US012509662B2

(12) United States Patent
Yao

(10) Patent No.: US 12,509,662 B2
(45) Date of Patent: Dec. 30, 2025

(54) GENERATION REGULATABLE FUSOGENIC ONCOLYTIC HERPES SIMPLEX VIRUS TYPE 1 VIRUS AND METHODS OF USE

(71) Applicant: THE BRIGHAM AND WOMEN'S HOSPITAL, INC., Boston, MA (US)

(72) Inventor: Feng Yao, Southborough, MA (US)

(73) Assignee: THE BRIGHAM AND WOMEN'S HOSPITAL, INC.

( * ) Notice: Subject to any disclaimer, the term of this patent is extended or adjusted under 35 U.S.C. 154(b) by 1175 days.

(21) Appl. No.: 17/296,879

(22) PCT Filed: Nov. 21, 2019

(86) PCT No.: PCT/US2019/062527
§ 371 (c)(1),
(2) Date: May 25, 2021

(87) PCT Pub. No.: WO2020/112471
PCT Pub. Date: Jun. 4, 2020

(65) Prior Publication Data

US 2023/0026342 A1 Jan. 26, 2023

Related U.S. Application Data

(60) Provisional application No. 62/772,293, filed on Nov. 28, 2018.

(51) Int. Cl.

| | |
|---|---|
| ***C12N 7/00*** | (2006.01) |
| ***A61K 31/65*** | (2006.01) |
| ***A61K 35/763*** | (2015.01) |
| ***A61P 35/00*** | (2006.01) |

(52) U.S. Cl.
CPC ................ *C12N 7/00* (2013.01); *A61K 31/65* (2013.01); *A61K 35/763* (2013.01); *A61P 35/00* (2018.01); *C12N 2710/16621* (2013.01); *C12N 2710/16632* (2013.01); *C12N 2710/16671* (2013.01)

(58) Field of Classification Search
None
See application file for complete search history.

(56) References Cited

U.S. PATENT DOCUMENTS

| | | | | |
|---|---|---|---|---|
| 2008/0008686 A1 | 1/2008 | Yao | | |
| 2010/0015687 A1* | 1/2010 | Yao | C12N 15/86 | 435/235.1 |
| 2016/0074448 A1* | 3/2016 | Campadelli | A61P 9/00 | 435/235.1 |
| 2019/0083555 A1* | 3/2019 | Zhou | C12N 15/86 | |

OTHER PUBLICATIONS

Wang et al., Journal of Biological Chemistry vol. 289 Nunber 52, pp. 3795-3805 (Year: 2014).*
Debray et al., Virology vol. 145, Issue 1, Aug. 1985, pp. 36-48 (Year: 1985).*
Yao et al., "Development of a Regulatable Oncolytic Herpes Simplex Virus Type 1 Recombinant Virus for Tumor Therapy", Journal of Virology, vol. 84, No. 16, Aug. 15, 2010 (Aug. 15, 2010) pp. 8163-8171.
Wang et al., "p32 is a novel target for viral protein ICP34. 5 of herpes simplex virus type 1 and facilitates viral nuclear egress." Journal of Biological Chemistry 289.52 (2014): 35795-35805.
Avitabile et al., "Herpes simplex virus glycoprotein K, but not its syncytial allele, inhibits cell-cell fusion mediated by the four fusogenic glycoproteins, gD, GB, gH, and gL." Journal of virology 77.12 (2003): 6836-6844.

* cited by examiner

*Primary Examiner* — Shanon A. Foley
*Assistant Examiner* — Myron G Hill
(74) *Attorney, Agent, or Firm* — NIXON PEABODY LLP; David S. Resnick; Jeanne N. Jodoin

(57) ABSTRACT

Malignant tumors that are resistant to conventional therapies represent significant therapeutic challenges. An embodiment of the present invention provides a new generation regulatable fusogenic oncolytic herpes simplex virus-1 that is more effective at selective killing target cells, such as tumor cells. In various embodiments presented herein, the oncolytic virus described herein is suitable for treatment of solid tumors, as well as other cancers.

19 Claims, 11 Drawing Sheets

Specification includes a Sequence Listing.

SEQUENCE LISTING

<160> NUMBER OF SEQ ID NOS: 10

<210> SEQ ID NO 1
<211> LENGTH: 142090
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
gaggagcggc tagaccccgg aaacgggccc cccccaaaac acaccccccg ggggcgcgcg 60
cggcccttta aaggcgggcg gcgggcagcc cgggcccccc gcggccgcga ctagcgagtt 120
agacaggcaa gcactactcg cctctgcacg cacatgcttg cctgtcaaac tctaccaccc 180
cggcacgctc tctgtctcca tggcccgccg ccgccatcgc ggcccccgcc gcccccggcc 240
gcccgggccc acgggcgcgg tcccaaccgc acagtcccag gtaacctcca cgcccaactc 300
ggaacccgtg gtcaggagcg cgcccgcggc cgccccgccg ccgccccccg ccccccatta 360
gcatgcccct cccgccgacg caacaggggc ttggcctgcg tcggtgcccc ggggcttccc 420
gccttcccga agaaactcat taccataccc ggaaccccag gggaccaatg cgggttcatt 480
gagcgacccg cgggccaatg cgcgaggggc cgtgtgttcc gccaaaaaag caattaacat 540
aacccggaac cccaggggag tggttacgcg cggcgcggga ggcggggaat accggggttg 600
cccattaagg gccgcgggaa ttgccggaag cgggaagggc ggccggggcc gcccattaat 660
gagtttctaa ttaccatccg ggaagcggaa caaggcctct gcaatttttt aattcccagc 720

```
ccgggaaggg ggcggcccgg cccactgggc gggggttacc gcccagtggg ccgggccccg    780
acgactcggc ggacgctggt tggccgggcc ccgccgcgct ggcggccgcc gattggccag    840
tcccgccctc cgagggcggg cccgcctcgg gggcgggccg gctccaagcg tatatatgcg    900
cggctcctgc catcgtctct ccggagagcg gcttggtgcg gagctcccgg gagctccgcg    960
gaagacccag gccgcctcgg gtgtaacgtt agaccgagtt cgccgggccg gctccgcggg   1020
ccagggcccg ggcacgggcc tcgggcccca ggcacggccc gatgaccgcc tcggcctccg   1080
ccacccggcg ccggaaccga gcccggtcgg cccgctcgcg ggcccacgag ccgcggcgcg   1140
ccaggcgggc ggccgaggcc cagaccacca ggtggcgcac ccggacgtgg ggcgagaagc   1200
gcacccgcgt gggggtcgcg ggggtcgcgg gggtcgcggg gggcttcggc gccccctccc   1260
cgcccgcgcg tcgcaggcgc aggcgcgcca ggtgctctgc ggtgacgcgc aggcggaggg   1320
cgaggcgcgg cggaaggcgg aagggggag gggggtggg aggggttagc cccgcccccc   1380
gggcccgcgc cgggcggtgg ggaccggggg cggggggcgg cggcggtggg ccgggcctct   1440
ggcgccggct cgggcgggg gctgtccggc cagtcgtcgt cgtcgtcgtc ggacgcggac   1500
tcgggaacgt ggagccactg gcgcagcagc agcgaacaag aaggcggggg cccctggcgg   1560
ggggcggcgg cggggcggcc gcgggcgcgc tcctgaccac gggttccgag ttgggcgtgg   1620
aggttacctg ggactggcgg ttgggaccgc gcccgtgggc ccgggcggcc gggggcggcg   1680
ggggccgcga tggcggcggc gggccatgga gacagagagc gtgccggggt ggtagagttt   1740
gacaggcaag catgtgcgtg cagaggcgag tagtgcttgc ctgtctaact cgctagtctc   1800
ggccgggggg ggcccgggct gcccgccgcc cgcctttaaa gggccgcgcg ccccccgcca   1860
gtgggccccc gccttcttgt tcgctgctgc tgcgccagtg gctccacgtt cccgagtccg   1920
cgtccgacga cgacgacgac gactggccgg acagcccccc gcccgagccg gcgccagagg   1980
cccggcccac cgccgccgcc ccccgccccc ggtccccacc gcccggcgcg ggcccggggg   2040
gcggggctaa cccctcccac ccccccctccg cccttccgc cttccgccgc gcctcgccct   2100
ccgcctgcgc gtcaccgccg agcacctggc gcgcctgcgc ctgcgacgcg cgggcggggg   2160
ggggcgccga agccccccg acccccgcga cccccgcgac ccccacgcgg gtgcgcttct   2220
cgccccacgt ccgggtgcgc cacctggtgg tctgggcctc ggccgcccgc ctggcgcgcc   2280
gcggctcgtg ggcccgcgag cgggccgacc gggctcggtt ccggcgccgg gtggcggagg   2340
ccgaggcggt catcgggccg gcctggggcc cgaggcccgt gcccgggccc ggcccgcgga   2400
gccggcccgg cgaactcggt ctaacgttac acccgaggcg gcctgggtct tccgcggagc   2460
tcccgggagc tccgcaccaa gccgctctcc ggagagacga tggcaggagc cgcgcatata   2520
tacgcttgga gccggcccgc ccccgaggcg ggcccgccct cggagggcgg gactggccaa   2580
tcggcggccg ccagcgcggc ggggcccggc caaccagcgt ccgccgagtc gtcggggccc   2640
ggcccactgg gcggtaactc ccgcccagtg ggccgggccg cccacttccc ggtatggtaa   2700
ttaaaaactt gcagaggcct tgttccgctt cccggtatgg taattagaaa ctcattaatg   2760
ggcggccccg gccgcccttc ccgcttccgg caattcccgc ggcccttaat gggcaacccc   2820
ggtattcccc gcctcccgcg ccgcgcgtaa ccactcccct ggggttccgg gttatgttaa   2880
ttgctttttt ggcggaacac acggcccctc gcgcattggc ccgcgggtcg ctcaatgaac   2940
ccgcattggt cccctggggt tccgggtatg gtaatgagtt tcttcgggaa ggcgggaagc   3000
cccggggcac cgacgcaggc caagcccctg ttgcgtcggc gggaggggca tgctaatggg   3060
```

-continued

```
gttctttggg ggacaccggg ttggtccccc aaatcggggg ccgggccgtg catgctaatg   3120

atattctttg ggggcgccgg gttggtcccc ggggacgggg ccgctccgcg gtgggcctgc   3180

ctcccctggg acgcgcggcc attgggggaa tcgtcactgc cgcccctttg ggagggggaa   3240

aggcgtgggg tataagttag ccctggcccg acggtctggt cgcatttgca cctcggcact   3300

cggagcgaga cgcagcagcc aggcagactc gggccgcccc ctctccgcat caccacagaa   3360

gccccgccta cgttgcgacc cccagggacc ctccgtcagc gaccctccag ccgcatacga   3420

ccccccgggg atcctctagg gcctctgagc tattccagaa gtagtgaaga ggcttttttg   3480

gaggcctagg cttttgcaaa aagctccgga tcgatcctga gaacttcagg gtgagtttgg   3540

ggacccttga ttgttctttc tttttcgcta ttgtaaaatt catgttatat ggagggggca   3600

aagttttcag ggtgttgttt agaatgggaa gatgtccctt gtatcaccat ggaccctcat   3660

gataattttg tttctttcac tttctactct gttgacaacc attgtctcct cttattttct   3720

tttcattttc tgtaactttt tcgttaaact ttagcttgca tttgtaacga atttttaaat   3780

tcacttttgt ttatttgtca gattgtaagt actttctcta atcacttttt tttcaaggca   3840

atcagggtat attatattgt acttcagcac agttttagag aacaattgtt ataattaaat   3900

gataaggtag aatatttctg catataaatt ctggctggcg tggaaatatt cttattggta   3960

gaaacaacta catcctggtc atcatcctgc ctttctcttt atggttacaa cgatatacac   4020

tgtttgagat gaggataaaa tactctgagt ccaaaccggg cccctctgct aaccatgttc   4080

atgccttctt ctttttccta cagctcctgg gcaacgtgct ggttattgtg ctgtctcatc   4140

attttggcaa agaattgtaa tacgactcac tatagggcga attgatatgt ctagattaga   4200

taaaagtaaa gtgattaaca gcgcattaga gctgcttaat gaggtcggaa tcgaaggttt   4260

aacaacccgt aaactcgccc agaagctagg tgtagagcag cctacattgt attggcatgt   4320

aaaaaataag cgggctttgc tcgacgcctt agccattgag atgttagata ggcaccatac   4380

tcacttttgc cctttagaag gggaaagctg gcaagatttt ttacgtaata acgctaaaag   4440

ttttagatgt gctttactaa gtcatcgcga tggagcaaaa gtacatttag gtacacggcc   4500

tacagaaaaa cagtatgaaa ctctcgaaaa tcaattagcc tttttatgcc aacaaggttt   4560

ttcactagag aatgcattat atgcactcag cgctgtgggg cattttactt taggttgtgt   4620

attggaagat caagagcatc aagtcgctaa agaagaaagg gaaacaccta ctactgatag   4680

tatgccgcca ttattacgac aagctatcga attatttgat caccaaggtg cagagccagc   4740

cttcttattc ggccttgaat tgatcatatg cggattagaa aaacaactta aatgtgaaag   4800

tgggtccgcg tacagcggat cccgggaatt cagatcttat taaagcagaa cttgtttatt   4860

gcagcttata atggttacaa ataaagcaat agcatcacaa atttcacaaa taaagcattt   4920

ttttcactgc attctagttg tggtttgtcc aaactcatca atgtatctta tcatgtctgg   4980

tcgacccggg acgagggaaa acaataaggg acgcccccgt gtttgtgggg aggggggggt   5040

cgggcgctgg gtggtctctg gccgcgccca ctacaccagc caatccgtgt cggggaggtg   5100

gaaagtgaaa gacacgggca ccacacacca gcgggtcttt tgtgttggcc ctaataaaaa   5160

aaactcaggg gatttttgct gtctgttggg aaataaaggt ttacttttgt atcttttccc   5220

tgtctgtgtt ggatgtatcg cgggggtgcg tgggagtggg ggtgcgtggg agtgggggtg   5280

cgtgggagtg gggggtgcgtg ggagtggggg cccacgcacc cccactccca cgcaccccca   5340

cacccacgca cccccgcgat acatccaaca cagacaggga aaagatacaa aagtaaacct   5400

ttatttccca acagacagca aaaatcccct gagttttttt tattagggcc aacacaaaag   5460
```

acccgctggt gtgtggtgcc cgtgtctttc actttccacc tccccgacac ggattggctg 5520
gtgtagtggg cgcggccaga gaccacccag cgcccgaccc cccctcccc acaaacgggg 5580
ggcccggaga gccgcggcac ccggacgcgc ccggaaagtc tttcgcacca ccggcgatcg 5640
gcacggccgc gcccccgctt ttataaaggc tcagatgacg cagcaaaaac aggccacagc 5700
accacatggg taggtgatgt aattttattt tcctcgtctg cggcctaatg gatttccggg 5760
cgcggtgccc ctgtctgcag agcacttaac ggattgatat ctcgcgggca cgcgcgccct 5820
taatggaccg gcgcggggcg gggggccgga tacccacacg ggcggggggg ggtgtcgcgg 5880
gccgtctgct ggcccgcggc cacataaaca atgactcggg gcctttctgc ctctgccgct 5940
tgtgtgtgcg cgcgccggct ctgcggtgtc ggcggcggcg gcggcggtgg ccgccgtgtt 6000
cggtctcggt agccggccgg cgggtggact cgcgggggc cggagggggg gaggcagggg 6060
gggggagggt ggggatcagg acttccactt cccgtccttc catcccccgt tcccctcggt 6120
tgttcctcgc ctcccccaac accccgccgc tttccgttgg ggttgttatt gttgtcggga 6180
tcgtgcgggc cgggggtcgc cggggcaggg gcgggggcgt gggcgggggt gctcgtcgat 6240
cgaccgggct cagtgggggc gtggggtggg tgggagaagg cgaggagact ggggtggggg 6300
tgtcggtggg tggttgtttt ttccccccctg ccttccaccc tccggccccc cgcgagtcca 6360
cccgccggcc ggctaccgag accgaacacg gcggccaccg ccgccgccgc cgccgacacc 6420
gcagagccgg cgcgcgcaca cacaagcggc agaggcagaa aggccccgag tcattgttta 6480
tgtggccgcg ggccagcaga cggcccgcga cacccccccc cccccgtgtg gggatccggc 6540
cccccgcccc cgccgcccat taagggcgcg cgtgcccgcg gatatcatcc gttaagtgct 6600
ctgcagacag gggcaccgcg cccggaaatc cattaggccg cagacgagga aaataaaatt 6660
acatccctac ccatgtggtg ctgtggcctg tttttgctgc gtcatctgag cctttataaa 6720
agcgggggcg cggccgtgcc gatcgccggt ggtgcgaaag actttccggg cgcgtccggg 6780
ccccccgccg ctaaacccca tcccgccccc gggaccccac atataagccc ccagccacac 6840
gcaagaacag acacgcagaa cggctgtgtt tattttaaat aaaccgatgt cggaataaac 6900
aaacacaaac acccgcgacg gggggacggc ggggacggag ggaggggggg gacgggggac 6960
ggaaacagac acaaaaaaca accacaaaaa aaaaaaacaa ccacccaccg acaccccccc 7020
cccagtctcc tcgccttctc cccccacccc acgcccccac tgagcccggt cgatcgacga 7080
gcacccccgc ccccgccccc gcccctgccc cggcgacccc cggcccgcac gatcccgaca 7140
acaataatcc gtcccccgtc ccccctccc tccgtcccct ccgtcccccc tcgcgggggt 7200
ttgtgtttgt ttattccgac atcggtttat ttaaaataaa cacagccgtt ctgcgtgtct 7260
gttcttgcgt gtggctgggg gcttatatgt ggggtcccgg gggcgggatg gggtttagcg 7320
gcggggggcg gcgcgccgga cggggcgctg gagatagcgg cccccgggga ccgggggacc 7380
ggggctgggt atcccgaggt ggggatgtgg gcgggggtgc gcgggagggg tcggtggtgg 7440
gggtggtggt ggtgggggta gtaggaatgg tggggggggg gagggcgctg gttggtcaaa 7500
aaagggaggg acgggggccg gcagaccgac ggcgacaacg ctccccggcg gccgggtcgc 7560
ggctcttacg agcggcccgg cccgcgctcc caccccccgg gccgtgtcct tgctttcccc 7620
ccgtctcccc ccccgccttc tcctcctcct cctcgttttt ccaaaccccg cccacccggc 7680
ccggcccggc ccggcccggc caccgccgcc cacccaccca cctcgggata cccagccccg 7740
gtcccccgtt ccccgggggc cgttatctcc agcgccccgt ccggcgcgcc gccccccgcc 7800

```
gctaaacccc atcccgcccc cgggacccca catataagcc cccagccaca cgcaagaaca    7860
gacacgcaga acggctacga ggaggaggag gagaaggcgg ggggggagac ggggggaaag    7920
caaggacacg gcccgggggg tgggagcgcg ggccgggccg ctcgtaagag ccgcgacccg    7980
gccgccgggg agcgttgtcg ccgtcggtct gccggccccc gtccctccct tttttgacca    8040
accagcgccc tcccccccgc gcgggccggg ccgctcgtaa gagccgcgac ccggccgccg    8100
gggagcgttg tcgccgtcgg tctgccggcc cccgtccctc ccttttttga ccaaccagcg    8160
ccctcccccc caccaccatt cctactacca ccaccaccac cacccccacc accgacacct    8220
cccgcgcacc cccgcccaca tccccccacc ccgcaccacg agcacggggt gggggtagca    8280
ggggatcaaa ggggggcaaa gccggcgggg cggttcgggg gggcgggaga ccgagtaggc    8340
ccgcccatac gcggcccctc ccggcagcca cgccccccag cgtcgggtgt cacggggaaa    8400
gagcagggga gagggggga gaggggagag ggggggagag ggggtatata aaccaacgaa    8460
aagcgcggga acggggatac ggggcttgtg tggcacgacg tcgtggttgt gttactgggc    8520
aaacacttgg ggactgtagg tttctgtggg tgccgaccct aggcgctatg gggattttgg    8580
gttgggtcgg gcttattgcc gttggggttt tgtgtgtgcg ggggggcttg tcttcaaccg    8640
aatatgttat tcggagtcgg gtggctcgag aggtggggga tatattaaag gtgccttgtg    8700
tgccgctccc gtctgacgat cttgattggc gttacgagac cccctcggct ataaactatg    8760
ctttgataga cggtatattt ttgcgttatc actgtcccgg attggacacg gtcttgtggg    8820
ataggcatgc ccagaaggca tattgggtta accccttttt atttgtggcg ggttttctgg    8880
aggacttgag tcaccccgcg tttcctgcca acacccagga aacagaaacg cgcttggccc    8940
tttataaaga gatacgccag gcgctggaca gtcgcaagca ggccgccagc cacacacctg    9000
tgaaggctgg gtgtgtgaac tttgactatt cgcgcacccg ccgctgtgta gggcgacagg    9060
atttgggacc taccaacgga acgtctggac ggaccccggt tctgccgccg gacgatgaag    9120
cgggcctgca accgaagccc ctcaccacgc cgccgcccat catcgccacg tcggacccca    9180
ccccgcgacg ggacgccgcc acaaaaagca gacgccgacg accccactcc cggcgcctct    9240
aacgatgcct cgacggaaac ccgtccgggt tcggggggcg aaccggccgc ctgtcgctcg    9300
tcagggccgg cgggcgctcc tcgccgccct agaggctgtc ccgctggtgt gacgttttcc    9360
tcgtccgcgc cccccgaccc tcccatggat ttaacaaacg ggggggtgtc gcctgcggcg    9420
acctcggcgc ctctggactg gaccacgttt cggcgtgtgt ttctgatcga cgacgcgtgg    9480
cggcccctga tggagcctga gctggcgaac cccttaaccg cccacctcct ggccgaatat    9540
aatcgtcggt gccagaccga agaggtgctg ccgccgcggg aggatgtgtt ttcgtggact    9600
cgttattgca cccccgacga ggtgcgcgtg gttatcatcg gccaggaccc atatcaccac    9660
cccggccagg cgcacggact tgcgtttagc gtgcgcgcga acgtgccgcc tcccccgagt    9720
cttcggaatg tcttggtggc cgtcaagaac tgttatcccg aggcacggat gagcggccac    9780
ggttgcctgg aaaagtgggc gcgggacggc gtcctgttac taaacacgac cctgaccgtc    9840
aagcgcgggg cggcggcgtc ccactctaga atcggttggg accgcttcgt gggcggagtt    9900
atccgccggt tggccgcgcg ccgccccggc ctggtgttta tgctctgggg cgcacacgcc    9960
cagaatgcca tcaggccgga ccctcgggtc cattgcgtcc tcaagttttc gcacccgtcg   10020
cccctctcca aggttccgtt cggaacctgc cagcatttcc tcgtggcgaa ccgatacctc   10080
gagacccggt cgatttcacc catcgactgg tcggtttgaa aggcatcgac gtccggggtt   10140
tttgtcggtg gggcttttg ggtatttccg atgaataaag acggttaatg gttaaacctc   10200
```

```
tggtctcata cgggtcggtg atgtcgggcg tcgggggaga gggagttccc tctgcgcttg  10260
cgattctagc ctcgtggggc tggacgttcg acacgccaaa ccacgagtcg gggatatcgc  10320
cagatacgac tcccgcagat tccattcggg gggccgctgt ggcctcacct aaccaacctt  10380
tacacggggg cccggaacgg gaggccacag cgccgtcttt ctccccaacg cgcgcggatg  10440
acggcccgcc ctgtaccgac gggccctacg tgacgtttga taccctgttt atggtgtcgt  10500
cgatcgacga attagggcgt cgccagctca cggacaccat ccgcaaggac ctgcggttgt  10560
cgctggccaa gtttagcatt gcgtgcacca agacctcctc gttttcggga aacgccccgc  10620
gccaccacag acgcggggcg ttccagcgcg gcacgcgggc gccgcgcagc aacaaaagcc  10680
tccagatgtt tgtgttgtgc aaacgcgccc acgccgctcg agtgcgagag cagcttcggg  10740
tcgttattca gtcccgcaag ccgcgcaagt attacacgcg atcttcggac gggcggctct  10800
gccccgccgt ccccgtgttc gtccacgagt tcgtctcgtc cgagccaatg cgcctccacc  10860
gagataacgt catgctggcc tcgggggccg agtaaccgcc cccccccccc ccccgccccc  10920
cccccccccc cccccccccc cctccccccc cccccccccc tcttccccccg tgacacccga  10980
cgctgggggg cgtggctgcc gggaggggcc gcgtatgggc gggcctactc ggtctcccgc  11040
ccccccgaac cgcccccgccg gctttgcccc ccgcgatctt cggacgggcg gctctgcccc  11100
gccgtccccg tgttcgtcca cgagttcgtc tcgtccgagc caatgcgcct ccaccgagat  11160
aacgtcatgc tggcctcggg ggccgagtaa ccgccccccc cccatgccac cctcactgcc  11220
cgtcgcgcgt gtttgatgtt aataaataac acataaattt ggctggttgt ttgttgtctt  11280
taatggaccg cccgcaaggg gggggggcg tttcagtgtc gggtgacgag cgcgatccgg  11340
ccgggatcct aggaccccaa aagtttgtct gcgtattcca gggtggggct cagttgaatc  11400
tcccgcagca cctctaccag caggtccgcg gtgggctgga gaaactcggc cgtcccgggg  11460
caggcggttg tcgggggtgg aggcgcggcg cccaccccgt gtgccgcgcc tggcgtctcc  11520
tctgggggcg acccgtaaat ggttgcagtg atgtaaatgg tgtccgcggt ccagaccacg  11580
gtcaaaatgc cggccgtggc gctccgggcg ctttcgccgc gcgaggagct gacccaggag  11640
tcgaacggat acgcgtacat atgggcgtcc cacccgcgtt cgagcttctg gttgctgtcc  11700
cggcctataa agcggtaggc acaaaattcg gcgcgacagt cgataatcac caacagccca  11760
atgggggtgt gctggataac aacgcctccg cgcggcaggc ggtcctggcg ctcccggccc  11820
cgtaccatga tcgcgcgggt gccgtactca aaaacatgca ccacctgcgc ggcgtcgggc  11880
agtgcgctgg tcagcgaggc cctggcgtgg cataggctat acgcgatggt cgtctgtgga  11940
ttggacatct cgcggtgggt agtgagtccc ccgggccggg ttcggtggaa ctgtaagggg  12000
acggcgggtt aatagacaat gaccacgttc ggatcgcgca gagccgatag tatgtgctca  12060
ctaatgacgt catcgcgctc gtggcgctcc cggagcggat ttaagttcat gcgaaggaat  12120
tcggaggagg tggtgcggga catggccacg tacgcgctgt tgaggcgcag gttgccgggc  12180
gtaaagcaga tggcgacctt gtccaggcta aggccctggg agcgcgtgat ggtcatggca  12240
agcttggagc tgatgccgta gtcggcgttt atggccatgg ccagctccgt agagtcaatg  12300
gactcgacaa actcgctgat gttggtgttg acgacggaca tgaagccgtg ttggtcccgc  12360
aagaccacgt aaggcagggg ggcctcttcc agtaactcgg ccacgttggc cgtcgcgtgc  12420
cgcctccgca gctcgtccgc aaaggcaaac acccgtgtgt acgtgtatcc catgagcgta  12480
taattgtccg tctgcagggc gacggacatc agcccccgc gcggcgagcc ggtcagcatc  12540
```

-continued

```
tcgcagcccc ggaagataac gttgtccacg tacgtgctaa agggggcgac ttcaaatgcc  12600
tccccgaaga gctcttggag gattcggaat ctcccgagga aggcccgctt cagcagcgca  12660
aactgggtgt gaacggcggc ggtggtctcc ggttccccgg gggtgtagtg gcagtaaaac  12720
acgtcgagct gttgttcgtc cagccccgcg aaaataacgt cgaggtcgtc gtcgggaaaa  12780
tcgtccgggc ccccgtcccg cggccccagt tgcttaaaat caaacgcacg ctcgccgggg  12840
gcgcctgcgt cggccattac cgacgcctgc gtcggcaccc ccgaagattt ggggcgcaga  12900
gacagaatct ccgccgttag ttctcccatg cgggcgtacg cgagggtcct ctgggtcgca  12960
tccaggcccg ggcgctgcag aaagttgtaa aaggagataa gcccgctaaa tatgagccgc  13020
gacaggaacc tgtaggcaaa ctccaccgaa gtctccccct gagtctttac aaagctgtcg  13080
tcacgcaaca ctgcctcgaa ggcccggaac gtcccactaa acccaaaaac cagttttcgc  13140
aggcgcgcgg tcaccgcgat ctggctgttg aggacgtaag tgacgtcgtt gcgggccacg  13200
accagctgct gtttgctgtg cacctcgcag cgcatgtgcc ccgcgtcctg gtcctggctc  13260
tgcgagtagt tggtgatgcg gctggtgttg gccgtgagcc acttttcaat agtcaggccg  13320
ggctggtgtg tcagccgtcg gtattcgtca aactccttga ccgacacgaa cgtaagcacg  13380
gggagggtta acacgacgaa ctccccctca cgggtcacct tcaggtaggc gtggagcttg  13440
gccatgtacg cgctcacctc tttgtgggag gagaacagcc gcgtccagcc ggggaggttg  13500
gcggggttgg tgatgtagtt ttccgggacg acgaagcgat ccacgaactg catgtgctcc  13560
tcggtgatgg gcaggccgta ctccagcacc ttcatgaggt taccgaactc gtgctcgacg  13620
caccgtttgt tgttaataaa aatggcccag ctatacgaga ggcgggcgta ctcgcgcagc  13680
gtgcgggtgc agatgaggta cgtgagcacg ttctcgctct ggcggacgga acaccgcagt  13740
ttctggtgct cgaaggcgac tccagggacg ccgtctgcgt cggcgagccc acacacacca  13800
acacgggccg caggcgggcc gcgtactggg gggtgtggta cagggcgtta atcatccacc  13860
agcaatacac cacggccgtg aggaggtgac gcccaaggag cccggcctcg tcgatgacga  13920
tcacgttgct gcgggtaaag gccggcagcg ccccgtgggt ggccggggcc aaccgcgtca  13980
gggcgccctc ggccaacccc agggtccgtt ccagggcggc cagggcgcga aactcgttcc  14040
gcaactcctc gcccccggag gcggccaggg cgcgcttcgt gaggtccaaa atcacctccc  14100
agtagtacgt cagatctcgt cgctgcaggt cctccagcga ggcggggttg ctggtcaggg  14160
tgtacgggta ctgtcccagt tgggcctgga cgtgattccc gcgaaaccca aattcatgaa  14220
agatggtgtt gatgggtcgg ctgagaaagg cgcccgagag tttggcgtac atgttttggg  14280
ccgcaatgcg cgtggcgccc gtcaccacac agtccaagac ctcgttgatt gtctgcacgc  14340
acgtgctctt tccggagcca gcgttgccgg tgataagata caccgcgaac ggaaactccc  14400
tgaggggcag gcctgcgggg gactctaagg ccgccacgtc ccggaaccac tgcagacggg  14460
gcacttgcgc tccgtcgagc tgttgttgcg agagctctcg gatgcgctta aggattggct  14520
gcaccccgtg catagacgta aaatttaaaa aggcctcggc cctccctgga acggctggtc  14580
ggtccccggg ttgctgaagg tgcggcgggc cgggtttctg tccgtctagc tggcgctccc  14640
cgccggccgc cgccatgacc gcaccacgct cgtgggcccc cactacgcgt gcgcgggggg  14700
acacggaagc gctgtgctcc cccgaggacg gctgggtaaa ggttcacccc acccccggta  14760
cgatgctgtt ccgtgagatt ctccacgggc agctggggta taccgagggc cagggggtgt  14820
acaacgtcgt ccggtccagc gaggcgacca cccggcagct gcaggcggcg atctttcacg  14880
cgctcctcaa cgccaccact taccgggacc tcgaggcgga ctggctcggc cacgtggcgg  14940
```

cccgcggtct gcagccccaa cggctggttc gccggtacag gaacgcccgg gaggcggata 15000
tcgccggggt ggccgagcgg gtgttcgaca cgtggcggaa cacgcttagg acgacgctgc 15060
tggactttgc ccacgggttg gtcgcctgct ttgcgccggg cggcccgagc ggcccgtcaa 15120
gcttccccaa atatatcgac tggctgacgt gcctggggct ggtccccata ttacgcaagc 15180
gacaagaagg gggtgtgacg cagggtctga gggcgtttct caagcagcac ccgctgaccc 15240
gccagctggc cacggtcgcg gaggccgcgg agcgcgccgg ccccgggttt tttgagctgg 15300
cgctggcctt cgactccacg cgcgtggcgg actacgaccg cgtgtatatc tactacaacc 15360
accgccgggg cgactggctc gtgcgagacc ccatcagcgg gcagcgcgga gaatgtctgg 15420
tgctgtggcc ccccttgtgg accggggacc gtctggtctt cgattcgccc gtccagcggc 15480
tgtttcccga gatcgtcgcg tgtcactccc tccgggaaca cgcgcacgtc tgccggctgc 15540
gcaataccgc gtccgtcaag gtgctgctgg ggcgcaagag cgacagcgag cgcggggtgg 15600
ccggtgccgc gcgggtcgtt aacaaggtgt tgggggagga cgacgagacc aaggccgggt 15660
cggccgcctc gcgcctcgtg cggcttatca tcaacatgaa gggcatgcgc cacgtaggcg 15720
acattaacga caccgtgcgt gcctacctcg acgaggccgg ggggcacctg atagacgccc 15780
cggccgtcga cggtaccctc cctggattcg gcaagggcgg aaacaaccgc gggtctgcgg 15840
gccaggacca ggggggcgg gcgccgcagc ttcgccaggc cttccgcacg gccgtggtta 15900
acaacatcaa cggcgtgttg gagggctata taaataacct gtttggaacc atcgagcgcc 15960
tgcgcgagac caacgcgggc ctggcgaccc aattgcagga gcgcgaccgc gagctccggc 16020
gcgcaacagc gggggccctg gagcgccagc agcgcgcggc cgacctggcg gccgagtccg 16080
tgaccggtgg atgcggcagc cgccctgcgg gggcggacct gctccgggcc gactatgaca 16140
ttatcgacgt cagcaagtcc atggacgacg acacgtacgt cgccaacagc tttcagcacc 16200
cgtacatccc ttcgtacgcc caggacctgg agcgcctgtc gcgcctctgg gagcacgagc 16260
tggtgcgctg ttttaaaatt ctgtgtcacc gcaacaacca gggccaagag acgtcgatct 16320
cgtactccag cggggcgatc gccgcattcg tcgcccccta ctttgagtca gtgcttcggg 16380
ccccccgggt aggcgcgccc atcacgggct ccgatgtcat cctgggggag gaggagttat 16440
gggatgcggt tttaaaaaac ccgcctgcaa acgtacctga cagacatcgc ggccctgttc 16500
gtcgcggacg tccagcacgc agcgctgccc ccgccccct ccccggtcgg cgccgatttc 16560
cggcccggcg cgtccccgcg gggccggtcc agatcgcggt cgcccggaag aactgcgcca 16620
ggcgcgccgg accagggcgg gggcatcggg caccgggatg gccgccgcga cggccgacga 16680
tgaggggtcg gccgccacca tcctcaagca ggccatcgcc ggggaccgca gcctggtcga 16740
ggcggccgag gcgattagcc agcagacgct gctccgcctg gcctgcgagg tgcgccaggt 16800
cggcgaccgc cagccgcggt ttaccgccac cagcatcgcg cgcgtcgacg tcgcgcctgg 16860
gtgccggttg cggttcgttc tggacgggag tcccgaggac gcctatgtga cgtcggagga 16920
ttactttaag cgctgctgcg gccagtccag ttatcgcggc ttcgcggtgg cggtcctgac 16980
ggccaacgag gaccacgtgc acagcctggc cgtgcccccc ctcgttctgc tgcaccggtt 17040
ctccctgttc aaccccaggg acctcctgga ctttgagctt gcctgtctgc tgatgtacct 17100
ggagaactgc ccccgaagcc acgccacccc gtcgaccttt gccaaggttc tggcgtggct 17160
cggggtcgcg ggtcgccgca cgtccccatt cgaacgcgtt cgctgccttt tcctccgcag 17220
ttgccactgg gtcctaaaca cactcatgtt catggtgcac gtaaaaccgt tcgacgacga 17280
gttcgtcctg ccccactggt acatggcccg gtacctgctg gccaacaacc cgccccccgt 17340
tctctcggcc ctgttctgtg ccaccccgac gagctcctca ttccggctgc cggggccgcc 17400
cccccgctcc gactgcgtgg cctataaccc cgccgggatc atggggagct gctgggcgtc 17460
ggaggaggtg cgcgcgcctc tggtctattg gtggctttcg gagaccccaa aacgacagac 17520
gtcgtcgctg ttttatcagt tttgttgaat tttaggaaat aaacccggtt ttgtttctgt 17580
ggcctcccga cggatgcgcg tgtccttcct ccgtcttggt gggtgggtgt ctgtgtatcg 17640
cgtcccatct gtgcggagag ggggggcatg tcggcacgta ttcggacaga ctcaagcaca 17700
cacgggggag cgctcttgtc tcagggcaat gtttttattg gtcaaactca ggcaaacaga 17760
aacgacatct tgtcgtcaaa gggatacaca aacttccccc cctctcccca tactcccgcc 17820
agcaccccgg taaacaccaa ctcaatctcg cgcaggattt cgcgcaggtg atgagcgcag 17880
tccacggggg ggagcacaag ggccgcgggg tatagatcga cggggacgcc gaccgactcc 17940
ccgcctccgg gacagacacg cacgacgcgc cgccagtagt gctctgcgtc cagcaaggcg 18000
ccgccgcgga aggcagtggg gggcaagggg tcgctagcct caaaggggga cacccgaacg 18060
ctccagtact ccgcgtccaa ccgtttatta aacgcgtcca cgataaggcg gtcgcaggcg 18120
tcctccataa ggccccgggc cgtgagtgcg tcctcctccg gcacgcctgc cgttgtcagg 18180
cccaggaccc gtcgcagcgt gtcgcgtacg accccggccg ccgtggtgta cgcgggcccg 18240
cggagaggaa atcccccaag atggtcagtg ttgtcgcggg agttccagaa ccacactccc 18300
gcctggttcc aggcgactgc gtgggtgtag acgccctcga gggccaggca cagtgggtgc 18360
cgcagccgga ggccgttggc cctaagcacg gctcccacgg ccgtctcgat ggcccgccgg 18420
gcgtcctcga tcaccccgga agccgcatcc gcgtcttggg ggtccacgtt aaagacaccc 18480
cagaacgcac ccccatcgcc cccgcagacc gcgaacttca ccgagctggc cgtctcctcg 18540
atctgcaggc agacggcggc cattacccca cccaggagct gccgcagcgc agggcaggcg 18600
tcgcacgtgt ccgggaccag gcgctccaag acggccccgg cccagggctc tgagggagcg 18660
gccaccacca gcgcgtccag tcttgctagg cccgtccggc cgtgggggtc cgccagcccg 18720
ctccccccga ggtcggccag ggccaccagg agctgggcgc gaagtccggg gaagcaaaac 18780
cgcgccgtcc agacgggccc gacggccgcg ggcgggtcta acagttggat gattttagtg 18840
gcgggatgcc accgcgccac cgcctcccgc accgcgggca ggaggcatcc ggctgccgcc 18900
gaggccacgc cgggccaggc tcgcgggggg aggacgaccc tggcccccac cgcgggccag 18960
gcccccagga gcgcggcgta agcggccgcg gccccgcgca ccaggtcccg tgccgactcg 19020
gccgtggccg gcacggtgaa cgtgggccaa cccggaaacc ccaggacggc aaagtacggg 19080
acgggtcccc cccggacctc aaactcgggc cccagaaagg caaagacggg ggccagggcc 19140
ccgggggcgg cgtggaccgt ggtatgccac tgccggaaaa gggcgacgag cgccggcgcg 19200
gagaacttct cgccggcgct tacaaagtag tcgtaatcgc ggggcagcag cacccgtgcc 19260
gtgactcgtt gcgggtgccc gcgtggccgc aggcccacct cgcacacctc gaccaggtcc 19320
ccgaacgcgc cctccttctt gatcggcgga aacgcaagag tctggtattc gcgcgcaaat 19380
agcgcggttc cggtggtgat gttaacggtc agcgaagcgg cggacgcgca ctgggggggtg 19440
tcgcgaatgg ccgccaggcg cgcccacgcc agccgcgcgt cgggatgctc ggcaacgcgc 19500
gccgccaggg ccatagggtc gatgtcaatg ttggcctccg cgaccaggag agcggcgcga 19560
ggggcggcgg gcgggcccca cgacgctctc tcaactttca ccaccagtcc cgtgcgtggg 19620
tccgagccga tacgcagcgg ggcgaacagg gccaccggcc cggtctggcg ctccagggcc 19680

```
gccaggacgc acgcgtacag cgcccgccac agagtcgggt tctccagggg ctccagcggg  19740
gaggcggccg gcgtcgtcgc ggcgcgggcg gccgccacga cggcctggac ggagacgtcc  19800
gcggagccgt agaaatcccg cagctccgtc gcggtgacgg agacctccgc aaagcgcgcg  19860
cgaccctccc ctgcggcgtt gcgacataca aaatacacca gggcgtggaa gtactcgcga  19920
gcgcgggggg gcagccatac cgcgtaaagg gtaatggcgc tgacgctctc ctccacccac  19980
acgatatctg cggtgtccat cgcacggccc ctaaggatca cgggcggtct gtgggtccca  20040
tgctgccgtg cctggccggg cccggtgggt cgcggaaacc ggtgacgggg ggggggcggt  20100
ttttggggtt ggggtggggg tgggaaacgg cccgggtccg ggggccaact tggcccctcg  20160
gtgcgttccg gcaacagcgc cgccggtccg cggacgacca cgtaccgaac gagtgcggtc  20220
ccgagactta tagggtgcta aagttcaccg ccccctgcat catgggccag gcctcggtgg  20280
ggagctccga cagcgccgcc tccaggatga tgtcagcgtt ggggttggcg ctggatgagt  20340
gcgtgcgcaa acagcgcccc cacgcaggca cgcgtagctt gaagcgcgcg cccgcaaact  20400
cccgcttgtg ggccataagc agggcgtaca gctgcctgtg ggtccggcag gcgctgtggt  20460
cgatgtggtg ggcgtccaac aaccccacga ttgtctgttt ggtgaggttt ttaacgcgcc  20520
ccgccccggg aaacgtctgc gtgcttttgg ccatctgcac gccaaacagt tcgccccaga  20580
ttatcttgaa cagcgccacc gcgtggtccg tctcgctaac ggacccgcgc gggggacagc  20640
cgcttagggc gtcggcgacg cgcttgacgg cttcctccga gagcagaagt ccgtcggtta  20700
cgttacagtg gcccagttcg aacaccagct gcatgtagcg gtcgtagtgg ggggtcagta  20760
ggtccagcac gtcatcgggg ccgaaggtcc tcccagatcc cccggccgcc gagtcccaat  20820
gcaggcgcgc ggccatggtg ctgcacaggc acaacagctc ccagacgggg gttacgttca  20880
gggtgggggg cagggccacg agctccagct ctccggtgac gttgatcgtg gggatgacgc  20940
ccgtggcgta gtggtcatag atccgccgaa atatggcgct gctgcgggtg gccatgggaa  21000
cgcggagaca ggcctccagc aacgccaggt aaataaaccg cgtgcgtccc atcaggctgt  21060
tgaggttgcg catgagcgcg acaatttccg ccggcgcgac atcggaccgg aggtattttt  21120
cgacgaaaag acccacctcc tccgtctcgg cggcctgggc cggcagcgac gcctcgggat  21180
cccggcaccg cagctcccgt agatcgcgct gggccctgag ggcgtcgaaa tgtacgcccc  21240
gcaaaaacag acagaagtcc tttggggtca gggtatcgtc gtgtccccag aagcgcacgc  21300
gtatgcagtt tagggtcagc agcatgtgaa ggatgttaag gctgtccgag agacacgcca  21360
gcgtgcatct ctcaaagtag tgtttgtaac ggaatttgtt gtagatgcgc gacccccgcc  21420
ccagcgacgt gtcgcatgcc gacgcgtcac agcgcccctt gaaccggcga cacagcaggt  21480
ttgtgacctg ggagaactgc gcgggccact ggccgcagga actgaccacg tgattaagga  21540
gcatgggcgt aaagacgggc tccgagcgcg ccccggagcc gtccatgtaa atcagtagct  21600
ccccccttgcg gagggtgcgc acccgtccca gggactggta cacggacacc atgtccggtc  21660
cgtagttcat gggttttacg taggcgaaca tgccatcaaa gtgcagggga tcgaagctga  21720
ggcccacggt tacgaccgtc gtgtatataa ccacgcggta ttggccccac gtggtcacgt  21780
ccccgagggg ggtgagcgag tgaagcaaca gcacgcggtc cgtaaactga cggcagaacc  21840
gggccacgat ctccgcgaag gagaccgtcg acgaaaaaat gcagatgtta tcgccccccgc  21900
caaggcgcgc ttccagctcc ccaaagaacg tggccccccg ggcgtccgga gaggcgtccg  21960
gagacgggcc gctcggcggc ccgggcgggc gcagggcagc ctgcaggagc tcggtcccca  22020
```

-continued

```
gacgcgggag aaacaggcac cggcgcgccg aaaacccggg catggcgtac tcgccgacca  22080
ccacatgcac gttttttcg ccccggagac cgcacaggaa gtccaccaac tgcgcgttgg  22140
cggttgcgtc catggcgatg atccgaggac aggtgcgcag caggcgtagc attaacgcat  22200
ccacgcggcc cagttgctgc atcgttggcg aatagagctg gcccagcgtc gacataacct  22260
cgtccagaac gaggacgtcg tagttgttca gaaggttggg gcccacgcga tgaaggcttt  22320
ccacctggac gataagtcgg tggaaggggc ggtcgttcat aatgtaattg gtggatgaga  22380
agtaggtgac aaagtcgacc aggcctgact cagcgaaccg cgtcgccagg gtctgggtaa  22440
aactccgacg acaggagacg acgagcacac tcgtgtccgg agagtggatc gcttcccgca  22500
gccagcggat cagcgcggta gtttttcccg accccattgg cgcgcggacc acagtcacgc  22560
acctggccgt cggggcgctc gcgttgggga aggtgacggg tccgtgctgc tgccgctcga  22620
tcgttgtttt cgggtgaacc cggggcaccc attcggccaa atcccccccg tacaacatcc  22680
gcgctagcga tacgctcgac gtgtactgtt cgcactcgtc gtccccaatg ggacgcccgg  22740
cccccagagg atctcccgac tccgcgcccc ccacgaaagg catgaccggg gcgcggacgg  22800
cgtggtgggt ctggtgtgtg caggtggcga cgtttgtggt ctctgcggtc tgcgtcacgg  22860
ggctcctcgt cctggcctct gtgttccggg cacggtttcc ctgcttttac gccacggcga  22920
gctcttatgc cggggtgaac tccacggccg aggtgcgcgg gggtgtagcc gtgcccctca  22980
ggttggacac gcagagcctt gtgggcactt atgtaatcac ggccgtgttg ttgttggccg  23040
cggccgtgta tgccgtggtc ggcgccgtga cctcccgcta cgaccgcgcc ctggacgcgg  23100
gccgccgtct ggctgcggcc cgcatggcca tgccgcacgc cacgctgatc gccggaaacg  23160
tctgctcttg gttgctgcag atcaccgtcc tgttgctggc ccatcgcacc agccagctgg  23220
cccacctggt ttacgtcctg cactttgcgt gtctggtgta ttttgcggcc catttttgca  23280
ccagggggt cctgagcggg acgtatctgc gtcaggtgca cggcctgatg gagccggccc  23340
cgactcatca tcgcgtcgtt ggcccggctc gagccgtgct gacaaacgcc ttgctgttgg  23400
gcgtcttcct gtgcacggcc gacgccgcgg tatccctgaa taccatcgcc gcgttcaact  23460
ttaattttc ggccccgggc atgctcatat gcctgaccgt gctgttcgcc cttctcgtcg  23520
tatcgctgtt gttggtggtc gagggggtgt tgtgtcacta cgtgcgcgtg ttggtgggcc  23580
cccacctggg ggccgtggcc gccacgggca tcgtcggcct ggcatgcgag cactattaca  23640
ccaacggcta ctacgttgtg gagacgcagt ggccgggggc ccagacggga gtccgcgtcg  23700
ccctcgccct ggtcgccgcc tttgccctcg gcatggccgt gctccgctgc acccgcgcct  23760
atctgtatca caggcggcac cacaccaaat tttttatgcg catgcgcgac acgcgacacc  23820
gcgcacattc cgccctcaag cgcgtacgca gttccatgcg cggatcgcga gacggccgcc  23880
acaggcccgc acccggcagc ccgcccggga ttcccgaata tgcggaagac ccctacgcga  23940
tctcatacgg cggccagctc gaccggtacg gagattccga cggggagccg atttacgacg  24000
aggtggcgga cgaccaaacc gacgtattgt acgccaagat acaacacccg cggcacctgc  24060
ccgacgacga gcccatctat gacaccgttg gggggtacga ccccgagccc gccgaggacc  24120
ccgtgtacag caccgtccgc cgttggtagc tgtttggttc cgttttaata aaccgtttgt  24180
gtttaacccg accgtggtgt atgtctggtg tgtggcgtcc gatcccgtta ctatcaccgt  24240
tccccccaaa ccccggcgat tgtgggtttt tttaaaaacg acacgcgtgc gaccgtatac  24300
agaacattgt tgttttttat tcgctatcgg acatgggggg tggaaactgg gtggcggggc  24360
aggcgcctcc gggggttcgc cggtgagtgt ggcgcgaggg gggatccgac gaacgcaggc  24420
```

gctgtctccc cggggcccgc gtaaccccgc gcatatccgg gggcacgtag aaattacctt 24480
cctcttcgga ctcgatatcc acgacgtcaa agtcgtgggc ggtcagcgag acgacctccc 24540
cgtcgtcggt gatgaggacg ttgtttcggc agcagcaggg ccgggtcccg gagaacgaga 24600
ggcccatagc tcggcgagcg tgtcgtcgaa cgccaggcgg ctgcttcgct gtatggcctt 24660
atagatctcc ggatcgatgc ggacgggggt aatgatcagg gcgatcggaa cggcctggtt 24720
cgggagaatg gacgccttgc tgggtcctgc ggccccgaga gccccggcgc cgtcctccag 24780
gcggaacgtt acgccctcct ccgcgctagt gcggtgcctg ccgataaacg tcaccagatg 24840
cgggtggggg gggcagtcgg ggaagtggct gtcgagcacg tagccctgca ccaagatctg 24900
cttaaagttc gggtgacggg ggttcgcgaa gacgggctcg cggcgtacca gatccccgga 24960
gctccaggac acgggggaga tggtgtggcg tccgaggtcg gggtgccaa acagaagcac 25020
ctccgagaca acgccgctat ttaactccac caaggcccga tccgcggcgg agcaccgcct 25080
tttttcgccc gaggcgtggg cctctgacca ggcctggtct tgcgtgacga gagcctcctc 25140
cgggccgggg acgcgcccgg gcgcgaagta tcgcacgctg ggcttcggga tcgaccggat 25200
aaatgcccgg aacgcctccg gggaccggtg tgccatcaag tcctcgtacg cggaggccgt 25260
ggggtcgctg gggtccatgg ggtcgaaagc gtacttggcc cggcatttga cctcgtaaaa 25320
ggccaggggg gtcttgggga ctggggccaa gtagccgtga atgtcccgag gacagacgag 25380
aatatccagg gacgccccga ccatccccgt gtgaccgtcc atgaggaccc cacacgtatg 25440
cacgttctct tcggcgaggt cgccgggttc gtggaagata aagcgccgcg tgtcggcgcc 25500
ggcctcgccg ccgtcgtccg cgcggcccac gcagtagcga aacagcaggc ttcgggccgt 25560
cggctcgttc acccgcccga acatcaccgc cgaagactgt acatccggcc gcaggctggc 25620
gttgtgcttc agccactggg gcgagaaaca cggaccctgg gggccccagc ggagggtgga 25680
tgcggtcgtg aggccccgcc ggagcagggc ccatagctgg cagtcggcct ggttttgcgt 25740
ggccgcctcg taaaacccca tgaggggccg gggcgccacg gcgtccgcgg cggccggggg 25800
cccgcggcgc gtcaggcgcc ataggtgccg gccgagtccg cggtccacca tacccgcctc 25860
ctcgaggacc acggccaggg aacacagata atccaggcgg gcccagaggg gaccgatggc 25920
cagaggggcg cggacgccgc gcagcaaccc gcgcaggggc gctcgaacgt ctcggctagt 25980
atatgggagg gcagcgcgtt ggggatcacc gacgccgacc acatagagtc aaggtccggg 26040
gagtcgggat cggcgtccgg gtcgcgggcg tgggtgcccc caggagatag cggaatgtct 26100
ggggtcggag gccctgaggc gtcagaaagt gccggcgacg cggcccgggg cttttcgtct 26160
gcggtgtcgg tggcgtgctg atcacgtggg gggttaacgg gcgaatggga gctcgggtcc 26220
acaactgacg tcgtctgggg tgggggggc aggggacgga aggtggttgt tagcggaaga 26280
ctgttagggc gggggcgctt gggggggctg tcggggccac gaggggtgtc ctcggccagg 26340
gcccaggaac gcttagtcac ggtgcgtccc ggcggacatg ctgggcctcc cgtggactcc 26400
atttccgaga cgacgtgggg ggagcggtgg ttgagcgcgc cgccgggtga acgctgattc 26460
tcacgacagc gcgtgccgcg cgcacgggtt ggtgtgacac aggcgggaca ccagcaccag 26520
gagaggctta agctcgggag gcagcgccac cgacgacagt atcgccttgt gtgtgtgctg 26580
gtaatttata caccgatccg taaacgcgcg ccgaatcttg ggattgcgga ggtggcgccg 26640
gatgccctct gggacgtcat acgccaggcc gtgggtgttg gtctcggccg agttgacaaa 26700
cagggctggg tgcagcacgc ggcgataggc gagcagggcc agggcgaagt ccagcgacag 26760
ctggttgttg aaatactggt aaccgggaaa ccgggtcacg ggtacgccca ggctcggggc 26820
gacgtacacg ctaaccacca actccagcag cgtctggcca agggcgtaca ggtcaaccgc 26880
taacccgacg tcgtgcttca ggcggtggtt ggtaaattcg gcccgttcgt tgttaaggta 26940
tttcaccaac agctccgggg gctggttata cccgtgaccc accagggtgt gaaagttggc 27000
tgtggttagg gcggtgggca tgccaaacat ccggggggac ttgaggtccg gctcctggag 27060
gcaaaactgc ccccgggcga tcgtggagtt ggagttgagg gtgacgaggc taaagtcggc 27120
gaggacggcc cgccggagcg agacggcgtc cgaccgcagc atgacgagga tgttggcgca 27180
cttgatatcc aggtggctga tcccgcaggt ggtgtttaaa aacacaacgg cgcgggccag 27240
ctccgtgaag cactggtgga gggccgtcga gaccgagggg tttgttgtgc gcagggacgc 27300
cagttggccg atatacttac cgaggtccat gtcgtacgcg gggaacacta tctgtcgttg 27360
ttgcagcgag aacccgaggg gcgcgatgaa gccgcggatg ttgtgggtgc ggccggcgcg 27420
tagagcgcac tccccgacca acagggtcgc gatgagctca acggcaaacc actccttttc 27480
ctttatggtc ttaacggcaa gcttatgttc gcgaatcagt tggacgtcgc cgtatccccc 27540
agaccccccg aagcttcggg ccccggggat ctcgagggtc gtgtagtgta gggcggggtt 27600
gatggcgaac acggggctgc atagcttgcg gatgcgcgtg agggtaagga tgtgcgaggg 27660
ggacgagggg ggtgcggtta acgccgcctg ggatctgcgc aggggcgggc ggttcagttt 27720
ggccgccgta ccgggcgtct cgggggacgc gcggcgatga gacgagcggc tcattcgcca 27780
tcgggatagt cccgcgcgaa gccgctcgcg gaggccggat cggtggcggg acccgtggga 27840
ggagcgggag ccggcggcgt cctggagaga ggggccgctg gggcgcccgg aggccccgtg 27900
tgggttggag tgtatgtagg atgcgagcca atccttgaag gactgttggc gtgcaccttg 27960
ggggctgagg ttagctgcca catgaccagc aggtcgctgt ctgcgggact catccatcct 28020
tcggccaggt cgccgtcttc ccacagagaa gcgttggtcg ctgcttcctc gagttgctcc 28080
tcctggtccg caagacgatc gtccacggcg tccaggcgct caccaagcgc cggatcgagg 28140
taccgtcggt gtgcggttag aaagtcacga cgcgccgctt gctcctccac gcgaatttta 28200
acacaggtcg cgcgctgtcg catcatctct aagcgcgcgc gggactttag ccgcgcctcc 28260
aattccaagt gggccgcctt tgcagccata aaggcgccaa caaaccgagg atcttgggtg 28320
ctgacgccct cccggtgcag ctgcagggtc tggtccttgt aaatctcggc tcggaggtgc 28380
gtctcggcca ggcgtcggcg cagggccgcg tgggcggcat ctcggtccat tccgccaccc 28440
tgcgggcgac ccggggggtg ctctgatagt ctcgcgtgcc caaggcccgt gatcggggta 28500
cttcgccgcc gcgacccgcc acccggtgtg cgcgatgttt ggtcagcagc tggcgtccga 28560
cgtccagcag tacctggagc gcctcgagaa acagaggcaa cttaaggtgg gcgcggacga 28620
ggcgtcggcg ggcctcacaa tgggcggcga tgccctacga gtgccctttt tagatttcgc 28680
gaccgcgacc cccaagcgcc accagaccgt ggtcccgggc gtcgggacgc tccacgactg 28740
ctgcgagcac tcgccgctct tctcggccgt ggcgcggcgg ctgctgttta atagcctggt 28800
gccggcgcaa ctaaaggggc gtgatttcgg gggcgaccac acggccaagc tggaattcct 28860
ggcccccgag ttggtacggg cggtggcgcg actgcggttt aaggagtgcg cgccggcgga 28920
cgtggtgcct cagcgtaacg cctactatag cgttctgaac acgtttcagg ccctccaccg 28980
ctccgaagcc tttcgccagc tggtgcactt tgtgcgggac tttgcccagc tgcttaaaac 29040
ctccttccgg gcctccagcc tcacggagac cacgggcccc ccaaaaaaac gggccaaggt 29100
ggacgtggcc acccacggcc ggacgtacgg cacgctggag ctgttccaaa aaatgatcct 29160

```
tatgcacgcc acctactttc tggccgccgt gctcctcggg gaccacgcgg agcaggtcaa  29220
cacgttcctg cgtctcgtgt ttgagatccc cctgtttagc gacgcggccg tgcgccactt  29280
ccgccagcgc gccaccgtgt ttctcgtccc ccggcgccac ggcaagacct ggtttctagt  29340
gcccctcatc gcgctgtcgc tggcctcctt tcgggggatc aagatcggct acacggcgca  29400
catccgcaag gcgaccgagc cggtgtttga ggagatcgac gcctgcctgc ggggctggtt  29460
cggttcggcc cgagtggacc acgttaaagg ggaaaccatc tccttctcgt ttccggacgg  29520
gtcgcgcagt accatcgtgt ttgcctccag ccacaacaca aacgtaagtc ctcttttctt  29580
tcgcatggct ctcccaaggg gccccgggtc gacccgaccc acacccaccc acccacccac  29640
atacacacac aaccagacgc gggaggaaag tctgccccgt gggcactgat ttttattcgg  29700
gatcgcttga ggaggcccgg gcaacggccc gggcaacggt ggggcaactc gtagcaaata  29760
ggcgactgat gtacgaagag aagacacaca ggcgccaccc ggcgctggtc ggggggatgt  29820
tgtccgcgcc gcaccgtccc ccgacgacct cttgcagacg gtccgtgatg caaggacggc  29880
gggggcctg cagcagggtg accgtatcca cgggatggcc aaagagaagc ggacacaggc  29940
tagcatcccc ctggaccgcc agggtacact gggccatctt ggcccacaga cacggggcga  30000
cgcagggaca ggactccgtt acgacggagg agagccacag tgcgttggcg gaatcgatgt  30060
ggggcggcgg ggcgcaggac tcgcagcccc ccgggtggtt ggtgatcctg gccaggagcc  30120
atcccagatg gcgggccctg cttcccggtg gacagagcga ccccaggtcg ctgtccatgg  30180
cccagcagta gatctggccg ctggggaggt gccaccaggc ccccgggccc aaggcgcaac  30240
acgcgcccgg ctccgggggg gtcttcgcgg ggaccagata cgcgccatcc agctcgccga  30300
ccactggctc ctccgcgagc tgttcggtgg ttgggtcggg ggtttcctcc ggggggggtgg  30360
ccgcccgtat gcgggcgaac gtgagggtgc acaggagcgg ggtcaggggg tgcgtcacgc  30420
tccggaggtg gacgatcgcg cagtagcggc gctcgcggtt aaagaaaaag agggcaaaga  30480
aggtgttcgg gggcaaccgc agcgccttgg ggcgcgtcag atacagaaaa atctcgcaga  30540
agagggcgcg cccggggtct gggttaggaa gggccacctg acacagaggc tcggtgagga  30600
ccgttagaca ccgaaagatc ttgagccgct cgtccgcccg aacgacgcgc cacacaaaga  30660
cggagttgac aatgcgcgcg atagagtcga cgtccgtccc caggtcgtcg actctgtcgc  30720
gcgtgccgcg agctccggcc cgggaatccg gccggggcaa ggtccccggg ggaccaggcg  30780
gcgccagggg ccgccggggt cccagctgcg ccatgccggg ggcgggggga gggcaaaccc  30840
cagaggcggg ggccaacggc gcggggagga gtgggtgggc gaggtggccg ggggaaggcg  30900
cccgctagcg agaacggccg ttcccggacg acaccttgcg acaaaaccta aggacagcgg  30960
cccgcgcgac ggggtccgag aggctaaggt aggccgcgat gttaatggtg aacgcaaagc  31020
cgccgggaaa gacaactatg ccacagaggc ggcgattaaa ccccaggcag aggtaggcgt  31080
agctttcccc gggcaggtat tgctcgcaga ccctgcgtgg ggctgtggag gggacggcct  31140
ccatgaagcg acatttactc tgctcgcgtt tactgacgtc accatccatc gccacggcga  31200
ttggacgatt gttaagccgc agcgtgtctc cgcttgtgct gtagtagtca aaaacgtaat  31260
ggccgtcgga gtcggcaaag cgggccggga ggtcgtcgcc gagcgggacg acccgccgcc  31320
cccgaccgcc ccgtcccccc aggtgtgcca ggacggccag ggcatacgcg gtgtgaaaaa  31380
aggcgtcggg ggcggtcccc tcgacggcgc gcatcaggtt ctcgaggaga atggggaagc  31440
gcctggtcac ctcccccagc cacgcgcgtt ggtcggggcc aaagtcatag cgcaggcgct  31500
```

gtgagattcg agggccgccc tgaagcgcgg cccggatggc ctggcccagg gcccggaggc 31560
acgccagatg tatgcgcgca gtaaaggcga cctcggcggc gatgtcaaag ggcggcagga 31620
cggggcgcgg gtggcgcagg ggcacctcga gcgcgggaaa gcggagcagc agctccgcct 31680
gcccagcggg agacagctgg tgggggcgca cgacgcgttc tgcggcgcag gcctcggtca 31740
gggccgtggc cagcgccgag gacagcagcg ggggcgggcg cgtcgcccgc cccacgccac 31800
ggagttctcg taggagacga cgacgaagcg ctgcttggtt ccgtagtggt ggcgcaggac 31860
cacggagata gaacgacggc tccacagcca gtccggccgg tcgccgccgg ccagggcttc 31920
ccatccgcga tccaaccact cgaccagcga ccgcggcttt gcggtaccag gggtcagggt 31980
tagaacgtcg ttcaggatgt cctcgccccc gggcccgtgg ggcactgggg ccacaaagcg 32040
gcccccgcct gggggctcca gacccgccaa caccgcatct gcgtcagccg cccccatggc 32100
gcccccgctg acggcctggt gaaccagggc gccctggcgg agccccgatg caacgccaca 32160
ggccgcacgc ccggtccgag cgcggaccgg gtggcggcgg gtgacgtcct gcactgcccg 32220
ctgaaccaac gcgaggatct cctcgttctc ctgcgcgatg gacacgtcct gggccgcggt 32280
cgtgtcgccg ccgggggccg tcagctgctc ctccggggag atgggggggt cggacgcccc 32340
gacgatgggc gggtctgcgg gcgcccccgc gtggggccgg gccaagggct gcggacgcgg 32400
ggacgcgctt tcccccagac ccatggacag gtgggccgca gcctccttcg cggccggcgg 32460
ggcggcggcg ccaagcagag cgacgtagcg gcacaaatgc cgacagacgc gcatgatgcg 32520
cgtgctgtcg gccgcgtagc gcgtgttggg ggggacgagc tcgtcgtaac taaacagaat 32580
cacgcgggca cagctcgccc ccgagcccca cgcaaggcgc agcgccgcca cggcgtacgg 32640
gtcatagacg ccctgtgcgt cacacaccac gggcaaggag acgaacaacc ccccggcgct 32700
ggacgcacgc ggaaggaggc cagggtgtgc cggcacgacg ggggccagaa gctcccccac 32760
cgcatccgcg ggcacgtagg cggcaaacgc cgtgcaccac ggggtacagt cgccggtggc 32820
atgagcccga gtctggattt cgacctggaa gtttgcggcc gtcccgagtc cggggcggcc 32880
gcgcatcagg gcggccagag ggattcccgc ggccgccagg cactcgctgg atatgatgac 32940
gtgaaccaaa gacgagggcc gacccgggac gtggccgaga tcgtactgga cctcgttggc 33000
caagtgcgcg ttcatggttc gggggtgggt gtgggtgtgt aggcgatgcg ggtcccccga 33060
gtccgcggga agggcgcggg tttggcgcgc gtatgcgtat tcgccaacgg aggcgtgcgt 33120
gcttatgcgc ggcgcgtttc ttctgtctcc agggaatccg aggccaggac tttaacctgc 33180
tctttgtcga cgaggccaac tttattcgcc cggatgcggt ccagacgatt atgggctttc 33240
tcaaccaggc caactgcaag attatcttcg tgtcgtccac caacaccggg aaggccagta 33300
cgagcttttt gtacaacctc cgcggggccg ccgacgagct tctcaacgtg gtgacctata 33360
tatgcgatga tcacatgccg cgggtggtga cgcacacaaa cgccacggcc tgttcttgtt 33420
atatcctcaa caagcccgtt ttcatcacga tggacggggc ggttcgccgg accgccgatt 33480
tgtttctggc cgattccttc atgcaggaga tcatcggggg ccaggccagg gagaccggcg 33540
acgaccggcc cgttctgacc aagtctgcgg gggagcggtt tctgttgtac cgcccctcga 33600
ccaccaccaa cagcggcctc atggcccccg atttgtacgt gtacgtggat cccgcgttca 33660
cggccaacac ccgagcctcc gggaccggcg tcgctgtcgt cgggcggtac cgcgacgatt 33720
atatcatctt cgccctggag cacttttttc tccgcgcgct cacgggctcg gcccccgccg 33780
acatcgcccg ctgcgtcgtc cacagtctga cgcaggtcct ggccctgcat cccggggcgt 33840
ttcgcggcgt ccgggtggcg gtcgagggaa atagcagcca ggactcggcc gtcgccatcg 33900

```
ccacgcacgt gcacacagag atgcaccgcc tactggcctc ggagggggcc gacgcgggct  33960
cgggccccga gcttctcttc taccactgcg agcctcccgg gagcgcggtg ctgtacccct  34020
ttttcctgct caacaaacag aagacgcccg cctttgaaca ctttattaaa aagtttaact  34080
ccgggggcgt catggcctcc caggagatcg tttccgcgac ggtgcgcctg cagaccgacc  34140
cggtcgagta tctgctcgag cagctgaata acctcaccga aaccgtctcc cccaacacgg  34200
acgtccgtac gtattccgga aaacggaacg gcgcctcgga tgaccttatg gtcgccgtca  34260
ttatggccat ctaccttgcg gcccaggccg gacctccgca cacattcgct cccatcacac  34320
gcgtttcgtg agcgcccaat aaacacaccc aggtatgcta cgcacgacca cggtgtcgcc  34380
tgttaagggg gggggaaggg ggtgttggcg ggaagcgtgg gaacacgggg gattctctca  34440
cgaccggcac cagtaccacc cccctgtgaa cacagaaacc ccaacccaaa tcccataaac  34500
atacgacaca caggcatatt ttggaatttc ttaggttttt atttatttag gtatgctggg  34560
gtttctccct ggatgcccac ccccaccccc ccccgtgggt ctagccgggc cttagggata  34620
gcgtataacg ggggccatgt ctccggaccg cacaacggcc gcgccgtcaa aggtgcacac  34680
ccgaaccacg ggagccaggg ccaaggtgtc tcctagttgg cccgcgtggg tcagccaggc  34740
gacgagcgcc tcgtagagcg gcagccttcg ctctccatcc tgcatcaggg ccggggcttc  34800
ggggtgaatg agctgggcgg cctcccgcgt gacactctgc atctgcagga gagcgttcac  34860
gtacccgtcc tgggcactta gcgcaaagag ccgggggatt agcgtaagga tgatggtggt  34920
tccctccgtg atcgagtaaa ccatgttaag gaccagcgat cgcagctcgg cgtttacggg  34980
gccgagttgt tggacgtccg ccagcagcga gaggcgactc ccgttgtagt acagcacgtt  35040
gaggtctggc agccctccgg ggtttctggg gctggggttc aggtcccgga tgcccctggc  35100
cacgagccgc gccacgattt cgcgcgccag gggcgatgga agcggaacgg gaaaccgcaa  35160
cgtgaggtcc agcgaatcca ggcgcacgtc cgtcgcttgg ccctcgaaca cgggcgggac  35220
gaggctgatg gggtccccgt tacagagatc tacgggggag gtgttgcgaa ggttaacggt  35280
gccggcgtgg gtgaggccca cgtccagggg gcaggcgacg attcgcgtgg gaagcacccg  35340
ggtgatgacc gcggggaagc gccttcggta cgccagcaac agccccaacg tgtcgggact  35400
gacgcctccg gagacgaagg attcgtgcgc cacgtcggcc agcgtcagtt gccggcggat  35460
ggtcggcagg aataccaccc gcccttcgca gcgctgcagc gccgccgcat cggggcgcga  35520
gatgcccgag ggtatcgcga tgtcagtttc aaagccgtcc gccagcatgg cgccgatcca  35580
cgcggcaggg agtgcagtgg tggttcgggt ggcgggagga gcgcggtggg ggtcagcggc  35640
gtagcagaga cgggcgacca acctcgcata ggacgggggg tgggtcttag ggggttggga  35700
ggcgacaggg accccagagc atgcgcgggg aggtctgtcg ggcccagacg caccgagagc  35760
gaatccgtcc atggagtccc ggcctgggtt ttatggggcc cggccctcgg aatcgcggct  35820
tgtcggcggg gacaaagggg gcggggctag ggggcttgcg gaaacagaag acgtgtggga  35880
taaaagaatc gcactacccc aaggaagggc ggggcggttt attacagagc cagtcccttg  35940
agcggggatg cgtcatagac gagatactgc gcgaagtggg tctcccgcgc gtgggcttcc  36000
ccgttgcggg cgctgcggag gagggcgggg tcgctggcgc aggtgagcgg gtaggcctcc  36060
tgaaacaggc cacacgggtc ctccacgagt tcgcggcacc ccgggggggcg cttaaactgt  36120
acgtcgctgg cggcggtggc cgtggacacc gccgaacccg tctccacgat caggcgctcc  36180
aggcagcgat gtttggcggc gatgtcggcc gacgtaaaga acttaaagca ggggctgagc  36240
```

accggcgagg ccccgttgag gtggtaggcc ccgttataga gcaggtcccc gtacgaaaat 36300
cgctgcgacg cccacgggtt ggccgtggcc gcgaaggccc gggacgggtc gctctggccg 36360
tggtcgtaca tgagggcggt gacatccccc tccttgtccc ccgcgtaaac gcccccggcg 36420
gcgcgtcccc gggggttgca gggccggcgg aagtagttga cgtcggtcga cacgggggtg 36480
gcgataactc acacacggcg tcctggccgt ggtccatccc tgcgcgccgc ggcacctggg 36540
cgcccccgaa cacggggacg ggctgggccg gccccaggcg gtttcccgcc acgaccgcgt 36600
tccgcaggta cacggctgcc gcgttgtcca gtagaggggg agccccgcgg cccaggtaaa 36660
agttttgggg aaggttgccc atgtcggtga cggggttgcg gacggttgcc gtggccacga 36720
cggcggtgta gcccacgccc aggtccacgt tcccgcgcgg ctgggtgagc gtgaagttta 36780
cccccccgcc agtttcatgc cgggccacct ggagctggcc caggaagtac gcctccgacg 36840
cgcgctccga gaacagcacg ttctcagtca caaagcggtc ctgtcggacg acggtgaacc 36900
caaacccggg atggaggccc gtcttgagct gatgatgcaa ggccacggga ctgatcttga 36960
agtaccccgc catgagcgcg taggtcagcg cgttctcccc ggccgcgctc tcgcggacgt 37020
gctgcacgac gggctgtcgg atcgacgaaa agtagttggc ccccagagcc ggggggacca 37080
gggggacctg ccgcgacagg tcgcgcaggg ccggggggaa attgggcgcg ttcgccacgt 37140
ggtcggcccc ggcgaacagc gcgtggacgg ggaggggggta aaaatagtcg ccattttgga 37200
tggtatggtc cagatgctgg ggggccatca gcaggattcc ggcgtgcaac gccccgtcga 37260
atatgcgcat gttggtggtg gacgcggtgt tggcgcccgc gtcgggcgcc gccgagcaga 37320
gcagcgccgt tgtgcgttcg gccatgttgt gggccagcac ctgcagcgtg agcatggcgg 37380
gcccgtccac taccacgcgc ccgttgtgaa acatggcgtt gaccgtgttg gccaccagat 37440
tggccggggc agggggtgcg cggggccgtc acggggcgct ggggcaatcc tcgccggggg 37500
tgatctccgg gaccaccatg ttctgcaggg tggcgtatac gcggtcgaag cgaacccccg 37560
cggtgcagca gcggccccgc gagaaggcgg gcaccatcac gtagtagtaa atcttgtggt 37620
gcacggtcca gtccgccccc cggtgcggcc ggtcgtccgc ggcgtccgcg gctcgggcct 37680
gggtgttgtg cagcagctgg ccgtcgttgc ggttgaagtc cgcggtcgcc acgttacacg 37740
ccgctgcgta cacggggtcg tggccccccg cgctaacccg gcagtcgcga tggcggtcca 37800
gggccgcgcg ccgcatcagg gcgtcgcagt cccacacgag ggtggcagc agcgccgggt 37860
ctcgcattag gtgattcagt tcggcttgcg cctgcccgcc cagttccggg ccggtcaggg 37920
taaagtcatc aaccagctgg gccagggcct cgacgtgcgc caccaggtcc cggtacacgg 37980
ccatgcactc ctcgggaagg tctcccccga ggtaggtcac gacgtacgag accagcgagt 38040
agtcgttcac gaacgccgcg caccgcgtgt tgttccagta gctggtgatg cactggacca 38100
cgagccgggc cagggcgcag aagacgtgct cgctgccgtg tatggcggcc tgcagcaggt 38160
aaaacaccgc cgggtagttg cggtcttcga acgccccgcg aacggcggcg atggtggcgg 38220
gggctggcgt ggcgtcccac ccccagctcc aggccccggg cgtcccggaa cgccgccgga 38280
catagcgcca ggggcaagtt gccgttcacc acgcgccagg tggcctggat ctcccccggg 38340
ccggccgggg gaacgtcccc ccccggcagc tccacgtcgg ccaccccccac gaagaagtcg 38400
aacgcggggt gcagctcaag agccaggttg gcgttgtcgg gctgcataaa ctgctccggg 38460
gtcatctggc cttccgcgac ccatcggacc cgcccgtggg ccaggcgctg cccccaggcg 38520
ttcaaaaaca gctgctgcat gtctgcggcg gggccggccg gggccgccac gtacgccccg 38580
tacggattgg cggcttcgac ggggtcgcgg ttaaggcccc cgaccgccgc gtcaacgttc 38640
atcagcgaag ggtggcacac ggtcccgatc gcgtgttcca gagacaggcg cagcacctgg 38700
cggtccttcc cccaaaaaaa cagctggcgg ggcgggaagg cgcggggatc cgggtggccg 38760
ggggcggggc taggtccccg gcgtgcgcgg caaaccgttc catgaccgga ttgaacaggc 38820
ccaggggcag gacgaacgtc aggtccatgg cgcccaccag gggtaggga acgttggtgg 38880
cggcgtagat gcgcttctcc agggcctcca aaaagatcag cttctcgccg atggacacca 38940
gatccgcgcg cacgcgcgtc gtctgggggg cgctctcgag ctcgtccagc gtctgccggt 39000
tcaggtcgag ctgctcctcc tgcatctcca gcaggtggcg gcccacgtcg tccagacttc 39060
gcacggcctt gcccatcacg agcgccgtga ccaggttggc cccgttcagg accatctcgc 39120
cgtacgtcac cggcacgtcg gcttcggtgt cctccacttt caggaaggac tgcaggaggc 39180
gctgtttgat cggggcggtg gtgacgagca ccccgtcgac cggacgcccg cgcgtgtcgg 39240
catgcgtcag acggggcacg gccacggagg gctgcgtggc cgtggtgagg tccacgagcc 39300
aggcctcgac ggcctcccgg cggtggcccg ccttgcccag gaaaaagctc gtctcgcaga 39360
agcttcgctt tagctcggcg accagggtcg cccgggccac cctggtggcc aggcggccgt 39420
tgtccaggta tcgttgcatc ggcaacaaca aagccagggg cggcgccttt tccagcagca 39480
cgtgcagcat ctggtcggcc gtgccgcgct caaacgcccc gaggacggcc tggacgttgc 39540
gagcgagctg ttggatggcg cgcaactggc gatgcgcgct gatacccgtc ccgtccaggg 39600
cctcccccgt gagcagggcg atggcctcgg tggccaggct gaaggcggcg ttcagggccc 39660
ggcggtcgat aatcttggtc atgtaattgt gtgtgggttg ctcgatgggg tgcgggccgt 39720
cgcgggcaat cagcggctgg tggacctcga actgtacgcg cccctcgttc atgtaggcca 39780
gctccggaaa cttggtacac acgcacgcca ccgacaaccc gagctccaga aagcgcacga 39840
gcgacagggt gttgcaatac gaccccaaca gggcgtcgaa ctcgacgtca tacaggctgt 39900
ttgcatcgga gcgcacgcgg gaaaaaaaat cgaacaggcg tcgatgcgac gccacctcga 39960
tcgtgctaag gagggacccg gtcggcacca tggccgcggc ataccggtat cccggagggt 40020
cgcggttggg agcggccatg ggtcgcgtg gagatcggct gtctctagcg atattggccc 40080
ggggaggcta agatccaccc caacgcccgg ccacccgtgt acgtgcccga cggcccaagg 40140
tccaccgaaa gacacgacgg gcccggaccc aaaaaggcgg gggatgctgt gtgagaggcc 40200
gggtgtcggt cggggggaa aggcaccggg agaaggctgc ggcctcgttc caggagaacc 40260
cagtgtcccc aacagacccg gggacgtggg atccaagctt gatctctatc actgataggg 40320
agatctctat cactgatagg gatcccaggc cttatatacc ccccccgccc ccccccgtta 40380
gaacgcgacg ggtgcattca agatggccct ggtccaaaag cgtgccagga agaaattggc 40440
agaggcggca aagctgtccg ccgccgccac ccacatcgag gccccggccg cgcaggctat 40500
ccccagggcc cgtgtgcgca ggggatcggt gggcggcagc atttggttgg tggcgataaa 40560
gtggaaaagc ccgtccggac tgaaggtctc gtgggcggcg gcgaacaagg cacacagggc 40620
cgtgcctccc aaaaacacgg acatccccca aaacacgggc gccgacaacg gcagacgatc 40680
cctcttgatg ttaacgtaca ggaggagcgc ccgcaccgcc cacgtaacgt agtagccgac 40740
gatggcggcc aggatacagg ccggcgccac caccccttccg gtcagcccgt aatacatgcc 40800
cgctgccacc atctccaacg gcttcaggac caaaaacgac caaaggaaca gaatcacgcg 40860
ctttgaaaag accggctggg tatggggcgg aagacgcgag tatgccgaac tgacaaaaaa 40920
gtcagaggtg ccgtacgagg acaatgaaaa ctgttcctcc agtggcagtt ctccctcctc 40980

```
cccccccaaag gcggcctcgt cgaccagatc tcgatccacc agaggaaggt catcccgcat  41040
ggtcatgggg tgtgcggtgg aggtggggag accgaaaccg caaagggtcg cttacgtcag  41100
caggatcccg agatcaaaga cacccgggtt cttgcacaaa caccacccgg gttgcatccg  41160
cggaggcgag tgttttgata aggccgttcc gcgccttgat ataacctttg atgttgacca  41220
caaaacccgg aatttacgcc tacgccccaa tgcccacgca agatgaggta ggtaaccccc  41280
cccccgtggg tgtgacgttg cgtttagttc attggaggcc aaggggaaaa tggggtgggg  41340
aggaaacgga aaacccagta ggccgtgttg ggaacacgcc cggggttgtc ctcaaaaggc  41400
agggtccata ctacggaagc cgtcgttgta ttcgagacct gcctgtgcga cgcacgtcgg  41460
ggttgcctgt gtccggttcg gccccaccgc gtgcggcacg cacgaggacg agtccgcgtg  41520
ctttattggc gttccaagcg ttgccctcca gtttctgttg tcggtgttcc cccataccca  41580
cgcccacatc caccgtaggg ggcctctggg ccgtgtcacg tcgccgcccg cgatggagct  41640
tagctacgcc accaccatgc actaccggga cgttgtgttt tacgtcacaa cggaccgaaa  41700
ccgggcctac tttgtgtgcg gggggtgtgt ttattccgtg ggcggccgt gtgcctcgca  41760
gcccggggag attgccaagt ttggtctggt cgttcgaggg acaggcccag acgaccgcgt  41820
ggtcgccaac tatgtacgaa gcgagctccg acaacgcggc ctgcaggacg tgcgtcccat  41880
tggggaggac gaggtgtttc tggacagcgt gtgtcttcta aacccgaacg tgagctccga  41940
gctggatgtg attaacacga acgacgtgga agtgctggac gaatgtctgg ccgagtactg  42000
cacctcgctg cgaaccagcc cgggtgtgct aatatccggg ctgcgcgtgc gggcgcagga  42060
cagaatcatc gagttgtttg aacacccaac gatagtcaac gtttcctcgc actttgtgta  42120
taccccgtcc ccatacgtgt tcgccctggc ccaggcgcac ctcccccggc tcccgagctc  42180
gctggaggcc ctggtgagcg gcctgtttga cggcatcccc gccccacgcc agccacttga  42240
cgcccacaac ccgcgcacgg atgtggttat cacgggccgc cgcgccccac gacccatcgc  42300
cgggtcgggg gcggggtcgg ggggcgcggg cgccaagcgg gccaccgtca gcgagttcgt  42360
gcaagtcaaa cacattgacc gcgtgggccc cgctggcgtt tcgccggcgc ctccgccaaa  42420
caacaccgac tcaagttccc tggtgcccgg ggcccaggat tccgccccgc ccggccccac  42480
gctaagggag ctgtggtggg tgttttatgc cacagaccgg gcgctggagg agccccgcgc  42540
cgactctggc ctcacccgcg aggaggtacg tgccgtacgt gggttccggg agcaggcgtg  42600
gaaactgttt ggctccgcgg gggccccgcg ggcgtttatc ggggccgcgt tgggcctgag  42660
ccccctccaa aagctagccg tttactacta tatcatccac cgagagaggc gcctgtcccc  42720
cttccccgcg ctagtccggc tcgtaggccg gtacacacag cgccacggcc tgtacgtccc  42780
tcggcccgac gacccagtct tggccgatgc catcaacggg ctgtttcgcg acgcgctggc  42840
ggccggaacc acagccgagc agctcctcat gttcgacctt ctcccccaa aggacgtgcc  42900
ggtgggaagc gacgtgcagg ccgacagcac cgctctgctg cgctttatag aatcgcaacg  42960
tctcgccgtc cccgggggg tgatctcccc cgagcacgtc gcgtaccttg gtgcgttcct  43020
gagcgtgctg tacgctggcc gcgggcgcat gtccgcagcc acgcacaccg cgcggctgac  43080
aggggtgacc tccctggtgc tagcggtggg tgacgtggac cgtctttccg cgtttgaccg  43140
cggagcggcg ggcgcggcca gccgcacgcg ggccgccggg tacctggatg tgcttcttac  43200
cgttcgtctc gctcgctccc aacacggaca gtctgtgtaa cagaccccaa taaacgtatg  43260
tcgctaccac acccttgtgt gtcaatggac gcctctccgg gggggaaggg aaaacaaaga  43320
ggggctgggg gagcggcacc accggggcct gaacaaacaa accacagaca cggttacagt  43380
```

```
ttattcggtc gggcggagaa acggccgaag ccacgccccc tttattcgcg tctccaaaaa  43440
aacgggacac ttgtccggag aacctttagg atgccagcca gggcggcggt aatcataacc  43500
acgcccagcg cagaggcggc cagaaacccg ggcgcaattg cggccacggg ctgcgtgtca  43560
aaggctagca aatgaatgac ggttccgttt ggaaatagca acaaggccgt ggacggcacg  43620
tcgctcgaaa acacgcttgg ggcgccctcc gtcggcccgg cggcgatttg ctgctgtgtg  43680
ttgtccgtat ccaccagcaa cacagacatg acctccccgg ccggggtgta gcgcataaac  43740
acggccccca cgagccccag gtcgcgctgg ttttgggtgc gcaccagccg cttggactcg  43800
atatcccggg tggagccttc gcatgtcgcg gtgaggtagg ttaggaacag tgggcgtcgg  43860
acgtcgacgc cggtgagctt gtagccgatc ccccggggca gaggggagtg ggtgacgacg  43920
tagctggcgt tgtgggtgat gggtaccagg atccgtggct cgacgttggc agactgcccc  43980
ccgcaccgat gtgaggcctc agggacgaag gcgcggatca gggcgttgta gtgtgcccag  44040
cgcgtcaggg tcgaggcgag gccgtgggtc tgctgggcca ggacttcgac cggggtctcg  44100
gatcgggtgg cttgagccag cgcgtccagg ataaacacgc tctcgtctag atcaaagcgc  44160
agggaggccg cgcatggcga aaagtggtcc ggaagccaaa agagggtttt ctggtggtcg  44220
gcccgggcca gcgcggtccg gaggtcggcg ttggtcgctg cggcgacgtc ggacgtacac  44280
agggccgagg ctatcagaag gctccggcgg gcgcgttccc gctgcaccgc cgaggggacg  44340
cccgccaaga acggctgccg gaggacagcc gaggcgtaaa atagcgcccg gtggacgacc  44400
ggggtggtca gcacgcggcc ccctagaaac tcggcataca gggcgtcgat gagatgggct  44460
gcgctgggcg ccactgcgtc gtacgccgag gggctatcca gcacgaaggc cagctgatag  44520
cccagcgcgt gtaatgccaa gctctgttcg cgctccagaa tctcggccac caggtgctgg  44580
agccgagcct ctagctgcag gcgggccgtg ggatccaaga ctgacacatt aaaaaacaca  44640
gaatccgcgg cacagcccgc ggccccgcgg gcggccaacc cggcaagcgc gcgcgagtgg  44700
gccaaaaagc ctagcaggtc ggagaggcag accgcgccgt ttgcgtgggc ggcgttcacg  44760
aaagcaaaac ccgacgtcgc gagcagcccc gttaggcgcc agaagagagg gggacgcggg  44820
ccctgctcgg cgcccgcgtc ccccgagaaa aactccgcgt atgcccgcga caggaactgg  44880
gcgtagttcg tgccctcctc cgggtagccg cccacgcggc ggagggcgtc cagcgcggag  44940
ccgttgtcgg cccgcgtcag ggaccctagg acaaagaccc gataccgggg gccgcccggg  45000
ggcccgggaa gagcccccgg ggggttttcg tccgcggggt ccccgacccg atctagcgtc  45060
tggcccgcgg ggaccaccat cacttccacc ggagggctgt cgtgcatgga tatcacgagc  45120
cccatgaatt cccgcccgta gcgcgcgcgc accagcgcgg catcgcaccc gagcaccagc  45180
tcccccgtcg tccagatgcc cacgggccac gtcgaggccg acggggagaa atacacgtac  45240
ctacctgggg atctcaacag gccccgggtg gccaaccagg tcgtggacgc gttgtgcagg  45300
tgcgtgatgt ccagctccgt cgtcgggtgc cgccgggccc caaccggcgg tcgggggggc  45360
ggtgtatcac gcggcccgct cgggtggctc gccgtcgcca cgttgtctcc ccgcgggaac  45420
gtcagggcct cggggtcagg gacggccgaa aacgttaccc aggcccggga acgcagcaac  45480
acggaggcgg ttggattgtg caagagaccc ttaagggggg cgaccgcggg gggaggctgg  45540
gcggtcggct cgaccgtgat gggggcgggc aggctcgcgt tcgggggccg gccgagcagg  45600
taggtcttcg agatgtaaag cagctggccg gggtcccgcg gaaactcggc cgtggtgacc  45660
aatacaaaac aaaagcgctc ctcgtaccag cgaagaaggg gcagagatgc cgtagtcagg  45720
```

```
tttagttcgt ccggcggcgc cagaaatccg cgcggtggtt tttgggggtc gggggtgttt  45780
ggcagccaca gacgcccggt gttcgtgtcg cgccagtaca tgcggtccat gcccaggcca  45840
tccaaaaacc atgggtctgt ctgctcagtc cagtcgtgga cctgacccca cgcaacgccc  45900
aaaagaataa cccccacgaa ccataaacca ttccccatgg gggaccccgt ccctaaccca  45960
cggggcccgt ggctatggca gggcttgccg ccccgacgtt ggctgcgagc cctgggcctt  46020
cacccgaact tgggggttgg ggtggggaaa aggaagaaac gcgggcgtat tggccccaat  46080
ggggtctcgg tggggtatcg acagagtgcc agccctggga ccgaaccccg cgtttatgaa  46140
caaacgaccc aacacccgtg cgttttattc tgtcttttta tttccgtcat agcgcgggtt  46200
ccttccggta ttgtctcctt ccgtgtttca gttagcctcc cccatctccc gggcaaacgt  46260
gcgcgccagg tcgcagatcg tcggtatgga gcctggggtg gtgacgtggg tctggaccat  46320
cccggaggta agttgcagca gggcgtcccg gcagccggcg ggcgattggt cgtaatccag  46380
gataaagacg tgcatgggac ggaggcgttt ggccaagacg tccaaggccc aggcaaacac  46440
gttatacagg tcgccgttgg gggccagcaa ctcgggggcc cgaaacaggg taaataacgt  46500
gtccccgata tggggtcgtg ggcccgcgtt gctctggggc tcggcaccct ggggcggcac  46560
ggccgtcccc gaaagctgtc cccaatcctc ccgccacgac ccgccgccct gcagataccg  46620
caccgtattg gcaagcagcc cgtaaacgcg gcgaatcgcg gccaacatag ccaggtcaag  46680
ccgctcgccg gggcgctggc gtttggccag gcggtcgatg tgtctgtcct ccggaagggc  46740
ccccaacacg atgtttgtgc cgggcaaggt cggcgggatg agggccacga acaccagcac  46800
ggcctggggg gtcatgctgc ccataaggta tcgcgcggcc gggtagcaca ggagggcggc  46860
gatgggatgg cggtcgaaga tgagggtgag ggccgggggc ggggcatgtg agctcccagc  46920
ctcccccccg atatgaggag ccagaacggc gtcggtcacg gcataaggca tgcccattgt  46980
tatctgggcg cttgtcatta ccaccgccgc gtccccggcc gatatctcac cctggtcgag  47040
gcggtgttgt gtggtgtaga tgttcgcgat tgtctcggaa gcccccagca cctgccagta  47100
agtcatcggc tcgggtacgt agacgatatc gtcgcgcgaa cccagggcca ccagcagttg  47160
cgtggtggtg gttttcccca tcccgtgagg accgtctata taaacccgca gtagcgtggg  47220
cattttctgc tccaggcgga cttccgtggc ttcttgctgc cggcgagggc gcaacgccgt  47280
acgtcggttg ctatggccgc gagaacgcgc agcctggtcg aacgcagacg cgtgttgatg  47340
gcaggggtac gaagccatac gcgcttctac aaggcgcttg ccaaagaggt gcgggagttt  47400
cacgccacca agatctgcgg cacgctgttg acgctgttaa gcgggtcgct gcagggtcgc  47460
tcggtgttcg aggccacacg cgtcacctta atatgcgaag tggacctggg accgcgccgc  47520
cccgactgca tctgcgtgtt cgaattcgcc aatgacaaga cgctgggcgg ggtttgtgtc  47580
atcatagaac taaagacatg caaatatatt tcttccgggg acaccgccag caaacgcgag  47640
caacgggcca cggggatgaa gcagctgcgc cactccctga agctcctgca gtccctcgcg  47700
cctccgggtg acaagatagt gtacctgtgc cccgtcctgg tgtttgtcgc ccaacggacg  47760
ctccgcgtca gccgcgtgac ccggctcgtc ccgcagaagg tctccggtaa tatcaccgca  47820
gtcgtgcgga tgctccagag cctgtccacg tatacggtcc ccatggagcc taggacccag  47880
cgagcccgtc gccgccgcgg cggcgctgcc cgggggtctg cgagcagacc gaaaaggtca  47940
ccctctgggg cacgcgaccc gcccgggcca gcggcccgcc aggtaccacc cgccgaccaa  48000
acccccgcct ccacggaggg cgggggggtg cttaagagga tcgcggcgct cttctgcgtg  48060
cccgtggcca ccaagaccaa accccgagct gcctccgaat gagagtgttt cgttccttcc  48120
```

```
ccctcccccc gcgtcagaca aaccctaacc accgcttaag cggcccccgc gaggtccgaa  48180
gactcatttg gatccggcgg gagccacctg acaacagccc ccgggtttcc ccacgccaga  48240
cgccggtccg ctgtgccatc gctccccttc atcccacccc catcttgtcc ccaaataaaa  48300
caaggtctgg tagttaggac aacgaccgca gttctcgtgt gttattgtcg ctctccgcct  48360
ctcgcagatg gacccgtatt gcccatttga cgctctggac gtctgggaac acaggcgctt  48420
catagtcgcc gattcccgaa acttcatcac ccccgagttc ccccgggact tttggatgtc  48480
gcccgtcttt aacctccccc gggagacggc ggcggagcag gtggtcgtcc tgcaggccca  48540
gcgcacagcg gctgccgctg ccctggagaa cgccgccatg caggcggccg agctccccgt  48600
cgatatcgag cgccggttac gcccgatcga acggaacgtg cacgagatcg caggcgccct  48660
ggaggcgctg gagacggcgg cggccgccgc cgaagaggcg gatgccgcgc gcggggatga  48720
gccggcgggt gggggcgacg ggggggcgcc cccgggtctg gccgtcgcgg agatggaggt  48780
ccagatcgtg cgcaacgacc cgccgctacg atacgacacc aacctccccg tggatctgct  48840
acatatggtg tacgcgggcc gcggggcgac cggctcgtcg ggggtggtgt tcgggacctg  48900
gtaccgcact atccaggacc gcaccatcac ggactttccc ctgaccaccc gcagtgccga  48960
ctttcgggac ggccggatgt ccaagacctt catgacggcg ctggtcctgt ccctgcagtc  49020
gtgcggccgg ctgtatgtgg gccagcgcca ctattccgcc ttcgagtgcg ccgtgttgtg  49080
tctctacctg ctgtaccgaa acacgcacgg ggccgccgac gatagcgacc gcgctccggt  49140
cacgttcggg gatctgctgg gccggctgcc ccgctacctg gcgtgcctgg ccgcggtgat  49200
cgggaccgag ggcggccggc cacagtaccg ctaccgcgac gacaagctcc ccaagacgca  49260
gttcgcggcc ggcgggggcc gctacgaaca cggagcgctg gcgtcgcaca tcgtgatcgc  49320
cacgctgatg caccacgggg tgctcccggc ggccccgggg gacgtccccc gggacgcgag  49380
cacccacgtt aaccccgacg gcgtggcgca ccacgacgac ataaaccgcg ccgccgccgc  49440
gttcctcagc cggggccaca acctattcct gtgggaggac cagactctgc tgcgggcaac  49500
cgcgaacacc ataacggccc tgggcgttat ccagcggctc ctcgcgaacg gcaacgtgta  49560
cgcggaccgc ctcaacaacc gcctgcagct gggcatgctg atccccggag ccgtcccttc  49620
ggaggccatc gcccgtgggg cctccgggtc cgactcgggg gccatcaaga gcggagacaa  49680
caatctggag gcgctatgtg ccaattacgt gcttccgctg taccgggccg acccggcggt  49740
cgagctgacc cagctgtttc ccggcctggc cgccctgtgt cttgacgccc aggcggggcg  49800
gccggtcggg tcgacgcggc gggtggtggt atgtcatcgg gggcccgcca ggcggcgctg  49860
ggcgcctcac cgccctggaa ctcatcaacc gcacccgcac aaaccccacc cccgtggggg  49920
aggttatcca cgcccacgac gccctggcga tccaatacga acaggggctt ggcctgctgg  49980
cgcagcaggc acgcattggc ttgggctcca acaccaagcg tttctccgcg ttcaacgtta  50040
gcagcgacta cgacatgttg tactttttat gtctggggtt cattccacag tacctgtcgg  50100
cggtttagtg ggtggtgggc gagggggag ggggcattag ggagaaagaa caagagcctc  50160
cgttgggttt tctttgtgcc tgtactcaaa aggtcatacc ccgtaaacgg cgggctccag  50220
tcccggcccg gcggttggcg tgaacgcaac ggcgggagct gggttagcgt ttagtttagc  50280
attcgctctc gcctttccgc ccgcccccga ccgttgagcc tttttttttt tttttttttt  50340
ttcgtccacc aaagtctctg tgggtgcgcg catggcagcc gatgccccgg gagaccggat  50400
ggaggagccc ctgccagaca gggccgtgcc catttacgtg gctgggtttt tggccctgta  50460
```

-continued

```
tgacagcggg gactcgggcg agttggcatt ggatccggat acggtgcggg cggccctgcc  50520
tccggataac ccactcccga ttaacgtgga ccaccgcgct ggctgcgagg tggggcgggt  50580
gctggccgtg gtcgacgacc cccgcgggcc gttttttgtg gggctgatcg cctgcggcaa  50640
ctggagcgcg tcctcgagac ggccgccagc gctgcgattt tcgagcgccg cgggccgccg  50700
ctctcccggg aggagcgcct gttgtacctg atcaccaact acctgccctc ggtctccctg  50760
gccacaaaac gcctgggggg cgaggcgcac cccgatcgca cgctgttcgc gcacgtagcg  50820
ctgtgcgcga tcgggcggcg ccttggcact atcgtcacct acgacaccgg tctcgacgcc  50880
gccatcgcgc cctttcgcca cctgtcgccg gcgtctcgcg agggggcgcg gcgactggcc  50940
gccgaggccg agctcgcgct atccggacgc acctgggcgc ccggcgtgga ggcgctgccc  51000
acccgctgct ttccaccgcc gttaacaaca tgatgctgcg ggaccgctgg agcctggtgg  51060
ccgagcggcg gcggcaggcc gggatcgccg gacacaccta cctccaggcg agcgaaaaat  51120
tcaaaatgtg gggggcggag cctgtttccg cgccggcgcg cgggtataag aacggggccc  51180
cggagtccac ggacataccg cccggctcga tcgctgccgc gccgcagggt gaccggtgcc  51240
caatcgtccg tcagcgcggg gtcgcctcgc ccccggtact gccccccatg aaccccgttc  51300
caacatcggg caccccggcc cccgcgccgc ccggcgacgg gagctacctg tggatcccgg  51360
cctcccatta caaccagctc gtcgccggcc acgccgcgcc ccaaccccag ccgcattccg  51420
cgtttggttt cccggctgcg gcgggggccg tggcctatgg gcctcacggc gcgggtcttt  51480
cccagcatta ccctccccac gtcgcccatc agtatcccgg ggtgctgttc tcgggaccca  51540
gcccactcga ggcgcagata gccgcgttgg tgggggccat agccgcggac cgccaggcgg  51600
gcggtcagcc ggccgcggga gaccctgggg tccgggggtc gggaaagcgt cgccggtacg  51660
aggcggggcc gtcggagtcc tactgcgacc aggacgaacc ggacgcggac tacccgtact  51720
accccgggga ggctcgaggc gggccgcgcg gggtcgactc tcggcgcgcg gcccgccagt  51780
ctcccgggac caacgagacc atcacggcgc tgatgggggc ggtgacgtct ctgcagcagg  51840
aactggcgca catgcgggct cggaccagcg cccccctatgg aatgtacacg ccggtggcgc  51900
actatcgccc tcaggtgggg gagccggaac caacaacgac ccacccggcc ctttgtcccc  51960
cggaggccgt gtatcgcccc ccaccacaca gcgcccccta cggtcctccc cagggtccgg  52020
cgtcccatgc ccccactccc ccgtatgccc cagctgcctg cccgccaggc ccgccaccgc  52080
ccccatgtcc ttccacccag acgcgcgccc ctctaccgac ggagcccgcg ttcccccccg  52140
ccgccaccgg atcccaaccg gaggcatcca acgcggaggc cggggccctt gtcaacgcca  52200
gcagcgcagc acacgtggac gttgacacgg cccgcgccgc cgatttgttc gtctctcaga  52260
tgatgggggc ccgctgattc gccccggtct ttggtaccat gggatgtctt actgtatatc  52320
tttttaaata aaccaggtaa taccaaataa gacccattgg tgtatgttct ttttttttta  52380
ttgggagggg cgggtaggcg ggtagcttta caatgcaaaa gcctttgacg tggaggaagg  52440
cgtggggggg aggaaatcgg cactgaccaa gggggtccgt tttgtcacgg gaaaggaaga  52500
ggaaaaggcg cggcacccgg gggagttatg tgttcctttt tctttcttcc cacacacaca  52560
caaaaggcgt accaaacaaa aaaaccaaaa gatgcgcatg cggtttaaca cccgtggttt  52620
ttatttacaa caaacccccc gtcacaggtc gtcctcgtcg gcgtcaccgt ctttgttggg  52680
aacttgggtg tagttggtgt tgcggcgctt gcgcatgacc atgtcggtga ccttggcgct  52740
gagcagcgcg ctcgtgccct tcttcttggc cttgtgttcc gtgcgctcca tggccgacac  52800
cagggccatg taccgtatca tctccctggc ctcggctagc ttggcctcgt caaagtcgcc  52860
```

gccctcctcg ccctccccgg acgcgtccgg gttggtgggg ttcttgagct ccttggtggt 52920
tagagggtac agggccttca tggggttgct ctgcagccgc atgacgtaac gaaaggcgaa 52980
gaaggccgcc gccaggccgg ccaggaccaa cagacccacg gccagcgccc caaaggggtt 53040
ggacatgaag gaggacacgc ccgacacggc cgataccacg ccgcccacga tgcccatcac 53100
caccttgccg accgcgcgcc ccaggtcgcc catcccctcg aagaacgcgc ccaggcccgc 53160
gaacatggcg gcgttggcgt cggcgtggat gaccgtgtcg atgtcggcga agcgcaggtc 53220
gtgcagctgg ttgcggcgct ggacctccgt gtagtccagc aggccgctgt ccttgatctc 53280
gtggcgggtg tacacctcca gggggacaaa ctcgtgatcc tccagcatgg tgatgttgag 53340
gtcgatgaag gtgctgacgg tggtgatgtc ggcgcggctc agctggtggg agtacgcgta 53400
ctcctcgaag tacacgtagc cccaccgaa ggtgaagtag cgccggtgtc ccacggtgca 53460
cggctcgatc gcatcgcgcg tcagccgcag ctcgttgttc tcccccagct gcccctcgac 53520
caacgggccc tggtcttcgt accgaaagct gaccaggggg cggctgtagc aggccccggg 53580
ccgcgagctg atgcgcatcg agttttggac gatcacgttg tccgcggcga ccggcacgca 53640
cgtggagacg gccatcacgt cgccgagcat ccgcgcgctc acccgccggc ccacggtgac 53700
cgaggcgatg gcgttggggt tcagcttgcg ggcctcgttc cacagggtca gctcgtgatt 53760
ctgtagctcg caccacgcga tggcaacgcg gcccaacata tcgttgacat ggcgctgtat 53820
gtggttgtac gtaaactgca gccgggcgaa ctcgatggag gaggtggtct tgatgcgctc 53880
cacggacgcg ttggcgctgg ccccgggcgg cgggggcgtg gggtttgggg gcttgcggct 53940
ctgctctcgg aggtgttccc gcacgtacag ctccgcgagc gtgttgctga gaaggggctg 54000
gtacgcgatc agaaagcccc cattggccag gtagtactgc ggctggccca ccttgatgtg 54060
cgtcgcgttg tacctgcggg cgaagatgcg gtccatggcg tcgcgggcgt ccttgccgat 54120
gcagtccccc aggtccacgc gcgagagcgg gtactcggtc aggttggtgg tgaaggtggt 54180
ggatatggcg tcggaggaga atcggaagga gccgccgtac tcggagcgca gcatctcgtc 54240
cacttcctgc cacttggtca tggtgcagac cgacgggcgc tttggcaccc agtcccaggc 54300
cacggtgaac ttgggggtcg tgagcaggtt ccgggtggtc ggcgccgtgg cccgggcctt 54360
ggtggtgagg tcgcgcgcgt agaagccgtc gacctgcttg aagcggtcgg cggcgtagct 54420
ggtgtgttcg gtgtgcgacc cctcccggta gccgtaaaac ggggacatgt acacaaagtc 54480
gccagtcgcc agcacaaact cgtcgtacgg gtacaccgag cgcgcgtcca cctcctcgac 54540
gatgcagttt accgtcgtcc cgtaccggtg gaacgcctcc acccgcgagg ggttgtactt 54600
gaggtcggtg gtgtgccagc cccggctcgt gcgggtcgcg gcgttggccg gtttcagctc 54660
catgtcggtc tcgtggtcgt cccggtgaaa cgcggtggtc tccaggttgt tgcgcacgta 54720
cttggccgtg gaccgacaga ccccccttggc gttgatcttg tcgatcacct cctcgaaggg 54780
gacgggggcg cggtcctcaa agatccccat aaactgggag tagcggtggc cgaaccacac 54840
ctgcgaaacg gtgacgtctt tgtagtacat ggtggccttg aacttgtacg gggcgatgtt 54900
ctccttgaag accaccgcga tgccctccgt gtagttctga ccctcgggcc gggtcgggca 54960
gcggcgcggc tgctcgaact gcaccaccgt ggcgcccgtg gggggtgggc acacgtaaaa 55020
gtttgcatcg gtgttctccg ccttgatgtc ccgcaggtgc tcgcgcaggg tggcgtggcc 55080
cgcggcgacg gtcgcgcccc cttggcgttg atcttgtcga tcacctcctc gaaggggacg 55140
ggggcgcggt cctcaaagat ccccataaac tgggagtagc ggtggccgaa ccacacctgc 55200

```
gaaacggtga cgtctttgta gtacatggtg gccttgaact tgtacggggc gatgttctcc  55260
ttgaagacca ccgcgatgcc ctccgtgtag ttctgaccct cgggccgggt cgggcagcgg  55320
cgcggctgct cgaactgcac caccgtggcg cccgtggggg gtgggcacac gtaaaagttt  55380
gcatcggtgt tctccgcctt gatgtcccgc aggtgctcgc gcagggtggc gtggcccgcg  55440
gcgacggtcg cgttgtcgcc ggcggggcgg gggcgttggg ttttcggttt ttgttcttct  55500
tcggtttcgg gtcccccgtt ggggcggcgc caagggcggg cggcgccgga gtggcagggc  55560
ccccgttcgc cgcctgggtc gcggccgcga ccccaggcgt gccgggggaa ctcggagccg  55620
ccgacgccac caggaccccc agcgtcaacc ccaagagcgc ccatacgacg aaccaccggc  55680
gcccccacga gggggcgccc tggtgcatgg cgggactacg gggcccgtc gtgcccccg  55740
tcaggtagcc tgggggcgag gtgctggagg accgagtaga ggatcgagaa aacgtcgcgg  55800
tcgtagacca cgaccgaccg ggggccgata cagccgtcgg gggcgctctc gacgatggcc  55860
accagcggac agtcggagtc gtacgtgaga tatacgccgg gcgggtaacg gtaacgacct  55920
tcggaggtcg ggcggctgca gtccgggcgg cgcaactcga gctccccgca ccggtagacc  55980
gaggcaaaga gtgtggtggc gataatcagc tcgcgaatat atcgccaggc ggcgcgctga  56040
gtgggcgtta ttccggaaat gccgtcaaaa cagtaaaacc tctgaaattc gctgacggcc  56100
caatcagcac ccgagccccc cgcccccatg atgaaccggg cgagctcctc cttcaggtgc  56160
ggcaggagcc ccacgttctc gacgctgtaa tacagcgcgg tgttgggggg ctgggcgaag  56220
ctgtgggtgg agtgatcaaa gaggggcccg ttgacgagct cgaagaagcg atgggtgatg  56280
ctggggagca gggccgggtc cacctggtgt cgcaggagag acgctcgcat gaaccggtgc  56340
gcgtcgaaca cgcccggcgc cgagcggttg tcgatgaccg tgcccgcgcc cgccgtcagg  56400
gcgcagaagc gcgcgcgcgc cgcaaagccg ttggcgaccg cggcgaacgt cgcgggcagc  56460
acctcgccgt ggacgctgac ccgcagcatc ttctcgagct ccccgcgctg ctcgcggacg  56520
cagcgcccca ggctggccaa cgaccgcttc gtcaggcggt ccgcgtacag ccgccgtcgc  56580
tcccgtacgt ccgcggccgc ttgcgtggcg atgtccccc acgtctcggg cccctgcccc  56640
ccgggcccgc ggcgacggtc ttcgtcctcg cccccgcccc cgggagctcc caaccccgt  56700
gccccttcct ctacggcgac acggtccccg tcgtcgtcgg ggcccgcgcc gcccttgggc  56760
gcgtccgccg cgcccccgc ccccatgcgc gccagcacgc gacgcagcgc ctcctcgtcg  56820
cactgttcgg ggctgacgag gcgccgcaag agcggcgtcg tcaggtggtg gtcgtagcac  56880
gcgcggatga gcgcctcgat ctgatcgtcg ggtgacgtgg cctgaccgcc gattattagg  56940
gcgtccacca tatccagcgc cgccaggtgg ctcccgaacg cgcgatcgaa atgctccgcc  57000
cgccgcccga acagcgccag ttccacggcc accgcggcgg tctcctgctg caactcgcgc  57060
cgcgccagcg cggtcaggtt gctggcaaac gcgtccatgg tggtctggcc ggcgcggtcg  57120
ccggacgcga gccagaatcg caattcgctg atggcgtaca ggccgggcgt ggtggcctga  57180
aacacgtcgt gcgcctccag cagggcgtcg gcctccttgc ggaccgagtc gttctcgggc  57240
gacgggtggg gctgcccgtc gcccccgcg gtccgggcca gcgcatggtc caacacggag  57300
agcgcccgcg cgcggtcggc gtccgacagc ccggcggcgt ggggcaggta ccgccgcagc  57360
tcgttggcgt ccagccgcac ctgcgcctgc tgggtgacgt ggttacagat acggtccgcc  57420
aggcggcggg cgatcgtcgc cccctggttc gccgtcacac acagttcctc gaaacagacc  57480
gcgcaggggt gggacgggtc gctaagctcc ggggggacga taaggcccga ccccaccgcc  57540
cccaccataa actcccgaac gcgctccagc gcggcggtgg cgccgcgcga gggggtgatg  57600
```

aggtggcagt agtttagctg ctttagaaag ttctcgacgt cgtgcaggaa acacagctcc 57660
atatggacgg tcccgccata cgtatccagc ctgacccgtt ggtgatacgg acagggtcgg 57720
gccaggccca tggtctcggt gaaaaacgcc gcgacgtctc ccgcggtcgc gaacgtctcc 57780
aggctgccca ggagccgctc gccctcgcgc cacgcgtact ctagcagcaa ctccagggtg 57840
accgacagcg gggtgagaaa ggccccggcc tgggcctcca ggcccggcct cagacgacgc 57900
cgcagcgccc gcacctgaag cgcgttcagc ttcagttggg ggagcttccc ccgtccgatg 57960
tgggggtcgc accgccggag cagctctatc tgaaacacat aggtctgcac ctgcccgagc 58020
agggctaaca acttttgacg ggccacggtg ggctcggaca ccggggcggc catctcgcgg 58080
cgccgatctg taccgcggcc ggagtatgcg gtggaccgag gcggtccgta cgctacccgg 58140
tgtctggctg agccccgggg tccccctctt cggggcggcc tcccgcgggc ccgccgaccg 58200
gcaagccggg agtcggcggc gcgtgcgttt ctgttctatt cccagacacc gcggagagga 58260
atcgcggccc gcccagagat atagacacgg aacacaaaca agcacggatg tcgtagcaat 58320
aatttatttt acacacatcc ccgccccgcc ctaggttccc ccaccccccca accccctcaca 58380
gcatatccaa cgtcaggtct cccttttttgt cggggggccc ctccccaaac gggtcatccc 58440
cgtggaacgc ccgtttgcgg ccggcaaatg ccggtcccgg ggcccccggg ccgccgaacg 58500
gcgtcgcgtt gtcgtcctcg cagccaaaat ccccaaagtt aaacacctcc ccggcgttgc 58560
cgagttggct gactagggcc tcggcctcgt gcgccacctc cagggccgcg tccgtcgacc 58620
actcgccgtt gccgcgctcc agggcacgcg cggtcagctc catcatctcc tcgcttaggt 58680
actcgtcctc caggagcgcc agccagtcct cgatctgcag ctgctgggtg cggggcccca 58740
ggcttttcac ggtcgccacg aacacgctac tggcgacggc cgccccgccc tcggagataa 58800
tgccccggag ctgctcgcac agcgagcttt cgtgcgctcc gccgccgagg ttcgaggccg 58860
cgcacacaaa cccggcccgg ggacaggcca ggacgaactt gcgggtgcgg tcaaaaataa 58920
ggagcgggca cgcgtttttg ccgcccatca ggctggccca gttcccggcc tgaaacacac 58980
ggtcgttgcc ggccatgccg tagtatttgc tgatgctcaa ccccaacacg accatggggc 59040
gcgccgccat gacgggccgc agcaggttgc agctggcgaa catggacgtc cacgcgcccg 59100
gatgcgcgtc cacggcgtcc atcagcgcgc gggccccggc ctccaggccc gccccgccct 59160
gcgcggacca cgcggccgcc gcctgcacgc tggggggacg gcgggacccc gcgatgatgg 59220
ccgtgagggt gttgatgaag tatgtcgagt gatcgcagta ccgcagaatc tggtttgcca 59280
tgtagtacat cgccagctcg ctcacgttgt tgggggccag gttaataaag tttatcgcgc 59340
cgtagtccag ggaaaacttt ttaatgaacg cgatggtctc gatgtcctcg cgcgacagga 59400
gccgggcggg aagctggttg cgttggaggg ccgtccagaa ccactgcggg ttcggctggt 59460
tggaccccgg gggcttgccg ttggggaaga tggccgcgtg gaactgcttc agcagaaagc 59520
ccagcggtcc gaggaggatg tccacgcgct tgtcgggctt ctggtaggcg ctctggaggc 59580
tggcgacccg cgccttggcg gcctcggacg cgttggcgct cgcgcccgcg aacaacacgc 59640
ggctcttgac gcgcagctcc ttgggaaacc ccagggtcac gcgggcaacg tcgccctcga 59700
agctgctctc ggcgggggcc gtctggccgg ccgttaggct gggggcgcag atagccgccc 59760
cctccgagag cgcgaccgtc agcgttttgg ccgacagaaa cccgttgtta aacatgtcca 59820
tcacgcgccg ccgcagcacc ggttggaatt gattgcgaaa gttgcgcccc tcgaccgact 59880
gcccggcgaa caccccgtgg cactggctca gggccaggtc ctgatacacg gcgaggttgg 59940

```
atcgccgccc gagaagctga agcagggggc atggcccgca cgcgtacggg tccagcgtca  60000
gggacatggc gtggttggcc tcgcccagac cgtcgcgaaa cttgaagttc ctcccctcca  60060
ccaggttgcg catcagctgc tccacctcgc ggtccacgac ctgcctgacg ttgttcacca  60120
ccgtatgcag ggcctcgcgg ttggtgatga tggtctccag ccgccccatg gccgtgggga  60180
ccgcctggtc cacgtactgc agggtctcga gttcggccat gacgcgctcg gtcgccgcgc  60240
ggtacgtctc ctgcatgatg gtccgggcgg tctcggatcc gtccgcgcgc ttcagggccg  60300
agaaggcggc gtagtttccc agcacgtcgc agtcgctgta catgctgttc atggtcccga  60360
agacgccgat ggctccgcgg gcggcgctgg cgaacttggg atggcgcgcc cggaggcgca  60420
tgagcgtcgt gtgtacgcag gcgtggcgcg tgtcgaaggt gcacaggttg cagggcacgt  60480
cggtctggtt ggagtccgcg acgtatcgaa acacgtccat ctcctggcgc ccgacgatca  60540
cgccgccgtc gcagcgctcc aggtaaaaca gcatcttggc cagcagcgcc ggggaaaacc  60600
cacacagcat ggccaggtgc tcgccggcaa attcctgggt tccgccgacg aggggcgcgg  60660
tgggccgacc ctcgaacccg ggcaccacgt gtccctcgcg gtccacctgt gggttggccg  60720
ccacgtgggt cccgggcacg aggaagaagc ggtaaaagga gggtttgctg tggtcctttg  60780
ggtccgccgg accggcgtcg tccacctcgg tgagatggag ggccgagttg gtgctaaata  60840
ccatggcccc cacgagtccc gcggcgcgcg ccaggtacgc cccgacggcg ttggcgcggg  60900
ccgcggccgt gtcctggccc tcgcacagcg gccacgcgga gatgtcggtg ggcggctcgt  60960
cgaagacggc catcgacacg atagactcga gggccagggc ggcgtctccg gccatgacgg  61020
aggccaggcg ctgttcgaac ccgcccgccg ggcccttgcc gccgccgtcg cgcccacccc  61080
gcggggtctt accctggctg gcttcgaagg ccgtgaacgt aatgtcggcg gggagggcgg  61140
cgccctcgtg gttttcgtca aacgccaggt gggcggccgc gcgggccacg gcgtccacgt  61200
ttcggcatcg cagtgccacg gcggcgggtc ccacgaccgc ctcgaacagg aggcggttga  61260
gggggcggtt aaaaaacgga agcgggtagg taaaattctc cccgatcgat cggtggttgg  61320
cgttgaacgg ctcggcgatg acccggctaa aatccggcat gaacagctgc aacggataca  61380
cgggtatgcg gtgcacctcc gccccgccta tggttacctt gtccgagcct cccaggtgca  61440
gaaaggtgtt gttgatgcac acggcctcct tgaagccctc ggtaacgacc agatacagga  61500
gggcgcggtc cgggtccagg ccgaggcgct cacacagcgc ctcccccgtc gtctcgtgtt  61560
tgaggtcgcc gggccggggg gtgtagtccg aaaagccaaa atggcggcgt gcccgctcgc  61620
agagtcgcgt caggtttggg gcctgggtgc tggggtccag gtgccggccg ccgtgaaaga  61680
cgtacacgga cgagctgtag tgcgatggcg tcagtttcag ggacaccgcg gtacccccga  61740
gccccgtcgt gcgagaaccc acgaccacgg ctacgttggc ctcaaagccg ctctccacgg  61800
tcaggcccac gaccaggggc gccacggcga cgtcggcatc gccgctgcgc gccgacagta  61860
acgccagaag ctcgatgcct tcggacggac acgcgcgagc gtacacgtat cccaggggcc  61920
cggggggac cttgatggtg gttgccgtct tgggctttgt ctccatgtcc tcctggcaat  61980
cggtccgcaa acggaggtaa tcccggcacg acgacggacg cccgacgagg tatgtctccc  62040
gagcgtcaaa atccgggggg gggggggggg ggggggcggc gacggtcaag gggagggtgg  62100
gagaccgggg ttggggaatg aatccctacc cttcacagac aacccccggg taaccacggg  62160
gtgccgatga accccggcgg ctggcaacgc ggggtccctg cgagaggcac agatgcttac  62220
ggtcaggtgc tccgggccgg gtgcgtctga tatgcggttg gtatatgtac actttacctg  62280
ggggcgtgcc ggaccgcccc agcccctccc acaccccgcg cgtcatcagc cggtgggcgt  62340
```

```
ggccgctatt ataaaaaaag tgagaacgcg aagcgttcgc actttgtcct aataatatat  62400
atattattag gacaaagtgc gaacgcttcg cgttctcact tttttataa tagcggccac  62460
gcccaccggc tacgtcacgc tcctgtcggc cgccggcggt ccataagccc ggccggccgg  62520
gccgacgcga ataaaccggg ccgccggccg gggcgccgcg cagcagctcg ccgcccggat  62580
ccgccagaca aacaaggccc ttgcacatgc cggcccgggc gagcctgggg gtccggtaat  62640
tttgccatcc cacccaagcg gcttttgggg tttttcctct tccccctcc ccacatcccc  62700
cctctttagg ggttcgggtg ggaacaaccg cgatgttttc cggtggcggc ggcccgctgt  62760
cccccggagg aaagtcggcg gccagggcgg cgtccgggtt ttttgcgccc gccggccctc  62820
gcggagccgg ccggggaccc ccgccttgtt tgaggcaaaa cttttacaac ccctacctcg  62880
ccccagtcgg gacgcaacag aagccgaccg ggccaaccca gcgccatacg tactatagcg  62940
aatgcgatga atttcgattc atcgccccgc gggtgctgga cgaggatgcc cccccggaga  63000
agcgcgccgg ggtgcacgac ggtcacctca agcgcgcccc caaggtgtac tgcggggggg  63060
acgagcgcga cgtcctccgc gtcgggtcgg gcggcttctg gccgcggcgc tcgcgcctgt  63120
ggggcggcgt ggaccacgcc ccggcggggt tcaaccccac cgtcaccgtc tttcacgtgt  63180
acgacatcct ggagaacgtg gagcacgcgt acggcatgcg cgcggcccag ttccacgcgc  63240
ggtttatgga cgccatcaca ccgacgggga ccgtcatcac gctcctgggc ctgactccgg  63300
aaggccaccg ggtggccgtt cacgtttacg gcacgcggca gtacttttac atgaacaagg  63360
aggaggttga caggcaccta caatgccgcg ccccacgaga tctctgcgag cgcatggccg  63420
cggccctgcg cgagtccccg ggcgcgtcgt tccgcggcat ctccgcggac cacttcgagg  63480
cggaggtggt ggagcgcacc gacgtgtact actacgagac gcgccccgct ctgttttacc  63540
gcgtctacgt ccgaagcggg cgcgtgctgt cgtacctgtg cgacaacttc tgcccggcca  63600
tcaagaagta cgagggtggg gtcgacgcca ccacccggtt catcctggac aaccccgggt  63660
tcgtcacctt cggctggtac cgtctcaaac cgggccggaa caacacgcta gcccagccgc  63720
gggccccgat ggccttcggg acatccagcg acgtcgagtt taactgtacg gcggacaacc  63780
tggccatcga ggggggcatg agcgacctac cggcatacaa gctcatgtgc ttcgatatcg  63840
aatgcaaggc ggggggggag gacgagctgg cctttccggt ggccgggcac ccggaggacc  63900
tggttattca gatatcctgt ctgctctacg acctgtccac caccgccctg gagcacgtcc  63960
tcctgttttc gctcggttcc tgcgacctcc ccgaatccca cctgaacgag ctggcggcca  64020
ggggcctgcc cacgcccgtg gttctggaat tcgacagcga attcgagatg ctgttggcct  64080
tcatgaccct tgtgaaacag tacggccccg agttcgtgac cgggtacaac atcatcaact  64140
tcgactggcc cttcttgctg gccaagctga cggacattta caaggtcccc ctggacgggt  64200
acggccgcat gaacggccgg ggcatgtttc gcgtgtggga catagccag agccacttcc  64260
agaagcgcag caagataaag gtgaacggca tggtgaacat cgacatgtac gggatcataa  64320
ccgacaagat caagctctcg agctacaagc tcaacgccgt ggccgaagcc gtcctgaagg  64380
acaagaagaa ggacctgagc tatcgcgaca tccccgccta ctacgccacc gggcccgcgc  64440
aacgcggggt gatcggcgag tactgcatac aggattccct gctggtgggc cagctgtttt  64500
ttaagttttt gccccatctg gagctctcgg ccgtcgcgcg cttggcgggt attaacatca  64560
cccgcaccat ctacgacggc cagcagatcc gcgtctttac gtgcctgctg cgcctggccg  64620
accagaaggg ctttattctg ccggacaccc aggggcgatt taggggcgcc gggggggagg  64680
```

```
cgcccaagcg tccggccgca gcccgggagg acgaggagcg gccagaggag gaggggggagg  64740
acgaggacga acgcgaggag ggcgggggcg agcgggagcc ggagggcgcg cgggagaccg  64800
ccggccggca cgtggggtac cagggggcca gggtccttga ccccacttcc gggtttcacg  64860
tgaaccccgt ggtggtgttc gactttgcca gcctgtaccc cagcatcatc caggcccaca  64920
acctgtgctt cagcacgctc tccctgaggg ccgacgcagt ggcgcacctg gaggcgggca  64980
aggactacct ggagatcgag gtgggggggc gacggctgtt cttcgtcaag gctcacgtgc  65040
gagagagcct cctcagcatc ctcctgcggg actggctcgc catgcgaaag cagatccgct  65100
cgcggattcc cccagagcagc cccgaggagg ccgtgctcct ggacaagcag caggccgcca  65160
tcaaggtcgt gtgtaactcg gtgtacgggt tcacgggagt gcagcacgga ctcctgccgt  65220
gcctgcacgt tgccgcgacg gtgacgacca tcggccgcga gatgctgctc gcgacccgcg  65280
agtacgtcca cgcgcgctgg gcggccttcg aacagctcct ggccgatttc ccggaggcgg  65340
ccgacatgcg cgcccccggg ccctattcca tgcgcatcat ctacggggac acggactcca  65400
tatttgtgct gtgccgcggc ctcacggccg ccgggctgac ggccatgggc gacaagatgg  65460
cgagccacat ctcgcgcgcg ctgtttctgc cccccatcaa actcgagtgc gaaaagacgt  65520
tcaccaagct gctgctgatc gccaagaaaa agtacatcgg cgtcatctac gggggtaaga  65580
tgctcatcaa gggcgtggat ctggtgcgca aaaacaactg cgcgtttatc aaccgcacct  65640
ccagggccct ggtcgacctg ctgttttacg acgataccgt atccggagcg gccgccgcgt  65700
tagccgagcg ccccgcagag gagtggctgg cgcgacccct gcccgaggga ctgcaggcgt  65760
tcggggccgt cctcgtagac gcccatcggc gcatcaccga cccggagagg gacatccagg  65820
actttgtcct caccgccgaa ctgagcagac acccgcgcgc gtacaccaac aagcgcctgg  65880
cccacctgac ggtgtattac aagctcatgg cccgccgcgc gcaggtcccg tccatcaagg  65940
accggatccc gtacgtgatc gtggcccaga cccgcgaggt agaggagacg gtcgcgcggc  66000
tggccgccct ccgcgagcta gacgccgccg ccccagggga cgagcccgcc ccccccgcgg  66060
ccctgccctc cccgaccaag cgcccccggg agacgccgtc gcatgccgac cccccgggag  66120
gcgcgtccaa gccccgcaag ctgctggtgt ccgagctggc cgaggatccc gcatacgcca  66180
ttgcccacgg cgtcgccctg aacacggact attacttctc ccacctgttg ggggcggcgt  66240
gcgtgacatt caaggccctg tttgggaata acgccaagat caccgagagt ctgttaaaaa  66300
ggtttattcc cgaagtgtgg caccccccgg acgacgtggc cgcgcggctc cgggccgcag  66360
ggttcggggc ggtgggtgcc ggcgctacgg cggaggaaac tcgtcgaatg ttgcatagag  66420
cctttgatac tctagcatga gcccccgtc gaagctgatg tccctcattt tacaataaat  66480
gtctgcggcc gacacggtcg gaatctccgc gtccgtgggt ttctctgcgt tgcgccggac  66540
cacgagcaca aacgtgctct gccacacgtg ggcgacgaac cggtaccccg ggcacgcggt  66600
gagcatccgg tctatgagcc ggtagtgcag gtgggcggac gtgccgggaa agatgacgta  66660
cagcatgtgg cccccgtaag tggggtccgg gtaaaacaac agccgcgggt cgcacgcccc  66720
gcctccgcgc aggatcgtgt ggacgaaaaa aagctcgggt tggccaagaa tcccggccaa  66780
gaggtcctgg agggggcgt tgtggcggtc ggccaacacg accaaggagg ccaggaaggc  66840
gcgatgctcg aatatcgtgt tgatctgctg cacgaaggcc aggattaggg cctcgcggct  66900
ggtggcggcg aaccgcccgt ctcccgcgtt gcacgcggga cagcaacccc cgatgcctag  66960
gtagtagccc atcccggaga gggtcaggca gttgtcggcc acggtctggt ccagacagaa  67020
gggcagcgac acgggagtgg tcttcaccag gggcaccgag aacgagcgca cgatggcgat  67080
```

ctcctcggag ggcgtctggg cgagggcggc gaaaaggccc cgatagcgct ggcgctcgtg 67140
taaacacagc tcctgtttgc gggcgtgagg cggcaggctc ttccgggagg cccgacgcac 67200
cacgcccaga gtcccgccgg ccgcagagga gcacgaccgc cggcgctcct tgccgtgata 67260
gggcccgggc cgggagccgc ggcgatgggg gtcggtatca tacataggta cacagggtgt 67320
gctccaggga caggagcgag atcgagtggc gtctaagcag cgcgcccgcc tcacggacaa 67380
atgtggcgag cgcggtgggc tttggtacaa atacctgata cgtcttgaag gtgtagatga 67440
gggcacgcaa cgctatgcag acacgcccct cgaactcgtt cccgcaggcc agcttggcct 67500
tgtggagcag cagctcgtcg ggatgggtgg cggggggatg gccgaacaga acccaggggt 67560
caacctccat ctccgtgatg gcgcacatgg ggtcacagaa catgtgctta aagatggcct 67620
cgggccccgc ggcccgcagc aggctcacaa accggccccc gtccccgggc tgcgtctcgg 67680
ggtccgcctc gagctggtcg acgacgggta cgatacagtc gaagaggctc gtgttgtttt 67740
ccgagtagcg gaccacggag gcccggagtc tgcgcagggc cagccagtaa gcccgcacca 67800
gtaacaggtt acacagcagg cattctccgc cggtgcgccc gcgcccccgg ccgtgtttca 67860
gcacggtggc catcagaggg cccaggtcga ggtcgggctg ggcatcgggt tcggtaaact 67920
gcgcaaagcg cggagccacg tcgcgcgtgc gtgccccgcg atgcgcttcc caggactggc 67980
ggaccgtggc gcgacgggcc tccgcggcag cgcgcagctg gggccccgac tcccagacgg 68040
cgggggtgcc ggcgaggagc agcaggacca gatccgcgta cgcccacgta tccggcgact 68100
cctccggctc gcggtccccg gcgaccgtct cgaattcccc gttgcgagcg gcggcgcgcg 68160
tacagcagct gtccccgccc ccgcgccgac cctccgtgca gtccaggaga cgggcgcaat 68220
ccttccagtt catcagcgcg gtggtgagcg acggctgcgt gccggatccc gccgccgacc 68280
ccgccccctc ctcgcccccg gaggccaagg ttccgatgag ggcccgggtg gcagactgcg 68340
ccaggaacga gtagttggag tactgcacct tggcggctcc cggggagggc gagggcttgg 68400
gttgcttctg ggcatgccgc ccgggcaccc cgccgtcggt acggaagcag cagtggagaa 68460
aaaagtgccg gtggatgtcg tttatggtga gggcaaagcg tgcgaaggag ccgaccaggg 68520
tcgccttctt ggtgcgcaga aagtggcggt ccatgacgta cacaaactcg aacgcggcca 68580
cgaagatgct agcggcgcag tggggcgccc ccaggcattt ggcacagaga aacgcgtaat 68640
cggccaccca ctggggcgag aggcggtagg tttgcttgta cagctcgatg gtgcggcaga 68700
ccagacaggg ccggtccagc gcgaaggtgt cgatggccgc cgcggaaaag ggcccggtgt 68760
ccaaaagccc ctccccacag ggatccgggg gcgggttgcg gggtcctccg cgcccgcccg 68820
aaccccctcc gtcgcccgcc cccccgcggg cccttgaggg ggcggtgacc acgtcggcgg 68880
cgacgtcctc gtcgagcgta ccgacgggcg gcacacctat cacgtgactg gccgccagga 68940
gctcggcgca gagagcctcg ttaagagcca ggaggctggg atcgaaggcc acatacgcgc 69000
gctcgaacgc ccccgccttc cagctgctgc cgggggactc ttcgcacacc gcgacgctcg 69060
ccaggacccc ggggggcgaa gttgccatgg ctgggcggga ggggcgcacg cgccagcgaa 69120
ctttacggga cacaatcccc gactgcgcgc tgcggtccca gaccctggag agtctagacg 69180
cgcgctacgt ctcgcgagac ggcgcgcatg acgcggccgt ctggttcgag gatatgaccc 69240
ccgccgagct ggaggttgtc ttcccgacta cggacgccaa gctgaactac ctgtcgcgga 69300
cgcagcggct ggcctccctc ctgacgtacg ccgggcctat aaaagcgccc gacgacgccg 69360
ccgccccgca gaccccggac accgcgtgtg tgcacggcga gctgctcgcc cgcaagcggg 69420

-continued

```
aaagattcgc ggcggtcatt aaccggttcc tggacctgca ccagattctg cggggctgac  69480
gcgcgcgctg ttgggcggga cggttcgcga accctttggt gggtttacgc gggcacgcac  69540
gctcccatcg cgggcgccat ggcgggactg ggcaagccct accccggcca cccaggtgac  69600
gccttcgagg gtctcgttca gcgaattcgg cttatcgtcc catctacgtt gcggggcggg  69660
gacggggagg cgggccccta ctctccctcc agcctcccct ccaggtgcgc ctttcagttt  69720
catggccatg acgggtccga cgagtcgttt cccatcgagt atgtactgcg gcttatgaac  69780
gactgggccg aggtcccgtg caacccttac ctgcgcatac agaacaccgg cgtgtcggtg  69840
ctgtttcagg ggtttttca tcgcccacac aacgcccccg ggggcgcgat tacgccagag  69900
cggaccaatg tgatcctggg ctccaccgag acgacggggc tgtccctcgg cgacctggac  69960
accatcaagg ggcggctcgg cctggatgcc cggccgatga tggccagcat gtggatcagc  70020
tgctttgtgc gcatgccccg cgtgcagctc gcgtttcggt tcatgggccc cgaagatgcc  70080
ggacggacga gacggatcct gtgccgcgcc gccgagcagg ctattacccg tcgccgccga  70140
acccggcggt cccgggaggc gtacggggcc gaggccgggc tgggggtggc tggaacgggt  70200
ttccgggcca ggggggacgg ttttggcccg ctccccttgt taacccaagg gccctcccgc  70260
ccgtggcacc aggccctgcg gggtcttaag cacctacgga ttggcccccc cgcgctcgtt  70320
ttggcggcgg gactcgtcct gggggccgct atttggtggg tggttggtgc tggcgcgcgc  70380
ctataaaaaa ggacgcaccg ccgccctaat cgccagtgcg ttccggacgc cttcgcccca  70440
cacagccctc ccgtccgaca cccccatatc gcttcccgac ctccggtccc gatggccgtc  70500
ccgcaatttc accgccccag caccgttacc accgatagcg tccgggcgct tggcatgcgc  70560
gggctcgtct tggccaccaa taactctcag tttatcatgg ataacaacca cccgcacccc  70620
cagggcaccc aaggggccgt gcgggagttt ctccgcggtc aggcggcggc gctgacggac  70680
cttggtctgg cccacgcaaa caacacgttt accccgcagc ctatgttcgc gggcgacgcc  70740
ccggccgcct ggttgcggcc cgcgtttggc ctgcggcgca cctattcacc gtttgtcgtt  70800
cgagaacctt cgacgcccgg gaccccgtga ggcccgggga gttccttctg ggtgtttta  70860
atcaataaaa gaccacacca acgcacgagc cttgcgttta atgtcgtgtt tattcaaggg  70920
agtgggatag ggttcgacgg ttcgaaactt aacacacaaa ataatcgagc gcgtctagcc  70980
cagtaacatg cgcacgtgat gtaggctggt cagcacggcg tcgctgtgat gaagcagcgc  71040
ccggcgggtc cgctgtaact gctgttgtag gcggtaacag gcgcggatca gcaccgccag  71100
ggcgctacga ccggtgcgtt gcacgtagcg tcgcgacaga actgcgtttg ccgatacggg  71160
cggggggccg aattgtaagc gcgtcacctc ttgggagtca tcggcggata acgcactgaa  71220
tggttcgttg gttatggggg agtgtggttc ccgagggagt gggtcgagcg cctcggcctc  71280
ggaatccgag aggaacaacg aggtggtgtc ggagtcttcg tcgtcagaga catacagggt  71340
ctgaagcagc gacacgggcg ggggggtagc gtcaatgtgt agcgcgaggg aggatgccca  71400
cgaagacacc ccagacaagg agctgcccgt gcgtggattt gtggacgacg cggaagccgg  71460
gacggatggg cggttttgcg gtgcccggaa ccgaaccgcc ggatactccc cgggtgctac  71520
atgcccgttt tggggctggg gttggggctg gggctggggc ggggggtggg gggggttggg  71580
gtggggctgg ggtggggctg gggttggggc tggggctggg gctggggctg gggtggggtt  71640
ggggttgggg ctggggctgg ggtggggtgg ggctggggtg gggttggggc tggggttggg  71700
gctggggttg gggctggggt ggggctgggg ttggggttgg ggttggggct ggggttgggg  71760
ctggggcgcg gacaggcggt tgacggtcaa atgcccccgg gggcgcgcag atgtggtggg  71820
```

cgtggccacc ggctgccggg taggggggcg gcggggaacc gggcctccgg gcgtaacacc 71880
gccctccagc gtcaaggatg tggggggcgg gcctgacgtc gggggcgggg tgacgggttg 71940
gaccgcggga ggcgggggag agggacctgc gggagaggat gaggtcggct cggccgggtt 72000
gcggcctaaa acaggggccg tggggtcggc ggggtcccag ggtgaaggga gggattcccg 72060
cgattcggac agcgacgcga cagcggggcg cgtaaggcgc cgctgcggcc cgcctacggg 72120
aaccctgggg ggggttggcg cgggacccga ggttagcggg gggcggcggt tttcgccccc 72180
gggcaaaacc gtgccggttg cgaccggggg cggaacggga tcgataggga gagcgggaga 72240
agcctggccg gcgaactggg gaccgagcgg gaggggcaca ccagacacca aagcgtggag 72300
cgctggctct gggggtttgg gaggggccgg ggggcgcgcg aaatcggtaa ccggggcgac 72360
cgtgtcgggg agggcaggcg gccgccaacc ctgggtggtc gcggaagcct gggtggcgcg 72420
cgccagggag cgtgcccggc ggtgtcggcg cgcgcgcgac ccggacgaag aagcggcaga 72480
agcgcgggag gaggcggggg ggcgggggc ggtggcatcg gggggcgccg gggaactttg 72540
gggggacggc aagcgccgga agtcgtcgcg ggggcccacg ggcgccggcc gcgtgctttc 72600
ggccgggacg cccggtcgtg cttcgcgagc cgtgactgcc ggcccagggg gccgcggtgc 72660
acactgggac gtggggacgg actgatcggc ggtgggcgaa agggggtccg gggcaaggag 72720
gggcgcgggg ccgccggagt cgtcagacgc gagctcctcc aggccgtgaa tccatgccca 72780
catgcgaggg gggacgggct cgccgggggt ggcgtcggtg aatagcgtgg gggccaggct 72840
tccgggcccc aacgagccct ccgtcccaac aaggtccgcc gggccggggg tcgggttcgg 72900
gaccgagggg ctctggtcgt cgggggcgcg ctggtacacc ggatgccccg ggaatagctc 72960
ccccgacagg agggaggcgt cgaacggccg cccgaggata gctcgcgcga ggaaggggtc 73020
ctcgtcggtg gcgctggcgg cgaggacgtc ctcgccgccc gccacaaacg ggagctcctc 73080
ggtggcctcg ctgccaacaa accgcacgtc ggggggggccg ggggggtccg ggttttccca 73140
caacaccgcg accggggtca tggagatgtc cacgagcacc agacacggcg ggcccccgggc 73200
gaggggccgc tcggcgatga gcgcggacag gcgcgggagc tgtgccgcca gacacgcgtt 73260
ttcaatcggg ttcaggtcgg cgtgcaggag gcggacggcc cacgtctcga tgtcggacga 73320
cacggcatcg cgcaaggcgg cgtccggccc gcgagcgcgt gagtcaaaca gcgtgagaca 73380
cagctccagc tccgactcgc gggaaaaggc cgtggtgttg cggagcgcca cgacgacggg 73440
cgcgcccagg agcactgccg ccagcaccag gtccatggcc gtaacgcgcg ccgcgggggt 73500
gcggtgggtg gcggcggccg gcacggcgac gtgctggccc gtgggccggt agagggcgtt 73560
ggggggagcg gggggtgacg cctcgcgccc ccccgagggg ctcagcgtct gcccagattc 73620
cagacgcgcg gtcagaaggg cgtcgaaact gtcatactct gtgtagtcgt ccggaaacat 73680
gcaggtccaa agagcggcca gagcggtgct tgggagacac atgcgcccga ggacgctcac 73740
cgccgccagc gcctgggcgg gactcagctt tcccagcgcg gcgccgcgct cggttcccag 73800
ctcggggacc gagcgccagg gcgccagggg gtcggtttcg gacaacttgc cgcggcgcca 73860
gtctgccagc cgcgtgccga acatgaggcc ccgggtcgga gggcctccgg tcgaaaacac 73920
tggcagcacg cggatgcggg cgtctggatg cggggtcagg cgctgcacga atagcatgga 73980
atctgctgcg ttctgaaacg cacgggggag ggtgagatgc atgtactcgt gttggcggac 74040
cagatccagg cgccaaaagg tgtaaatgtg ttccggggag ctggccacca gcgccaccag 74100
cacgtcgttc tcgttaaagg aaacgcggtg cctagtggag ctgtggggcc cgagcggcgg 74160
tcccggggcc gccgcgtcac ccccccattc cagctgggcc cagcgacacc caaactcgcg 74220
cgtgagagtg gtcgcgacga gggcgacgta gagctcggcc gccgcatcca tcgaggcccc 74280
ccatctcgcc tggcggtggc gcacaaagcg tccgaagagc tgaaagttgg cggcctgggc 74340
gtcgctgagg gccagctgaa gccggttgat gacggtgatg acgtacatgg ccgtgacggt 74400
cgaggccgac tccagggtgt ccgtcggaag cggggggcga atgcatgccg cctcgggaca 74460
catcagcagc gcgccgagct tgtcggtcac ggccgggaag cagagcgcgt actgcagtgg 74520
cgttccatcc gggaccaaaa agctgggggc gaacggccga tccagcgtac tggtggcctc 74580
gcgcagcacc aggggccccg ggcctccgct cactcgcagg tacgcctcgc cccggcggcg 74640
cagcatctgc gggtcggcct cttggccggg tggggcggac gcccgggcgc gggcgtctag 74700
ggcgcgaaga tccacgagca ggggcgcggg cgcggcggcc gcgcccgcgc ccgtctggcc 74760
tgtggccttg gcgtacgcgc tatataagcc catgcggcgt tggatgagct cccgcgcgcc 74820
ccggaactcc tccaccgccc atggggccag gtccccggcc accgcgtcga attccgccaa 74880
caggcccccc agggtgtcaa agttcatctc ccaggccacc cttggcacca cctcgtcccg 74940
cagccgggcg ctcaggtcgg cgtgttgggc cacgcgcccc ccgagctcct ccacggcccc 75000
ggcccgctcg gcgctcttgg cgcccaggac gccctggtac ttggcgggaa ggcgctcgta 75060
gtcccgctgg gctcgcagcc ccgacacagt gttggtggtg tcctgcaggg cgcgaagctg 75120
ctcgcatgcc gcgcgaaatc cctcgggcga tttccaggcc cccccgcgaa cgcggccgaa 75180
gcgaccccat acctcgtccc actccgcctc ggcctcctcg agagacctcc gcagggcctc 75240
gacgcggcga cgggtgtcga agagcgcctg caggcgcgcg ccctgtcgcg tcaggaggcc 75300
cgggccgtcg ccgctggccg cgtttagcgg gtgcgtctca aaggtacgct gggcatgttc 75360
caaccaggcg accgcctgca cgtcgagctc gcgcgccttc tccgtctggt ccaacagaat 75420
ttcgacctga tccgcgatct cctccgccga gcgcgcctgg tccagcgtct tggccacggt 75480
cgccgggacg gcgaccacct tcagcagggt cttcagattg gccagaccct cggcctcgag 75540
ctgggcccgg cgctcgcgcg cggccagcac ctcccgcagc cccgccgtga cccgctcggt 75600
ggcttcggcg cgctgctgtt tggcgcgcac cacggcgtcc ttggtatcgg ccaggtcctg 75660
tcgggtcacg aatgcgacgt agtcggcgta cgccgtgtcc ttcacggggc tctggtccac 75720
gcgctccagc gccgccacgc acgccaccag cgcgtcctcg ctcgggcagg gcagggtgac 75780
ccctgcccgg acaagctcgg cggccgccgc cgggtcgttg cgcaccgcgg atatctcctc 75840
cgcggcggcg gccaggtcca gcgccacgct tccgatcgcg cgccgcgcgt cggcccggag 75900
ggcgtccagg cgatcgcgga tatccacgta ctcggcgtag cccttttgaa aaaacggcac 75960
gtactggcgc agggccggca cgccccccaa gtcttccgac aggtgtagga cggcctcgtg 76020
gtagtcgata aacccgtcgt tcgcctgggc ccgctccagc agcccccccg ccagccgcag 76080
aagccgcgcc aggggctcgg tgtccacccg aaacatgtcg gcgtacgtgt cggccgcggc 76140
cccgaaggcc gcgctccagt cgatgcggtg aatggctgcg agcgggggga gcatggggtg 76200
gcgctggttc tcgggggtgt atgggttaaa cgcaagggcc gtctccaggg caagggtcac 76260
cgccttggcg ttggttccca gcgcctgttc ggcccgcttt cggaagtccc gggggttgta 76320
gccgtgcgtg cccgccagcg cctgcaggcg acggagctcg accacgtcaa actcggcacc 76380
gctttccacg cggtccagca cggcctccac gtcggcggcc cagcgctcgt ggctactgcg 76440
ggcgcgctgg gccgccatct tctctctcag gtcggcgatg gcggcctcaa gttcgtcggc 76500
gcggcgtcgc gtggcgccga tgacctttcc cagctcctgc agggcgcgcc cgctgggggga 76560

```
gtggtccccg gccgtccctt cggcgtgcaa caggcccccg aacctgccct cgtggcccgc  76620
gaggctttcc cgcgcgccgg tggtcgcgcg cgtcgcggcc tggatcaggg aggcatgctc  76680
tccctccggt tggttggcgg cccggcgcac ctggacgaca aggtcggctg ccgccgaccc  76740
taaggtcgtg agctgggcga tggccccccg cgcgtccagg gccaaccgag tcgccttgac  76800
gtatcccgcg gcgctgtcgg ccatggccgc taggaaggcc aggggggagg ccgggtcgct  76860
ggcggccgcg cccagggccg tcaccgcgtc gaccaggacg cggtgcgccc gcacggccgc  76920
atccaccgtc gacgcggggt ctgccgtcgc gacggcggcg ctgccggcgt tgatggcgtt  76980
cgagacggcg tgggctatga tcggggcgtg atcggcgaag aactgcaaga gaaacggagt  77040
ctctggggcg tcggcgaaca ggttcttcag caccaccacg aagctgggat gcaagccaga  77100
cagagccgtc gccgtgtccg gagtcgggtg ctccagggca tctcggtact gccccagcag  77160
cccccacatg tccgcccgca gtgccgccgt aacctcaggg ggcgcccccc gaacggcctc  77220
ggggaggtcc gaccagcccg ccggcaggga ggcccgcagg gtcgccagga cggccggaca  77280
ggcctttagc cccacaaagt cagggagggg gcgcaggacc ccctggagtt tgtgcaagaa  77340
cttctcccgg gcgtcgcggg ccaccttcgc ccgctcccgc gctccctcga gcattgcctc  77400
cagggagcgc gcgcgctccc gcaaacgggc acgcgcatcg gggcgagct ctgccgtcag   77460
cttggcggca tccatggccc gcgcctgccg cagcgcttcc tcggccatgc gcgtggcctc  77520
tggcgacagc ccgccgtcgt cggggtaggg cgacgcgccg ggcgcaggaa caaaggccgc  77580
gtcgctgtcc agctgctggc ccagggccgc atctagggcg tcgaagcgcc gcagctcggc  77640
cagacccgag ctgcggcgcg cctgctggtc gttaatgtcg cggatgctgc gcgccagctc  77700
gtccagcggc ttgcgttcta tcagcccttg gttggcggcg tccgtcagga cggagagcca  77760
ggccgccagg tcctcggggg cgtccagcgt ctggccccgc tggatcagat cccgcaacag  77820
gatggccgtg gggctggtcg cgatcggggg cggggcggga atggcggcgc gctgcgcgat  77880
gtcccgcgtg tgctggtcga agacaggcag ggactcgagc agctggacca cgggcacgac  77940
ggcggccgaa gccacgtgaa accggcggtc gttgttgtcg ctggcctgta gagccttggc  78000
gctgtatacg gccccccggt aaaagtactc cttaaccgcg ccctcgatcg cccgacgggc  78060
ctgggtccgc acctcctcca gccgaacctg aacggcctcg gggcccaggg ggggtgggcg  78120
cggagccccc tgcggggccg ccccggccgg ggcgggcatt acgccgaggg gcccggcgtg  78180
ctgtgagacc gcgtcgaccc cgcgagcgag ggcgtcgagg gcctcgcgca tctggcgatc  78240
ctccgcctcc accctaatct cttcgccacg ggcaaatttg gccagagcct ggactctata  78300
cagaagcggt tctgggtgcg tcggggtggc gggggcaaaa agggtgtccg ggtgggcctg  78360
cgagcgctcc agaagccact cgccgaggcg tgtatacaga ttggccggcg gggccgcgcg  78420
aagctgcagc tccaggtccg cgagttcccc gtaaaaggcg tccgtctccc gaatgacatc  78480
cctagccaca aggatcagct tcgccagcgc caggcgaccg atcagagagt tttcgtccag  78540
cacgtgctgg acgaggggca gatgggcggc cacgtcggcc aggctcaggc gcgtggaggc  78600
cagaaagtcc cccacggccg ttttccgggg cagcatgctc agggtaaact ccagcagggc  78660
ggcggccggg ccggccaccc cggcctgggt gtgcgtccgg gccccgttct cgatgagaaa  78720
ggcgaggacg cgttcaaaga aaaaaataac acagagctcc agcagccccg gagaagccgg  78780
atacggcgac cgtaaggcgc tgatggtgag ccgcgaacac gcggcgccct cgcgggccag  78840
ggtggcggag cacgcggtga acttaaccgc cgtggcggcc acgtttgggt gggcctcgaa  78900
```

cagctgggcg aggtctgcgc ccgggggctc gggtgagcgg cgagtcttca gcgcctcgag 78960
ggcctgtgag gacgccggaa ccatgggccc gtcgtcctcg cccgcctcgg cgaccggcgg 79020
cccggccggg tcggggggtg ccgaggcgag gacaggctcc ggaacggagg cggggaccgc 79080
ggccccgacg gggtttgcc tttgggggtg ggtttcttct tggttttggc aggggggcc 79140
gagcgtttcg ttttctcccc cgaagtcagg tcttcgacgc tggaaggcgg agtccaggtg 79200
ggtcggcggc gcttgggaag gccggccgag tagcgtgccc ggtgccgacc aaccgggacg 79260
acgcccatct ccaggacccg catgtcgtcg tcatcttctt cggccgcctc tgcggcgggg 79320
gtcttggggg cggagggagg cggtggtggg atcgcggagg gtgggtcggc ggaggggga 79380
tccgtgggtg gggtaccctt tagggccacc gcccatacat cgtcgggcgc ccgattcggg 79440
cgcttggcct ctggttttgc cgacggaccg gccgtccccc gggatgtctc ggaggccctg 79500
tcgtcgcgac gggcccgggt cggtggcggc gactgggcgg ctgtgggcgg gtgtggcccc 79560
ggccccctc cccctcccg ggggcccacg ccgacgcagg gctcccccag gcccgcgatc 79620
tcgccccgca gggggtgcgt gatggccacg cgccgttcgc tgaacgcttc gtcctgcatg 79680
taagtctcgc tggccccgta aagatgcaga gccgcggccg tcaagtccgc aggagccgcg 79740
ggttccgggc ccgacggcac gaaaaacacc atggctcccg cccaccgtac gtccgggcga 79800
tcgcgggtgt aatacgtcag gtatggatac atgtccccg cccgcacttt ggcgatgaac 79860
gcgggggtgc cctccggaag gccatgcggg tcaaaaaggt atgcggtgtc gccgtccctg 79920
aacagcccca tccctagggg gccaatggtt aggagcgtgt acgacagggg gcgcagggcc 79980
cacgggccgg cgaagaacgt gtgtgcgggg cattgtgtct ccagcaggcc tgccgcgggc 80040
tccccgaaga agcccacctc gccgtatacg cgcgagaaga cacagcgcag tccgccgcgc 80100
gcccctgggt actcgaggaa gttggggagc tcgacgatcg aacacatgcg cggcggccca 80160
gggcccgcag tcgcgcgcgt ccactcgccc ccctcgacca aacatccctc gatggcctcc 80220
gcggacagaa cgtcgcgagg gcccacatca aatatgaggc tgagaaagga cagcgacgag 80280
cgcatgcacg ataccgaccc ccccggctcc aggtcgggcg cgaactggtt ccgagcaccg 80340
gtgaccacga tgtcgcgatc cccccgcgt tccatcgtgg agtgcggtgg ggtgcccgcg 80400
atcatatgtg ccctgcgggc cagagacccg gcctgtttat ggaccggacc cccggggtta 80460
gtgttgtttc cgccacccac gcccccgtac catggccccg gttcccctga ttaggctacg 80520
agtcgcggtg atcgcttccc aaaaaccgag ctgcgtttgt ctgtcttggt cttcccccc 80580
cccagcccgc acaccataac accgagaaca acacacgggg gtgggcggaa cataataaag 80640
ctttattggt aactagttaa cggcaagtcc gtgggtggcg cgacggtgtc ctccgggatc 80700
atctcgtcgt cctcgacggg ggtgttggaa tgaggcgcct cctcgcggtc cacctggcgt 80760
gggccgtgcc cataggcctc cggcttctgt gcgtccatgg gcgtaggcgc ggggagactg 80820
tttccggcgt cgcggacctc caggtccctg ggagcctccg gtccggctaa cggacgaaac 80880
gcggaagcgc gaaacacgcc gtcggtgacc cgcaggagct cgttcatcag taaccaatcc 80940
atactcagcg taacggccag cccctggcga gacagatcca cggagtccgg aaccgcggtc 81000
gtctggccca gggggccgag gctgtagtcc ccccaggccc ctaggtcgcg acggctcgta 81060
agcacgacgc ggtcggccgc ggggctttgc gggggggcgt cctcgggcgc atgcgccatt 81120
acctctcgga tggccgcggc gcgctggtcg gccgagctga ccaagggcgc cacgaccacg 81180
gcgcgctccg tctgcaggcc cttccacgtg tcgtggagtt cctggacaaa ctcggccacg 81240
ggctcgggtc ccgcggccgc gcgcgcggct tgatagcagg ccgacagacg ccgccagcgc 81300
gctagaaact gacccatgaa acaaaacccg gggacctggt ctcccgacag cagcttcgac 81360
gcccgggcgt gaatgccgga cacgacggac agaaacccgt gaatttcgcg ccggaccacg 81420
gccagcacgt tgtcctcgtg cgacacctgg gctgccagct cgtcgcacac ccccaggtgc 81480
gccgtggttt cggtgatgac ggaacgcagg ctcgcgaggg acgcgaccag cgcgcgcttg 81540
gcgtcgtgat acatgctgca gtactgactc accgcgtccc ccatggcctc gggggggccag 81600
ggccccaggc ggtcgggcgt gtccccgacc accgcataca ggcggcgccc gtcgctctcg 81660
aaccgacact cgaaaaaggc ggagagcgtg cgcatgtgca gccgcagcag cacgatggcg 81720
tcctccagtt ggcgaatcag ggggtcggcg cgctcggcga ggtcctgcag cacccccccgg 81780
gcagccaggg cgtacatgct aatcaacagg aggctggtgc ccacctcggg gggcgggggg 81840
ggctgcagtt ggaccagggg ccgcagctgc tcgacggcac ccctggagat cacgtacagc 81900
tcccggagca gctgctctat gttgtcggcc atctgcatag tggggccgag gccgccccgg 81960
gcggccggtt cgaggagagt gatcagcgcg cccagtttgg tgcgatggcc ctcgaccgtg 82020
gggagatagc ccagcccaaa gtcccgggcc caggccaaca cacgcagggc gaactcgacc 82080
gggcggggaa ggtaggccgc gctacacgtg gccctcagcg cgtccccaac caccagggcc 82140
agaacgtagg ggacgaagcc cgggtcggcg aggacgttgg ggtgaatgcc ctcgagggcg 82200
gggaagcgga tctgggtcgc cgcggccagg tggacagagg gggcatggct gggctgcccg 82260
acggggagaa gcgcggacag cggcgtggcc ggggtggtgg gggtgatgtc ccagtgggtc 82320
tgaccataca cgtcgatcca gatgagcgcc gtctcgcgga gaaggctggg ttgaccggaa 82380
ctaaagcggc gctcggccgt ctcaaactcc cccacgagcg cccgccgcag gctcgccaga 82440
tgttccgtcg gcacggccgg ccccatgata cgcgccagcg tctggctcag aacgcccccc 82500
gacaggccga ccgcctcaca gagccgcccg tgcgtgtgct cgctggcgcc ctggacccgc 82560
ctgaaagttt ttacgtagtt ggcatagtac ccgtattccc gcgccagacc aaacacgttc 82620
gaccccgcga gggcaatgca cccaaagagc tgctggactt cgccgagtcc gtggccggcg 82680
ggcgtccgcg cggggacgcc cgccgccaga aacccctcca gggccgaaag gtagtgcgtg 82740
cagtgcgagg gcgtgaaccc agcgtcgatc agggtgttga tcaccacgga gggcgaattg 82800
gtattctgga tcaacgtcca cgtctgctgc agcagagcca gcagccgctg ctgggcgccg 82860
gcggagggct gctccccgag ctgcagcagg ctggagacgg caggctggaa gactgccagt 82920
gccgacgaac tcaggaacgg cacgtcggga tcaaacacgg ccacgtccgt ccgcacgcgc 82980
gccattagcg tccccggggg cgcacaggcc gagcgcgggc tgacgcggct gagggccgtc 83040
gacacgcgca cctcctcgcg gctgcgaacc atcttgttgg cctccagtgg cggaatcatt 83100
atggccgggt cgatctcccg cacggtgtgc tgaaactgcg ccaacagggg cggcgggacc 83160
acagcccccc gctcgggggt cgtcaggtac tcgtccacca gggccaacgt aaagagggcc 83220
cgtgtgaggg gagtgagggt cgcgtcgtct atgcgctgga ggtgcgccga gaacagcgtc 83280
acccgattac tcaccagggc caagaaccgg aggccctctt gcacgaacgg ggcggggaag 83340
agcaggctgt acaccggggt ggtaaggttc gcgctgggct gccccaacgg gaccggcgcc 83400
agcttgagcg acgtctcccc aagggcctcg atggaggtcc gcgggctcat ggccaagcag 83460
ctcttggtga cggtttgcca gcggtctatc cactccacgg cgcactggcg gacgcggacc 83520
ggccccaggg ccgccgcggt gcgcaggccg gcggactcca gcgcatggga cgtgtcggag 83580
ccggtgaccg cgaggatggt gtccttgatg acctccatct cccggaaggc ctggtcgggg 83640
gcctcgggga gagccaccac caagcggtgt acgagcaacc cggggaggtt ctcggccaag 83700
agcgccgtct ccggaagccc gtgggcccgg tggagcgcgc acaggtgttc cagcagcggc 83760
cgccagcatg cccgcgcgtc tgccggggcg atggccgttc ccgacaacag aaacgccgcc 83820
atggcggcgc gcagcttggc cgtggccaga aacgccgggt cgtccgcccc gtttgccgtc 83880
tcggccgtgg gggttggcgg ttggcgaagg ccggctaggc tcgccaatag gcgctgcata 83940
ggtccgtccg agggcggacc ggcgggtgag gtcgtgacga cgggggcctc ggacgggaga 84000
ccgcggtctg ccatgacgcc cggctcgcgt gggtggggga cagcgtagac caacgacgag 84060
accgggcggg aatgactgtc gtgcgctgta gggagcggcg aattatcgat cccccgcggc 84120
cctccaggaa ccccgcaggc gttgcgagta ccccgcgtct tcgcggggtg ttatacggcc 84180
acttaagtcc cggcatcccg ttcgcggacc caggcccggg ggattgtccg gatgtgcggg 84240
cagcccggac ggcgtgggtt gcggactttc ggcggggcgg cccaaatggc cctttaaacg 84300
tgtgtatacg gacgcgccgg gccagtcggc caacacaacc caccggaggc ggtagccgcg 84360
tttggctgtg gggtgggtgg ttccgccttg cgtgagtgtc ctttcgaccc ccccctcccc 84420
cgggtcttgc taggtcgcga tctgtggtcg caatgaagac caatccgcta cccgcaaccc 84480
cttccgtgtg gggcgggagt accgtggaac tcccccccac cacacgcgat accgcggggc 84540
agggcctgct tcggcgcgtc ctgcgccccc cgatctctcg ccgcgacggc ccagtgctcc 84600
ccagggggtc gggaccccgg agggcggcca gcacgctgtg gttgcttggc ctggacggca 84660
cagacgcgcc ccctggggcg ctgaccccca acgacgatac cgaacaggcc ctggacaaga 84720
tcctgcgggg caccatgcgc ggggggcgg ccctgatcgg ctccccgcgc catcatctaa 84780
cccgccaagt gatcctgacg gatctgtgcc aacccaacgc ggatcgtgcc gggacgctgc 84840
ttctggcgct gcggcacccc gccgacctgc ctcacctggc ccaccagcgc gccccgccag 84900
gccggcagac cgagcggctg ggcgaggcct ggggccagct gatggaggcg accgccctgg 84960
ggtcggggcg agccgagagc gggtgcacgc gcgcgggcct cgtgtcgttt aacttcctgg 85020
tggcggcgtg tgccgcctcg tacgacgcgc gcgacgccgc cgatgcggta cgggcccacg 85080
tcacggccaa ctaccgcggg acgcgggtgg gggcgcgcct ggatcgtttt tccgagtgtc 85140
tgcgcgccat ggttcacacg cacgtcttcc cccacgaggt catgcggttt ttcgggggc 85200 tggtgtcgtg ggtcacccag gacgagctag cgagcgtcac cgccgtgtgc gccgggcccc 85260
aggaggcggc gcacaccggc cacccgggcc ggccccgctc ggccgtgatc ctcccggtgt 85320
gtgcgttcgt ggacctggac gccgagctgg ggctgggggg cccgggcgcg gcgtttctgt 85380
acctggtatt cacttaccgc cagcgccggg accaggagct gtgttgtgtg tacgtgatca 85440
agagccagct ccccccgcgc gggttggagc cggccctgga gcggctgttt gggcgcctcc 85500
ggatcaccaa cacgattcac ggcaccgagg acatgacgcc cccggcccca aaccgaaacc 85560
ccgacttccc cctcgcgggc ctggccgcca atccccaaac cccgcgttgc tctgctggcc 85620
aggtcacgaa cccccagttc gccgacaggc tgtaccgctg gcagccggac ctgcgggggc 85680
gccccaccgc acgcacctgt acgtacgccg cctttgcaga gctcggcatg atgcccgagg 85740
atagtccccg ctgcctgcac cgcaccgagc gctttggggc ggtcagcgtc cccgttgtca 85800
tcctggaagg cgtggtgtgg cgccccggcg agtggcgggc ctgcgcgtga gcgtagcaaa 85860
cgccccgccc acacaacgct ccgcccccaa ccccttcccc gctgtcactc gttgttcgtt 85920
gacccggacg tccgccaaat aaagccactg aaacccgaaa cgcgagtgtt gtaacgtcct 85980
ttgggcggga ggaagccaca aaatgcaaat gggatacatg gaaggaacac acccccgtga 86040
ctcaggacat cggcgtgtcc ttttgggttt cactgaaact ggcccgcgcc ccacccctgc 86100
gcgatgtgga taaaaagcca gcgcgggtgg tttagggtac cacaggtggg tgctttggaa 86160
acttgtcggt cgccgtgctc ctgtgagctt gcgtccctcc ccggtttcct ttgcgctccc 86220
gccttccgga cctgctctcg cctatcttct ttggctctcg gtgcgattcg tcaggcagtg 86280
gccttgtcga atctcgaccc caccactcgc cggacccgcc gacgtcccct ctcgagcccg 86340
ccgaaacccg ccgcgtctgt tgaaatggcc agccgccccg ccgcatcctc tcccgtcgaa 86400
gcgcgggccc cggttggggg acaggaggcc ggcggcccca gcgcagccac ccagggggag 86460
gccgccgggg cccctctcgc ccgcggccac cacgtgtact gccagcgagt caatggcgtg 86520
atggtgcttt ccgacaagac gcccgggtcc gcgtcctacc gcatcagcga tagcaacttt 86580
gtccaatgtg gttccaactg caccatgatc atagacggag acgtggtgcg cgggcgcccc 86640
caggacccgg gggccgcggc atccccccgct cccttcgttg cggtgacaaa catcggagcc 86700
ggcagcgacg gcgggaccgc cgtcgtggca ttcgggggaa ccccacgtcg ctcggcgggg 86760
acgtctaccg gtacccagac gaccgacgtc cccaccgagg cccttggggg ccccccctcct 86820
cctccccgct tcaccctggg tggcggctgt tgttcctgtc gcgacacacg gcgccgctct 86880
gcggtattcg ggggggaggg ggatcccgtc ggccccgcgg agttcgtctc ggacgaccgg 86940
tcgtccgatt ccgactcgga tgactcggag gacaccgact cggagacgct gtcacacgcc 87000
tcctcggacg tgtccggcgg ggccacgtac gacgacgccc ttgactccga ttcgtcatcg 87060
gatgactccc tgcagataga tggccccgtg tgtcgcccgt ggagcaatga caccgcgccc 87120
ctggatgttt gccccgggac cccccggcccg ggcgccgacg ccggtggtcc ctcagcggta 87180
gacccacacg caccgacgcc aggggccggc gctggtcttg cggccgatcc cgccgtggcc 87240
cgggacgacg cggaggggct ttcggacccc cggccacgtc tgggaacggg cacggcctac 87300
cccgtccccc tggaactcac gcccgagaac gcggaggccg tggcgcgctt tctgggagat 87360
gccgtgaacc gcgaacccgc gctcatgctg gagtactttt gccggtgcgc ccgcgaggaa 87420
accaagcgtg tcccccccag gacattctgc agccccccctc gcctcacgga ggacgacttt 87480
gggcttctca actacgcgct cgtggagatg cagcgcctgt gtctggacgt tcctccggtc 87540
ccgccgaacg catacatgcc ctattatctc agggagtatg tgacgcggct ggtcaacggg 87600
ttcaagccgc tggtgagccg gtccgctcgc ctttaccgca tcctgggggt tctggtgcac 87660
ctgcggatcc ggacccggga ggcctccttt gaggagtggc tgcgatccaa ggaagtggcc 87720
ctggactttg gcctgacgga aaggcttcgc gagcacgaag cccagctggt gatcctggcc 87780
caggctctgg accattacga ctgtctgatc cacagcacac cgcacacgct ggtcgagcgg 87840
gggctgcaat cggccctgaa gtatgaggag ttttacctaa agcgctttgg cgggcactac 87900
atggagtccg tcttccagat gtacacccgc atcgccggct tttggcctg ccgggccacg 87960
cgcggcatgc gccacatcgc cctggggcga gaggggtcgt ggtgggaaat gttcaagttc 88020
ttttccaccg cctctacgac caccagatcg taccgtcgac ccccgccatg ctgaacctgg 88080
ggacccgcaa ctactacacc tccagctgct acctggtaaa cccccaggcc accacaaaca 88140
aggcgaccct gcgggccatc accagcaacg tcagcgccat cctcgcccgc aacgggggca 88200
tcgggctatg cgtgcaggcg tttaacgact ccggccccgg gaccgctagc gtcatacccg 88260
ccctcaaggt cctcgactcg ctggtggcgg cgcacaacaa agagagcgcg cgtccaaccg 88320
gcgcgtgcgt gtacctggag ccgtggcaca ccgacgtgcg ggccgtgctc cggatgaagg 88380

```
gggtcctcgc cggcgaagag gcccagcgct gcgacaatat cttcagcgcc ctctggatgc  88440
cagacctgtt tttcaagcgc ctgattcgcc acctggacgg cgagaagaac gtcacatgga  88500
ccctgttcga ccgggacacc agcatgtcgc tcgccgactt tcacggggag gagttcgaga  88560
agctctacca gcacctcgag gtcatggggt tcggcgagca gatacccatc caggagctgg  88620
cctatggcat tgtgcgcagt gcggccacga ccgggagccc cttcgtcatg ttcaaagacg  88680
cggtgaaccg ccactacatc tacgacaccc agggggcggc catcgccggc tccaacctct  88740
gcaccgagat cgtccatccg gcctccaagc gatccagtgg ggtctgcaat ctgggaagcg  88800
tgaatctggc ccgatgcgtc tccaggcaga cgtttgactt tgggcggctc cgcgacgccg  88860
tgcaggcgtg cgtgctgatg gtgaacatca tgatcgacag cacgctacaa cccacgcccc  88920
agtgcacccg cggcaacgac aacctgcggt ccatgggaat cggcatgcag ggcctgcaca  88980
cggcctgcct gaagctgggg ctggatctgg agtctgtcga atttcaggac ctgaacaaac  89040
acatcgccga ggtgatgctg ctgtcggcga tgaagaccag caacgcgctg tgcgttcgcg  89100
gggccagtcc cttcaaccac tttaagcgca gcatgtatcg cgccggccgc tttcactggg  89160
agcgctttcc ggacgcccgg ccgcggtacg agggcgagtg ggagatgcta cgccagagca  89220
tgatgaaaca cggcctgcgc aacagccagt ttgtcgcgct gatgcccacc gccgcctcgg  89280
cgcagatctc ggacgtcagc gagggctttg cccccctgtt caccaacctg ttcagcaagg  89340
tgacccggga cggcgagacg ctgcgcccca acacgctcct gctaaaggaa ctggaacgca  89400
cgtttagcgg gaagcgcctc ctggaggtga tggacagtct cgacgccaag cagtggtccg  89460
tggcgcaggc gctcccgtgc ctggagccca cccacccccct ccggcgattc aagaccgcgt  89520
ttgactacga ccagaagttg ctgatcgacc tgtgtgcgga ccgcgccccc tacgtcgacc  89580
atagccaatc catgaccctg tatgtcacgg agaaggcgga cgggaccctc ccagcctcca  89640
ccctggtccg ccttctggtc cacgcatata agcgcggact aaaaacaggg atgtactact  89700
gcaaggttcg caaggcgacc aacagcgggg tctttggcgg cgacgacaac attgtctgca  89760
cgagctgcgc gctgtgcccg acaacccccct ccgcgccagg cccgccgcca ctgtcgtcgc  89820
cgtcccacgc gctcccccgc tgccatggat tccgcggccc cagccctctc ccccgctctg  89880
acggcccata cgggccagag cacgccggcg gacctggcga tccagattcc aaagtgcccc  89940
gaccccgaga ggtacttcta cacctcccag tgtcccgaca ttaaccacct gcgctccctc  90000
agcatcctta accgctggct ggaaaccgag cttgttttcg tgggggacga ggaggacgtc  90060
tccaagcttt ccgagggcga gctcagcttt taccgcttcc tcttcgcttt cctgtcggcc  90120
gccgacgacc tggttacgga aaacctgggc ggcctctccg gcctgtttga gcagaaggac  90180
attctccact actacgtgga gcaggaatgc atcgaagtcg tacactcgcg cgtgtacaac  90240
atcatccagc tggtgctttt tcacaacaac gaccaggcgc gccgcgagta cgtggccggc  90300
accatcaacc acccggccat ccgcgccaag gtggactggc tggaagcgcg ggtgcgggaa  90360
tgcgcctccg ttccggaaaa gttcatcctc atgatcctca tcgagggcat ctttttttgcc  90420
gcctcgtttg ccgccatcgc ctaccttcgc accaacaacc ttctgcgggt cacctgccag  90480
tcaaacgacc tcatcagccg ggacgaggcc gtgcacacga cggcctcgtg ttacatctac  90540
aacaactacc tcggcgggca cgccaagccc ccgcccgacc gcgtgtacgg gctgttccgc  90600
caggcggtcg agatcgagat cggatttatc cgatcccagg cgccgacgga cagccatatc  90660
ctgagcccgg cggcgctggc ggccatcgaa aactacgtgc gattcagcgc ggatcgcctg  90720
ttgggcctta tccacatgaa gccactgttt tccgccccac cccccgacgc cagctttccg  90780
```

```
ctgagcctca tgtccaccga caaacacacc aatttttttcg agtgtcgcag cacctcctac  90840
gccggggcgg tcgtcaacga tctgtgaggg tcgcggcgcg cttctacccg tgtttgccca  90900
taataaacct ctgaaccaaa ctttgggtct cattgtgatt cttgtcaggg acgcgggggt  90960
gggagaggat aaaaggcggc gcaaaaagca gtaaccaggt ccgtccagat tctgagggca  91020
taggatacca taattttatt ggtgggtcgt ttgttcgggg acaagcgcgc tcgtctgacg  91080
tttgggctac tcgtcccaga atttggccag gacgtccttg tagaacgcgg gtgggggggc  91140
ctgggtccgc agctgctcca gaaacctgtc ggcgatatca ggggccgtga tatgccgggt  91200
cacaatagat cgcgccaggt tttcgtcgcg gatgtcctgg tagataggca ggcgtttcag  91260
aagagtccac ggcccccgct ccttggggcc gataagcgat atgacgtact taatgtagcg  91320
gtgttccacc agctcggtga tggtcatggg atcggggagc cagtccaggg actctggggc  91380
gtcgtggatg acgtggcgtc gccggctggc cacataactg cggtgctctt ccagcagctg  91440
cgcgttcggg acctggacga gctcgggcgg ggtgagtatc tccgaggagg acgacctggg  91500
gccggggtgg cccccggtaa cgtcccgggg atccaggggg aggtcctcgt cgtcttcgta  91560
tccgccggcg atctgttggg ttagaatttc ggtccacgag acgcgcatct cggtgccgcc  91620
ggcggccggc ggcaaagggg gcctggtttc cgtggagcgc gagctggtgt gttcccggcg  91680
gatggcccgc cgggtctgag agcgactcgg gggggtccag tgacattcgc gcagcacatc  91740
ctccacggag gcgtaggtgt tattgggatg gaggtcggtg tggcagcgga caaagagggc  91800
caggaactgg gggtagctca tcttaaagta ctttagtata tcgcgacagt tgatcgtggg  91860
aatgtagcag gcgctaatat ccaacacaat atcacagccc atcaacagga ggtcagtgtc  91920
tgtggtgtac acgtacgcga ccgtgttggt gtgatagagg ttggcgcagg catcgtccgc  91980
ctccagctga cccgagttaa tgtaggcgta ccccagggcc cggagaacgc gaatacagaa  92040
cagatgcgcc agacgcaggg ccggcttcga gggcgcggcg gacggcagcg cggctccgga  92100
cccggccgtc ccccgggtcc ccgaggccag agaggtgccg cgccggcgca tgttggaaaa  92160
ggcagagctg ggtctggagt cggtgatggg ggaaggcggt ggagaggcgt ccacgtcact  92220
ggcctcctcg tccgtccggc attgggccgt cgtgcgggcc aggatggcct tggctccaaa  92280
cacaaccggc tccatacaat tgaccccgcg atcggtaacg aagatgggga aaagggactt  92340
ttgggtaaac acctttaata agcgacagag gcagtgtagc gtaatggcct cgcggtcgta  92400
actggggtat cggcgctgat atttgaccac caacgtgtac atgacgttcc acaggtccac  92460
ggcgatgggg gtgaagtacc cggccggggc cccaaggccc tggcgcttga ccagatggtg  92520
tgtgtgggca aacttcatca tcccgaacaa acccatgtca ggtcgattgt aactgcggat  92580
cggcctaact aaggcgtggt tggtgcgacg gtccgggaca cccgagtctg tctctctgtg  92640
tatggtgacc cagacaacaa caccgacaca agaggacaat aatccgttag gggacgctct  92700
ttataatttc gatggcccaa ctccacgcgg attggtgcag caccctgcat gcgccggtgt  92760
gggccaaact tccccccgct cattgcctct tccaaaaggg tgtggcctaa cgagctgggg  92820
gcgtatttaa tcaggctagc gcggcgggcc tgccgtagtt tctggctcgg tgagcgacgg  92880
tccggttgct tgggtcccct ggctgccagc aaaaccccac cctcgcagcg gcatacgccc  92940
cctccgcgtc ccgcacccga gaccccggcc cggctgccct caccaccgaa gcccacctcg  93000
tcactgtggg gtgttcccag cccgcattgg gatgacggat tcccctggcg gtgtggcccc  93060
cgcctccccc gtggaggacg cgtcggacgc gtccctcggg cagccggagg agggggcgcc  93120
```

ctgccaggtg gtcctgcagg gcgccgaact taatggaatc ctacaggcgt ttgccccgct 93180
gcgcacgagc cttctggact cgcttctggt tatgggcgac cggggcatcc ttatccataa 93240
cacgatcttt ggggagcagg tgttcctgcc cctggaacac tcgcaattca gtcggtatcg 93300
ctggcgcgga cccacggcgg cgttcctgtc tctcgtggac cagaagcgct ccctcctgag 93360
cgtgtttcgc gccaaccagt acccggacct acgtcgggtg gagttggcga tcacgggcca 93420
ggccccgttt cgcacgctgg ttcagcgcat atggacgacg acgtccgacg gcgaggccgt 93480
tgagctagcc agcgagacgc tgatgaagcg cgaactgacg agctttgtgg tgctggttcc 93540
ccagggaacc cccgacgttc agttgcgcct gacgaggccg cagctcacca aggtccttaa 93600
cgcgaccggg gccgatagtg ccacgcccac cacgttcgag ctcggggtta acggcaaatt 93660
ttccgtgttc accacgagta cctgcgtcac atttgctgcc cgcgaggagg gcgtgtcgtc 93720
cagcaccagc acccaggtcc agatcctgtc caacgcgctc accaaggcgg gccaggcggc 93780
cgccaacgcc aagacggtgt acggggaaaa tacccatcgc accttctctg tggtcgtcga 93840
cgattgcagc atgcgggcgg tgctccggcg actgcaggtc gccgggggca ccctcaagtt 93900
cttcctcacg acccccgtcc ccagtctgtg cgtcaccgcc accggtccca acgcggtatc 93960
ggcggtattt ctcctgaaac cccagaagat ttgcctggac tggctgggtc atagccaggg 94020
gtctccttca gccgggagct cggcctcccg ggcctctggg agcgagccaa cagacagcca 94080
ggactccgcg tcggacgcgg tcagccacgg cgatccggaa gacctcgatg gcgctgcccg 94140
ggcgggagag gcgggggcct cgcacgcctg tccgatgccg tcgtcgacca cgcgggtcac 94200
tcccacgacc aagcgggggc gctcgggggg cgaggatgcg cgcgcggaca cggccctaaa 94260
gaaacctaag acggggtcgc ccaccgcacc cccgcccaca gatccagtcc ccctggacac 94320
ggaggacgac tccgatgcgg cggacgggac ggcggcccgt cccgccgctc cagacgcccg 94380
gagcggaagc cgttacgcgt gttactttcg cgacctcccg accggagaag caagccccgg 94440
cgccttctcc gccttccggg ggggccccca aaccccgtat ggttttggat tcccctgacg 94500
gggcggggcc ttggcggccg cccaactctc gcaccatccc gggttaatgt aaataaactt 94560
ggtattgccc aacactctcc cgcgtgtcgc gtgtggttca tgtgtgtgcc tggcgtcccc 94620
caccctcggg ttcgtgtatt tcctttccct gtccttataa aagccgtatg tggggcgctg 94680
acggaaccac cccgcgtgcc atcacggcca aggcgcggga tgctccgcaa cgacagccac 94740
cgggccgcgt ccccggagga cggccaggga cgggtcgacg acggacggcc acacctcgcg 94800
tgcgtggggg ccctggcgcg ggggttcatg catatctggc ttcaggccgc cacgctgggt 94860
tttgcgggat cggtcgttat gtcgcgcggg ccgtacgcga atgccgcgtc tggggcgttc 94920
gccgtcgggt gcgccgtgct gggctttatg cgcgcacccc ctcccctcgc gcggcccacc 94980
gcgcggatat acgcctggct caaactggcg gccggtggag cggcccttgt tctgtggagt 95040
ctcggggagc ccggaacgca gccgggggcc ccgggcccgg ccacccagtg cctggcgctg 95100
ggcgccgcct atgcggcgct cctggtgctc gccgatgacg tctatccgct ctttctcctc 95160
gccccggggc ccctgttcgt cggcaccctg gggatggtcg tcggcgggct gacgatcgga 95220
ggcagcgcgc gctactggtg gatcggtggg cccgccgcgg ccgccttggc cgcggcggtg 95280
ttggcgggcc cgggggcgac caccgccagg gactgcttct ccagggcgtg ccccgaccac 95340
cgccgcgtct gcgtcatcgt cgcaggcgag tctgtttccc gccgcccccc ggaggaccca 95400
gagcgacccg gggaccccgg gccaccgtcc cccccgacac cccaacgatc ccaggggccg 95460
ccggccgatg aggtcgcacc ggccggggta gcgcggcccg aaaacgtctg ggtgcccgtg 95520
gtcacctttc tgggggcggg cgcgctcgcc gtcaagacgg tgcgagaaca tgcccgggaa 95580
acgccgggcc cgggcctgcc gctgtggccc caggtgtttc tcggaggcca tgtggcggtg 95640
gccctgacgg agctgtgtca ggcgcttatg ccctgggacc ttacggaccc gctgctgttt 95700
gttcacgccg gactgcaggt catcaacctc gggttggtgt ttcggttttc cgaggttgtc 95760
gtgtatgcgg cgctaggggg tgccgtgtgg atttcgttgg cgcaggtgct ggggctccgg 95820
cgtcgcctgc acaggaagga ccccggggac ggggcccggt tggcggcgac gcttcggggc 95880
ctcttcttct ccgtgtacgc gctggggttt ggggtggggg cgctgctgtg ccctccgggg 95940
tcaacgggcg ggtggtcggg cgattgatat atttttcaat aaaaggcatt agtcccgaag 96000
accgccggtg tgtgatgatt tcgccataac acccaaaccc cggatggggc ccgggtataa 96060
attccggaag gggacacggg ctaccctcac taccgagggc gcttggtcgg gaggccgcat 96120
cgaacgcaca cccccatccg gtggtccgtg tggaggtcgt ttttcagtgc ccggtctcgc 96180
tttgccggga acgctagccg atccctcgcg agggggaggc gtcgggcatg gccccggggc 96240
gggtgggcct tgccgtggtc ctgtggagcc tgttgtggct cggggcgggg gtggccgggg 96300
gctcggaaac tgcctccacc gggcccacga tcaccgcggg agcggtgacg aacgcgagcg 96360
aggcccccac atcggggtcc cccgggtcag ccgccagccc ggaagtcacc cccacatcga 96420
ccccaacccc caacaatgtc acacaaaaca aaaccacccc caccgagccg gccagccccc 96480
caacaacccc caagcccacc tccacgccca aaagcccccc cacgtccccc cgccccaacc 96540
caagaacaac acccccccg ccaagtcggg ccgccccact aaaccccccg ggcccgtgtg 96600
gtgcgaccgc cgcgacccat tggcccggta cggctcgcgg gtgcagatcc gatgccggtt 96660
tcggaattcc acccgcatgg agttccgcct ccagatatgg cgttactcca tgggtccgtc 96720
ccccccaatc gctccggctc ccgacctaga ggaggtcctg acgaacatca ccgcccccacc 96780
cgggggactc ctggtgtacg acagcgcccc caacctgacg gacccccacg tgctctgggc 96840
ggaggggggcc ggcccgggcg ccgaccctcc gttgtattct gtcaccgggc cgctgccgac 96900
ccagcggctg attatcggcg aggtgacgcc cgcgacccag ggaatgtatt acttggcctg 96960
gggccggatg gacagcccgc acgagtacgg gacgtgggtg cgcgtccgca tgttccgccc 97020
cccgtctctg accctccagc cccacgcggt gatggagggt cagccgttca aggcgacgtg 97080
cacggccgcc gcctactacc cgcgtaaccc cgtggagttt gtctggttcg aggacgaccg 97140
ccaggtgttt aacccgggcc agatcgacac gcagacgcac gagcaccccg acgggttcac 97200
cacagtctct accgtgacct ccgaggctgt cggcggccag gtccccccgc ggaccttcac 97260
ctgccagatg acgtggcacc gcgactccgt gatgttctcg cgacgcaatg ccaccgggct 97320
ggccctggtg ctgccgcggc caaccatcac catggaattt ggggtccggc atgtggtctg 97380
cacggccggc tgcgtccccg agggcgtgac gtttgcctgg ttcctggggg acgacccctc 97440
accggcggct aagtcggccg ttacggccca ggagtcgtgc gaccaccccg ggctggctac 97500
ggtccggtcc accctgccca tttcgtacga ctacagcgag tacatctgtc ggttgaccgg 97560
atatccggcc gggattcccg ttctagagca ccacggcagt caccagcccc cacccaggga 97620
ccccaccgag cggcaggtga tcgaggcgat cgagtgggtg gggattggaa tcggggttct 97680
cgcggcgggg gtcctggtcg taacggcaat cgtgtacgtc gtccgcacat cacagtcgcg 97740
gcagcgtcat cggcggtaac gcgagacccc cccgttacct ttttaatatc tatatagttt 97800
ggtccccctc tatcccgccc accgctgggc gctataaagc cgccaccctc tcttccctca 97860
ggtcatcctt ggtcgatccc gaacgacaca cggcgtggag caaaacgcct ccccctgagc 97920
cgctttccta ccaacacaac ggcatgcctc tgcgggcatc ggaacacgcc taccggcccc 97980
tgggccccgg gacaccccc atgcgggctc ggctccccgc cgcggcctgg gttggcgtcg 98040
ggaccatcat cgggggagtt gtgatcattg ccgcgttggt cctcgtgccc tcgcgggcct 98100
cgtgggcact ttccccatgc gacagcggat ggcacgagtt caacctcggg tgcatatcct 98160
gggatccgac ccccatggag cacgagcagg cggtcggcgg ctgtagcgcc ccggcgaccc 98220
tgatcccccg cgcggctgcc aaacagctgg ccgccgtcgc acgcgtccag tcggcaagat 98280
cctcgggcta ctggtgggtg agcggagacg gcattcgggc ctgcctgcgg ctcgtcgacg 98340
gcgtcggcgg tattgaccag ttttgcgagg agcccgccct cgcatatgct actatccccg 98400
cagtcccggg ggctttgttc agtttgtaac ttcgacccgc aacgcgctgg ggctgccgtg 98460
aggcgcgtgt actgcggtct gtctcgtctc ctcttctccc cttccctccc cctccgcatc 98520
ccaggatcac accggccaac gagggttggg ggggtccggc acggacccaa aataataaac 98580
acacaatcac gtgcgataaa aagaacacgc ggtcccctgt ggtgtttttg gttattttta 98640
ttaaatctcg tcgacaaaca gggggaaagg ggcgtggtct agcgacggca gcacgggcgg 98700
aggcgttcac cggctccggc gtccttcgcg tttaagcttg gtcaggaggg cgctcagggc 98760
ggcgacgttg gtcgggccgt cgttggtcag ggcgttggct cgatggcggg cgaggacggg 98820
cgaggggctc aacggcgggg gcgggggccg gggcggcccg gggggggaaa tagggcggat 98880 cccccccgt cgtacagggg gttttccgcc tcaatgtacg gggaggccgg cgctgcattc 98940
gccgtgttca cgcagacggt ttcgtagacc cgcatccatg gtatttcctc gtagacacgc 99000
cccccgtcct cgctcacggt ctcgtatatt gactcgtcgt cctcgtaggg ggcgtgccgt 99060
tcgcgggccg aggcggcgtg ggtggctttg cggcgggcgt cgtcgtcgtc gtcgtcggcc 99120
gtcagatacg tggcttccat ctggtcgggt tctccctccg gggcgggtcc ccacacccgt 99180
ggccgatcga ggctccccag agacgcgcgc cggacaagaa gggggcacgt cgccgccggc 99240
ggtcgcctgt cgggtcccgc gacgttacgg gccgggaggc gcgggggcac ctcccccatg 99300
tgcgtgtaat acgtggccgg ctgtgcggcc gcagcggggg gctcggcgac cgggtcgtcc 99360
gcatccggaa gcgggggccc cgcgccgtcc gcacggcgcc tccggaaccg ccgggtggac 99420
ggcgcggggg tcgagtgtag gcgaggtcgg gggaggggcg ggggctcgtt gtcgcgccgc 99480
gcccgctgaa tcttttcccg acaggtccca ccccccgcgc gatgcccccc cgggccgcgg 99540
gccatgtcgt ccgggggagg ccccgcggac cacgtcgtcc ggcgagacgc cacgagccgc 99600
aggatggact cgtagtggag cgacggcgcc ccgctgcgga gcagatccgc ggccagggcg 99660
gccccgaacc aagccttgat gctcaactcc atccgggccc agctgggggc ggtcatcgtg 99720
gggaacaggg gggcggtggt ccgacagaaa cgctcctggc tgtccaccgc ggcccgcaga 99780
tactcgttgt tcaggctgtc ggtggcccag acgccgtacc cggtgagggt cgcgttgatg 99840
atatactggg cgtggtgatg gacgatcgac agaacctcca ccgtggatac cacggtatcc 99900
acggtcccgt acgtaccgcc gctccgcttg ccggtctgcc acaggttggc taggcacgtc 99960
aggtggccca ggacgtcgct gaccgccgcc ctgagcgcca tgcactgcat ggagccggtc 100020
gtgccgctgg gaccccggtc cagatggcgc gcgaacgttt ccgcgggcgc ctccgggctg 100080
ccgccgagcg ggaggaaccg gcgattggag ggactcagcc ggtgacatac gtgcttgtcc 100140
gtcgtccaca gcatccagga cgcccaccgg tacagcacgg agacgtaggc caggagctcg 100200
ttgagccgca gtgcggtgtc ggtgctgggg cggcttgggt ccgccgggcg cataaagaac 100260
atgtactgct gaatccgatg gagggcgtcg cgcaggccgg ccacggtggc ggcgtacttg 100320
gccgccgcgg ccccgctctt gaacggggtg cgcgccagca gctttggcgc cagggtgggc 100380
cgcagcagca cgtgaaggct ggggtcgcag tcgcccacgg ggtcctcggg gacgtccagg 100440
ccgctgggca ccaccgtctg caggtacttc cagtactgcg tgaggatggc gcggctcaac 100500
tggccgccgg gcagctccac ctcgcccagc gcctgggtgg cggccgaagc gtagtgccgg 100560
atgtactcgt agtgcgggtc gctggcgagc ccgtccacga tcaaactctc gggaaccgtg 100620
ttgtgttgcc gcgcggccaa ccggacgctg cgatcggtgc aggtcagaaa cgccggctgc 100680
gcgtcgtcgg agcgctgccg caaggcgccc acggccgcgc taaggagccc ctccggggtg 100740
gggagcagac acccgccgaa gatgcgccgc tcgggaacgc ccgcgttgtc gccgcggatc 100800
aggttggcag gcgtcaggca ccgcgccagc cgcagggagc tcgcgccgcg cgtccggcgc 100860
tgcatggtga cgcccgttcg gtcgggaccc gccggtcgga gttatgccgc gtccagggcc 100920
atcggggcgc tttttatcgg gaggagctta tgggcgtggc gggcctccca gcccggtcgc 100980
gcgcctcccc gacacgtgcg cccgcagggc ggcggccccc tcgtctccca tcagcagttt 101040
cctaaactgg gacatgatgc cacccgcgga cccgcgggcc aacacggacc cgccgcttac 101100
gggggcgggg gggaagggct ccaggtcctt gagcagaaag gcggggtctg ccgtcccgga 101160
cacgggggcc cggggcgcgg aggaggcggg gcgcagatcc acgtgctccg cggccgcgcg 101220
gacgtccgcc cagaacttgg cgggggtggt gcgcgcgtac aggggctggg tcgctcggag 101280
gacacacgcg tagcgcaggg gggtgtacgt gcccacctcg gggccgtga atccccccgtc 101340
aaacgcggcc agtgtcacgc acgccaccac ggtgtcggca aaacccagca gccgctgcag 101400
gacgagcccg gcggccagaa tggcgcgcgt ggtcgcagcg tcgtcccggc gccggtgcgc 101460
gtccccgcac gcccgggcgt actttaaggt cactgtcgcc agggccgtgt gcagcgcgta 101520
caccgcagcg cccagcacgg cgttgagccc gctgttggcg agcagccggc gcgctgcggt 101580
gtcgcccagc gcctcgtgct cggcccccac gaccgcgggg cttcccaggg gcagggcgcg 101640
aaacagctcc tcccgcgcca cgtccgcaaa ggcggggtgg tgcacgtgcg ggtgcaggcg 101700
cgcccccacg accaccgaga gccactggac cgtctgctcc gccatcaccg ccaacacatc 101760
cagcacgcgc cccaggaagg cggcctcccg cgtcaaaacg caccggacgg cgtcgggatt 101820
gaagcgggcg agcagggccc cggtggccag gtacgtcatg cggccggcat agcgggcggc 101880
cacgcgacag tcgcggtcca gcagcgcgcg caccccgggc cagtacagca gggaccccag 101940
cgagctgcga aacaccgcgg cgtcggggcc ggattggggg gacactaacc cccccgcgct 102000
cagtaacggc acggccgcgg ccccgacggg acgcaacgcc gtgaggctcg cgaactgccg 102060
cctcagctcg gcagccctgt cgtccaggtc cgacccgcgc gcctctgcgt gaaggcgcgt 102120
cccgcatacc cacccgttga tggccagccg cacgacggca tccgccaaaa agctcatcgc 102180
ctgggcgggg ctggtttttg ttcgacgatc cgtcaggtca agaatcccat cgcccgtgat 102240
ataccaggcc aacgcctcgc cctgctgcag ggtttggcgg aaaaacaccg cggggttgtc 102300
gggggaggcg aagtgcatga cccccacgcg cgataacccg aacgcgctat ccggacacgg 102360
gtaaaacccg gccggatgcc ccagggctag ggcggagcgc acggactcgt cccacacggc 102420
aacctgaggg gccagtcgat ccaacgggaa tgccgcccgg agctccgggc ccggcacgcg 102480
tccctccaga acctccacct tgggcgggga acgggccccg ccgccgtcct ccggcccgac 102540
gtcttccggg tagtcgtcct cctcgtactg cagttcctct aggaacagcg gcgacggcgc 102600
cacccgcgaa ccgccgaccc gccccaaaat agcccgcgcg tcgacgggac ccaggtatcc 102660
cccctgccgg gcctgcggag gaccgcgggg aacctcatca tcatcgtcca ggcgaccgcg 102720
caccgactgg ctacgggccg catcgggccc ggggcgctgc cgggacgctc ggcgatggga 102780
tgagggcggg gcttccgacg cgcgccgtcg tcgggctcgc gggccttccc gtcgacggcg 102840
cacgggcggc tcgtcgcccg ccatctcctc cagagcctct agctcgctgt cgtcatcccc 102900
gcggaacacc gcacgcaggt accccatgaa ccccacccca tcgcccgctg gctcgtccgc 102960
cacgggcgag gcgcgggggc gggtggatgc gcgcctcctg cgccccgcgg gttcgcgagc 103020
cgacatggtg gcgatagacg cgggttatcg gatgtccgct accccccaaa aaagaaaaag 103080
accccacagc gcggatggag gtcggggtag gtgccgccgg accccctcgc gatgggaatg 103140
gacgggagcg acggggccgg cgcaaaaaac gcagtatctc ccgcgaaggc tacccgccgc 103200
cccagccccc ggccaaatgc ggaaacggtc ccgcgctctc gcctttatac gcgggccgcc 103260
ctgcgacaca atcacccgtc cgtggtttcg aatctacacg acaggcccgc agacgcggct 103320
aacacacacg ccggcaaccc agaccccagt gggttggttg cgcggtcccg tctcctggct 103380
agttctttcc cccaccacca aataatcaga cgacaaccgc aggtttttgt aatgtatgtg 103440
ctcgtgttta ttgtggatac gaaccgggga cgggagggga aaacccagac gggggatgcg 103500
ggtccggtcg cgccccctac ccaccgtact cgtcaattcc aagggcatcg gtaaacatct 103560
gctcaaactc gaagtcggcc atatccagag cgccgtaggg ggcggagtcg tggggggtaa 103620
atcccggacc cggggaatcc ccgtccccca acatgtccag atcgaaatcg tctagcgcgt 103680
cggcatgcgc catcgccacg tcctcgccgt ctaagtggag ctcgtccccc aggctgacat 103740
cggtcggggg ggccgtcgac agtctgcgcg tgtgtcccgc ggggagaaag gacaggcgcg 103800
gagccgccag ccccgcctct tcgggggcgt cgtcgtccgg gagatcgagc aggccctcga 103860
tggtagaccc gtaattgttt ttcgtacgcg cgcggctgta cgcgtgttcc cgcatgaccg 103920
cctcggaggg cgaggtcgtg aagctggaat acgagtccaa cttcgcccga atcaacacca 103980
taaagtaccc agaggcgcgg gcctggttgc catgcagggt gggaggggtc gtcaacggcg 104040
cccctggctc ctccgtagcc gcgctgcgca ccagcgggag gttaaggtgc tcgcgaatgt 104100
ggtttagctc ccgcagccgg cgggcctcga ttggcactcc ccggacggtg agcgctccgt 104160
tgacgaacat gaagggctgg aacagacccg ccaactgacg ccagctctcc aggtcgcaac 104220
agaggcagtc aaacaggtcg ggccgcatca tctgctcggc gtacgcggcc cataggatct 104280
cgcgggtcaa aaatagatac aaatgcaaaa acagaacacg cgccagacga gcggtctctc 104340
ggtagtacct gtccgcgatc gtggcgcgca gcatttctcc caggtcgcga tcgcgtccgc 104400
gcatgtgcgc ctggcggtgc agctgccgga cgctggcgcg caggtaccgg tacagggccg 104460
agcagaagtt ggccaacacg gttcgatagc tctcctcccg cgcccgtagc tcggcgtgga 104520
agaaacgaga gagcgcttcg tagtagagcc cgaggccgtc gcgggtggcc ggaagcgtcg 104580
ggaaggccac gtcgccgtgg gcgcgaatgt cgatttgggc gcgttcgggg acgtacgcgt 104640
ccccccattc caccacatcg ctgggcagcg ttgataggaa tttacactcc cggtacaggt 104700
cggcgttggt cggtaacgcc gaaaacaaat cctcgttcca ggtatcgagc atggtacata 104760
gcgcggggcc cgcgctaaag cccaagtcgt cgaggagacg gttaaagagg gcggcggggg 104820
ggacgggcat gggcggggag ggcatgagct gggcctggct caggcgcccc gttgcgtaca 104880
gcggaggggc cgccggggtg tttttgggac ccccggccgg gcgggggggt ggtggcgaag 104940
cgccgtccgc gtccatgtcg gcaaacagct cgtcgaccaa gaggtccatt gggtggggtt 105000
gatacgggaa agacgatatc gggcttttga tgcgatcgtc cccgcccgcc cagagagtgt 105060
gggacgcccg acggcgcggg aagagaaaaa cccccaaacg cgttagagga ccggacggac 105120
cttatggggg gaagtgggca gcgggaaccc cgtccgttcc cgaggaatga cagcccgtgg 105180
tcgccacccc gcatttaagc aacccgcacg ggccgccccg tacctcgtga cttcccccca 105240
cattggctcc tgtcacgtga aggcaaaccg agggcggctg tccaacccac cccccgccac 105300
ccagtcacgg tccccgtcgg attgggaaac aaaggcacgc aacgccaaca ccgaatgaac 105360
ccctgttggt gctttattgt ctgggtacgg aagtttttca ctcgacgggc cgtctggggc 105420
gagaagcgga gcgggctggg gctcgaggtc gctcggtggg gcgcgacgcc gcagaacgcc 105480
ctcgagtcgc cgtggccgcg tcgacgtcct gcaccacgtc tggattcacc aactcgttgg 105540
cgcgctgaat caggtttttg ccctcgcaga ccgtcacgcg gatggtggtg atgccaagga 105600
gttcgttgag gtcttcgtct gtgcgcggac gcgacatgtc ccagagctgg accgccgcca 105660
tccgggcatg catggccgcc aggcgcccaa ccgcggcgca gaagacgcgc ttgttaaagc 105720
cggccacccg gggggtccat ggcgcgtcgg ggtttggggg ggcggtgcta aagtgcagct 105780
ttctggccag cccctgcgcg ggtgtcttgg atcgggttgg cgccgtcgac gcgggggcgt 105840
ctgggagtgc ggcggattct ggctgggccg atttcctgcc gcgggtggtc tccgccgccg 105900
gggccgcggg ggccttagtc gccacccgct gggttcgggg ggcccggggg gcggtggtgg 105960
gtgtgcgtcc ggcccctccg gacccagcgg gcggcggagg cgcccgcgca ggccccgggg 106020
cggacaaaac cgccccggaa acgggacgcc gcgtccgggg gacctccggg tgttcgtcgt 106080
cttcggatga cgagcccccg tagagggcat aatccgactc gtcgtactgg acgaaacgga 106140
cctcgcccct tgggcgcgcg cgtgtctgta gggcgccacg gcgggaggtg tcaggcggac 106200
tatcgggact cgccatacat gaagacgggg tgtagtacag atcctcgtac tcatcgcgcg 106260
gaacctcccg cggacccgac ttcacggagc ggcgagaggt catggttcca cgaacacgct 106320
agggtcggat gcgcggacaa ttaggcctgg gttcggacgg cgggggtggt gcaggtgtgg 106380
agaggtcgag cgataggggc ggcccgggag agaagagagg gtccgcaaaa cccactgggg 106440
atgcgtgagt ggccctctgt gggcggtggg ggagagtctt ataggaagtg catataacca 106500
caacccatgg gtctaaccaa tccccagggg ccaagaaaca gacacgcccc aaacggtctc 106560
ggtttccgcg aggaagggga agtcctggga caccctccac ccccacccct caccccacac 106620
agggcgggtt caggcgtgcc cggcagccag tagcctctgg cagatctgac agacgtgtgc 106680
gataatacac acgcccatcg aggccatgcc tacataaaag ggcaccaggg cccccggggc 106740
agacatttgg ccagcgtttt gggtctcgca ccgcgcgccc ccgatcccat cgcgcccgcc 106800
ctcctcgccg ggcggctccc cgtgcgggcc cgcgtctccc gccgctaagg cgacgagcaa 106860
gacaaacaac aggcccgccc gacagaccct tctggggggg cccatcgtcc ctaacaggaa 106920
gatgagtcag tggggatccg gggcgatcct tgtccagccg gacagcttgg gtcgggggta 106980
cgatggcgac tggcacacgg ccgtcgctac tcgcgggggc ggagtcgtgc aactgaacct 107040
ggtcaacagg cgcgcggtgg cttttatgcc gaaggtcagc ggggactccg gatgggccgt 107100
cgggcgcgtc tctctggacc tgcgaatggc tatgccggct gacttttgtg cgattattca 107160
cgcccccgcg ctatccagcc cagggcacca cgtaatactg ggtcttatcg actcggggta 107220
ccgcggaacc gttatggccg tggtcgtagc gcctaaaagg acgcgggaat ttgcccccgg 107280
gaccctgcgg gtcgacgtga cgttcctgga catcctggcg accccccccgg ccctcaccga 107340 gccgatttcc ctgcggcagt tcccgcaact ggcgcccccc cctccaaccg gggccgggat 107400
acgcgcagat ccttggttgg agggggcgct cggggaccca agcgtgactc ctgccctacc 107460
ggcgcgacgc cgagggcggt ccctcgtcta tgccggcgag ctgacgccgg ttcagacgga 107520
acacggggac ggcgtacgag aagccatcgc cttccttcca aaacgcgagg aggatgccgg 107580
tttcgacatt gtcgtccgtc gcccggtcac cgtcccggca aacggcacca cggtcgtgca 107640
gccatccctc cgcatgctcc acgcggacgc cgggcccgcg gcctgctatg tgctggggcg 107700
gtcgtcgctc aacgcccgcg gcctcctggt cgttcctacg cgctggctcc ccgggcacgt 107760
atgtgcgttt gttgtttaca accttacggg ggttcctgtg accctcgagg ccggcgccaa 107820
ggtcgcccag ctcctggttg cgggggcgga cgctcttcct tggatccccc cggacaactt 107880
tcacgggacc aaagcgcttc gaaactaccc caggggtgtt ccggactcaa ccgccgaacc 107940
caggaacccg ccgctcctgg tgtttacgaa cgagtttgac gcggaggccc ccccgagcga 108000
gcgcgggacc gggggttttg gctctaccgg tatttagccc atagcttggg gttcgttccg 108060
ggcaataaaa aacgtttgta tctcatcttt cctgtgtgta gttgtttctg ttggatgcct 108120
gtgggtctat cacacccgcc cctccatccc acaaacacag aacacacggg ttggatgaaa 108180
acacgcattt attgacccaa aacacacgga gctgctcgag atgggccagg gcgaggtgcg 108240
gttggggagg ctgtaggtct gggaacggac acgcggggac acgattccgg tttggggtcc 108300
gggagggcgt cgccgtttcg ggcggcaggc gccagcgtaa cctccggggg cggcgtgtgg 108360
gggtgcccca aggagggcgc ctcggtcacc ccaagccccc ccgagcgggt tcccccggca 108420
accccgaagg cggagaggcc aagggcccgt tcggcgatgg ccacatcctc catgaccacg 108480
tcgctctcgg ccatgctccg aatagcctgg gagacgagca catccgcgga cttgtcagcc 108540
gcccccacgg acatgtacat ctgcaggatg gtggccatac acgtgtccgc caggcgccgc 108600
atcttgtcct gatgggccgc cacggccccg tcgatcgtgg gggcctcgag cccggggtgg 108660
tggcgcgcca gtcgttctag gttcaccatg caggcgtggt acgtgcgggc caaggcgcgg 108720
gccttcacga ggcgtcgggt gtcgtccagg gaccccaggg cgtcatcgag cgtgatgggg 108780
gcgggaagta gcgcgttaac gaccaccagg gcctcctgca gccgcggctc cgcctccgag 108840
ggcggaacgg ccgcgcggat catctcatat tgttcctcgg ggcgcgctcc ccagccacat 108900
atagccccga gaagagaagc catcgcgggc gggtactggc ccttgggcgc gcggacgcaa 108960
tggggcagga agacgggaac cgcgggggaga ggcgggcggc cgggactccc gtggaggtga 109020
ccgcgcttta tgcgaccgac gggggcgtta ttacctcttc gatcgccctc ctcacaaact 109080
ctctactggg ggccgagccg gtttatatat tcagctacga cgcatacacg cacgatggcc 109140
gtgccgacgg gcccacggag caagacaggt tcgaagagag tcgggcgctc taccaagcgt 109200
cgggcgggct aaatggcgac tccttccgag taaccttttg tttattgggg acggaagtgg 109260
gtgggaccca ccaggcccgc gggcgaaccc gacccatgtt cgtctgtcgc ttcgagcgag 109320
cggacgacgt cgccgcgcta caggacgccc tggcgcacgg gaccccgcta caaccggacc 109380
acatcgccgc caccctggac gcggaggcca cgttcgcgct gcatgcgaac atgatcctgg 109440
ctctcaccgt ggccgtcaac aacgccagcc cccgcaccgg acgcgacgcc gccgcggcgc 109500
agtatgatca gggcgcgtcc ctacgctcgc tcgtggggcg cacgtccctg ggacaacgcg 109560
gccttaccac gctatacgtc caccacgagg cgcgcgtgct ggccgcgtac cgcagggcgt 109620
attatggaag cgcgcagagt cccttctggt ttcttagcaa attcgggcct gacgaaaaaa 109680
gcctggtgct caccactcgg tactacctgc ttcaggccca gcgtctgggg ggcgcggggg 109740
ccacgtacga cctgcaggcc atcaaggaca tctgcgccac ctacgcgatt ccccacgccc 109800
cccgccccga caccgtcagc gccgcgtccc tgacctcgtt tgccgccatc acgcggttct 109860
gttgcacgag ccagtacgcc cgcggggccg cggcggccgg gtttccgctt tacgtggagc 109920
gccgtattgc ggccgacgtc cgcgagacca gtgcgctgga gaagttcata acccacgatc 109980
gcagttgcct gcgcgtgtcc gaccgtgaat tcattacgta catttacctg gcccattttg 110040
agtgtttcag ccccccgcgc ctagccacgc atcttcgggc cgtgacgacc caggacccca 110100
accccgcggc caacacggag cagccctcgc ccctgggcag ggaggccgtg gaacaatttt 110160
tttgccacgt gcgcgcccaa ctgaatatcg gggagtacgt caaacacaac gtgacccccc 110220
gggagaccgt cctggatggc gatacggcca aggcctacct gcgcgctcgc acgtacgcgc 110280
ccggggccct gacgcccgcc cccgcgtatt gcggggccgt ggactccgcc accaaaatga 110340
tggggcgttt ggcggacgcc gaaaagctcc tggcccccgc gggtggcccg cgttggcgcc 110400
cgccagtccc ggggaggata cggcgggcgg cacgccgccc ccacagacct gcggaatcgt 110460
caagcgcctc ctgagactgg ccgccacgga acaacaggac accacgcccc cggcgatcgc 110520
ggcgcttatc cgtaatgcgg cggtgcagac tcccctgccc gtctaccgga tatccatggt 110580
ccccacggga caggcatttg ccgcgctggc ctgggacgac tgggcccgca taacgcggga 110640
cgctcgcctg gccgaagcgg tcgtgtccgc cgaagcggcg gcgcaccccg accacggcgc 110700
gctgggcagg cggctcacgg atcgcatccg cgcccagggc cccgtgatgc cccctggcgg 110760
cctggatgcc ggggggcaga tgtacgtgaa tcgcaacgag atatttaacg gcgcgctggc 110820
aatcacaaac atcatcctgg atctcgacat cgccctgaag gagcccgtcc cctttcgccg 110880
gctccacgag gccctgggcc actttaggcg cggggctctg gcggcggttc agctcctgtt 110940
tcccgcggcc cgcgtggacc ccgacgcata tccctgttat tttttcaaaa gcgcatgtcg 111000
gcccggcccg gcgtccgtgg gttccggcag cggactcggc aacgacgacg acggggactg 111060
gtttccctgc tacgacgacg ccggtgatga ggagtgggcg gaggacccgg gcgccatgga 111120
cacatcccac gatcccccgg acgacgaggt tgcctacttt gacctgtgcc acgaagtcgg 111180
ccccacggcg gaacctcgcg aaacggattc gcccgtgtgt tcctgcaccg acaagatcgg 111240
actgcgggtg tgcatgcccg tccccgcccc gtacgtcgtc cacggttctc taacgatgcg 111300
gggggtggca cgggtcatcc agcaggcggt gctgttggac cgagattttg tggaggccat 111360
cgggagctac gtaaaaaact tcctgttgat cgatacgggg gcccgggcgc catggacaca 111420
tcccacgatc ccccggacga cgaggttgcc tactttgacc tgtgccacga agtcggcccc 111480
acggcggaac ctcgcgaaac ggattcgccc gtgtgttcct gcaccgacaa gatcggactg 111540
cgggtgtgca tgcccgtccc cgccccgtac gtcgtccacg gttctctaac gatgcggggg 111600
gtggcacggg tcatccagca ggcggtgctg ttggaccgag attttgtgga ggccatcggg 111660
agctacgtaa aaaacttcct gttgatcgat acgggggtgt acgcccacgg ccacagcctg 111720
cgcttgccgt attttgccaa aatcgccccc gacgggcctg cgtgcggaag gctgctgcca 111780
gtgtttgtga tcccccccgc ctgcaaagac gttccggcgt ttgtcgccgc gcacgccgac 111840
ccgcggcgct tccattttca cgccccgccc acctatctcg cttccccccg ggagatccgt 111900
gtcctgcaca gcctgggtgg ggactatgtg agcttctttg aaaggaaggc gtcccgcaac 111960
gcgctggaac actttgggcg acgcgagacc ctgacggagg tcctgggtcg gtacaacgta 112020
cagccggatg cggggggggac cgtcgagggg ttcgcatcgg aactgctggg gcggatagtc 112080
gcgtgcatcg aaacccactt tcccgaacac gccggcgaat atcaggccgt atccgtccgg 112140
cgggccgtca gtaaggacga ctgggtcctc ctacagctag tccccgttcg cggtaccctg 112200
cagcaaagcc tgtcgtgtct gcgctttaag cacggccggg cgagtcgcgc cacggcgcgg 112260
acattcgtcg cgctgagcgt cggggccaac aaccgcctgt gcgtgtcctt gtgtcagcag 112320
tgctttgccg ccaaatgcga cagcaaccgc ctgcacacgc tgtttaccat tgacgccggc 112380
acgccatgct cgccgtccgt tccctgcagc acctctcaac cgtcgtcttg ataacggcgt 112440
acggcctcgt gctcgtgtgg tacaccgtct tcggtgccag tccgctgcac cgatgtattt 112500
acacggtacg ccccaccggc accaacaacg acaccgccct cgtgtggatg aaaatgaacc 112560
agaccctatt gtttctgggg gccccgacgc acccccccaa cgggggctgg cgcaaccacg 112620
cccatatctg ctacgccaat cttatcgcgg gtagggtcgt gcccttccag gtcccacccg 112680
acgccacgaa tcgtcggatc atgaacgtcc acgaggcagt taactgtctg gagaccctat 112740
ggtacacacg ggtgcgtctg gtggtcgtag ggtggttcct gtatctggcg ttcgtcgccc 112800
tccaccaacg ccgatgtatg tttggtgtcg tgagtcccgc ccacaagatg gtggccccgg 112860
ccacctacct cttgaactac gcaggccgca tcgtatcgag cgtgttcctg cagtccccct 112920
acacgaaaat tacccgcctg ctctgcgagc tgtcggtcca gcggcaaaac ctggttcagt 112980
tgtttgagac ggacccggtc accttcttgt accaccgccc cgccatcggg gtcatcgtag 113040
gctgcgagtt gatgctacgc tttgtggccg tgggtctcat cgtcggcacc gctttcatat 113100
cccggggggc atgtgcgatc acatacccc tgtttctgac catcaccacc tggtgttttg 113160
tctccaccat cggcctgaca gagctgtatt gtattctgcg gcggggcccg gcccccaaga 113220
acgcagacaa ggccgccgcc ccggggcgat ccaaggggct gtcgggcgtc tgcgggcgct 113280
gttgttccat catcctgtcg ggcatcgcaa tgcgattgtg ttatatcgcc gtggtggccg 113340
gggtggtgct cgtggcgctt cactacgagc aggagatcca gaggcgcctg tttgatgtat 113400
gacgtcacat ccaggccggc ggaaaccgga acggcatatg caaactggaa actgtcctgt 113460
cttggggccc acccacccga cgcgtcatat gtaaatgaaa atcgttcccc cgaggccatg 113520
tgtagcctgg atcccaacga ccccgcccat gggtcccaat tggccgtccc gttaccaaga 113580
ccaacccagc cagcgtatcc acccccgccc gggtccccgc ggaagcggaa cggtgtatgt 113640
gatatgctaa ttaaatacat gccacgtact tatggtgtct gattggtcct tgtctgtgcc 113700
ggaggtgggg cgggggcccc gcccgggggg cggaactagg aggggtttgg gagagccggc 113760
cccggcacca cgggtataag gacatccacc acccggccgg tggtggtgtg cagccgtgtt 113820
ccaaccacgg tcacgcttcg gtgcctctcc ccgattcggg cccggtcgct tgctaccggt 113880
gcgccaccac cagaggccat atccgacacc ccagccccga cggcagccga cagcccggtc 113940
atggcgactg acattgatat gctaattgac ctcggcctgg acctctccga cagcgatctg 114000
gacgaggacc cccccgagcc ggcggagagc cgccgcgacg acctggaatc ggacagcaac 114060
ggggagtgtt cctcgtcgga cgaggacatg gaagaccccc acggagagga cggaccggag 114120
ccgatactcg acgccgctcg cccggcggtc cgcccgtctc gtccagaaga ccccggcgta 114180
cccagcaccc agacgcctcg tccgacggag cggcagggcc ccaacgatcc tcaaccagcg 114240
ccccacagtg tgtggtcgcg cctcggggcc cggcgaccgt cttgctcccc cgagcggcac 114300
gggggcaagg tggcccgcct ccaacccccca ccgaccaaag cccagcctgc ccgcggcgga 114360
cgccgtgggc gtcgcagggg tcggggtcgc ggtggtcccg gggccgccga tggtttgtcg 114420
gacccccgcc ggcgtgcccc cagaaccaat cgcaacccgg ggggaccccg ccccggggcg 114480
gggtggacgg acggccccgg cgccccccat ggcgaggcgt ggcgcggaag tgagcagccc 114540
gacccacccg gaggcccgcg gacacggagc gtgcgccaag caccccccccc gctaatgacg 114600
ctggcgattg cccccccgcc cgcggacccc cgcgccccgg ccccggagcg aaaggcgccc 114660
gccgccgaca ccatcgacgc caccacgcgg ttggtcctgc gctccatctc cgagcgcgcg 114720
gcggtcgacc gcatcagcga gagcttcggc cgcagcgcac aggtcatgca cgacccctttt 114780
ggggggcagc cgtttcccgc cgcgaatagc ccctgggccc cggtgctggc gggccaagga 114840
gggccctttg acgccgagac cagacgggtc tcctgggaaa ccttggtcgc ccacggcccg 114900
agcctctatc gcacttttgc cggcaatcct cgggccgcat cgaccgccaa ggccatgcgc 114960
gactgcgtgc tgcgccaaga aaatttcatc gaggcgctgg cctccgccga cgagacgctg 115020
gcgtggtgca agatgtgcat ccaccacaac ctgccgctgc gcccccagga ccccattatc 115080
gggacggccg cggcggtgct ggataacctc gccacgcgcc tgcggccctt tctccagtgc 115140
tacctgaagg cgcgaggcct gtgcggcctg gacgaactgt gttcgcggcg gcgtctggcg 115200
gacattaagg acattgcatc cttcgtgttt gtcattctgg ccaggctcgc caaccgcgtc 115260
gagcgtggcg tcgcggagat cgactacgcg acccttggtg tcggggtcgg agagaagatg 115320
catttctacc tccccggggc ctgcatggcg ggcctgatcg aaatcctaga cacgcaccgc 115380
caggagtgtt cgagtcgtgt ctgcgagttg acggccagtc acatcgtcgc ccccccgtac 115440
gtgcacggca aatattttta ttgcaactcc ctgttttagg tacaataaaa acaaaacatt 115500
tcaaacaaat cgccccacgt gttgtccttc tttgctcatg gccggcgggg cgtgggtcac 115560
ggcagatggc gggggtgggc ccggcgtacg gcctgggtgg gcggagggaa ctaacccaac 115620
gtataaatcc gtccccgctc caaggccggt gtcatagtgc ccttaggagc ttcccgcccg 115680
ggcgcatccc cccttttgca ctatgacagc gacccccctc accaacctgt tcttacgggc 115740
cccggacata acccacgtgg cccccccctta ctgcctcaac gccacctggc aggccgaaac 115800
ggccatgcac accagcaaaa cggactccgc ttgcgtggcc gtgcggagtt acctggtccg 115860
cgcctcctgt gagaccagcg gcacaatcca ctgctttttc tttgcggtat acaaggacac 115920
ccaccatacc cctccgctga ttaccgagct ccgcaacttt gcggacctgg ttaaccaccc 115980
gccggtccta cgcgaactgg aggataagcg cggggtgcgg ctgcggtgtg cgcggccgtt 116040
tagcgtcggg acgattaagg acgtctctgg gtccggcgcg tcctcggcgg gagagtacac 116100
gataaacggg atcgtgtacc actgccactg tcggtatccg ttctcaaaaa catgctggat 116160
gggggcctcc gcggccctac agcacctgcg ctccatcagc tccagcggca tggccgcccg 116220
cgcggcagag catcgacgcg tcaagattaa aattaaggcg tgatttccaa ccccccatga 116280
atgtgtgtaa cccccccccc aaaaaaaataa agagccgtaa cccaaccaaa ccaggcgtgg 116340
tgtgagtttg tggacccaaa gccctcagag acaatgcgac aggccagtat ggaccgtgat 116400
acttttattt attaactcac aggggcgctt accgccacag gaataccaga ataatgacca 116460
ccacaatcgc gaccacccca aatacagcat ggcgccacac cacgccacaa cagccctgtc 116520
gccggtatgg ggcatgatca gacgagccgc gcgccgcgcg ttgggccctg tacagctcgc 116580
gcgaattgac cctaggaggc cgccacgcgc ccgagttttg cgttcgtcgc tggtcgtcgg 116640
gcgccaaagc cccggacggc tgttcggtcg aacgaacggc cacgacagtg gcataggttg 116700
gggggtggtc cgacatagcc tcggcgtacg tcgggaggcc cgacaagagg tcccttgtga 116760
tgtcgggtgg ggccacaagc ctggtttccg gaagaaacag gggggttgcc aataacccgc 116820
cagggccaaa actccggcgc tgcgcacgtc gttcggcgcg gcgccgggcg cgccgagcgg 116880
ctcgctgggc ggcttggcgt gagcggcccc gctccgacgc ctcgccctct ccggaggagg 116940
ttggcggaat tggcacggac gacaggggcc cagcagagta cggtggaggt gggtccgtgg 117000
gggtgtccag atcaataacg acaaacggcc cctcgttcct accagacaag ctatcgtagg 117060
ggggcggggg atcagcaaac gcgttccccg cgctccatag acccgcgtcg ggttgcgccg 117120
cctccgaagc catggatgcg ccccaaagcc acgactcccg cgcgctaggt ccttggggta 117180
agggaaaagg ccctactccc catccaagcc agccaagtta acgggctacg ccttcgggga 117240
tgggactggc accccggcgg attttgttgg gctggtacgc gtcgcccaac cgagggccgc 117300
gtccacggga cgcgcctttt ataaccccgg ggtcattccc aacgatcaca tgcaatctaa 117360
ctggctcccc tctcccctct cccccctct ccccagcagg agcggggtgt tgcgccgggg 117420
gacgtctgga ggagcgggag gtgcgcggga cggtggatga ggaacaggag ttgttgcgcg 117480
gtgagttgtc gctgtgagtt gtgttgttgg gcaggtgtgg tggatgacgt gacgtgtgac 117540
gtgcggattg cgccgtgctt tgttggtgtt gttttacctg tggcagcccg ggcccccgc 117600 gggcgcgcgc gcgcgcaaaa aaggcgggcg gcggccccg ctcctccccc gcccctcccc 117660
cgctcctccc ccgctccccc ccgcccccgg ccccgccccc acccccccg cgcgcgcacg 117720 ccgcccggac cgccgcccgc ccttttgcg cccgcgcgcg cccgcggggg gccctggctg 117780
ccacaggtaa aacaacacca acaaagcacg gcgcaatccg cacgtcacac gtcacgtcat 117840
ccaccaccct gcccaacaac acaactcaca gcgacaactc ccgcgcaaca actcctgttc 117900
ctcatccaca cgtcaccgcg cccctcccgc tcctccagac gtaccccggc gcaacacccg 117960
ctcctgctac accccaccgc ccctccccag ccccagccct ccccagcccc agccctcccc 118020
cgggaggggg cgaggggcgg gagggggcga ggggcgggag ggggcgaggg gcggtggtgg 118080
ggcgcgggcg cccccggagg gttggatctc tgacctgaga ttggcggcac tgaggagaga 118140
tgcccgaacc cccccgaggg agcgcgggac gcggtgggga gggctggggc tggggagggc 118200
ggggcggggg ggcggggcgg gggggggggg gggggggggc gggggccccc cccccccccc 118260
cccccccccc cccccccccc cccccccccg cccccccccg ccccccgccc ccccccgccc 118320 ctcgcccccct cccgcccctc gccccctccc gcccctcgaa taaacaacgc tactgcaaaa 118380
cttaatcagg tcgttgccgt ttattgcgtc ttcgggtttc acaagcgccc cgccccgtcc 118440
cggcccgtta cagcaccccg tccccctcga acgcgccgcc gcgtcttcgt cccaggcgcc 118500
ttcccagtcc acaacgtccc gtcgcggggg cgtggccaag cccgcctccg cccccagcac 118560
ctccacggcc cccgccgccg ccagcacggt gccgctgcgg cccgtggccg aggcccagcg 118620
aatcccgggc ggcgccggcg gcagggcccc cgggccgtcg tcgtcgtcgc cgcgcagcac 118680
cagcgggggg gcgtcgtcgt cgggctccag cagggcgcgg gcgcaaaagt ccctccgcgg 118740
cccgcgccac cgggccgggc cggcgcgcac cgcctcgcgc cccagcgcca cgtacacggg 118800
ccgcagcggc gcgcccaggc cccagcgcgc gcaggcgcgg tgcgagtggg cctcctcctc 118860
gcagaagtcc ggcgcgccgg gcgccatggc gtcggtggtc cccgaggccg ccgcccggcc 118920
gtccagcgcc ggcagcacgg cccggcggta ctcgcgcggg gacatgggca ccggcgtgtc 118980
cgggccgagc gcgtgcgcac gcggtagcgc cgttgccgcc gcggcacggc gcagcggcgg 119040
cgcgtcgggg tacaggcgcg cgtgcgcggc ctccacgcgc gcgaagaccc ccgggccgaa 119100
cacgcggccc gaggccagca ccgtgcggcg caggtcccgc gccgccggcc agcgcacggc 119160
gcactgcacg gcgggcagca ggtcgcacgc caggtaggcg tgctgccgcg acaccgcggg 119220
cccgtcggcg ggccagtcgc aggcgcgcac ggtgttgacc acgatgagcc gccggtcgcc 119280
ggcgctggcg agcagcccca gaaactccac ggccccggcg aaggccaggt cccgcgtgga 119340
cagcagcagc acgccctgcg cgcccagcgc cgacacgtcg ggggcgccgg tccagttgcc 119400
cgcccaggcg gccgtgtccg gcccgcacag ccggttggcc agggccgcca gcaggcagga 119460
cagcccgccg cgctcggcgg accactccgg cggccccccc gaggccccgc cgccggccag 119520
gtcctcgccc ggcagcggcg agtacagcac caccacgcgc acgtcctcgg ggtcggggat 119580
ctggcgcatc caggccgcca ggcggcgcag cgggcccgag gcgcgcgggg ggccaaagag 119640
gcggcccccg gcggccccgt gggggtgggg gcccccaccc ccacggggcc gccgggggcc 119700
gcctctttgg ccccctgcgc gcctcgggcc cgctgcgccg catggcggcc tggatgcgcc 119760
agatccccga ccccgaggac gtgcgcgtgg tggtgctgta ctcgccgctg ccgggcgagg 119820
acctggccgg cggcggggcc tcgggggggc cgccggagtg gtccgccgag cgcggcgggc 119880
tgtcctgcct gctggcggcc ctggccaacc ggctgtgcgg gccggacacg gccgcctggg 119940
cgggcaactg gaccggcgcc cccgacgtgt cggcgctggg cgcgcagggc gtgctgctgc 120000
tgtccacgcg ggacctggcc ttcgccgggg ccgtggagtt tctggggctg ctcgccagcg 120060
ccggcgaccg gcggctcatc gtggcaacac cgtgcgcgcc tgcgactggc ccgccgacgg 120120
gcccgcggtg tcgcggcagc acgcctacct ggcgtgcgac ctgctgcccg ccgtgcagtg 120180
cgccgtgcgc tggccggcgg cgcgggacct gcgccgcacg gtgctggcct cgggccgcgt 120240
gttcggcccg gggtcttcg cgcgcgtgga ggccgcgcac gcgcgcctgt accccgacgc 120300
gccgccgctg cgcctgtgcc gcggcggcaa cgtgcgctac cgcgtgcgca cgcgcttcgg 120360
cccggacacg ccggtgccca tgtccccgcg cgagtaccgc cgggccgtgc tgccggcgct 120420
ggacggccgg gcggcggcct cggggaccac cgacgccatg gcgcccggcg cgccggactt 120480
ctgcgaggag gaggcccact cgcaccgcgc ctgcgcgcgc tggggcctgg gcgcgccgct 120540
gcggcccgtg tacgtggcgc tggggcgcga ggcggtgcgc gccggcccgg cccggtggcg 120600
cgggccgcgg agggactttt gcgcccgcgc cctgctggag cccgacgacg acgccccccc 120660
gctggtgctg cgcggcgacg acgacgacgg cccgggggcc ctgccgccgg cgccgcccgg 120720
gattcgctgg gcctcggcca cgggccgcag cggcaccgtg ctggcggcgg cgggggccgt 120780
ggaggtgctg gggcggaggg cgggctggcc acgcccccgc gcgggacgtt gtggactggg 120840
aaggcgcctg ggcgaagacg cggcggcgcg tcgagggggga cggggtgctg tacgggccgg 120900
gacggggcgg ggcgcttgtg aaacccgaag acgcaataaa cggcaacgac ctgattaagt 120960
tttgcagtag cgttgtttat tcgaggggcg ggagggggcg aggggcggcc ggcccgcaca 121020
gccggttggc cagggccgcc agcaggcagg acagcccgcc gcgctcggcg gaccactccg 121080
gcggcccccc cgaggccccg ccgccggcca ggtcctcgcc cggcagcggc gagtacagca 121140
ccaccacgcg cacgtcctcg gggtcgggga tctggcgcat ccaggccgcc atgcggcgca 121200
gcgggcccga ggcgcgcagg gggccaaaga ggcggccccc ggcggccccg tgggggtggg 121260
ggttctcgtc gtcgtcgccg ccgcacgcgg cctgggcggc gggggcgggc ccggcgcacc 121320
gcgcggcgat cgaggccagg gcccgcgggt caaacatgag ggccggtcgc caggggacgg 121380
ggaacagcgg gtggtccgtg agctcggcca cggcgcgcgg ggagcagtag gcctccaggg 121440
cggcggccgc gggcgccgcc gtgtggctgg gcccccgggg ctgccgccgc cagccgccca 121500
gggggtcggg gccctcggcg ggccggcgcg acagcgccag gggcgcgggg cgggcctgcg 121560
ccgcggcgcc cgggccgccg cgggctgggc gggggtgggc tcgggcccgg gggcgtggag 121620
gggggcgcgg ggagggggc gcgggcgtcc gagccggggg cgtccgcgcc gctcttcttc 121680
gtcttcgggg gtcgcgggcc gccgcctccg ggcggccggg ccgggccggg actcttgcgc 121740
ttgcgcccct cccgcggcgc ggcggaggcg gcggcggccg ccagcgcgtc ggcggcgtcc 121800
ggtgcgctgg ccgccgccgc cagcaggggg cggaggctct ggttctcaaa cagcaggtcc 121860
gcggcggcgg cggccgcgga gctcggcagg cgcgggtccc gcggcagcgc ggggcccagg 121920
gccccggcga ccaggctcac ggcgcgcacg gcggccacgg cggcctcgct gccgccggcc 121980
acgcgcaggt ccccgcgcag gcgcatgagc accagcgcgt cgcgcacgaa ccgcagctcg 122040
cgcagccacg cgcgcaggcg gggcgcgtcg gcgtgcggcg gcggcgggga agcggggccc 122100
gcgggtccct ctggccgcgg ggggctggcg ggccgggccc cggccagccc cgggacggcc 122160
gccaggtcgc cgtcgaagcc ctcggccagc gcctccagga tcccgcggca ggcggccagg 122220
cactcgacgg ccacgcggcc ggcctgggcg cggcgcccgg cgtcggcgtc ggcgtggcgg 122280
gcggcgtcgg ggtcgtcgcc ccccacgggg gaggcgggcg cggcggacag ccgccccagg 122340
gcggcgagga tccccgcggc gccgtacccg gcgggcaccg cgcgctcgcc cggtgcggcg 122400
gcggcgacgg cggcgacccc ctcgtcatct gcgccggcgc cggggctccc cgcggccccc 122460
gtcagcgccg cgttctcgcg cgccaacagg ggcgcgtagg cgcggcgcag gctggtcagc 122520
aggaagccct tctgcgcgcg gtcgtatcgg cggctcatgg ccacggcggc cgccgcgtgc 122580
gccaggcccc gccgaagcgg ccggccgcca tggcgtagcc caggtggggc acggcccgcg 122640
ccacgctgcc ggtgatgaag gagctgctgt tgcgcgcggc gcccgagatc cggaagcagg 122700
cctggtccag cgccacgtcc ccggggacca cgcgcgggtt ctggagccac cccatggcct 122760
ccgcgtccgg gggcctgcgc ggggacctgc gcgtggccgg cggcagcggg ccgccgtggc 122820
cgccggcgcg ccgtggccgg tcgccggggc cctgggcccc gcgctgccgc gggacccgcg 122880
cctgccgagc tccgcggccg ccgccgccgc ggacctgctg tttgagaacc agagcctccg 122940
ccccctgctg gcggcggcgg ccagcgcacc ggacgccgcc gacgcgctgg cggccgccgc 123000
cgcctccgcc gcgccgcggg aggggcgcaa gcgcaagagt cccggcccgg cccggccgcc 123060
cggaggcggc ggcccgcgac ccccgaagac gaagaagagc ggcgcggacg cccccggctc 123120
ggcgcccgcg ccccccctccc cgcgcccccc tccacgcccc cgggcccagc ccacccccccc 123180 ccacccgcgg cggcccgggg cgccgcggcg caggcccgcc cccgcccctg gcgctgtcgc 123240
gccggccccc cgagggcccc gacccccggg cggctggcgg cggcagcccc gggggcccag 123300
ccacacggcg gcgcccgcgg ccgccgccct ggaggcctac tgctccccgc gcgccgtggc 123360
cgagctcacg gaccacccgc tgttccccgt cccctggcga ccggccctca tgtttgaccc 123420
gcgggccctg gcctcgatcg ccgcgcggtg cgccgggccc gcccccgccg cccaggccgc 123480
gtgcggcggc gacgacgacg agaacccccg gggggggggg gggggggggg gggggggtg 123540 gggggggggg gggggggggg gggggggggg tgggtgggga gtggcaagga agaaacaagc 123600
ccgaccacca gacagaaaat gtaaccatac ccaaaccgac tctgggggct gtttgtgggg 123660
tcggaaccat aggatgaaca aaccaccccg tacctcccgc acccaagggt gcgggtggct 123720
catcggcatc tgtccggtat gggttgttcc ccacccactc gcgttcggac gtcttagaat 123780
catggcggtt ttctatgccg acatcggttt ttcccccgca ataaacacga tgcgataaaa 123840
actgtttgta aaatttatta aggggacaaa atgccctagc acaggggtgg ggttagggcc 123900
gggtccccac acccaaacgc accaaacaga tgcaggcagt gggtcgagta cagccccgcg 123960
tacgaacacg tcgatgcgtg tgtcagacag caccagaaag cacaggccat caacaggtcg 124020
tgcatgtgtc ggtgggtttg gacgcggggg gccatggtgg tgataaagtt aatggccgcc 124080
gtccgccagg gccacagggg cgacgtctct tggttggccc ggagccactg ggtgtggacc 124140
agccgcgcgt ggcggcccaa catggcccct gtagccgggg gcgggggatc gcgcacgttt 124200
gcagcgcaca tgcgagacac ctcgaccacg gttcgaaaga aggcccggtg gtccgcgggc 124260
aacatcacca ggtgcgcaag cgcccgggcg tccagagggt agagccctga gtcatccgag 124320
gttggctcat cgcccgggtc ttgccgcaag tgcgtgtggg ttgggcttcc ggtgggcggg 124380
acgcgaaccg cggtgtggat cccgacgcgg gcccgagcgt atgctccatc ttgtggggag 124440
aaggggtctg ggctcgccag gggggcatac ttgcccgggc tatacagacc cgcgagccgt 124500
acgtggttcg cggggggtgc gtggggtccg gggctccctg ggagaccggg gttgtcgtgg 124560
atccctgggg tcacgcggta ccctggggtc tctgggagct cgcggtactc tgggttccct 124620
aggttctcgg ggtggtcgcg gaacccgggg ctcccgggga acacgcggtg tcctggggat 124680
tgttggcggt cggacggctt cagatggctt cgagatcgta gtgtccgcac cgactcgtag 124740
tagacccgaa tctccacatt gccccgccgc ttgatcatta tcaccccgtt gcgggggtcc 124800
ggagatcatg cgcgggtgtc ctcgaggtgc gtgaacacct ctggggtgca tgccggcgga 124860
cggcacgcct tttaagtaaa catctgggtc gcccggccca actggggccg ggggttgggt 124920
ctggctcatc tcgagagaca cggggggggaa ccaccctccg cccagagact cgggtgatgg 124980
tcgtacccgg gactcaacgg gttaccggat tacggggact gtcggtcacg gtcccgccgg 125040
ttcttcgatg tgccacaccc aaggatgcgt tgggggcgat ttcgggcagc agcccgggag 125100
agcgcagcag gggacgctcc gggtcgtgca cggcggttct ggccgcctcc cggtcctcac 125160
gccccctttt attgatctca tcgcgtacgt cggcgtacgt cctgggccca acccgcatgt 125220
tgtccaggaa ggtgtccgcc atttccaggg cccacgacat gcttttcccg acgagcagga 125280
agcggtccac gcaacggtcg ccgccggtcg cctcgacgag ggcgttcctc ctgcgggaag 125340
gcacgaacgc gggtgagccc ccgcgtcccc cctcctccgc ccccgcgtcc cccctcctcc 125400
gcccccgcgt ccccccctcct ccgcccccgc gtccccccctc ctccgccccc gcgtcccccc 125460
tcctccgccc ccgcgtcccc cctcctccgc ccacccaagg tgcttacccg tgcaaaaaag 125520
gcggaccggt gggtttctgt cgtcggaggc ccccggggtg cgtcccctgt gtttcgtggg 125580
tggggtgggc gggtctttcc cccccgcgtc cgcgtgtccc tttccgatgc gatcccgatc 125640
ccgagccggg gcgtcgcgat gccgacgccg tccgctccga cggccctctg cgactcccgc 125700
tcccggtccg cgtgctccgc agccgctccc gtcgttcgtg gccggcgccg tctgcgggcg 125760
tcggtcgcgc cgggccttta tgtgcgccgg agagacccgc cccccgccgc ccgggtccgc 125820
ccccggggcc ggcgcggagt cgggcacggc gccagtgctc gcacttcgcc ctaataatat 125880
atatatattg ggacgaagtg cgaacgcttc gcgttctcac ttcttttacc cggcggcccc 125940
gccccccttgg ggcggtcccg cccgccggcc aatggggggg cggcaaggcg ggcggcccaa 126000
gggccgcccg ccgtcccgtg gtcccggcgt ccggcgggcg ggaccggggg cccggggacg 126060
gccaacgggc gcgcggggct cgtatctcat taccgccgaa ccgggaagtc ggggcccggg 126120
ccccgccccc tgcccgttcc tcgttagcat gcggaacgga agcggaaacc gccggatcgg 126180
gcggtaatga gatgccatgc ggggcggggc gcggacccac ccgccctcgc gccccgtcca 126240
tggcagatgg cgcggatggg cggggccggg ggttcgacca acgggccgcg gccacgggcc 126300

-continued cccggcgtgc cggcgtcggg gcggggtcgt gcataatgga attccgttcg gggtgggccc 126360
gccgggggc ggggggccgg cggcctccgc tgctcctcct tcccgccggc ccctgggact 126420
atatgagccc gaggacgccc cgatcgtcca cacggagcgc ggctgccgac acggatccac 126480
gacccgacgc gggaccgcca gagacagacc gtcagacgct cgccgcgccg ggacgccgat 126540
acgcggacga agcgcgggag ggggatcggc cgtccctgtc ctttttcccc acccaagcat 126600
cgaccggtcc gcgctagttc cgcgtcgacg gcgggggtcg tcggggtccg tgggtctcgc 126660
cccctccccc catcgagagt ccgtaggtga cctaccgtgc tacgtccgcc gtcgcagccg 126720
tatccccgga ggatcgcccc gcatcggcga tggcgtcgga gaacaagcag cgccccggct 126780
ccccgggccc caccgacggg ccgccgccca ccccgagccc agaccgcgac gagcgggggg 126840
ccctcgggtg gggcgcggag acggaggagg gcggggacga ccccgaccac gaccccgacc 126900
acccccacga cctcgacgac gcccggcggg acgggagggc ccccgcggcg ggcaccgacg 126960
ccggcgagga cgccggggac gccgtctcgc cgcgacagct ggctctgctg gcctccatgg 127020
tagaggaggc cgtccggacg atcccgacgc ccgaccccgc ggcctcgccg ccccggaccc 127080
ccgcctttct agccgacgac gatgacgggg acgagtacga cgacgcagcc gacgccgccg 127140
gcgaccgggc cccggcccgg ggccgcgaac gggaggcccc gctacgcggc gcgtatccgg 127200
accccacgga ccgccgtcgc cgcgcccgcc ggcccagccg ccgcggagac gtcgtcacgg 127260
ccggcggcgg ccatcggcgt catcgacctc gtcggactcc gggtcctcgt cctcgtcgtc 127320
cgcatcctct tcgtcctcgt cgtccgacga ggacgaggac gacgacggca acgacgcggc 127380
cgaccacgca cgcgaggcgc gggccgtcgg gcggggtccg tcgagcgcgg cgccggaagc 127440
ccccgggcgg acgccgcccc cgcccgggcc accccccctc tccgaggccg cgcccaagcc 127500
ccgggcggcg gcgaggaccc ccgcggcctc cgcgggccgc atcgagcgcc gccgggcccg 127560
cgcggcggtg gccggccgcg acgccacggg ccgcttcacg gccgggcagc cccggcgggt 127620
cgagctggcg ccgacgcggc ctccggcgcc ttctcgcgcg ctacgcgacg ggtcgtcgcg 127680
gggagccgtg gcccggcgcc gggcccccgc ccccggggcg ggtgctgtac ggcggcctgg 127740
gcgacagccg cccgggcctc tggggggcgc ccgaggcgga ggaggcgcga cgccggttcg 127800
aggcctcggg cgccccggcg gccgtgtggg cgcccgagct gggcgacgcc gcgcagcagt 127860
acgccctgat cacgcggctg ctgtacaccc cggacgcgga ggccatgggg tggctccaga 127920
acccgcgcgt ggtccccggg gacgtggcgc tggaccaggc ctgcttccgg atctcgggcg 127980
ccgcgcgcaa cagcagctcc ttcatcaccg gcagcgtggc gcgggccgtg ccccacctgg 128040
gctacgccat ggcggccggc cgcttcggct ggggcctggc gcacgcggcg gccgccgtgg 128100
ccatgagccg ccgatacgac cgcgcgcaga agggcttcct gctgaccagc ctgcgccgcg 128160
cctacgcgcc cctgttggcg cgcgagaacg cggcgctgac gggggccgcg gggagccccg 128220
gcgccggcgc agatgacgag ggggtcgccg ccgtcgccgc cgccgcaccg ggcgagcgcg 128280
cggtgcccgc cgggtacggc gccgcgggga tcctcgccgc cctggggcgg ctgtccgccg 128340
cgcccgcctc ccccgtgggg ggcgacgggg cgtacagcag ccgcgtgatc agggcgtact 128400
gctgcgcggc gtcgcccgct cgggcgccca cacggccgcc ggggcgcccg aggcctcgac 128460
ccggcgtcgc gcctcctccg cctcgggcgc cccccagagg cccgggcggc tgtcgcccag 128520
gccgccgtac agcacccgcc ccgggggcgg gggcccggcg ccgggccacg gctccccgct 128580
gacgacccgt cgcgatagcg cgcgtagaag gcgccggagg ccgcgtcggc gtccagctcg 128640
acccgccggg gctgcccggc cgtgaagcgg cccgtggcgt cgcggccggc caccgccgcg 128700
cgggcccggc ggcgctcgat gcggcccgcg gaggccgcgg gggtcctcgc cgccgcccgg 128760
ggcttgggcg cggcctcgga gagggggggt ggcccgggcg ggggcggcgt ccgcccgggg 128820
gcttccggcg ccgcgctcga cggaccccgc ccgacggccc gcgcctcgcg tgcgtggtcg 128880
gccgcgtcgt tgccgtcgtc gtcctcgtcc tcgtcggacg acgaggacga agaggatgcg 128940
gacgacgagg acgaggaccc ggagtccgac gaggtcgatg acgccgatgg ccgccgccgg 129000
ccgtgacgac gtctccgcgg cggctgggcc ggcgggcgcg gcgacaggcg gtccgtgggg 129060
gccggatacg cgccgcgccg cccgggggct tccggcgccg cgctcgacgg accccgcccg 129120
acggcccgcg cctcgcgtgc gtggtcggcc gcgtcgttgc cgtcgtcgtc ctcgtcctcg 129180
tcggacgacg aggacgaaga ggatgcggac gacgaggacg aggacccgga gtccgacgag 129240
gtcgatgacg ccgatggccg ccgccggccg tgacgacgtc tccgcggcgg ctgggccggc 129300
gggcgcggcg acaggcggtc cgtggggtcc ggatacgcgc cgcgtagcgg ggcctcccgt 129360
tcgcggcccc gggccggggc ccggtcgccg gcggcgtcgg ctgcgtcgtc gtactcgtcc 129420
ccgtcatcgt cgtcggctag aaaggcgggg gtccggggcg gcgaggccgc ggggtcgggc 129480
gtcgggatcg tccggacggc ctcctctacc atggaggcca gcagagccag ctgtcgcggc 129540
gagacggcgt ccccggcgtc ctcgccggcg tcggtgcccg ccgcggggc cctcccgtcc 129600 cgccgggcgt cgtcgaggtc gtgggggtgg tcggggtcgt ggtcggggtc gtccccgccc 129660
tcctccgtct ccgcgcccca cccgagggcc ccccgctcgt cgcggtctgg gctcggggtg 129720
ggcggcggcc cgtcggtggg gcccggggag ccggggcgct gcttgttctc cgacgccatc 129780
gccgatgcgg ggcgatcctc ccccgacgac ccccgccgtc gacgcggaac tagcgcggac 129840
cggtcgatgc ttgggtgggg aaaaaggaca gggacggccg atccccctcc cgcgcttcgt 129900
ccgcgtatcg gcgtcccggc gcggcgagcg tctgacggtc tgtctctggc ggtcccgcgt 129960
cgggtcgtgg atccgtgtcg gcagccgcgc tccgtgtgga cgatcggggc gtcctcgggc 130020
tcatatagtc ccggggccgg cgggagggag gagcagcgga ggccgccggc cccccgcccc 130080
ccggcgggcc cgaccccgcc ccgacgccgg cacgccgggg gcccgtggcc gcggcccgtt 130140
ggtcgaaccc ccggccccgc ccatccgcgc catctgccat ggacggggcg cgagggcggg 130200
tgggtccgcg ccccgccccg catggcatct cattaccgcc cgatccggcg gtttccgctt 130260
ccgttccgca tgctaacgag gaacgggcag gggcggggc ccgggccccg acttcccggt 130320
tcggcggtaa tgagatacga gccccgcgcg cccgttggcc gtccccgggc ccccgtcccg 130380
cccgccggac gccgggacca cgggacgcgg agcggacggc gtcggcatcg cgacgccccg 130440
gctcgggatc gggatcgcat cggaaaggga cacgcggacg cgggggggaa agacccgccc 130500
accccaccca cgaaacacag gggacgcccc cgggggcccc gacgacagaa acccccggtc 130560
cgcctttttt gcacgggtaa gcgccttggg tgggcggagg agggggacg cgggggcgga 130620 ggagggggga cgcgggggcg gaggaggggg gagcgggggg gaggaggggg gacgcggggg 130680
cggaggaggg gggacgcggg ggcggaggag gggggggggg ggggagccac tgtggtcctc 130740
cgggcgtttt ctggatggcc gacatttccc caggcgcttt tgtgccttgt gtaaaagcgc 130800
ggcgtcccgc tctccgatcc ccgcccctgg gcacgcgcaa gcgcaagcgc cctgcccgcc 130860
ccctctcatc ggagtctgag gtcgaatccg agacagcctt ggagtctgag gtcgaatccg 130920
agacagcatc ggattcgacc gagtctgggg accaggagga agcccccgc atcggtggcc 130980 gtagggcccc ccggaggctt ggggggcggt tttttctgga catgtcggcg gaatccacca 131040
cggggacgga aacggatgcg tcggtgtcgg acgaccccga cgacacgtcc gactggtctt 131100
gtgacgacat tcccccacga cccaagcggg cccgggtaaa cctgcggctc actagctctc 131160
ccgatcggcg ggatggggtt atttttccta agatggggcg ggtccggtct acccgggaaa 131220
cgcagccccg ggcccccacc ccgtcggccc caagcccaaa tgcaatgctc cggcgctcgg 131280
tgcgccaggc ccagaggcgg agcagcgcac gatggacccc cgacctgggc tacatgcgcc 131340
agtgtatcaa tcagctgttt cgggtcctgc gggtcgcccg ggacccccac ggcagtgcca 131400
accgcctgcg ccacctgata cgcgactgtt acctgatggg atactgccga gcccgtctgg 131460
ccccgcgcac gtggtgccgc ttgctgcagg tgtccggcgg aacctggggc atgcacctgc 131520
gcaacaccat acgggaggtg gaggctcgat tcgacgccac cgcagaaccc gtgtgcaagc 131580
ttccttgttt ggaggccaga cggtacggcc cggagtgtga tcttagtaat ctcgagattc 131640
atctcagcgc gacaagcgat gatgaaatct ccgatgccac cgatctggag gccgccggtt 131700
cggaccacac gctcgcgtcc cagtccgaca cggaggatgc cccctccccc gttacgctgg 131760
aaaccccaga accccgcggg tccctcgctg tgcgtctgga ggatgagttt ggggagtttg 131820
actggacccc ccaggagggc tcccagccct ggctgtctgc ggtcgtggcc gataccagct 131880
ccgtggaacg cccgggccca tccgattctg ggcgggtcg cgcagcagaa gaccgcaagt 131940
gtctggacgg ctgccggaaa atgcgcttct ccaccgcctg cccctatccg tgcagcgaca 132000
cgtttctccg gccgtgagtc cggtcgcccc gaccccccttg tatgtcccca aaataaaaga 132060
ccaaaatcaa agcgtttgtc ccagcgtctt aatggcggga agggggagag aaacagacca 132120
cgcgtacatg gggggtgttt gggggtttat tgacatcggg gctacagggt ggtaaccgga 132180
tagcagatgt gaggaagtct gggccgttcg ccgcgaacgg cgatcagagg gtccgtttct 132240
tgcggaccac ggcccggtga tgtgggttgc tcgtctaaaa tctcgggcat acccatacac 132300
gcacaacacg gacgccgcac cgaatgggac gtcgtaaggg ggtgggaggt agctgggtgg 132360
ggtttgtgca gagcaatcag ggaccgcagc cagcgcatac aatcgcgctc ccgtccgttg 132420
gtcccgggca ggaccacgcc gtactggtat tcgtaccggc tgagcagggt ctccaggggg 132480
tggttgggtg ccgcggggaa cggggtccac gccacggtcc actcgggcaa aaaccgagtc 132540
ggcacggccc acggttctcc cacccacgcg tctggggtct tgatggcgat aaatcttacc 132600
ccgagccgga ttttttgggc gtattcgaga aacggcacac acagatccgc cgcgcctacc 132660
acccacaagt ggtagaggcg agggggctg ggttggtctc ggtgcaacag tcggaagcac 132720
gccacggcgt ccacgacctc ggtgctctcc aaggggctgt cctccgcaaa caggcccgtg 132780
gtggtgtttg gggggcagcg acaggaccta gtgcgcacga tcgggcgggt gggtttgggt 132840
aagtccatca gcggctcggc caaccgtcga aggttggccg ggcgaacgac gaccggggta 132900
cccaggggtt ctgatgccaa aatgcggcac tgcctaagca ggaagctcca cagggccggg 132960
cttgcgtcga cggaagtccg gggcagggcg ttgttctggt caaggagggt cattacgttg 133020
acgacaacaa cgcccatgtt ggtatattac aggcccgtgt ccggtttggg gcacttgcag 133080
atttgtaagg ccacgcacgg cggggagaca ggccgacgcg ggggctgctc taaaaattta 133140
agggccctac ggtccacaga cccgccttcc cgggggggcc cttggagcga ccggcagcgg 133200
aggcgtccgg gggaggggag ggttatttac gggggggtag gtcagggggt gggtcgtcaa 133260
actgccgctc cttaaaaccc cggggcccgt cgttcggggt gctcgttggt tggcactcac 133320
ggtgcggcga atggcctgtc gtaagttttg tcgcgtttac gggggacagg gcaggaggaa 133380
ggaggaggcc gtcccgccgg agacaaagcc gtcccgggtg tttcctcatg gcccctttta 133440
taccccagcc gaggacgcgt gcctggactc cccgcccccg gagaccccca aaccttccca 133500
caccacacca cccggcgatg ccgagcgcct gtgtcatctg caggagatcc tggcccagat 133560
gtacggaaac caggactacc ccatagagga cgaccccagc gcggatgccg cggacgatgt 133620
cgacgaggac gccccggacg acgtggccta tccggaggaa tacgcagagg agctttttct 133680
gcccggggac gcgaccggtc cccttatcgg ggccaacgac cacatccctc ccccgcgtgg 133740
cgcatctccc cccggtatac gacgacgcag ccgggatgag attggggcca cgggatttac 133800
cgcagaagag ctggacgcca tggacaggca ggcggctcga gccatcagcc gcggcggcaa 133860
gccccccctcg accatggcca agctggtgac tggcatgggc tttacgatcc acggagcgct 133920
caccccagga tcggaggggt gtgtctttga cagcagccac ccagattacc cccaacgggt 133980
aatcgtgaag gcggggtggt acacgagcac gagccacgag gcgcgactgc tgaggcgact 134040
ggaccacccg gcgatcctgc ccctcctgga cctgcatgtc gtctccgggg tcacgtgtct 134100
ggtcctcccc aagtaccagg ccgacctgta tacctatctg agtaggcgcc tgaacccact 134160
gggacgcccg cagatcgcag cggtctcccg gcagctccta agcgccgttg actacattca 134220
ccgccagggc attatccacc gcgacattaa gaccgaaaat atttttatta acacccccga 134280
ggacatttgc ctgggggact ttggtgccgc gtgcttcgtg cagggttccc gatcaagccc 134340
cttcccctac ggaatcgccg gaaccatcga caccaacgcc cccgaggtcc tggccgggga 134400
tccgtatacc acgaccgtcg acatttggag cgccggtctg gtgatcttcg agactgccgt 134460
ccacaacgcg tccttgttct cggccccccg cggccccaaa aggggcccgt gcgacagtca 134520
gatcacccgc atcatccgac aggcccaggt ccacgttgac gagttttccc cgcatccaga 134580
atcgcgcctc acctcgcgct accgctcccg cgcggccggg aacaatcgcc cgccttacac 134640
ccgaccggcc tggacccgct actacaagat ggacatagac gtcgaatatc tggtttgcaa 134700
agccctcacc ttcgacggcg cgcttcgccc cagcgccgca gagctgcttt gtttgccgct 134760
gtttcaacag aaatgaccgc ccccgggggg cggtgctgtt tgcgggttgg cacaaaaaga 134820
ccccgacccg cgtctgtggt gtttttggca tcatgtcgcc gggcgccatg cgtgccgttg 134880
ttcccattat cccattcctt ttggttcttg tcggtgtatc gggggttccc accaacgtct 134940
cctccaccac ccaaccccaa ctccagacca ccggtcgtcc ctcgcatgaa gcccccaaca 135000
tgacccagac cggcaccacc gactctccca ccgccatcag ccttaccacg cccgaccaca 135060
caccccccat gccaagtatc ggactggagg aggaggagga agaggaggag ggggccgggg 135120
atggcgaaca tcttaagggg ggagatggga cccgtgacac cctaccccag tccccgggtc 135180
cagccgtccc gttggccggg gatgacgaga aggacaaacc caaccgtccc gtagtcccac 135240
cccccggtcc caacaactcc cccgcgcgcc ccgagaccag tcgaccgaag acacccccca 135300
ccagtatcgg gccgctggca actcgaccca cgacccaact cccctcaaag ggcgaccct 135360
tggttccgac gcctcaacat accccgctgt tctcgttcct cactgcctcc cccgccctgg 135420
acaccctctt cgtcgtcagc accgtcatcc acaccttatc gtttgtgtgt attgttgcta 135480
tggcgacaca cctgtgtggt ggttggtcca gacgcgggcg acgcacacac cctagcgtgc 135540
gttacgtgtg cctgccgccc gaacgcgggt agggtatggg gcggggatgg ggagagccca 135600
cacgcggaaa gcaagaacaa taaaggcggc gggatctagt tgatatgcgt ctctgggtgt 135660
ttttggggtg tggtgggcgc ggggcggtca ttggacgggg gtgcagttaa atacatgccc 135720
gggacccatg aagcatgcgc gacttccggg cctcggaacc cacccgaaac ggccaacgga 135780
cgtctgagcc aggcctggct atccggagaa acagcacacg acttggcgtt ctgtgtgtcg 135840
cgatgtctct gcgcgcagtc tggcatctgg ggcttttggg aagcctcgtg ggggctgttc 135900
ttgccgccac ccatctggga cctgcggcca acacaacgga ccccttaacg cacgccccag 135960
tgtcccctca ccccagcccc ctggggggct ttgccgtccc cctcgtagtc ggtgggctgt 136020
gtgccgtagt cctgggggcg gcgtgtctgc ttgagctcct gcgtcgtacg tgccgcgggt 136080
gggggcgtta ccatccctac atggacccag ttgtcgtata attttttccc ccccccccct 136140
tctccgcatg ggtgatgtcg ggtccaaact cccgacacca ccagctggca tggtataaat 136200
caccggtgcg ccccccaaac catgtccggc agggggatgg ggggcgaatg cggagggcac 136260
ccaacaacac cgggctaacc aggaaatccg tggccccggc ccccaacaaa gatcgcggta 136320
gcccggccgt gtgacattat cgtccatacc taccacaccg acgaatcccc taagggggag 136380
gggccatttt acgaggagga ggggtataac aaagtctgtc tttaaaaagc aggggttagg 136440
gagttgttcg gtcataagct tcagtgcgaa cgaccaacta ccccgatcat cagttatcct 136500
taaggtctct tttgtgtggt gcgttccggt atgggggggg ctgccgccag gttgggggcc 136560
gtgattttgt ttgtcgtcat agtgggcctc catggggtcc gcggcaaata tgccttggcg 136620
gatgcctctc tcaagatggc cgaccccaat cgctttcgcg gcaaagacct tccggtcctg 136680
gaccagctga ccgaccctcc gggggtccgg cgcgtgtacc acatccaggc gggcctaccg 136740
gacccgttcc agccccccag cctcccgatc acggtttact acgccgtgtt ggagcgcgcc 136800
tgccgcagcg tgctcctaaa cgcaccgtcg gaggcccccc agattgtccg cggggcctcc 136860
gaagacgtcc ggaaacaacc ctacaacctg accatcgctt ggtttcggat gggaggcaac 136920
tgtgctatcc ccatcacggt catggagtac accgaatgct cctacaacaa gtctctgggg 136980
gcctgtccca tccgaacgca gccccgctgg aactactatg acagcttcag cgccgtcagc 137040
gaggataacc tggggttcct gatgcacgcc cccgcgtttg agaccgccgg cacgtacctg 137100
cggctcgtga agataaacga ctggacggag attacacagt ttatcctgga gcaccgagcc 137160
aagggctcct gtaagtacgc cctcccgctg cgcatccccc cgtcagcctg cctctccccc 137220
caggcctacc agcagggggt gacggtggac agcatcggga tgctgccccg cttcatcccc 137280
gagaaccagc gcaccgtcgc cgtatacagc ttgaagatcg ccgggtggca cgggcccaag 137340
gccccataca cgagcaccct gctgcccccg gagctgtccg agacccccaa cgccacgcag 137400
ccagaactcg ccccggaaga ccccgaggat tcggccctct tggaggaccc cgtggggacg 137460
gtggcgccgc aaatcccacc aaactggcac atcccgtcga tccaggacgc cgcgacgcct 137520
taccatcccc cggccacccc gaacaacatg ggcctgatcg ccggcgcggt gggcggcagt 137580
ctcctggcag ccctggtcat ttgcggaatt gtgtactgga tgcaccgccg cactcggaaa 137640
gccccaaagc gcatacgcct cccccacatc cgggaagacg accagccgtc ctcgcaccag 137700
cccttgtttt actagatacc cccccccctta atgggtgcgg ggggggtcag gtctgcgggg 137760
ttgggatggg accttaactc catataaagc gagtctggaa ggggggaaag gcggacagtc 137820
gataagtcgg tagcggggga cgcgcacctg ttccgcctgt cgcacccaca gctttttcgc 137880
gaaccgtccc gtttcgggat gccgtgccgc ccgttgcagg gcctggtgct cgtgggcctc 137940
tgggtctgtg ccaccagcct ggttgtccgc cccccccctta atgggtgcgg ggggggtcag 138000
gtctgcgggg ttgggatggg accttaactc catataaagc gagtctggaa ggggggaaag 138060
gcggacagtc gataagtcgg tagcggggga cgcgcacctg ttccgcctgt cgcacccaca 138120
gctttttcgc gaaccgtccc gtttcgggat gccgtgccgc ccgttgcagg gcctggtgct 138180
cgtgggcctc tgggtctgtg ccaccagcct ggttgtccgt ggccccacgg tcagtctggt 138240
atcaaactca tttgtggacg ccggggcctt ggggcccgac ggcgtagtgg aggaagacct 138300
gcttattctc ggggagcttc gctttgtggg ggaccaggtc ccccacacca cctactacga 138360
tggggtcgta gagctgtggc actaccccat gggacacaaa tgcccacggg tcgtgcatgt 138420
cgtcacggtg accgcgtgcc cacgtcgccc cgccgtggca tttgccctgt gtcgcgcgac 138480
cgacagcact cacagccccg catatcccac cctggagctg aatctggccc aacagccgct 138540
tttgcgggtc cggagggcga cgcgtgacta tgccggggtg tacgtgttac gcgtatgggt 138600
cggggacgca ccaaacgcca gcctgtttgt cctggggatg gccatagccg ccgaaggtac 138660
tctggcgtac aacggctcgg cccatggctc ctgcgccccg aaactgcttc cgtcttcggc 138720
cccgcgtctg gccccggcga gcgtatacca acccgcccct aacccggcct ccaccccctc 138780
gaccaccacc tccacccccct cgaccaccat ccccgctccc caagcatcga ccacaccctt 138840
ccccacggga gacccaaaac cccaacctca cggggtcaac cacgaacccc catcgaatgc 138900
cacgcgagcg acccgcgact cgcgatatgc gctaacggtg acccagataa tccagatagc 138960
catccccgcg tccattatag ccctggtgtt tctggggagc tgtatttgct ttatacacag 139020
atgtcaacgc cgctaccgac gctcccgccg cccgatttac agcccccaga tacccacggg 139080
catctcatgc gcggtgaacg aagcggccat ggcccgcctc ggagccgagc tcaaatcgca 139140
tccgagcacc ccccccaaat cccggcgccg gtcgtcacgc acgccaatgc cctccctgac 139200
ggccatcgcc gaagagtcgg agcccgcggg ggcggctggg cttccgacgc cccccgtgga 139260
ccccacgaca tccaccccaa cgcctcccct gttggtatag gtccacggcc actggccggg 139320
ggcaccacat aaccgaccgc agtcactgag ttgggaataa accggtatta tttacctata 139380
tccgtgtatg tccatttctt tcttcccccc ccccccggaa accaaagaag gaagcaaaga 139440
atggatggga ggagttcagg aagccgggga gagggcccgc ggcgcattta aggcgttgtt 139500
gtgttgactt tggctcttct ggcgggttgg tgcggtgctg tttgttgggc tcccatttta 139560
cccgaagatc ggctgctatc cccgggacat ggatcgcggg gcggtggtgg ggtttcttct 139620
cggtgtttgt gttgtatcgt gcttggcggg aacgcccaaa acgtcctgga gacgggtgag 139680
tgtcggcgag gacgtttcgt tgcttccagc tccggggcct acggggcgcg gcccgaccca 139740
gaaactacta tgggccgtgg aacccctgga tgggtgcggc cccttacacc cgtcgtgggt 139800
ctcgctgatg ccccccaagc aggtgcccga gacggtcgtg gatgcggcgt gcatgcgcgc 139860
tccggtcccg ctggcgatgg cgtacgcccc cccggcccca tctgcgaccg gggtctacg 139920 aacggacttc gtgtggcagg agcgcgcggc cgtggttaac cggagtctgg ttattcacgg 139980
ggtccgagag acggacagcg gcctgtatac cctgtccgtg ggcgacataa aggacccggc 140040
tcgccaagtg gcctcggtgg tcctggtggt gcaaccggcc ccagttccga ccccaccccc 140100
gaccccagcc gattacgacg aggatgacaa tgacgagggc gaggacgaaa gtctcgccgg 140160
cactcccgcc agcgggaccc cccggctccc gcctcccccc gcccccccga ggtcttggcc 140220
cagcgccccc gaagtctcac atgtgcgtgg ggtgaccgtg cgtatggaga ctccggaagc 140280
tatcctgttt tcccccgggg agacgttcag cacgaacgtc tccatccatg ccatcgccca 140340
cgacgaccag acctactcca tggacgtcgt ctggttgagg ttcgacgtgc cgacctcgtg 140400
tgccgagatg cgaatatacg aatcgtgtct gtatcacccg cagctcccag aatgtctgtc 140460
cccggccgac gcgccgtgcg ccgcgagtac gtggacgtct cgcctggccg tccgcagcta 140520

```
cgcggggtgt tccagaacaa accccccacc gcgctgttcg gccgaggctc acatggagcc 140580
cgtcccgggg ctggcgtggc aggcggcctc cgtcaatctg gagttccggg acgcgtcccc 140640
acaacactcc ggcctgtatc tgtgtgtggt gtacgtcaac gaccatattc acgcctgggg 140700
ccacattacc atcagcaccg cggcgcagta ccggaacgcg gtggtggaac agcccctccc 140760
acagcgcggc gcggatttgg ccgagcccac ccacccgcac gtcggggccc ctccccacgc 140820
gcccccaacc cacggcgccc tgcggttagg ggcggtgatg ggggccgccc tgctgctgtc 140880
tgcgctgggg ttgtcggtgt gggcgtgtat gacctgttgg cgcaggcgtg cctggcgggc 140940
ggttaaaagc agggcctcgg gtaaggggcc cacgtacatt cgcgtggccg acagcgagct 141000
gtacgcggac tggagctcgg acagcgaggg agaacgcgac caggtcccgt ggctggcccc 141060
cccggagaga cccgactctc cctccaccaa tggatccggc tttgagatct tatcaccaac 141120
ggctccgtct gtataccccc gtagcgacgg gcatcaatct cgccgccagc tcacaacctt 141180
tggatccgga aggcccgatc gccgttactc ccaggcctcc gattcgtccg tcttctggta 141240
aggcgcccca tcccgaggcc ccacgtcggt cgccgaactg ggcgaccgcc ggcgaggtgg 141300
acgtcggaga cgagctaatc gcgatttccg acgaacgcgg acccccccga catgaccgcc 141360
cgcccctcgc cacgtcgacc gcgccctcgc cacacccgcg acccccgggc tacacggccg 141420
ttgtctcccc gatggccctc caggctgtcg acgcccccctc cctgtttgtc gcctggctgg 141480
ccgctcggtg gctccggggg gcttccggcc tgggggccgt cctgtgtggg attgcgtggt 141540
atgtgacgtc aattgcccga ggcgcacaaa gggccggtgg tccgcctagc cgcagcaaat 141600
taaaaatcgt gagtcacagc gaccgcaact tcccacccgg agctttcttc cggcctcgat 141660
gacgtcccgg ctctccgatc ccaactcctc agcgcgatcc gacatgtccg tgccgcttta 141720
tcccacggcc tcgccagttt cggtcgaagc ctactactcg gaaagcgaag acgaggcggc 141780
caacgacttc ctcgtacgca tggccgccca acagtcggta ttaaggcgtt gacgcagacg 141840
cacccgctgc gtcggcatgg tgatcgcctg tctcctcgtg gccgttctgt cgggcggatt 141900
tggggcgctc ctgatgtggc tgctccgcta aaagaccgca tcgacacgcg cgtccttctt 141960
gtcgtctctc ttcccccca tcaccccgca atttgcaccc agcctttaac tacattaaat 142020
tgggttcgat tggcaatgtt gtctcccggt tgatttttgg gtgggtgggg agtgggtggg 142080
tggggagtgg                                                        142090
```

<210> SEQ ID NO 2
<211> LENGTH: 338
<212> TYPE: PRT
<213> ORGANISM: Herpes simplex virus 1

<400> SEQUENCE: 2

```
Met Leu Ala Val Arg Ser Leu Gln His Leu Ser Thr Val Val Leu Ile
1               5                   10                  15

Thr Ala Tyr Gly Leu Val Leu Val Trp Tyr Thr Val Phe Gly Ala Ser
            20                  25                  30

Pro Leu His Arg Cys Ile Tyr Ala Val Arg Pro Thr Gly Thr Asn Asn
        35                  40                  45

Asp Thr Ala Leu Val Trp Met Lys Met Asn Gln Thr Leu Leu Phe Leu
    50                  55                  60

Gly Ala Pro Thr His Pro Pro Asn Gly Gly Trp Arg Asn His Ala His
65                  70                  75                  80

Ile Cys Tyr Ala Asn Leu Ile Ala Gly Arg Val Val Pro Phe Gln Val
                85                  90                  95
```

Pro Pro Asp Ala Thr Asn Arg Arg Ile Met Asn Val His Glu Ala Val
100 105 110

Asn Cys Leu Glu Thr Leu Trp Tyr Thr Arg Val Arg Leu Val Val Val
115 120 125

Gly Trp Phe Leu Tyr Leu Ala Phe Val Ala Leu His Gln Arg Arg Cys
130 135 140

Met Phe Gly Val Val Ser Pro Ala His Lys Met Val Ala Pro Ala Thr
145 150 155 160

Tyr Leu Leu Asn Tyr Ala Gly Arg Ile Val Ser Ser Val Phe Leu Gln
165 170 175

Tyr Pro Tyr Thr Lys Ile Thr Arg Leu Leu Cys Glu Leu Ser Val Gln
180 185 190

Arg Gln Asn Leu Val Gln Leu Phe Glu Thr Asp Pro Val Thr Phe Leu
195 200 205

Tyr His Arg Pro Ala Ile Gly Val Ile Val Gly Cys Glu Leu Met Leu
210 215 220

Arg Phe Val Ala Val Gly Leu Ile Val Gly Thr Ala Phe Ile Ser Arg
225 230 235 240

Gly Ala Cys Ala Ile Thr Tyr Pro Leu Phe Leu Thr Ile Thr Thr Trp
245 250 255

Cys Phe Val Ser Thr Ile Gly Leu Thr Glu Leu Tyr Cys Ile Leu Arg
260 265 270

Arg Gly Pro Ala Pro Lys Asn Ala Asp Lys Ala Ala Ala Pro Gly Arg
275 280 285

Ser Lys Gly Leu Ser Gly Val Cys Gly Arg Cys Cys Ser Ile Ile Leu
290 295 300

Ser Gly Ile Ala Met Arg Leu Cys Tyr Ile Ala Val Val Ala Gly Val
305 310 315 320

Val Leu Val Ala Leu His Tyr Glu Gln Glu Ile Gln Arg Arg Leu Phe
325 330 335

Asp Val

<210> SEQ ID NO 3
<211> LENGTH: 1737
<212> TYPE: DNA
<213> ORGANISM: Homo sapiens

<400> SEQUENCE: 3
atgctgccgt gcctcgtagt gctgctggcg gcgctcctca gcctccgtct tggctcagac 60
gctcatggga cagagctgcc cagccctccg tctgtgtggt ttgaagcaga atttttccac 120
cacatcctcc actggacacc catcccaaat cagtctgaaa gtacctgcta tgaagtggcg 180
ctcctgaggt atggaataga gtcctggaac tccatctcca actgtagcca gaccctgtcc 240
tatgacctta ccgcagtgac cttggacctg taccacagca atggctaccg ggccagagtg 300
cgggctgtgg acggcagccg gcactccaac tggaccgtca ccaacacccg cttctctgtg 360
gatgaagtga ctctgacagt tggcagtgtg aacctagaga tccacaatgg cttcatcctc 420
gggaagattc agctacccag gcccaagatg gcccccgcaa atgacacata tgaaagcatc 480
ttcagtcact tccgagagta tgagattgcc attcgcaagg tgccgggaaa cttcacgttc 540
acacacaaga aagtaaaaca tgaaaacttc agcctcctaa cctctggaga agtgggagag 600
ttctgtgtcc aggtgaaacc atctgtcgct tcccgaagta acaaggggat gtggtctaaa 660
gaggagtgca tctccctcac caggcagtat ttcaccgtga ccaacgtcat catcttcttt 720

```
gcctttgtcc tgctgctctc cggagccctc gcctactgcc tggccctcca gctgtatgtg    780
cggcgccgaa agaagctacc cagtgtcctg ctcttcaaga agcccagccc cttcatcttc    840
atcagccagc gtccctcccc agagacccaa gacaccatcc acccgcttga tgaggaggcc    900
tttttgaagg tgtccccaga gctgaagaac ttggacctgc acggcagcac agacagtggc    960
tttggcagca ccaagccatc cctgcagact gaagagcccc agttcctcct ccctgaccct   1020
cacccccagg ctgacagaac gctgggaaac agggagcccc ctgtgctggg ggacagctgc   1080
agtagtggca gcagcaatag cacagacagc gggatctgcc tgcaggagcc cagcctgagc   1140
cccagcacag ggcccacctg ggagcaacag gtggggagca acagcagggg ccaggatgac   1200
agtggcattg acttagttca aaactctgag ggccgggctg gggacacaca gggtggctcg   1260
gccttgggcc accacagtcc cccggagcct gaggtgcctg ggggaagaaga cccagctgct   1320
gtggcattcc agggttacct gaggcagacc agatgtgctg aagagaaggc aaccaagaca   1380
ggctgcctgg aggaagaatc gcccttgaca gatggccttg gccccaaatt cgggagatgc   1440
ctggttgatg aggcaggctt gcatccacca gccctggcca agggctattt gaaacaggat   1500
cctctagaaa tgactctggc ttcctcaggg gccccaacgg gacagtggaa ccagcccact   1560
gaggaatggt cactcctggc cttgagcagc tgcagtgacc tgggaatatc tgactggagc   1620
tttgcccatg accttgcccc tctaggctgt gtggcagccc caggtggtct cctgggcagc   1680
tttaactcag acctggtcac cctgcccctc atctctagcc tgcagtcaag tgagtga      1737
```

```
<210> SEQ ID NO 4
<211> LENGTH: 1788
<212> TYPE: DNA
<213> ORGANISM: Homo sapiens

<400> SEQUENCE: 4

atgggtcggg ggctgctcag gggcctgtgg ccgctgcaca tcgtcctgtg gacgcgtatc     60
gccagcacga tcccaccgca cgttcagaag tcggatgtgg aaatggaggc ccagaaagat    120
gaaatcatct gccccagctg taataggact gcccatccac tgagacatat taataacgac    180
atgatagtca ctgacaacaa cggtgcagtc aagtttccac aactgtgtaa attttgtgat    240
gtgagatttt ccacctgtga caaccagaaa tcctgcatga gcaactgcag catcacctcc    300
atctgtgaga agccacagga agtctgtgtg gctgtatgga gaaagaatga cgagaacata    360
acactagaga cagtttgcca tgaccccaag ctcccctacc atgactttat tctggaagat    420
gctgcttctc caaagtgcat tatgaaggaa aaaaaaaagc ctggtgagac tttcttcatg    480
tgttcctgta gctctgatga gtgcaatgac aacatcatct tctcagaaga atataacacc    540
agcaatcctg acttgttgct agtcatattt caagtgacag gcatcagcct cctgccacca    600
ctgggagttg ccatatctgt catcatcatc ttctactgct accgcgttaa ccggcagcag    660
aagctgagtt caacctggga aaccggcaag acgcggaagc tcatggagtt cagcgagcac    720
tgtgccatca tcctggaaga tgaccgctct gacatcagct ccacgtgtgc caacaacatc    780
aaccacaaca cagagctgct gcccattgag ctggacaccc tggtggggaa aggtcgcttt    840
gctgaggtct ataaggccaa gctgaagcag aacacttcag agcagtttga gacagtggca    900
gtcaagatct ttccctatga ggagtatgcc tcttggaaga cagagaagga catcttctca    960
gacatcaatc tgaagcatga gaacatactc cagttcctga cggctgagga gcggaagacg   1020
gagttgggga aacaatactg gctgatcacc gccttccacg ccaagggcaa cctacaggag   1080
```

tacctgacgc ggcatgtcat cagctgggag gacctgcgca agctgggcag ctccctcgcc 1140
cgggggattg ctcacctcca cagtgatcac actccatgtg ggaggcccaa gatgcccatc 1200
gtgcacaggg acctcaagag ctccaatatc ctcgtgaaga acgacctaac ctgctgcctg 1260
tgtgactttg ggctttccct gcgtctggac cctactctgt ctgtggatga cctggctaac 1320
agtgggcagg tgggaactgc aagatacatg gctccagaag tcctagaatc caggatgaat 1380
ttggagaatg ttgagtcctt caagcagacc gatgtctact ccatggctct ggtgctctgg 1440
gaaatgacat ctcgctgtaa tgcagtggga gaagtaaaag attatgagcc tccatttggt 1500
tccaaggtgc gggagcaccc ctgtgtcgaa agcatgaagg acaacgtgtt gagagatcga 1560
gggcgaccag aaattcccag cttctggctc aaccaccagg gcatccagat ggtgtgtgag 1620
acgttgactg agtgctggga ccacgaccca gaggcccgtc tcacagccca gtgtgtggca 1680
gaacgcttca gtgagctgga gcatctggac aggctctcgg ggaggagctg ctcggaggag 1740
aagattcctg aagacggctc cctaaacact accaaatagc tcttctgg 1788

<210> SEQ ID NO 5
<211> LENGTH: 465
<212> TYPE: DNA
<213> ORGANISM: Homo sapiens

<400> SEQUENCE: 5
atgtacagga tgcaactcct gtcttgcatt gcactaagtc ttgcacttgt cacaaacagt 60
gcacctactt caagttctac aaagaaaaca cagctacaac tggagcattt actgctggat 120
ttacagatga ttttgaatgg aattaataat tacaagaatc ccaaactcac caggatgctc 180
acatttaagt tttacatgcc caagaaggcc acagaactga aacatcttca gtgtctagaa 240
gaagaactca aacctctgga ggaagtgcta aatttagctc aaagcaaaaa ctttcactta 300
agacccaggg acttaatcag caatatcaac gtaatagttc tggaactaaa gggatctgaa 360
acaacattca tgtgtgaata tgctgatgag acagcaacca ttgtagaatt tctgaacaga 420
tggattacct tttgtcaaag catcatctca acactgactt gataa 465

<210> SEQ ID NO 6
<211> LENGTH: 763
<212> TYPE: DNA
<213> ORGANISM: Homo sapiens

<400> SEQUENCE: 6
aatgtggccc cctgggtcag cctcccagcc accgccctca cctgccgcgg ccacaggtct 60
gcatccagcg gctcgccctg tgtccctgca gtgccggctc agcatgtgtc cagcgcgcag 120
cctcctcctt gtggctaccc tggtcctcct ggaccacctc agtttggcca gaaacctccc 180
cgtggccact ccagacccag gaatgttccc atgccttcac cactcccaaa acctgctgag 240
ggccgtcagc aacatgctcc agaaggccag acaaactcta gaattttacc cttgcacttc 300
tgaagagatt gatcatgaag atatcacaaa agataaaacc agcacagtgg aggcctgttt 360
accattggaa ttaaccaaga atgagagttg cctaaattcc agagagacct ctttcataac 420
taatgggagt tgcctggcct ccagaaagac ctcttttatg atggccctgt gccttagtag 480
tatttatgaa gacttgaaga tgtaccaggt ggagttcaag accatgaatg caaagcttct 540
gatggatcct aagaggcaga tctttctaga tcaaaacatg ctggcagtta ttgatgagct 600
gatgcaggcc ctgaatttca acagtgagac tgtgccacaa aaatcctccc ttgaagaacc 660
ggatttttat aaaactaaaa tcaagctctg catacttctt catgctttca gaattcgggc 720
agtgactatt gatagagtga tgagctatct gaatgcttcc taa 763

<210> SEQ ID NO 7
<211> LENGTH: 489
<212> TYPE: DNA
<213> ORGANISM: Homo sapiens

<400> SEQUENCE: 7
atgagaattt cgaaaccaca tttgagaagt atttccatcc agtgctactt gtgtttactt 60
ctaaacagtc attttctaac tgaagctggc attcatgtct tcattttggg ctgtttcagt 120
gcagggcttc ctaaaacaga agccaactgg gtgaatgtaa taagtgattt gaaaaaaatt 180
gaagatctta ttcaatctat gcatattgat gctactttat atacggaaag tgatgttcac 240
cccagttgca aagtaacagc aatgaagtgc tttctcttgg agttacaagt tatttcactt 300
gagtccggag atgcaagtat tcatgataca gtagaaaatc tgatcatcct agcaaacaac 360
agtttgtctt ctaatgggaa tgtaacagaa tctggatgca aagaatgtga ggaactggag 420
gaaaaaaata ttaaagaatt tttgcagagt tttgtacata ttgtccaaat gttcatcaac 480
acttcttga 489

<210> SEQ ID NO 8
<211> LENGTH: 19
<212> TYPE: DNA
<213> ORGANISM: Herpes simplex virus 1

<400> SEQUENCE: 8
tccctatcag tgatagaga 19

<210> SEQ ID NO 9
<211> LENGTH: 5606
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgccaa gcttggctgc aggtcaacac 420
cagagcctgc ccaacatggc acccccactc ccacgcaccc ccactcccac gcacccccac 480
tcccacgcac ccccactccc acgcaccccc actcccacgc acccccactc ccacgcaccc 540
ccactcccac gcacccccac tcccacgcac ccccactccc acgcatcccc gcgatacatc 600
caacacagac agggaaaaga tacaaaagta aacctttatt tcccaacaga cagcaaaaat 660
cccctgagtt ttttttattt agggccaaca caaaagaccc gctggtgtgt ggtgcccgtg 720
tctttcactt ttcccctccc cgacacggat tggctggtgt agtgggcgcg gccagagacc 780
acccagcgcc cgaccccccc ctccccacaa acacgggggg cgtcccttat tgttttccct 840
cgtcccgggt cgaccagaca tgataagata cattgatgag tttggacaaa ccacaactag 900

```
aatgcagtga aaaaaatgct ttatttgtga aatttgtgat gctattgctt tatttgtaac    960
cattataagc tgcaataaac aagttctgct ttaataagat ctgaattccc gggatccgct   1020
gtacgcggac ccactttcac atttaagttg tttttctaat ccgcatatga tcaattcaag   1080
gccgaataag aaggctggct ctgcaccttg gtgatcaaat aattcgatag cttgtcgtaa   1140
taatggcggc atactatcag tagtaggtgt ttccctttct tctttagcga cttgatgctc   1200
ttgatcttcc aatacgcaac ctaaagtaaa atgccccaca gcgctgagtg catataatgc   1260
attctctagt gaaaaacctt gttggcataa aaaggctaat tgattttcga gagtttcata   1320
ctgtttttct gtaggccgtg tacctaaatg tacttttgct ccatcgcgat gacttagtaa   1380
agcacatcta aaacttttag cgttattacg taaaaaatct tgccagcttt ccccttctaa   1440
agggcaaaag tgagtatggt gcctatctaa catctcaatg gctaaggcgt cgagcaaagc   1500
ccgcttattt tttacatgcc aatacaatgt aggctgctct acacctagct tctgggcgag   1560
tttacgggtt gttaaacctt cgattccgac ctcattaagc agctctaatg cgctgttaat   1620
cactttactt ttatctaatc tagacatatc aattcgccct atagtgagtc gtattacaat   1680
tctttgccaa aatgatgaga cagcacaata accagcacgt tgcccaggag ctgtaggaaa   1740
aagaagaagg catgaacatg gttagcagag gggcccggtt tggactcaga gtattttatc   1800
ctcatctcaa acagtgtata tcattgtaac cataaagaga aaggcaggat gatgaccagg   1860
atgtagttgt ttctaccaat aagaatattt ccacgccagc cagaatttat atgcagaaat   1920
attctacctt atcatttaat tataacaatt gttctctaaa actgtgctga agtacaatat   1980
aatataccct gattgccttg aaaaaaaagt gattagagaa agtacttaca atctgacaaa   2040
taaacaaaag tgaatttaaa aattcgttac aaatgcaagc taaagtttaa cgaaaaagtt   2100
acagaaaatg aaaagaaaat aagaggagac aatggttgtc aacagagtag aaagtgaaag   2160
aaacaaaatt atcatgaggg tccatggtga tacaagggac atcttcccat tctaaacaac   2220
accctgaaaa ctttgccccc tccatataac atgaatttta caatagcgaa aaagaaagaa   2280
caatcaaggg tccccaaact caccctgaag ttctcaggat cgatccggag ctttttgcaa   2340
aagcctaggc ctccaaaaaa gcctcttcac tacttctgga atagctcaga ggccctagag   2400
gatccccggc ggggtcgtat gcggctggag ggtcgcggac ggagggtccc tgggggtcgc   2460
aacgtaggcg gggcttctgt ggtgatgcgg agagggggcg gcccgagtct gcctggctgc   2520
tgcgtctcgc tccgagtgcc gaggtgcaaa tgcgaccaga ctgtcgggcc agggctaact   2580
tataccccac gcctttcccc tccccaaagg ggcggcagtg acgattcccc caatggccgc   2640
gcgtcccagg ggaggcaggc ccaccgcggg gcggccccgt ccccggggac caacccggcg   2700
cccccaaaga atatcattag catgcacggc ccggcccccg atttgggggc ccaacccggt   2760
gtcccccaaa gaaccccatt agcatgcccc tcccgccgac gcaacagggg cttggcctgc   2820
gtcggtgccc cggggcttcc cgccttcccg aagaaactca ttaccatacc cggaacccca   2880
ggggaccaat gcgggttcat tgagcgaccc gcgggccaat gcgcgagggg ccgtgtgttc   2940
cgccaaaaaa gcaattagca taacccggaa ccccagggga gtggttacgc gcggcgcggg   3000
aggcggggaa taccggggtt gcccattaag ggccgcggga attgccggaa gcgggaaggg   3060
cggccggggc cgcccattaa tgagtttcta attaccatac cgggaagcgg aacaaggcct   3120
cttgcaagtt tttaattacc ataccgggaa gtgggcggcc cggcccattg ggcggtaact   3180
cccgcccaat gggccgggcc ccgaagactc ggcggacgct ggttggccgg gccccgccgc   3240
```

-continued

```
gctggcggcc gccgattggc cagtcccgcc cccgaggcgg cccgccctgt gagggcgggc   3300
tggctccaag cgtatatatg cgcggctcct gccatcgtct ctccggagag cggcttggtg   3360
cggagctcga attcggtaat catggtcata gctgtttcct gtgtgaaatt gttatccgct   3420
cacaattcca cacaacatac gagccggaag cataaagtgt aaagcctggg gtgcctaatg   3480
agtgagctaa ctcacattaa ttgcgttgcg ctcactgccc gctttccagt cgggaaacct   3540
gtcgtgccag ctgcattaat gaatcggcca acgcgcgggg agaggcggtt tgcgtattgg   3600
gcgctcttcc gcttcctcgc tcactgactc gctgcgctcg gtcgttcggc tgcggcgagc   3660
ggtatcagct cactcaaagg cggtaatacg gttatccaca gaatcagggg ataacgcagg   3720
aaagaacatg tgagcaaaag gccagcaaaa ggccaggaac cgtaaaaagg ccgcgttgct   3780
ggcgtttttc cataggctcc gcccccctga cgagcatcac aaaaatcgac gctcaagtca   3840
gaggtggcga aacccgacag gactataaag ataccaggcg tttccccctg gaagctccct   3900
cgtgcgctct cctgttccga ccctgccgct taccggatac ctgtccgcct ttctcccttc   3960
gggaagcgtg gcgctttctc aatgctcacg ctgtaggtat ctcagttcgg tgtaggtcgt   4020
tcgctccaag ctgggctgtg tgcacgaacc ccccgttcag cccgaccgct gcgccttatc   4080
cggtaactat cgtcttgagt ccaacccggt aagacacgac ttatcgccac tggcagcagc   4140
cactggtaac aggattagca gagcgaggta tgtaggcggt gctacagagt tcttgaagtg   4200
gtggcctaac tacggctaca ctagaaggac agtatttggt atctgcgctc tgctgaagcc   4260
agttaccttc ggaaaaagag ttggtagctc ttgatccggc aaacaaacca ccgctggtag   4320
cggtggtttt tttgtttgca agcagcagat tacgcgcaga aaaaaaggat ctcaagaaga   4380
tcctttgatc ttttctacgg ggtctgacgc tcagtggaac gaaaactcac gttaagggat   4440
tttggtcatg agattatcaa aaaggatctt cacctagatc cttttaaatt aaaaatgaag   4500
ttttaaatca atctaaagta tatatgagta aacttggtct gacagttacc aatgcttaat   4560
cagtgaggca cctatctcag cgatctgtct atttcgttca tccatagttg cctgactccc   4620
cgtcgtgtag ataactacga tacgggaggg cttaccatct ggccccagtg ctgcaatgat   4680
accgcgagac ccacgctcac cggctccaga tttatcagca ataaaccagc cagccggaag   4740
ggccgagcgc agaagtggtc ctgcaacttt atccgcctcc atccagtcta ttaattgttg   4800
ccgggaagct agagtaagta gttcgccagt taatagtttg cgcaacgttg ttgccattgc   4860
tacaggcatc gtggtgtcac gctcgtcgtt tggtatggct tcattcagct ccggttccca   4920
acgatcaagg cgagttacat gatcccccat gttgtgcaaa aaagcggtta gctccttcgg   4980
tcctccgatc gttgtcagaa gtaagttggc cgcagtgtta tcactcatgg ttatggcagc   5040
actgcataat tctcttactg tcatgccatc cgtaagatgc ttttctgtga ctggtgagta   5100
ctcaaccaag tcattctgag aatagtgtat gcggcgaccg agttgctctt gcccggcgtc   5160
aatacgggat aataccgcgc cacatagcag aactttaaaa gtgctcatca ttggaaaacg   5220
ttcttcgggg cgaaaactct caaggatctt accgctgttg agatccagtt cgatgtaacc   5280
cactcgtgca cccaactgat cttcagcatc ttttactttc accagcgttt ctgggtgagc   5340
aaaaacagga aggcaaaatg ccgcaaaaaa gggaataagg gcgacacgga aatgttgaat   5400
actcatactc ttcctttttc aatattattg aagcatttat cagggttatt gtctcatgag   5460
cggatacata tttgaatgta tttagaaaaa taaacaaata ggggttccgc gcacatttcc   5520
ccgaaaagtg ccacctgacg tctaagaaac cattattatc atgacattaa cctataaaaa   5580
taggcgtatc acgaggccct ttcgtc                                         5606
```

-continued

```
<210> SEQ ID NO 10
<211> LENGTH: 1017
<212> TYPE: DNA
<213> ORGANISM: Herpes simplex virus 1

<400> SEQUENCE: 10

atgctcgccg tccgttccct gcagcacctc tcaaccgtcg tcttgataac ggcgtacggc      60

ctcgtgctcg tgtggtacac cgtcttcggt gccagtccgc tgcaccgatg tatttacgcg     120

gtacgcccca ccggcaccaa caacgacacc gccctcgtgt ggatgaaaat gaaccagacc     180

ctattgtttc tgggggcccc gacgcacccc cccaacgggg gctggcgcaa ccacgcccat     240

atctgctacg ccaatcttat cgcgggtagg gtcgtgccct tccaggtccc acccgacgcc     300

acgaatcgtc ggatcatgaa cgtccacgag gcagttaact gtctggagac cctatggtac     360

acacgggtgc gtctggtggt cgtagggtgg ttcctgtatc tggcgttcgt cgccctccac     420

caacgccgat gtatgtttgg tgtcgtgagt cccgcccaca agatggtggc cccggccacc     480

tacctcttga actacgcagg ccgcatcgta tcgagcgtgt tcctgcagta cccctacacg     540

aaaattaccc gcctgctctg cgagctgtcg gtccagcggc aaaacctggt tcagttgttt     600

gagacggacc cggtcacctt cttgtaccac cgccccgcca tcggggtcat cgtaggctgc     660

gagttgatgc tacgctttgt ggccgtgggt ctcatcgtcg gcaccgcttt catatcccgg     720

ggggcatgtg cgatcacata ccccctgttt ctgaccatca ccacctggtg ttttgtctcc     780

accatcggcc tgacagagct gtattgtatt ctgcggcggg gcccggcccc caagaacgca     840

gacaaggccg ccgccccggg gcgatccaag ggctgtcgg gcgtctgcgg gcgctgttgt      900

tccatcatcc tgtcgggcat cgcaatgcga ttgtgttata tcgccgtggt ggccggggtg     960

gtgctcgtgg cgcttcacta cgagcaggag atccagaggc gcctgtttga tgtatga       1017
```

GENERATION REGULATABLE FUSOGENIC ONCOLYTIC HERPES SIMPLEX VIRUS TYPE 1 VIRUS AND METHODS OF USE

CROSS-REFERENCE TO RELATED APPLICATIONS

This application is a 371 National Phase Entry of International Patent Application No. PCT/US2019/062527 filed Nov. 21, 2019, which claims benefit under 35 U.S.C. § 119(e) of U.S. Provisional Application No. 62/772,293 filed Nov. 28, 2018, the contents of which are incorporated herein by reference in their entirety.

GOVERNMENT SUPPORT

This invention was made with government support under AI000588, and AI093738 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 8, 2019, is named 043214-090140WOPT_SL.txt and is 204,542 bytes in size.

FIELD OF INVENTION

The present invention is directed compositions and methods of treating cancer using regulatable fusogenic oncolytic herpes simplex virus 1 (HSV-1) virus.

BACKGROUND

Oncolytic viral therapy entails harnessing the ability of a virus to reproduce in and lyse human cells and directing this viral replication-dependent lysis preferentially toward cancerous cells. Advances in cancer biology, together with a detailed understanding of the roles of host factors and virus-encoded gene products in controlling virus production in infected cells, have facilitated the use of some viruses as potential therapeutic agents against cancer (Aghi and Martuza, 2005; Parato et al., 2005). Herpes simplex virus (HSV) possesses several unique properties as an oncolytic agent (Aghi and Martuza, 2005). It can infect a broad range of cell types, leading to the replication of new virus and cell death. HSV has a short replication cycle (9 to 18 h) and encodes many non-essential genes that, when deleted, greatly restrict the ability of the virus to replicate in non-dividing normal cells. Because of its large genome, multiple therapeutic genes can be packaged into the genome of oncolytic recombinants.

The use of a replication-conditional strain of HSV-1 as an oncolytic agent was first reported for the treatment of malignant gliomas (Martuza et al., 1991). Since then, various efforts have been made in an attempt to broaden their therapeutic efficacy and increase the replication specificity of the virus in tumor cells. Not surprisingly, however, deletion of genes that impair viral replication in normal cells also leads to a marked decrease in the oncolytic activity of the virus for the targeted tumor cells (Advani et al., 1998; Chung et al., 1999). Currently, no oncolytic viruses that are able to kill only tumor cells while leaving normal cells intact are available. Consequently, the therapeutic doses of existing oncolytic viruses are significantly restricted (Aghi and Martuza, 2005). The availability of an oncolytic virus whose replication can be tightly controlled and adjusted pharmacologically would offer greatly increased safety and therapeutic efficacy. Such a regulatable oncolytic virus would minimize unwanted replication in adjacent and distant tissues as well as undesirable progeny virus overload in the target area after the tumor has been eliminated. This regulatory feature would also allow the oncolytic activity of the virus to be quickly shut down should adverse effects be detected (Aghi and Martuza, 2005; Shen and Nemunaitis, 2005). Work described herein presents a new generation of regulatable fusogenic variant of an oncolytic HSV that is significantly more effective at killing cancer cells than other oncolytic HSV viruses.

SUMMARY OF THE INVENTION

This invention described herein is a novel tetracycline-regulatable HSV-1 ICP0 null mutant based fusogenic oncolytic virus, QREO5-F, whose preferential replication ability in human cancer cells over normal cells is further enhanced through series propagation of virus in human cancer cell lines. It is shown herein that infection of multiple human cancer cell types that include breast cancer, liver cancer, melanoma, pancreatic cancer, ovarian cancer, and several different non-small cell lung cancer cells with QREO5-F lead to 36,000- to $5\times10^7$-fold tetracycline-dependent progeny virus production, while little viral replication and virus-associated cytotoxicity are observed in infected growing as well as growth-arrested normal human fibroblasts. QREO5-F is, thus, a replication-competent oncolytic virus in the presence of tetracycline/doxycycline, and a replication-defective virus in the absence of tetracycline/doxycycline.

Importantly, QREO5-F is highly effective against pre-established CT26.WT colon carcinoma tumor in immune-competent mice. QREO5-F virotherapy led to induction of effective tumor-specific immunity that can prevent the tumor growth following re-challenge with the same type of tumor cells. Collectively, QREO5-F is an excellent candidate with efficacy and safety features suitable for clinical development.

Accordingly, one aspect described herein provides an oncolytic Herpes Simplex Virus (HSV) comprising recombinant DNA, wherein the recombinant DNA comprises: a gene comprising a 5' untranslated region and a HSV-1, or HSV-2, VP5 gene that is operably linked to an VP5 promoter comprising a TATA element; a tetracycline operator sequence positioned between 6 and 24 nucleotides 3' to said TATA element, wherein the VP5 gene lies 3' to said tetracycline operator sequence; a gene sequence encoding tetracycline repressor operably linked to an HSV immediate-early promoter, wherein the gene sequence is located at the ICP0 locus; a variant gene that increases syncytium formation as compared to wild type, wherein the HSV-1, or HSV-2, variant gene is selected from the group consisting of: a glycoprotein K (gK) variant; a glycoprotein B (gB) variant; a UL24 variant; and UL20 gene variant; and a gene sequence encoding a functional ICP34.5 protein, wherein said oncolytic HSV does not encode functional ICP0 and does not contain a ribozyme sequence located in said 5' untranslated region of VP5.

In one embodiment of any aspect, the variant gene is a gK variant gene that encodes an amino acid substitution selected from the group consisting of: an Ala to Thr amino acid substitution corresponding to amino acid 40 of SEQ ID NO:

2; an Ala to "x" amino acid substitution corresponding to amino acid 40 of SEQ ID NO: 2, wherein "x" is any amino acid; an Asp to Asn amino acid substitution corresponding to amino acid 99 of SEQ ID NO: 2; a Leu to Pro amino acid substitution corresponding to amino acid 304 of SEQ ID NO: 2; and an Arg to Leu amino acid substitution corresponding to amino acid 310 of SEQ ID NO: 2.

In one embodiment of any aspect, the tetracycline operator sequence comprises two Op2 repressor binding sites.

In one embodiment of any aspect, the VP5 promoter is an HSV-1 or HSV-2 VP5 promoter.

In one embodiment of any aspect, the HSV immediate-early promoter is an HSV-1 or HSV-2 immediate-early promoter or the HCMV immediate-early promoter.

In one embodiment of any aspect, the HSV immediate-early promoter is selected from the group consisting of: ICP0 promoter, ICP4 promoter, ICP27 promoter, and ICP22 promoter.

In one embodiment of any aspect, the recombinant DNA is part of the HSV-1 genome. In one embodiment of any aspect, the recombinant DNA is part of the HSV-2 genome.

In one embodiment of any aspect, the oncolytic HSV described herein further comprises a pharmaceutically acceptable carrier In one embodiment of any aspect, the oncolytic HSV described herein further encodes at least one polypeptide that can increase the efficacy of the oncolytic HSV to induce an anti-tumor-specific immunity. In one embodiment, the at least one polypeptide encodes a product selected from the group consisting of: interleukin 2 (IL2), interleukin 12 (IL12), interleukin 15 (IL15), an anti-PD-1 antibody or antibody reagent, an anti-PD-L1 antibody or antibody reagent, an anti-OX40 antibody or antibody reagent, a CTLA-4 antibody or antibody reagent, a TIM-3 antibody or antibody reagent, a TIGIT antibody or antibody reagent, a soluble interleukin 10 receptor (IL10R), a fusion polypeptide between a soluble IL10R and IgG-Fc domain, a soluble TGFβ type II receptor (TGFBRII), a fusion polypeptide between a soluble TGFBRII and IgG-Fc domain, an anti-IL10R antibody or antibody reagent, an anti-IL10 antibody or antibody reagent, an anti-TGF-β1 antibody or antibody reagent, and an anti-TGFBRII antibody or antibody reagent.

In one embodiment of any aspect, the oncolytic HSV described herein further encodes fusogenic activity.

Another aspect described herein provides a composition comprising any of the oncolytic HSV described herein. In one embodiment, the composition further comprises a pharmaceutically acceptable carrier.

Another aspect described herein provides a method for treating cancer comprising administering any of the oncolytic HSV described herein or a composition thereof to a subject having cancer.

In one embodiment of any aspect, the cancer is a solid tumor.

In one embodiment of any aspect, the tumor is benign or malignant.

In one embodiment of any aspect, the subject is diagnosed or has been diagnosed as having a carcinoma, a melanoma, a sarcoma, a germ cell tumor, or a blastoma. In one embodiment of any aspect, the subject is diagnosed or has been diagnosed as having non-small-cell lung cancer, breast cancer, brain cancer, colon cancer, prostate cancer, liver cancer, lung cancer, ovarian cancer, skin cancer, head and neck cancer, kidney cancer, and pancreatic cancer.

In one embodiment of any aspect, the cancer is metastatic.

In one embodiment of any aspect, the oncolytic HSV is administered locally, regionally, or systemically. In one embodiment of aspect, the oncolytic HSV is administered directly to the tumor. In one embodiment of any aspect, the regional administration is the hepatic artery infusion, renal artery infusion, or the pulmonary infusion. In one embodiment of any aspect, the systemic administration is the intravenous infusion.

In one embodiment of any aspect, the method further comprises administering an agent that regulates the tet operator. In one embodiment, the agent is doxycycline or tetracycline. In one embodiment of any aspect, the agent is administered locally or systemically. In one embodiment of any aspect, the systemic administration is oral administration.

Another aspect described herein provides an oncolytic Herpes Simplex Virus (HSV) comprising recombinant DNA, wherein the recombinant DNA does not encode functional ICP0 and encodes fusogenic activity.

Definitions

All references cited herein are incorporated by reference in their entirety as though fully set forth.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. Definitions of common terms can be found in Singleton et al., *Dictionary of Microbiology and Molecular Biology* 3$^{rd}$ ed., J. Wiley & Sons New York, NY (2001); March, *Advanced Organic Chemistry Reactions, Mechanisms and Structure* 5$^{th}$ ed., J. Wiley & Sons New York, NY (2001); Michael Richard Green and Joseph Sambrook, *Molecular Cloning: A Laboratory Manual,* 4th ed., *Cold Spring Harbor Laboratory Press*, Cold Spring Harbor, NY, USA (2012); Davis et al., *Basic Methods in Molecular Biology*, Elsevier Science Publishing, Inc., New York, USA (2012); Jon Lorsch (ed.) *Laboratory Methods in Enzymology*: DNA, Elsevier, (2013); Frederick M. Ausubel (ed.), *Current Protocols in Molecular Biology* (CPMB), John Wiley and Sons, (2014); John E. Coligan (ed.), *Current Protocols in Protein Science* (CPPS), John Wiley and Sons, Inc., (2005); and Ethan M Shevach, Warren Strobe, (eds.) *Current Protocols in Immunology* (CPI) (John E. Coligan, ADA M Kruisbeek, David H Margulies, John Wiley and Sons, Inc., (2003); each of which provide one skilled in the art with a general guide to many of the terms used in the present application.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g. cancer) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligan-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The term "operably linked," as used herein, refers to the arrangement of various nucleic acid molecule elements relative to each other such that the elements are functionally connected and are able to interact with each other. Such elements may include, without limitation, a promoter, an enhancer, a polyadenylation sequence, one or more introns and/or exons, and a coding sequence of a gene of interest to be expressed. The nucleic acid sequence elements, when operably linked, can act together to modulate the activity of one another, and ultimately may affect the level of expression of the gene of interest, including any of those encoded by the sequences described above.

The term "vector," as used herein, refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both of which are incorporated herein by reference). Additionally, the techniques described herein and demonstrated in the referenced figures are also instructive with regard to effective vector construction.

The term "oncolytic HSV-1 vector" refers to a genetically engineered HSV-1 virus corresponding to at least a portion of the genome of HSV-1 that is capable of infecting a target cell, replicating, and being packaged into HSV-1 virions. The genetically engineered virus comprises deletions and or mutations and or insertions of nucleic acid that render the virus oncolytic such that the engineered virus replicates in- and kills-tumor cells by oncolytic activity. The virus may be attenuated or non-attenuated. The virus may or may not deliver a transgene—that differs from the HSV viral genome. In one embodiment, the oncolytic HSV-1 vector does not express a transgene to produce a protein foreign to the virus.

The term "promoter," as used herein, refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer or silencer to regulate transcription of the gene of interest. The promoter comprises a DNA regulatory sequence, wherein the regulatory sequence is derived from a gene, which is capable of binding RNA polymerase and initiating transcription of a downstream (3'-direction) coding sequence. A promoter generally comprises a sequence that functions to position the start site for RNA synthesis. The best-known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one can position the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter used, individual elements can function either cooperatively or independently to activate transcription. The promoters described herein may or may not be used in conjunction with an "enhancer," which refers to a cis-acting regulatory sequence involved in the transcriptional activation of a nucleic acid sequence, such as those for the genes, or portions or functional equivalents thereof, listed herein.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages may be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include, the HCMV immediate-early promoter, the beta-lactamase (penicillinase), lactose and tryptophan (trp) promoter systems.

A "gene," or a "sequence which encodes" a particular protein, is a nucleic acid molecule which is transcribed (in the case of DNA) and translated (in the case of mRNA) into a polypeptide in vitro or in vivo when placed under the control of one or more appropriate regulatory sequences. A gene of interest can include, but is no way limited to, cDNA from eukaryotic mRNA, genomic DNA sequences from eukaryotic DNA, and even synthetic DNA sequences. A transcription termination sequence will usually be located 3' to the gene sequence. Typically, a polyadenylation signal is provided to terminate transcription of genes inserted into a recombinant virus.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term "transgene" refers to a particular nucleic acid sequence encoding a polypeptide or a portion of a polypeptide to be expressed in a cell into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been inserted; (3) a nucleic acid sequence that serves to add additional copies of the same (i.e., homologous) or a similar nucleic acid sequence naturally occurring in the cell into which it has been inserted; or (4) a silent naturally occurring or homologous nucleic acid sequence whose expression is induced in the cell into which it has been inserted. A "mutant form" or "modified nucleic acid" or "modified nucleotide" sequence means a sequence that contains one or more nucleotides that are different from the wild-type or naturally occurring sequence, i.e., the mutant nucleic acid sequence contains one or more nucleotide substitutions, deletions, and/or insertions. In some cases, the gene of interest may also include a sequence encoding a leader peptide or signal sequence such that the transgene product may be secreted from the cell.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, nanobodies, humanized antibodies, chimeric antibodies, and the like.

The term "oncolytic activity," as used herein, refers to cytotoxic effects in vitro and/or in vivo exerted on tumor cells without any appreciable or significant deleterious effects to normal cells under the same conditions. The cytotoxic effects under in vitro conditions are detected by various means as known in prior art, for example, by staining with a selective stain for dead cells, by inhibition of DNA synthesis, or by apoptosis. Detection of the cytotoxic effects under in vivo conditions is performed by methods known in the art.

A "biologically active" portion of a molecule, as used herein, refers to a portion of a larger molecule that can perform a similar function as the larger molecule. Merely by way of non-limiting example, a biologically active portion of a promoter is any portion of a promoter that retains the ability to influence gene expression, even if only slightly. Similarly, a biologically active portion of a protein is any portion of a protein which retains the ability to perform one or more biological functions of the full-length protein (e.g. binding with another molecule, phosphorylation, etc.), even if only slightly.

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

With the aforementioned preliminary descriptions and definitions in mind, additional background is provided herein below to provide context for the genesis and development of the inventive vectors, compositions and methods described herein.

BRIEF DESCRIPTION OF THE DRAWINGS

Exemplary embodiments are illustrated in the referenced figures. It is intended that the embodiments and figures disclosed herein are to be considered illustrative rather than restrictive.

(FIG. 2A) Vero cells were seeded at $5\times10^5$ cells per 60 mm dish and (FIG. 2B) H1299 cells were seeded at $7.5\times10^5$ cells per 60 mm dish. At 48 h post-seeding, triplicate dishes of Vero cells and H1299 cells were infected with QREO5 and KTR27 at an MOI of 1 PFU/cell and 0.25 PFU/cell, respectively, in a volume of 0.5 ml. The number of PFU used herein was based on their titers determined on U2OS cells monolayers in the presence of tetracycline. After 1.5 h of incubation at 37° C., the inocula were removed and the cells were washed twice with acid-glycine saline (to remove membrane-bound extracellular virions) and then twice by DMEM. Infections were carried out in the absence or presence of tetracycline at 2.5 ug/ml. Infected cells were harvested at 72 h post-infection. Viral titers were determined on U2OS monolayers in the presence of tetracycline. Viral titers are expressed as means±standard deviation. Numbers located above the brackets indicate the fold difference in viral yield between the indicated infections.

(FIG. 7A) Human cancer cells MDA-MB 231, Panc-1, SK-Mel-28, SNU-398, and SK-OV-3 were seeded at 1.5×

$10^6$, $5\times10^5$, $7.5\times10^5$, $1.5\times10^6$ and $1.5\times10^6$ cells per 60 mm dish, respectively. At 48 h post-seeding, triplicate dishes were infected with QREO5-F at MOIs of 1 PFU/cell, 0.25 PFU/cell, 3 PFU/cell, 1 PFU/cell, and 0.5 PFU/cell, respectively. After 1.5 h of incubation at 37° C., the inocula were removed and the cells were washed twice with acid-glycine saline and then twice by DMEM. Infections were then carried out in the absence or presence of tetracycline at 2.5 μg/ml. Infected cells were harvested at 48, 72, 48, 48, and 72 h post-infection, respectively, and viral titers were determined on U2OS monolayers in the presence of tetracycline. (FIG. 7B) H1299, A549, and H1975 cells were seeded at $7.5\times10^5$, $1\times10^6$ and $7.5\times10^5$ cells per 60 mm dish, respectively. At 48 h post-seeding, triplicate dishes were infected with QREO5-F at MOIs of 0.25 PFU/cell, 0.1 PFU/cell, and 0.25 PFU/cell, respectively. After 1.5 h of incubation at 37° C., the inocula were removed and the cells were washed twice with acid-glycine saline and then twice by DMEM. Infections were then carried out in the absence or presence of tetracycline at 2.5 μg/ml. Infected cells were harvested at 48, 72 and 48 h post-infection, respectively, and viral titers were determined on U2OS monolayers in the presence of tetracycline. Numbers located above the brackets indicate the fold difference in viral yield between the indicated conditions.

(FIG. 8A) Triplicate dishes of infected cells were harvested at 48 h post-infection and viral titers were determined on U2OS monolayers in the presence of tetracycline. (FIG. 8B) Mock-infected and infected cells in the presence of tetracycline in triplicate dishes were harvested at 72 h post-infection. Viable cells were counted by trypan blue exclusion and graphed as a percentage of viable cells in the mock-infected controls, expressed as means±standard deviation. (FIG. 8C) Selective lysis of H1299 cells. Images cells infected with QREO5-F in the absence and presence of tetracycline, photographed at 72 h post-infection.

(FIG. 10A) Four QREO5-F cured mice and 5 naïve age-match female BALB/c mice were injected s.c. with $5\times10^5$ CT26.WT cells into the middle section between the rear left and right flanks. Tumor volumes were quantified every third day by a caliper. (FIG. 10B) Representative images of naïve mouse and QREO5-F-cured mouse.

DESCRIPTION OF THE INVENTION

Figure 1:
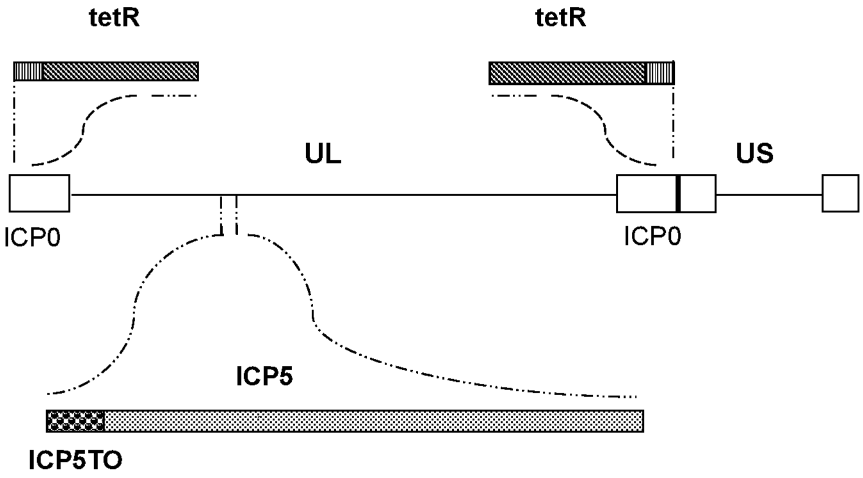
FIG. 1 shows a schematic diagram of the genome of HSV-1 recombinant QREO5. UL and US represent the unique long and unique short regions of the HSV-1 genome, respectively, which are flanked by their corresponding inverted repeat regions (open boxes). The replacement of the ICP0 coding sequences with DNA sequences encoding tetR (black box) and intron II of the rabbit β-globin gene (vertical line box) flanked by ICP0 sequences are shown above the diagram of the HSV-1 genome. An expanded DNA fragment containing the ICP5 open reading frame (grey box) under the control of the tetO-bearing HSV-1 ICP5 promoter (cross-hatched box).

Oncolytic viruses are genetically modified viruses that preferentially replicate in host cancer cells, leading to the production of new viruses and ultimately, cell death. Herpes simplex virus (HSV) possesses several unique properties as an oncolytic agent. It can infect a broad range of cell types and has a short replication cycle (9 to 18 h). The use of a replication-conditional strain of HSV-1 as an oncolytic agent was first reported for the treatment of malignant gliomas. Since then, various efforts have been made in an attempt to broaden their therapeutic efficacy and increase the replication specificity of the virus in tumor cells. Not surprisingly, however, deletion of genes that impair viral replication in normal cells also leads to a marked decrease in the oncolytic activity of the virus for the targeted tumor cells. Currently, no oncolytic viruses that are able to kill only tumor cells while leaving normal cells intact are available. Consequently, the therapeutic doses of existing oncolytic viruses are significantly restricted. The availability of an oncolytic virus whose replication can be tightly controlled and adjusted pharmacologically would offer greatly increased safety and therapeutic efficacy. Such a regulatable oncolytic virus would minimize the risk of uncontrolled replication in adjacent and distant tissues as well as undesirable progeny virus overload in the target area after the tumor has been eliminated. This regulatory feature would also allow the oncolytic activity of the virus to be quickly shut down should adverse effects be detected.

HSV replicates in epithelial cells and fibroblasts and establishes life-long latent infection in neuronal cell bodies within the sensory ganglia of infected individuals. During productive infection, HSV genes fall into three major classes based on the temporal order of their expression: immediate-early (IE), early (E), and late (L) (Roizman, 2001). The HSV-1 viral proteins directly relevant to the current invention are immediate-early regulatory protein, ICP0, and the viral major capsid protein ICP5 or VP5. Although not essential for productive infection, ICP0 is required for efficient viral gene expression and replication at low multiplicities of infection in normal cells and efficient reactivation from latent infection (Cai and Schaffer, 1989; Leib et al., 1989; Yao and Schaffer, 1995). ICP0 is needed to stimulate translation of viral mRNA in quiescent cells (Walsh and Mohr, 2004) and plays a fundamental role in counteracting host innate antiviral response to HSV infection. In brief, it prevents an IFN-induced nuclear block to viral transcription, down regulates TLR2/TLR9-induced inflammatory cytokine response to viral infection, suppresses TNF-α mediated activation of NF-κB signaling pathway, and interferes with DNA damage response to viral infection (Lanfranca et al., 2014). Given that tumor cells are impaired in various cellular pathways, such as DNA repair, interferon signaling, and translation regulation (Barber, 2015; Critchley-Thorne et al., 2009; Kastan and Bartek, 2004; Li and Chen, 2018;

Mohr, 2005; Zitvogel et al., 2015), it is not surprising that ICP0 deletion mutants replicate much more efficiently in cancer cells than in normal cells, in particular, quiescent cells and terminally differentiated cells. The oncolytic potential of ICP0 mutants was first illustrated by Yao and Schaffer (Yao and Schaffer, 1995), who showed that the plaque-forming efficiency of an ICP0 null mutant in human osteoscarcoma cells (U2OS) is 100- to 200-fold higher than in non-tumorigenic African green monkey kidney cells (Vero). It has been recently shown the defect in stimulator of interferon genes (STING) signaling pathway in U2OS cells leads to its demonstrated ability to efficiently support the growth of ICP0 null mutant (Deschamps and Kalamvoki, 2017).

Using the T-RExTM gene switch technology (Thermo Fisher/Invitrogen, Carlsbad, CA) invented by Dr. Feng Yao and a self-cleaving ribozyme, the first regulatable oncolytic virus, KTR27 (U.S. Pat. No. 8,236,941, which is incorporated herein by reference in its entirety), in which the HSV-1 ICP0 gene is replaced by DNA sequence encoding tetracycline repressor (tetR) was created, while the essential HSV-1 ICP27 gene is controlled by the tetO-bearing ICP27 promoter and a self-cleaving ribozyme in the 5' untranslated region of the ICP27 coding sequence. Recent DNA sequence analyses of a KTR27-derived fusogenic virus, named KTR27-F, indicates that in addition to the deletion of both copies of ICP0 gene, both copies of HSV-1 ICP34.5 gene are also deleted from the said KTR27-F virus. Moreover, PCR analyses of KTR27 viral DNA with the ICP34.5 gene-specific primers has revealed that like KTR27-F, KTR27 does not encode ICP0 gene and ICP34.5 gene. ICP34.5 gene is located 5' to the ICP0 gene in the inverted repeat region of HSV-1 genome that flanks the unique long sequence of HSV-1 genome. Various HSV-1 onclytic viruses are based on the deletion of ICP34.5 gene (Aghi and Martuza, 2005; Kaur et al., 2012; Lawler et al., 2017), including the recently FDA-approved talimogene laherparepvec (T-VEC) for treatment of advanced-stage melanoma (Rehman et al., 2016).

Building on the tet-dependent viral replication and onco-selectivity profiles of KTR27 and the notion that the self-cleaving ribozyme employed in construction of KTR27 for achieving higher degree of tet-dependent viral replication significantly restricts viral replication in cancer cells because of less than optimal expression of ICP27, a new ICP0 null mutant-based tetR-expressing oncolytic virus QREO5 that encodes the late HSV-1 major capsid protein VP5 under the control of the tetO-containing VP5 promoter was recently developed. Because VP5 is a late viral gene product, whose expression is dependent on the expression of viral IE genes, it was hypothesized that the late kinetics of the tetO-bearing VP5 promoter would allow for more stringent control of VP5 expression than that of ICP27 under the control of the tetO-bearing ICP27 promoter by tetR expressed from the IE ICP0 promoter. Indeed, QREO5 exhibits significantly superior tet-dependent viral replication than KTR27 in infected H1299 cells and Vero cells. Moreover, because the QREO5 genome contains no self-cleaving ribozyme and encodes wild-type ICP34.5 gene, it replicates 100- and 450-fold more efficiently than KTR27 in Vero cells and H1299 cells, respectively.

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state. HSV-1 contains a double-stranded, linear DNA genome, about 152 kilobases in length, which has been completely sequenced by McGeoch (McGeoch et al., J. Gen. Virol. 69: 1531 (1988); McGeoch et al., Nucleic Acids Res 14: 1727 (1986); McGeoch et al., J. Mol. Biol. 181: 1 (1985); Perry and McGeoch, J. Gen. Virol. 69:2831 (1988); Szpara M L et al., J Virol. 2010, 84:5303; Macdonald S J et al., J Virol. 2012, 86:6371). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

Accordingly, described herein is an oncolytic Herpes Simplex Virus (HSV) comprising recombinant DNA, wherein the recombinant DNA comprises: a gene comprising a 5' untranslated region and a HSV-1, or HSV-2, VP5 gene that is operably linked to an VP5 promoter comprising a TATA element; a tetracycline operator sequence positioned between 6 and 24 nucleotides 3' to said TATA element, wherein the VP5 gene lies 3' to said tetracycline operator sequence; a gene sequence encoding tetracycline repressor operably linked to an HSV immediate-early promoter, wherein the gene sequence is located at the ICP0 locus; a variant gene that increases syncytium formation as compared to wild type, wherein the HSV-1, or HSV-2, variant gene is selected from the group consisting of: a glycoprotein K (gK) variant; a glycoprotein B (gB) variant; a UL24 variant; and UL20 gene variant; and a gene sequence encoding a functional ICP34.5 protein, wherein said oncolytic HSV does not encode functional ICP0 and does not contain a ribozyme sequence located in said 5' untranslated region of VP5. In one embodiment, the recombinant DNA is derived from the HSV-1 genome. In an alternative embodiment, the recombinant DNA is derived from the HSV-2 genome. In one embodiment, the genome of the HSV comprising recombinant DNA consists of, consists essentially of, or comprises the sequence of SEQ ID NO. 1.

A distinguishing feature of the oncolytic virus described herein is that the viral genome expression a gene sequence that encodes functional ICP34.5. Infected cell protein 34.5 (ICP34.5) is a protein (e.g., a gene product) expressed by the γ34.5 gene in viruses, such as the herpes simplex virus. ICP34.5 is one of HSV neurovirulence factors (Chou J, Kern E R, Whitley R J, and Roizman B, Science, 1990). One of the functions of ICP34.5 is to block the cellar stress response to a viral infection, i.e., blocking the double-stranded RNA-dependent protein kinase PKR-mediated antiviral response (Agarwalla, P. K., et al. Method in Mol. Bio., 2012).

The oncolytic virus described herein is a ICP0 null virus. Infected cell polypeptide 0 (ICP0) is a protein encoded by the HSV-1 α0 gene. ICP0 is generated during the immediate-early phase of viral gene expression. ICP0 is synthesized and transported to the nucleus of the infected host cell, where it promotes transcription from viral genes, disrupts nuclear and cytoplasmic cellular structures, such as the microtubule network, and alters the expression of host genes. One skilled in the art can determine if the ICP0 gene product has been deleted or if the virus does not express functional forms of this gene product using PCR-based assays to detect the presence of the gene in the viral genome or the expression of the gene products, or using functional assays to assess their function, respectively.

In one embodiment, the gene that encodes these gene products contain a mutation, for example, an inactivating mutation, that inhibits proper expression of the gene product. For example, the gene may encode a mutation in the gene product that inhibits proper folding, expression, function, etc. of the gene product. As used herein, the term "inactivating mutation" is intended to broadly mean a mutation or alteration to a gene wherein the expression of that gene is significantly decreased, or wherein the gene product is rendered nonfunctional, or its ability to function is significantly decreased. The term "gene" encompasses both the regions coding the gene product as well as regulatory regions for that gene, such as a promoter or enhancer, unless otherwise indicated.

Ways to achieve such alterations include: (a) any method to disrupt the expression of the product of the gene or (b) any method to render the expressed gene nonfunctional. Numerous methods to disrupt the expression of a gene are known, including the alterations of the coding region of the gene, or its promoter sequence, by insertions, deletions and/or base changes. (See, Roizman, B. and Jenkins, F. J., *Science* 229: 1208-1214 (1985)).

An essential feature of the DNA of the present invention is the presence of a gene needed for virus replication that is operably linked to a promoter having a TATA element. A tet operator sequence is located between 6 and 24 nucleotides 3' to the last nucleotide in the TATA element of the promoter and 5' to the gene. The strength with which the tet repressor binds to the operator sequence is enhanced by using a form of operator which contains two op2 repressor binding sites (each such site having the nucleotide sequence: TCCCTATCAGTGATAGAGA (SEQ ID NO: 8)) linked by a sequence of 2-20, preferably 1-3 or 10-13, nucleotides. When repressor is bound to this operator, very little or no transcription of the associated gene will occur. If DNA with these characteristics is present in a cell that also expresses the tetracycline repressor, transcription of the gene will be blocked by the repressor binding to the operator and replication of the virus will not occur. However, if tetracycline, for example, is introduced, it will bind to the repressor, cause it to dissociate from the operator, and virus replication will proceed.

During productive infection, HSV gene expression falls into three major classes based on the temporal order of expression: immediate-early (α), early (β), and late (γ), with late genes being further divided into two groups, γ1 and γ2. The expression of immediate-early genes does not require de novo viral protein synthesis and is activated by the virion-associated protein VP16 together with cellular transcription factors when the viral DNA enters the nucleus. The protein products of the immediate-early genes are designated infected cell polypeptides ICP0, ICP4, ICP22, ICP27, and ICP47 and it is the promoters of these genes that are preferably used in directing the expression of tet repressor (tetR). The expression of a gene needed for virus replication is under the control of the tetO-containing promoters and these essential genes may be immediate-early, early or late genes, e.g., ICP4, ICP27, ICP8, UL9, gD and VP5. In one embodiment, the tetR has the sequence of SEQ ID NO: 9.

ICP0 plays a major role in enhancing the reactivation of HSV from latency and confers a significant growth advantage on the virus at low multiplicities of infection. ICP4 is the major transcriptional regulatory protein of HSV-1, which activates the expression of viral early and late genes. ICP27 is essential for productive viral infection and is required for efficient viral DNA replication and the optimal expression of subset of viral β genes and γ1 genes as well as viral γ2 genes. The function of ICP47 during HSV infection appears to be to down-regulate the expression of the major histocompatibility complex (MHC) class I on the surface of infected cells.

The recombinant DNA may also include at least one, and preferably at least two, sequences coding for the tetracycline repressor with expression of these sequences being under the control of an immediate early promoter, preferably ICP0 or ICP4. The sequence for the HSV ICP0 and ICP4 promoters and for the genes whose regulation they endogenously control are well known in the art (Perry, et al., J. Gen. Virol. 67:2365-2380 (1986); McGeoch et al., J. Gen. Virol. 72:3057-3075 (1991); McGeoch et al., Nucl. Acid Res. 14:1727-1745 (1986)) and procedures for making viral vectors containing these elements have been previously described (see US published application 2005-0266564).

These promoters are not only very active in promoting gene expression, they are also specifically induced by VP16, a transactivator released when HSV-1 infects a cell. Thus, transcription from ICP0 promoter is particularly high when repressor is most needed to shut down virus replication. Once appropriate DNA constructs have been produced, they may be incorporated into HSV-1 virus using methods that are well known in the art. One appropriate procedure is described in US 2005-0266564 but other methods known in the art may also be employed.

In various embodiments, the variant gene comprises at least one amino acid change that deviates from the wild-type sequence of the gene. In one embodiment, an oncolytic HSV described herein can contain two or more amino acid substitutions in at least one variant gene. The at least two amino acid substitutions can be found in the same gene, for example, the gK variant gene contains at least two amino acid substitutions. Alternatively, the at least two amino acid substitutions can be found in the at least two different genes, for example, the gK variant gene and the UL24 variant gene each contains at least one amino acid substitutions.

SEQ ID NO: 2 is the amino acid sequence encoding gK (strain KOS).

```
                                             (SEQ ID NO: 2)
MLAVRSLQHLSTVVLITAYGLVLVWYTVFGASPLHRCIYAVRPTGTNNDT

ALVWMKMNQTLLFLGAPTHPPNGGWRNHAHICYANLIAGRVVPFQVPPDA

TNRRIMNVHEAVNCLETLWYTRVRLVVVGWFLYLAFVALHQRRCMFGVVS

PAHKMVAPATYLLNYAGRIVSSVFLQYPYTKITRLLCELSVQRQNLVQLF

ETDPVTFLYHRPAIGVIVGCELMLRFVAVGLIVGTAFISRGACAITYPLF

LTITTWCFVSTIGLTELYCILRRGPAPKNADKAAAPGRSKGLSGVCGRCC

SIILSGIAMRLCYIAVVAGVVLVALHYEQEIQRRLFDV
```

Another distinguishing feature of the oncolytic virus described herein is that the viral genome sequence does not contain a ribozyme sequence, for example, at the 5' untranslated region of VP5. A ribozyme is an RNA molecule that is capable of catalyzing a biochemical reaction in a similar manner as a protein enzyme. Ribozymes are further described in, e.g., Yen et al., Nature 431:471-476, 2004, the contents of which are incorporated herein by reference in its entirety.

In one embodiment, the oncolytic HSV described herein further comprises at least one polypeptide that encodes a product (e.g., a protein, a gene, a gene product, or an antibody or antibody reagent) that can increase the efficacy of the oncolytic HSV to induce an anti-tumor-specific immunity. Exemplary products include, but are not limited to, interleukin 2 (IL2), interleukin 12 (IL12), interleukin 15 (IL15), an anti-PD-1 antibody or antibody reagent, an anti-PD-L1 antibody or antibody reagent, an anti-OX40 antibody or antibody reagent, a CTLA-4 antibody or antibody reagent, a TIM-3 antibody or antibody reagent, a TIGIT antibody or antibody reagent, a soluble interleukin 10 receptor (IL10R), a fusion polypeptide between a soluble IL10R and IgG-Fc domain, a soluble TGF-β type II receptor (TGFBRII), a fusion polypeptide between a soluble TGFBRII and IgG-Fc domain, an anti-IL10R antibody or antibody reagent, an anti-IL10 antibody or antibody reagent, an anti-TGF-β1 antibody or antibody reagent, and an anti-TGFBRII antibody or antibody reagent. In one embodiment, the product is a fragment of IL-2, IL-12, or IL-15, that comprises the same functionality of IL-2, IL-12, or IL-15, as described herein below. One skilled in the art can determine if an anti-tumor specific immunity is induced using stand techniques in the art, which are further described in, for example, Clay, T M, et al. Clinical Cancer Research (2001); Malyguine, A, et al. J Transl Med (2004); or Macchia I, et al. BioMed Research International (2013), each of which are incorporated herein by reference in their entireties.

Interleukin-2 (IL-2) is an interleukin, a type of cytokine signaling molecule in the immune system. IL-2 regulates the activities of white blood cells (for example, leukocytes and lymphocytes) that are responsible for immunity. IL-2 is part of the body's natural response to microbial infection, and in discriminating between foreign "non-self" and "self". It mediates its effects by binding to IL-2 receptors, which are expressed by lymphocytes. Sequences for IL-2, also known TCGF and lympokine, are known for a number of species, e.g., human IL-2 (NCBI Gene ID: 3558) polypeptide (e.g., NCBI Ref Seq NP_000577.2) and mRNA (e.g., NCBI Ref Seq NM_000586.3). IL-2 can refer to human IL-2, including naturally occurring variants, molecules, and alleles thereof. IL-2 refers to the mammalian IL-2 of, e.g., mouse, rat, rabbit, dog, cat, cow, horse, pig, and the like. The nucleic sequence of SEQ ID NO: 5 comprises the nucleic sequence which encodes IL-2.

SEQ ID NO: 5 is the nucleotide sequence encoding IL-2.

```
                                                         (SEQ ID NO: 5)
                                                                  atgta
 61 caggatgcaa ctcctgtctt gcattgcact aagtcttgca cttgtcacaa acagtgcacc
121 tacttcaagt tctacaaaga aaacacagct acaactggag catttactgc tggatttaca
181 gatgattttg aatggaatta ataattacaa gaatcccaaa ctcaccagga tgctcacatt
241 taagttttac atgcccaaga aggccacaga actgaaacat cttcagtgtc tagaagaaga
301 actcaaacct ctggaggaag tgctaaattt agctcaaagc aaaaactttc acttaagacc
361 cagggactta atcagcaata tcaacgtaat agttctggaa ctaaagggat ctgaaacaac
421 attcatgtgt gaatatgctg atgagacagc aaccattgta gaatttctga acagatggat
481 taccttttgt caaagcatca tctcaacact gacttgataa
```

Interleukin-12 (IL-12) is an interleukin naturally produced by dendritic cells, macrophages, neutrophils, and human B-lymphoblastoid cells (NC-37) in response to antigenic stimulation. IL-12 is involved in the differentiation of naive T cells into Th1 cells. It is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ. Sequences for IL-12a, also known P35, CLMF, NFSK, and KSF1, are known for a number of species, e.g., human IL-12a (NCBI Gene ID: 3592) polypeptide (e.g., NCBI Ref Seq NP_000873.2) and mRNA (e.g., NCBI Ref Seq NM 000882.3). IL-12 can refer to human IL-12, including naturally occurring variants, molecules, and alleles thereof. IL-12 refers to the mammalian IL-12 of, e.g., mouse, rat, rabbit, dog, cat, cow, horse, pig, and the like. The nucleic sequence of SEQ ID NO:6 comprises the nucleic sequence which encodes IL-12a.

SEQ ID NO: 6 is the nucleotide sequence encoding IL-12a.

```
                                                         (SEQ ID NO: 6)
                                                  aatgtggccc cctgggtcag
241 cctcccagcc accgccctca cctgccgcgg ccacaggtct gcatccagcg gctcgccctg
301 tgtccctgca gtgccggctc agcatgtgtc cagcgcgcag cctcctcctt gtggctaccc
361 tggtcctcct ggaccacctc agtttggcca gaaacctccc cgtggccact ccagacccag
421 gaatgttccc atgccttcac cactcccaaa acctgctgag ggccgtcagc aacatgctcc
```

-continued

```
481 agaaggccag acaaactcta gaattttacc cttgcacttc tgaagagatt gatcatgaag
541 atatcacaaa agataaaacc agcacagtgg aggcctgttt accattggaa ttaaccaaga
601 atgagagttg cctaaattcc agagagacct ctttcataac taatgggagt tgcctggcct
661 ccagaaagac ctcttttatg atggccctgt gccttagtag tatttatgaa gacttgaaga
721 tgtaccaggt ggagttcaag accatgaatg caaagcttct gatggatcct aagaggcaga
781 tctttctaga tcaaaacatg ctggcagtta ttgatgagct gatgcaggcc ctgaatttca
841 acagtgagac tgtgccacaa aaatcctccc ttgaagaacc ggatttttat aaaactaaaa
901 tcaagctctg catacttctt catgctttca gaattcgggc agtgactatt gatagagtga
961 tgagctatct gaatgcttcc taa
```

Interleukin-15 (IL-15) is an interleukin secreted by mononuclear phagocytes (and some other cells) following infection by virus(es). This cytokine induces cell proliferation of natural killer cells; cells of the innate immune system whose principal role is to kill virally infected cells. Sequences for IL-15 are known for a number of species, e.g., human IL-15 (NCBI Gene ID: 3600) polypeptide (e.g., NCBI Ref Seq NP_000585.4) and mRNA (e.g., NCBI Ref Seq NM_000576.1). IL-15 can refer to human IL-15, including naturally occurring variants, molecules, and alleles thereof. IL-15 refers to the mammalian IL-15 of, e.g., mouse, rat, rabbit, dog, cat, cow, horse, pig, and the like. The nucleic sequence of SEQ ID NO: 7 comprises the nucleic sequence which encodes IL-15.

SEQ ID NO: 7 is the nucleotide sequence encoding IL-15.

```
                                                          (SEQ ID NO: 7)
                atgaga atttcgaaac cacatttgag aagtatttcc atccagtgct
421 acttgtgttt acttctaaac agtcattttc taactgaagc tggcattcat gtcttcattt
481 tgggctgttt cagtgcaggg cttcctaaaa cagaagccaa ctgggtgaat gtaataagtg
541 atttgaaaaa aattgaagat cttattcaat ctatgcatat tgatgctact ttatatacgg
601 aaagtgatgt tcaccccagt tgcaaagtaa cagcaatgaa gtgctttctc ttggagttac
661 aagttatttc acttgagtcc ggagatgcaa gtattcatga tacagtagaa aatctgatca
721 tcctagcaaa caacagtttg tcttctaatg ggaatgtaac agaatctgga tgcaaagaat
781 gtgaggaact ggaggaaaaa aatattaaag aatttttgca gagttttgta catattgtcc
841 aaatgttcat caacacttct tga
```

Interleukin 10 receptor (IL10R), either soluble or wild-type, has been shown to mediate the immunosuppressive signal of interleukin 10, resulting in the inhibition of the synthesis of proinflammatory cytokines. This receptor is reported to promote survival of progenitor myeloid cells through the insulin receptor substrate-2/PI 3-kinase/AKT pathway. Activation of IL10R leads to tyrosine phosphorylation of JAK1 and TYK2 kinases. Two transcript variants, one protein-coding and the other not protein-coding, have been found for this gene. Sequences for IL10R are known for a number of species, e.g., human IL10R (NCBI Gene ID: 3587) polypeptide (e.g., NCBI Ref Seq NP_001549.2) and mRNA (e.g., NCBI Ref Seq NM_001558.3). IL10R can refer to human IL10R, including naturally occurring variants, molecules, and alleles thereof. IL10R refers to the mammalian IL10R of, e.g., mouse, rat, rabbit, dog, cat, cow, horse, pig, and the like. The nucleic sequence of SEQ ID NO: 3 comprises the nucleic sequence which encodes IL10R.

SEQ ID NO: 3 is the nucleotide sequence encoding IL10R.

```
                                                   (SEQ ID NO: 3)
                         atg ctgccgtgcc tcgtagtgct gctggcggcg ctcctcagcc

 121 tccgtcttgg ctcagacgct catgggacag agctgcccag ccctccgtct gtgtggtttg

 181 aagcagaatt tttccaccac atcctccact ggacacccat cccaaatcag tctgaaagta

 241 cctgctatga agtggcgctc ctgaggtatg gaatagagtc ctggaactcc atctccaact

 301 gtagccagac cctgtcctat gaccttaccg cagtgacctt ggacctgtac cacagcaatg

 361 gctaccgggc cagagtgcgg gctgtggacg gcagccggca ctccaactgg accgtcacca

 421 acacccgctt ctctgtggat gaagtgactc tgacagttgg cagtgtgaac ctagagatcc

 481 acaatggctt catcctcggg aagattcagc tacccaggcc caagatggcc cccgcaaatg

 541 acacatatga aagcatcttc agtcacttcc gagagtatga gattgccatt cgcaaggtgc

 601 cgggaaactt cacgttcaca cacaagaaag taaaacatga aaacttcagc ctcctaacct

 661 ctggagaagt gggagagttc tgtgtccagg tgaaaccatc tgtcgcttcc cgaagtaaca

 721 aggggatgtg gtctaaagag gagtgcatct ccctcaccag gcagtatttc accgtgacca

 781 acgtcatcat cttctttgcc tttgtcctgc tgctctccgg agccctcgcc tactgcctgg

 841 ccctccagct gtatgtgcgg cgccgaaaga agctacccag tgtcctgctc ttcaagaagc

 901 ccagcccctt catcttcatc agccagcgtc cctccccaga gacccaagac accatccacc

 961 cgcttgatga ggaggccttt ttgaaggtgt ccccagagct gaagaacttg gacctgcacg

1021 gcagcacaga cagtggcttt ggcagcacca agccatccct gcagactgaa gagccccagt

1081 tcctcctccc tgaccctcac ccccaggctg acagaacgct gggaaacagg gagcccccTg

1141 tgctggggga cagctgcagt agtggcagca gcaatagcac agacagcggg atctgcctgc

1201 aggagcccag cctgagcccc agcacagggc ccacctggga gcaacaggtg gggagcaaca

1261 gcaggggcca ggatgacagt ggcattgact tagttcaaaa ctctgagggc cgggctgggg

1321 acacacaggg tggctcggcc ttgggccacc acagtccccc ggagcctgag gtgcctgggg

1381 aagaagaccc agctgctgtg gcattccagg gttacctgag gcagaccaga tgtgctgaag

1441 agaaggcaac caagacaggc tgcctggagg aagaatcgcc cttgacagat ggccttggcc

1501 ccaaattcgg gagatgcctg gttgatgagg caggcttgca tccaccagcc ctggccaagg

1561 gctatttgaa acaggatcct ctagaaatga ctctggcttc ctcaggggcc ccaacgggac

1621 agtggaacca gcccactgag gaatggtcac tcctggcctt gagcagctgc agtgacctgg

1681 gaatatctga ctggagcttt gcccatgacc ttgcccctct aggctgtgtg gcagccccag

1741 gtggtctcct gggcagcttt aactcagacc tggtcaccct gcccctcatc tctagcctgc

1801 agtcaagtga gtga
```

Transforming growth factor beta receptor II (TGFBRII), either soluble or wild type form, is protein encoded by this gene forms a heteromeric complex with type II TGF-beta receptors when bound to TGF-beta, transducing the TGF-beta signal from the cell surface to the cytoplasm. Sequences for TGFBRII are known for a number of species, e.g., human TGFBRII (NCBI Gene ID: 7048) polypeptide (e.g., NCBI Ref Seq NP_001020018.1) and mRNA (e.g., NCBI Ref Seq NM_001024847.2). TGFBRII can refer to human TGFBRII, including naturally occurring variants, molecules, and alleles thereof. TGFBRII refers to the mammalian TGFBRII of, e.g., mouse, rat, rabbit, dog, cat, cow, horse, pig, and the like. The nucleic sequence of SEQ ID NO: 4 comprises the nucleic sequence which encodes TGFBRII.

SEQ ID NO: 4 is the nucleotide sequence encoding TGFBRII.

```
                                        (SEQ ID NO: 4)
             ATGGGTCG GGGGCTGCTC AGGGGCCTGT GGCCGCTGCA

 421 CATCGTCCTG TGGACGCGTA TCGCCAGCAC GATCCCACCG CACGTTCAGA AGTCGGATGT

 481 GGAAATGGAG GCCCAGAAAG ATGAAATCAT CTGCCCCAGC TGTAATAGGA CTGCCCATCC

 541 ACTGAGACAT ATTAATAACG ACATGATAGT CACTGACAAC AACGGTGCAG TCAAGTTTCC

 601 ACAACTGTGT AAATTTTGTG ATGTGAGATT TTCCACCTGT GACAACCAGA AATCCTGCAT

 661 GAGCAACTGC AGCATCACCT CCATCTGTGA GAAGCCACAG GAAGTCTGTG TGGCTGTATG

 721 GAGAAAGAAT GACGAGAACA TAACACTAGA GACAGTTTGC CATGACCCCA AGCTCCCCTA

 781 CCATGACTTT ATTCTGGAAG ATGCTGCTTC TCCAAAGTGC ATTATGAAGG AAAAAAAAAA

 841 GCCTGGTGAG ACTTTCTTCA TGTGTTCCTG TAGCTCTGAT GAGTGCAATG ACAACATCAT

 901 CTTCTCAGAA GAATATAACA CCAGCAATCC TGACTTGTTG CTAGTCATAT TTCAAGTGAC

 961 AGGCATCAGC CTCCTGCCAC CACTGGGAGT TGCCATATCT GTCATCATCA TCTTCTACTG

1021 CTACCGCGTT AACCGGCAGC AGAAGCTGAG TTCAACCTGG GAAACCGGCA AGACGCGGAA

1081 GCTCATGGAG TTCAGCGAGC ACTGTGCCAT CATCCTGGAA GATGACCGCT CTGACATCAG

1141 CTCCACGTGT GCCAACAACA TCAACCACAA CACAGAGCTG CTGCCCATTG AGCTGGACAC

1201 CCTGGTGGGG AAAGGTCGCT TTGCTGAGGT CTATAAGGCC AAGCTGAAGC AGAACACTTC

1261 AGAGCAGTTT GAGACAGTGG CAGTCAAGAT CTTTCCCTAT GAGGAGTATG CCTCTTGGAA

1321 GACAGAGAAG GACATCTTCT CAGACATCAA TCTGAAGCAT GAGAACATAC TCCAGTTCCT

1381 GACGGCTGAG GAGCGGAAGA CGGAGTTGGG GAAACAATAC TGGCTGATCA CCGCCTTCCA

1441 CGCCAAGGGC AACCTACAGG AGTACCTGAC GCGGCATGTC ATCAGCTGGG AGGACCTGCG

1501 CAAGCTGGGC AGCTCCCTCG CCCGGGGGAT TGCTCACCTC CACAGTGATC ACACTCCATG

1561 TGGGAGGCCC AAGATGCCCA TCGTGCACAG GGACCTCAAG AGCTCCAATA TCCTCGTGAA

1621 GAACGACCTA ACCTGCTGCC TGTGTGACTT TGGGCTTTCC CTGCGTCTGG ACCCTACTCT

1681 GTCTGTGGAT GACCTGGCTA ACAGTGGGCA GGTGGGAACT GCAAGATACA TGGCTCCAGA

1741 AGTCCTAGAA TCCAGGATGA ATTTGGAGAA TGTTGAGTCC TTCAAGCAGA CCGATGTCTA

1801 CTCCATGGCT CTGGTGCTCT GGGAAATGAC ATCTCGCTGT AATGCAGTGG GAGAAGTAAA

1861 AGATTATGAG CCTCCATTTG GTTCCAAGGT GCGGGAGCAC CCCTGTGTCG AAAGCATGAA

1921 GGACAACGTG TTGAGAGATC GAGGGCGACC AGAAATTCCC AGCTTCTGGC TCAACCACCA

1981 GGGCATCCAG ATGGTGTGTG AGACGTTGAC TGAGTGCTGG GACCACGACC CAGAGGCCCG

2041 TCTCACAGCC CAGTGTGTGG CAGAACGCTT CAGTGAGCTG GAGCATCTGG ACAGGCTCTC

2101 GGGGAGGAGC TGCTCGGAGG AGAAGATTCC TGAAGACGGC TCCCTAAACA CTACCAAATA

2161 GCTCTTCTGG
```

Antibodies or antibody reagents that bind to PD-1, or its ligand PD-L1, are described in, e.g., U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments the PD-1 antibodies include nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade. Also specifically contemplated herein are agents that disrupt or block the interaction between PD-1 and PD-L1, such as a high affinity PD-L1 antagonist.

Non-limiting examples of PD-1 antibodies include: pembrolizumab (Merck); nivolumab (Bristol Meyers Squibb); pidilizumab (Medivation); and AUNP12 (Aurigene). Non-limiting examples of PD-L1 antibodies can include atezolizumab (Genentech); MPDL3280A (Roche); MED14736 (AstraZeneca); MSB0010718C (EMD Serono); avelumab (Merck); and durvalumab (Medimmune).

Antibodies that bind to OX40 (also known as CD134), are described in, e.g., U.S. Pat. Nos. 9,006,399, 9,738,723, 9,975,957, 9,969,810, 9,828,432; PCT Published Patent Application Nos: WO2015153513, WO2014148895, WO2017021791, WO2018002339; and US Application Nos: US20180273632; US20180237534; US20180230227; US20120269825; which are incorporated by reference herein in their entireties.

Antibodies that bind to CTLA-4, are described in, e.g., U.S. Pat. Nos. 9,714,290, 6,984,720, 7,605,238, 6,682,736, 7,452,535; PCT Published Patent Application No: WO2009100140; and US Application Nos: US20090117132A, US20030086930, US20050226875, US20090238820; which are incorporated by reference herein in their entireties. Non-limiting examples of CTLA-4 antibodies include: ipilimumab (Bristol-Myers Squibb)

Antibodies that bind to TIM3, are described in, e.g., U.S. Pat. Nos. 8,552,156, 9,605,070, 9,163,087, 8,329,660; PCT Published Patent Application No: WO2018036561, WO2017031242, WO2017178493; and US Application Nos: US20170306016, US20150110792, US20180057591, US20160200815; which are incorporated by reference herein in their entireties.

Antibodies that bind to TIGIT (also known as CD134), are described in, e.g., U.S. Pat. Nos. 10,017,572, 9,713,641; PCT Published Patent Application No: WO2017030823; and US Application Nos: US20160355589, US20160176963, US20150322119; which are incorporated by reference herein in their entireties.

Antibodies that bind to Interleukin 10 receptor (IL10R) (e.g., soluble or wild-type) are described in, e.g., U.S. Pat. No. 7,553,932; and US Application Nos: US20040009939, US20030138413, US20070166307, US20090087440, and US201000028450, which are incorporated by reference herein in their entireties.

Antibodies that bind to TGFBRII (e.g., soluble or wild-type) are described in, e.g., U.S. Pat. No. 6,497,729; and US Application Nos: US2012114640, US20120021519, which are incorporated by reference herein in their entireties.

In one embodiment, the oncolytic HSV described herein further encodes fusogenic activity.

Another aspect provides an oncolytic Herpes Simplex Virus (HSV) comprising recombinant DNA that does not encode functional ICP0 and encodes fusogenic activity.

One aspect of the invention described herein provides a composition comprising any of the oncolytic HSV described herein. In one embodiment, the composition is a pharmaceutical composition. As used herein, the term "pharmaceutical composition" refers to the active agent in combination with a pharmaceutically acceptable carrier e.g. a carrier commonly used in the pharmaceutical industry.

In one embodiment, the composition further comprises at least one pharmaceutically acceptable carrier. Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the compositions of the invention to a cell in vitro or to a subject in vivo. A pharmaceutically acceptable carrier can contain a physiologically acceptable compound that acts, for example, to stabilize the composition or to increase the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the oncolytic HSV.

The oncolytic viruses described herein or composition thereof can be administered to a subject having cancer. In one embodiment, an agent that regulates the tet operator is further administered with the oncolytic viruses described herein or composition thereof. Exemplary agents include, but are not limited to, doxycycline or tetracycline.

In one embodiment, the cancer is a solid tumor. The solid tumor can be malignant or benign. In one embodiment, the subject is diagnosed or has been diagnosed with having a carcinoma, a melanoma, a sarcoma, a germ cell tumor, and a blastoma. Exemplary cancers include, but are in no way limited to, non-small-cell lung cancer, breast cancer, brain cancer, colon cancer, prostate cancer, liver cancer, lung cancer, ovarian cancer, skin cancer, head and neck cancer, kidney cancer, and pancreatic cancer. In one embodiment, the cancer is metastatic. These types of cancers are known in the art and can be diagnosed by a skilled clinician using standard techniques known in the art, for example blood analysis, blood cell count analysis, tissue biopsy, non-invasive imaging, and/or review of family history.

In cases where tumors are readily accessible, e.g., tumors of the skin, mouth or which are accessible as the result of surgery, virus can be applied topically. In other cases, it can be administered by injection or infusion. The agent that regulates the tet operator and tetR interaction, for example doxycycline or tetracycline, used prior to infection or at a time of infection can also be administered in this way or it can be administered systemically, for example, orally.

Although certain routes of administration are provided in the foregoing description, according to the invention, any suitable route of administration of the vectors may be adapted, and therefore the routes of administration described above are not intended to be limiting. Routes of administration may include, but are not limited to, intravenous, regional artery infusion, oral, buccal, intranasal, inhalation, topical application to a mucosal membrane or injection, including intratumoral, intradermal, intrathecal, intracisternal, intralesional or any other type of injection. Administration can be effected continuously or intermittently and will vary with the subject and the condition to be treated. One of skill in the art would readily appreciate that the various routes of administration described herein would allow for the inventive vectors or compositions to be delivered on, in, or near the tumor or targeted cancer cells. One of skill in the art would also readily appreciate that various routes of administration described herein will allow for the vectors and compositions described herein to be delivered to a region in the vicinity of the tumor or individual cells to be treated. "In the vicinity" can include any tissue or bodily fluid in the subject that is in sufficiently close proximity to the tumor or individual cancer cells such that at least a portion of the vectors or compositions administered to the subject reach their intended targets and exert their therapeutic effects.

Prior to administration, the oncolytic viruses can be suspended in any pharmaceutically acceptable solution including sterile isotonic saline, water, phosphate buffered saline, 1,2-propylene glycol, polyglycols mixed with water, Ringer's solution, etc. The exact number of viruses to be administered is not crucial to the invention but should be an "effective amount," i.e., an amount sufficient to cause cell lysis extensive enough to generate an immune response to released tumor antigens. Since virus is replicated in the cells after infection, the number initially administered will increase rapidly with time. Thus, widely different amounts of initially administered virus can give the same result by varying the time that they are allowed to replicate, i.e., the time during which cells are exposed to tetracycline. In general, it is expected that the number of viruses (PFU) initially administered will be between $1\times10^6$ and $1\times10^{10}$.

Tetracycline or doxycycline will be administered either locally or systemically to induce viral replication at a time of infection or 1-72 h prior to infection. The amount of tetracycline or doxycycline to be administered will depend upon the route of delivery. In vitro, 1 μg/ml of tetracycline is more than sufficient to allow viral replication in infected cells. Thus, when delivered locally, a solution containing anywhere from 0.1 μg/ml to 100 μg/ml may be administered. However, much higher doses of tetracycline or doxycycline (e.g., 1-5 mg/ml) can be employed if desired. The total amount given locally at a single time will depend on the size of the tumor or tumors undergoing treatment but in general, it is expected that between 0.5 and 200 ml of tetracycline or doxycycline solution would be used at a time. When given systemically, higher doses of tetracycline or doxycycline will be given but it is expected that the total amount needed will be significantly less than that typically used to treat bacterial infections (for example, with doxycycline, usually 1-2 grams per day in adults divided into 2-4 equal doses and, in children, 2.2-4.4 mg per kilogram of body weight, which can be divided into at least 2 doses, per day). It is expected that 5-100 mg per day should be effective in most cases. Dosing for tetracycline and doxycycline are well known in the art and can best be determined by a skilled clinician for a given patient.

The effectiveness of a dosage, as well as the effectiveness of the overall treatment can be assessed by monitoring tumor size using standard imaging techniques over a period of days, weeks and/or months. A shrinkage in the size or number of tumors is an indication that the treatment has been successful. If this does not occur or continue, then the treatment can be repeated as many times as desired. In addition, treatment with virus can be combined with any other therapy typically used for solid tumors, including surgery, radiation therapy or chemotherapy. In addition, the procedure can be combined with methods or compositions designed to help induce an immune response.

As used herein, the term "therapeutically effective amount" is intended to mean the amount of vector which exerts oncolytic activity, causing attenuation or inhibition of tumor cell proliferation, leading to tumor regression. An effective amount will vary, depending upon the pathology or condition to be treated, by the patient and his or her status, and other factors well known to those of skill in the art. Effective amounts are easily determined by those of skill in the art. In some embodiments a therapeutic range is from $10^3$ to $10^{12}$ plaque forming units introduced once. In some embodiments a therapeutic dose in the aforementioned therapeutic range is administered at an interval from every day to every month via the intratumoral, intrathecal, convection-enhanced, intravenous or intra-arterial route.

The invention provided herein can further be described in the following numbered paragraphs.

1. An oncolytic Herpes Simplex Virus (HSV) comprising recombinant DNA, wherein the recombinant DNA comprises:

a) a gene comprising a 5' untranslated region and a HSV-1, or HSV-2, VP5 gene that is operably linked to an VP5 promoter comprising a TATA element;

b) a tetracycline operator sequence positioned between 6 and 24 nucleotides 3' to said TATA element, wherein the VP5 gene lies 3' to said tetracycline operator sequence; c) a gene sequence encoding tetracycline repressor operably linked to an HSV immediate-early promoter, wherein the gene sequence is located at the ICP0 locus;

d) a variant gene that increases syncytium formation as compared to wild type, wherein the HSV-1, or HSV-2, variant gene is selected from the group consisting of: a glycoprotein K (gK) variant; a glycoprotein B (gB) variant; a UL24 variant; and UL20 gene variant; and e) a gene sequence encoding a functional ICP34.5 protein;

wherein said oncolytic HSV does not encode functional ICP0 and does not contain a ribozyme sequence located in said 5' untranslated region of VP5.

2. The oncolytic HSV of paragraph 1, wherein the variant gene is a gK variant gene that encodes an amino acid substitution selected from the group consisting of: an Ala to Thr amino acid substitution corresponding to amino acid 40 of SEQ ID NO: 2; an Ala to "x" amino acid substitution corresponding to amino acid 40 of SEQ ID NO: 2, wherein "x" is any amino acid; an Asp to Asn amino acid substitution corresponding to amino acid 99 of SEQ ID NO: 2; a Leu to Pro amino acid substitution corresponding to amino acid 304 of SEQ ID NO: 2; and an Arg to Leu amino acid substitution corresponding to amino acid 310 of SEQ ID NO: 2.

3. The oncolytic HSV of any preceding paragraph, wherein the tetracycline operator sequence comprises two Op2 repressor binding sites.

4. The oncolytic HSV of any preceding paragraph, wherein the VP5 promoter is an HSV-1 or HSV-2 VP5 promoter.

5. The oncolytic HSV of any preceding paragraph, wherein the immediate-early promoter is an HSV-1 or HSV-2 immediate-early promoter.

6. The oncolytic HSV of any preceding paragraph, wherein the HSV immediate-early promoter is selected from the group consisting of: ICP0 promoter and ICP4 promoter.

7. The oncolytic HSV of any preceding paragraph, wherein the recombinant DNA is part of the HSV-1 genome.

8. The oncolytic HSV of any preceding paragraph, wherein the recombinant DNA is part of the HSV-2 genome.

9. The oncolytic HSV of any preceding paragraph, further comprising a pharmaceutically acceptable carrier.

10. The oncolytic HSV of any preceding paragraph, further encoding at least one polypeptide that can increase the efficacy of the oncolytic HSV to induce an anti-tumor-specific immunity.

11. The oncolytic HSV of any preceding paragraph, wherein the at least one polypeptide encodes a product selected from the group consisting of: interleukin 2 (IL2), interleukin 12 (IL12), interleukin 15 (IL15), an anti-PD-1 antibody or antibody reagent, an anti-PD-L1 antibody or antibody reagent, an anti-OX40 antibody or antibody reagent, a CTLA-4 antibody or antibody reagent, a TIM-3 antibody or antibody reagent, a TIGIT antibody or antibody reagent, a soluble interleukin 10 receptor (IL10R), a fusion polypeptide between a soluble IL10R and IgG-Fc domain, a soluble TGFβ receptor (TGFBRII), a fusion polypeptide between a soluble TGFBRII and IgG-Fc domain, an anti-IL10R antibody or antibody reagent, an anti-IL10 antibody or antibody reagent, an anti-TGFβ1 antibody or antibody reagent, and an anti-TGFBRII antibody or antibody reagent.

12. The oncolytic HSV of any preceding paragraph, wherein the oncolytic HSV the further encodes fusogenic activity.

13. A composition comprising an oncolytic HSV of any preceding paragraph.

14. The composition of any preceding paragraph, further comprising a pharmaceutically acceptable carrier.

15. A method for treating cancer, the method comprising administering the oncolytic HSV of any preceding paragraph or the composition of any preceding paragraph to a subject having cancer.

16. The method of any preceding paragraph, wherein the cancer is a solid tumor.

17. The method of any preceding paragraph, wherein the tumor is benign or malignant.

18. The method of any preceding paragraph, wherein the subject is diagnosed or has been diagnosed as having cancer is selected from the list consisting of: a carcinoma, a melanoma, a sarcoma, a germ cell tumor, and a blastoma.

19. The method of any preceding paragraph, wherein the subject is diagnosed or has been diagnosed as having a cancer selected from the group consisting of: non-small-cell lung cancer, breast cancer, brain cancer, colon cancer, prostate cancer, liver cancer, lung cancer, ovarian cancer, skin cancer, head and neck cancer, kidney cancer, and pancreatic cancer.

20. The method of any preceding paragraph, wherein the cancer is metastatic.

21. The method of any preceding paragraph, further comprising administering an agent that regulates the tet operator-containing promoter.

22. The method of any preceding paragraph, wherein the agent is doxycycline or tetracycline.

23. The method of any preceding paragraph, wherein the agent is administered locally or systemically.

24. The method of any preceding paragraph, wherein the systemic administration is oral administration.

25. The method of any preceding paragraph, wherein the oncolytic virus is administered directly to the tumor.

26. An oncolytic Herpes Simplex Virus (HSV) comprising recombinant DNA, wherein the recombinant DNA does not encode functional ICP0; and encodes fusogenic activity.

EXAMPLES

Introduction

Human cancers are heterogeneous and contain multiple barriers that limit viruses from efficiently infecting distant tumor cells following initial viral replication (McKee et al., 2006; Nagano et al., 2008; Pluen et al., 2001). It has been elegantly demonstrated that intratumoral inoculation of oncolytic viruses enabling expression of viral fusogenic glycoproteins lead to syncytium formation of infected cells with neighboring cells, resulting in more efficient spread of viruses within the tumor as well as bystander killing of uninfected tumor cells through syncytium formation (Ahmed et al., 2003; Fu et al., 2003). It has been further indicated that syncytia caused by fusogenic lysis of tumor cells leads to the more efficient release and cross presentation of tumor antigens for priming tumor-specific T-cell response (Errington et al., 2006; Phan et al., 2003). Without being bound by a particular theory, it was thus hypothesized that a fusogenic variant of QREO5 could offer a significant immunological benefit in augmenting the anti-tumor response induced by QREO5.

HSV encodes several surface glycoproteins that involve the fusion of the viral envelope with the cell membrane as well as the fusion of an infected cell with adjacent cells, leading to syncytia. HSV variants exhibiting extensive syncytium formation consisting of as many as thousands of nuclei can be isolated by the propagation of virus in cell cultures (Pertel and Spear, Virology, 1996). Studies have shown that mutations in the cytoplasmic domain of HSV-1 glycoprotein B (gB) can lead to extensive syncytial (Baghian A et al., J Virol. 67:2396-2401, 1993; Bzik D J et al., Virology 137:185-190, 1984; Cai W H et al., J Virol 62:2596-2604, 1988; Engel J P et al., Virology 192:112-120, 1993; Diakidi-Kosta A et al., Gage P J et al., J Virol 67:2191-2201, 1993; Virus Res 93-99-108, 2003). HSV-1 syncytial mutations have also been identified in gene encoding for glycoprotein K (gK) (Bond V C et al., J Gen Virol 61:245-254, 1982; Bond V C and Person S, Virology 132: 368-376, 1984; Debroy C et al., et al., Virology 145:36-48, 1985; Hutchinson et al., J Virol 66:5603-5609; Pogue-Geile K L et al., Virology 136:100-109, 1984; Pogue-Geile K L et al., Virology 157:67-74, 1987), the UL20 gene (Melancon J M et al., J Virol 78:7329-7343, 2004) and the UL24 gene (Sanders P G et al., J Gen Virol 63:277-95, 1982; Jacobson J G et al., J Virol 63:1839-1843; Jacobson J G et al., Virology 242:161-169, 1998). Notably, UL20 interacts with both gB and gK (Foster T P et al., J Virol 82:6310-6323, 2008; Chouljenko V N et al., J Virol 84:8596-8606).

QREO5-F is a syncytium-forming QREO5 variant isolated by continuing propagations of QREO5 in human osteosarcoma U2OS cells followed by plaque-purification. Due to its robust fusogenic activity, QREO5-F is significantly more efficient than QREO5 in killing infected cancer cells at the low multiplicity of infection. QREO5-F and QREO5 replicate equally well in Vero cells and H1299 human lung cancer cells. It is shown herein that infection of multiple human cancer cell types with QREO5-F led to 36,000-to $5\times10^{7}$-fold tetracycline-dependent progeny virus production. Importantly, it is shown herein that QREO5-F is highly effective against pre-established CT26.WT colon carcinoma tumor in immune-competent mice. Moreover, localized intratumoral QREO5-F virotherapy led to induction of effective tumor-specific immunity that can prevent the tumor growth following re-challenge with the same type of tumor cells.

Materials and Methods

Cells, plasmids, and viruses. The osteosarcoma line U2OS and the African green monkey kidney cell line (Vero) were grown in Dulbecco's modified Eagle's medium (DMEM) supplemented with 10% fetal bovine serum (FBS) (Yao and Schaffer, 1995). U2OS cells express a cellular activity that can effectively complement the function of the HSV-1 IE regulatory protein ICP0 lacking in ICP0-mutant viruses (Yao and Schaffer, 1995). Primary human fibroblasts were grown in DMEM containing 10% FBS plus 1×non-essential amino acids (Yao and Eriksson, 1999).

Human breast cancer cells (MDA-MB-231), human colon cancer cells (HCT116), human non-small-cell lung cancer cells (H1299, A549, H1975), human liver cancer cells (SNU-398), and pancreatic cancer cells (Panc 1) were cultured in DMEM containing 10% FBS. Human melanoma cells (SK-MEL-28) were cultured in DMEM containing 10% FBS plus 1× non-essential amino acids and 1 mM sodium pyruvate. Human ovarian cancer cells (SK-OV-3) were cultured in RPMI-1640 medium containing 2 mM glutamine and 10% FBS. H1975 cells and SNU-398 cells were kindly provided by Dr. Chris A. French (Brigham and Women's Hospital) and Dr. Li Chai (Brigham and Women's Hospital), respectively. Panc 1 was the kind gift of Dr. Edward Hwang (Brigham and Women's Hospital). HCT116 cells were kindly provided by Dr. Albert Koong (Stanford University). Mouse colorectal carcinoma cells CT26.WT were purchased from ATCC and cultured in in DMEM containing 10% FBS.

pVP5 is an HSV-1 VP5-expressing plasmid, which was constructed by insertion of the Bgl II-Afe I-VP5 containing fragment of pKK1 into pcDNA3 at the Bgl II and Xho I sites. pKK1 was kindly provided by Dr. Prashant J. Desai (John Hopkins University). pTO-VP5 is a pVP5-derived plasmid, in which the expression of VP5 is under the control of the tetO-containing VP5 promoter.

K0R is an HSV-1 strain KOS derived ICP0 null mutant virus that encodes tetracycline repressor (tetR) at the ICP0 locus (Yao et al., 2006). K0R27-lacZ was derived from K0R in which the ICP27 coding sequence was replaced with the LacZ gene by homologous recombination (Yao et al., 2010). KTR27 is a 7134-derived recombinant virus that encodes tetR under the control of HSV-1 ICP0 promoter at the ICP0 locus, and the essential ICP27 gene under the control of the tetO-containing ICP27 promoter and a self-cleaving ribozyme located at the 5' untranslated region of ICP27 coding sequence (Yao et al., 2010) (U.S. Pat. No. 8,236, 941). K5ΔZ is a HSV-1 strain KOS-derived VP5-deletion mutant virus (Kindly provided by Dr. Prashant J. Desai, John Hopkins University), in which the HSV-1 VP5 gene is replaced by the LacZ gene. KTO-VP5 is a K5ΔZ-derived virus, which was constructed by replacing the lacZ in K5ΔZ with VP5 gene under the control of the tetO-containing VP5 promoter in plasmid pTO-VP5 according to protocol as previously described (Yao et al., 2010).

SDS-PAGE and western blot analysis. 60-mm dishes of Vero cells in duplicate were infected QREO5-F at an MOI of 3 PFU/cell in the absence and presence of tetracycline. Cell extracts were prepared at 16 hours post-infection as described previously (Yao and Schaffer, 1995). Proteins in cell extracts were resolved by sodium dodecyl sulfate-polyacrylamide gel electrophoresis (SDS-PAGE) and transferred to polyvinylidene difluoride (PVDF) membranes. Western blot analyses were performed (Yao and Schaffer, 1995) with monoclonal antibodies (Santa Cruz Biotechnology, Inc., Santa Cruz, CA) specific for HSV IE proteins ICP27 (sc-69806), and early-late gene products VP5 (sc-56989) and gD (sc-69802).

Mice and experimental tumors. Female BALB/c mice 6-7 weeks of age were purchased from Charles River Laboratories (Cambridge, MA). Mice were housed in metal cages at four mice per cage and maintained on a 12-h light/dark cycle. Mice were allowed to acclimatize for one week prior to experimentation. All animal experiments conducted in this study were approved by the Harvard Medical Area Standing Committee on Animals and the American Veterinary Medical Association, which is accredited by the Association for Assessment and Accreditation of Laboratory Animal Care (AAALAC) and meets National Institutes of Health standards as set forth in "The Guide for the Care and Use of Laboratory Animals."

A syngeneic mouse colon carcinoma model was established by implantation s.c. of $5\times10^5$ CT26. WT cells in a volume of 100 μl in both the left and right flanks of female BALB/c mice (n=24). Once tumors reached to 3-5 mm in diameter, mice were randomly divided into 3 different groups of 8 mice each, and tumors on one side of flanks were intratumorally injected with 100 ul of DMEM containing 1 ug of doxycycline, QREO5-F at $2\times10^6$ PFU containing no doxycycline, or QREO5-F at $2\times10^6$ PFU containing 1 ug doxycycline in a volume of 100 ul. The number of PFU used herein was based on the titer on the ICP0-expressing Vero cells monolayers in the presence of tetracycline. Tumors were received the same treatment on days 3 and 6 post initial inoculation. Tumor volumes were quantified every third day using calipers and the formula $V=(L\times W^2)/2$. Data are presented as means±SEM.

Illumina sequencing. QREO5-F viral DNA was prepared from QREO5-F-infected U2OS cells with Qiagen Genomic DNA kit. Quantitative real-time PCR analysis reveals close to 80% of total DNA represents QREO5-F viral DNA. The isolated DNA (2.2 ug) was used for library construction and sequencing at Translational Genomics Core Facility, Partners HealthCare, Cambridge, MA. Briefly, DNA was sheared to an average size of 550 bp, which then underwent library construction per the manufacturer's manual (Illumina TruSeq DNA PCR-Free Sample Preparation Kit). Libraries were then sequenced on the MiSeq instrument (Illumina) to generate 250 bp paired end reads. For both libraries, the sequencing yielded greater than 1,500,000 total pass filtered (PF) reads.

Genome assembly and variant calling was performed using the VirAMP pipeline on the web-based interface (Wan Y et al., 2015; www.viramp.com), using default paired-end sequence settings. VirAmp uses a semi-guided de novo assembly where assembly of short sequence reads into contigs is followed by a reference guided assembly to orient contigs and perform pairwise alignment. Variant calling uses MUMmer package tools to identify variation between the new assemblies and the reference sequence. The HSV-1 KOS strain (JQ673480.1) was used as the reference sequence for the assembly, as well as for variant calling.

Results

Construction and selection of QREO5. QREO5 is an HSV-1 recombinant virus that encodes tetR under the control of HSV-1 ICP0 promoter at the ICP0 locus, and the essential VP5 gene under the control of the tetO-containing VP5 promoter (FIG. 1). QREO5 was constructed first by co-infection of U2OS cells with KTO-VP5 and K0R27-lacZ followed plaque-purification on U2OS cells. The plaque-purified virus that exhibits highly tetracycline-dependent viral replication in U2OS cells and Vero cells was then propagated in MCF-7 human breast cancer cells for several passages followed by three round of plaque-purification.

Figure 2A:
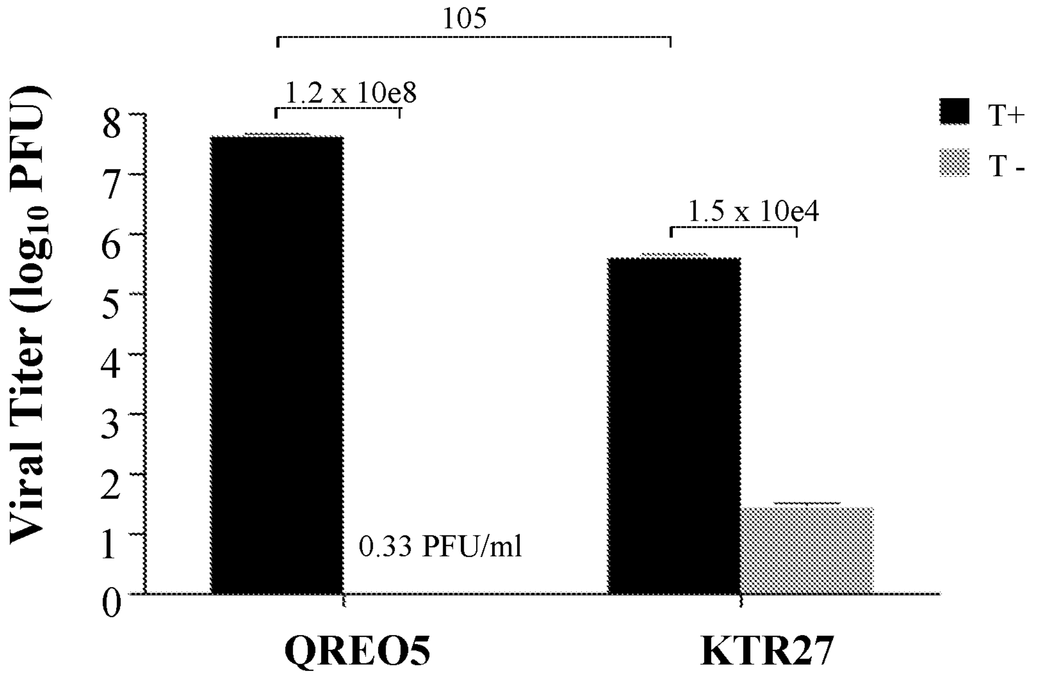
FIGS. 2A and 2B show QREO5 replicates significantly more efficiently than KTR27 in Vero cells and H1299 cells.
Figure 2B:
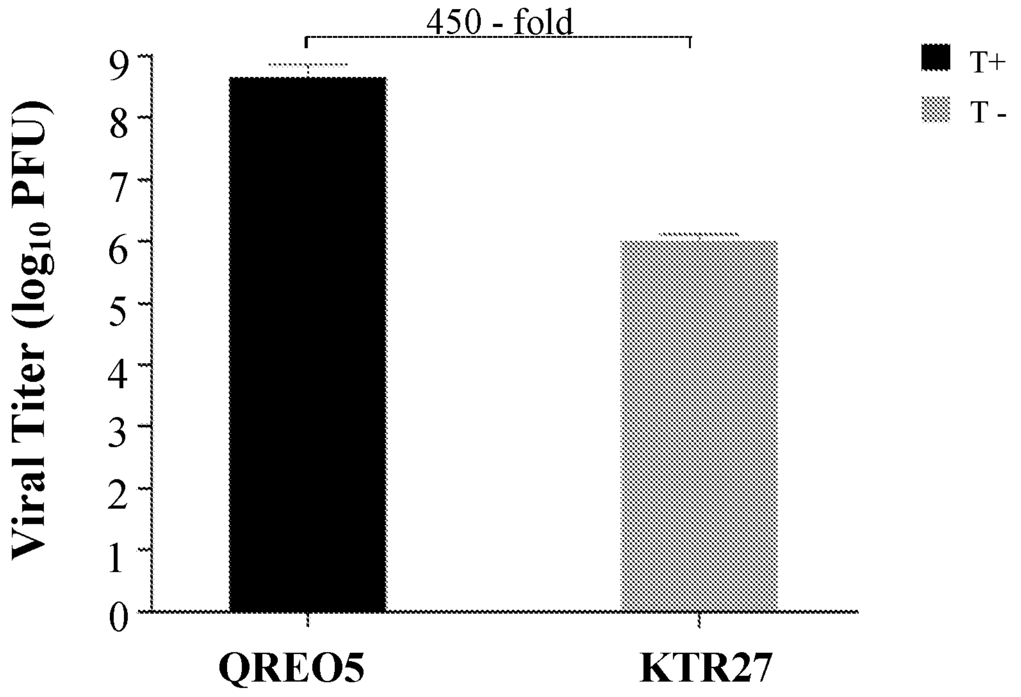

Replication of QREO5 in Vero cells and H1299 cells. To test if QREO5 replicates more efficiently than KTR27 in Vero cells, and if the replication of QREO5 can be more stringently controlled by tetracycline, Vero cells were infected with QREO5 and KTR27 at an MOI of 1 PFU/cell in the absence and presence of tetracycline and infected cells were harvested at 72 h post-infection. As shown in FIG. 2A, yields of QREO5 in Vero cells is $10^5$-fold higher than KTR27, and the fold of tetracycline-dependent viral replication of QREO5 in Vero cells is significant higher than that of KTR27. The result in FIG. 2B shows that yields of QREO5 is 450-fold higher than KTR27 in H1299 cells at an MOI of 0.25 PFU/cell.

Figure 3:
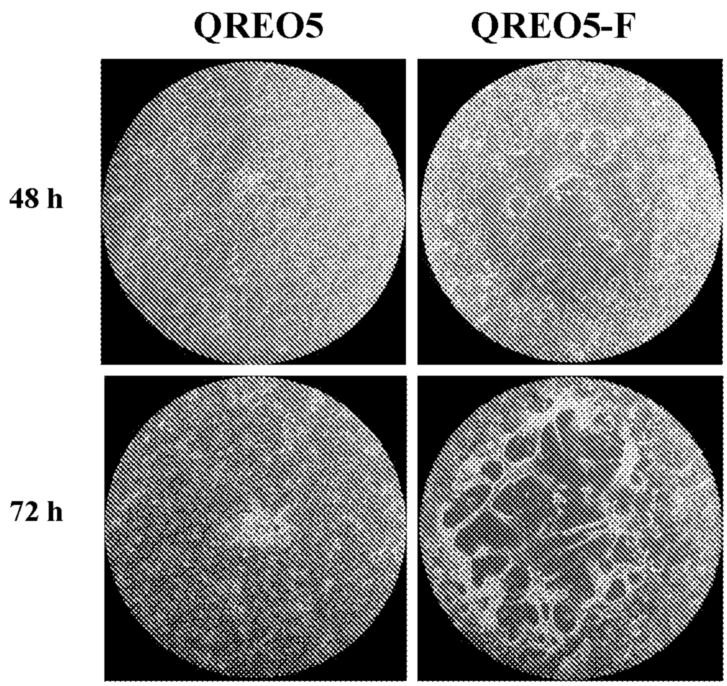
FIG. 3 shows Vero cells were seeded at $7.5\times10^5$ cells per 60 mm dish. Cells were infected with QREO5 or QREO5-F at 200 PFU/dish at 48 h post-cell seeding in the presence of tetracycline. QREO5 or QREO5-F plaques were photographed at 48 and 72 h post-infection.
Figure 4A:
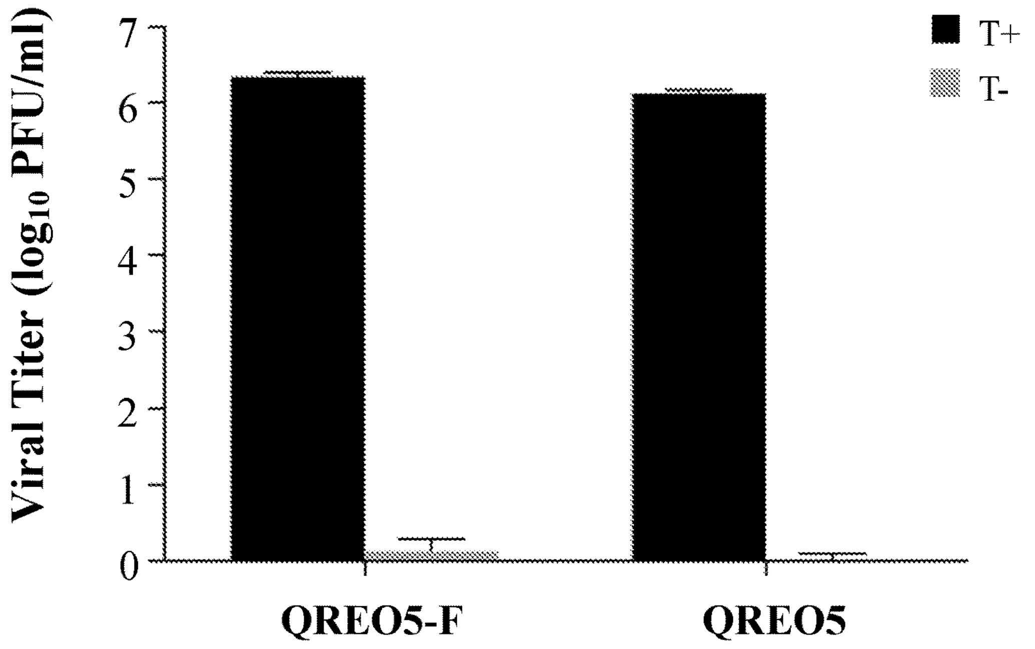
FIGS. 4A and 4B show QREO5-F and QREO5 replicate equally well in Vero cells and H1299 cells. Vero cells and H1299 cells were seeded at $7.5\times10^5$ cells per 60 mm dish. At 48 h post-cell seeding, Vero cells (FIG. 4A) and H1299 cells (FIG. 4B) were infected with QREO5 or QREO5-F at MOIs of 0.5 PFU/cell and 0.25 PFU/cell, respectively, in the presence or absence of tetracycline. Infected cells were harvested at 72 h post-infection (FIG. 4A) or 48 h post-infection (FIG. 4B). Viral titers were determined on U2OS monolayers in the presence of tetracycline. Viral titers are expressed as means±standard deviation.
Figure 4B:
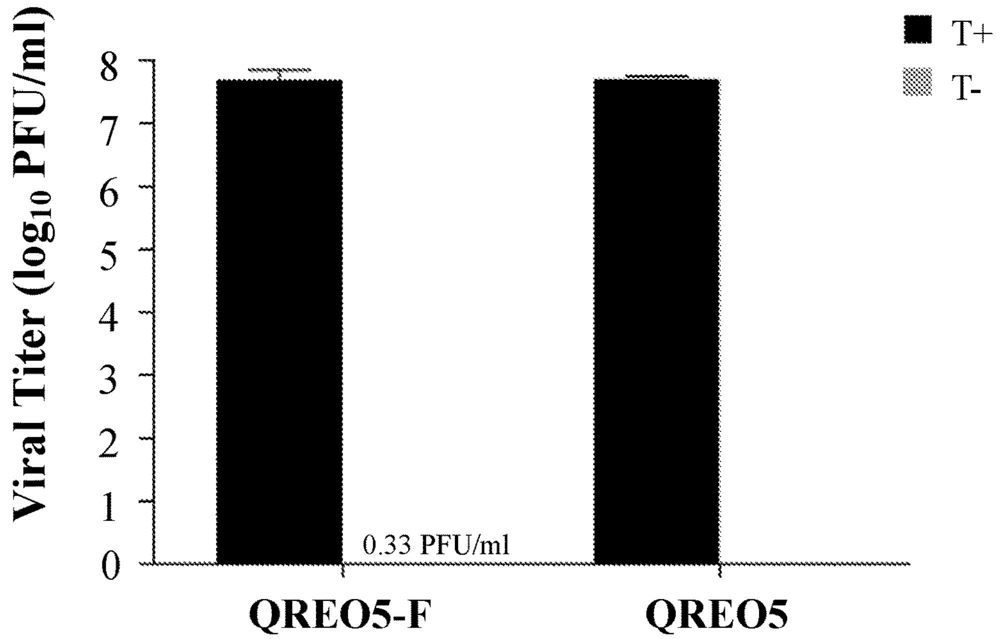

Selection of QREO5-F. To isolate fusogenic variants of QREO5, fusogenic variants-containing QREO5 stock was propagated in U2OS cells for 7 more passages. Fifty large fusogenic variants of QREO5 were plaque-purified and amplified in U2OS cells followed by testing their plaque-forming efficiency in U2OS cells, H1299 cells, A549, and MCF7 cells. QREO5-F is a second-round plaque-purified syncytium-forming QREO5 variant with a plaque size~30 times larger than that of parental QREO5 at 48 and 72 h post-infection in infected Vero cells (FIG. 3). QREO5-F replicates in Vero cells and H1299 cells as efficiently as QREO5 (FIG. 4).

Figure 5:
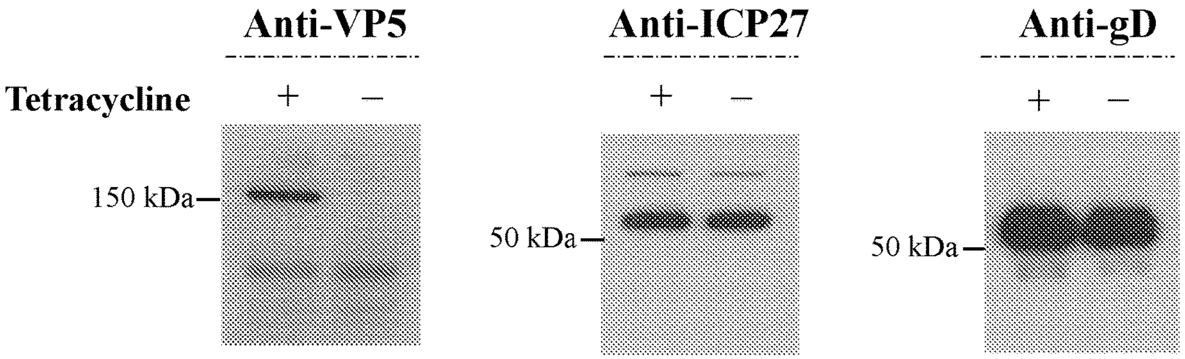
FIG. 5 shows no detectable VP5 expression in QREO5-F infected Vero cells in the absence of tetracycline. Vero cells were infected with QREO5-F at an MOI of 3 PFU/cell of in the presence and absence of tetracycline. Infected cell extracts were prepared at 16 hours post-infection, resolved by SDS-PAGE followed by western blot analysis with anti-ICP27, anti-gD, and anti-VP5 specific monoclonal antibodies.

The western blot analyses presented in FIG. 5 show that while similar levels of viral immediate-early gene ICP27 and early-late gene gD are expressed in the presence and absence of tetracycline, no VP5 expression was detected in QREO5-F-infected cells in the absence of tetracycline, indicating that the lack of de novo synthesis of infectious QREO5-F in the absence of tetracycline is the direct result of little or no VP5 expression.

Figure 6:
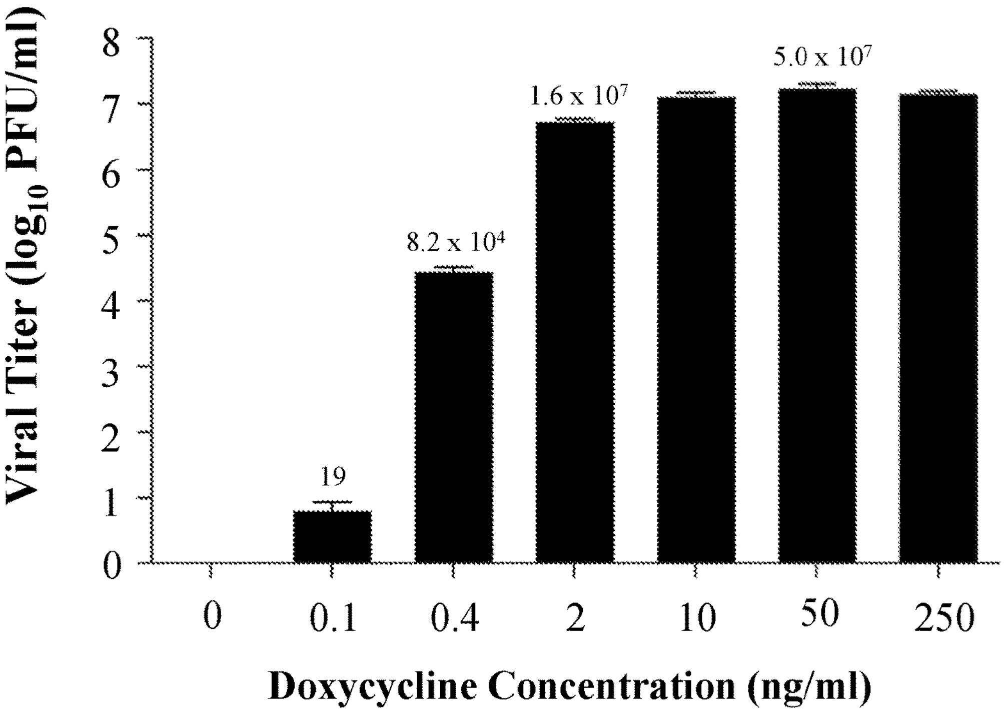
FIG. 6 shows QREO5-F replication is tightly regulated by doxycycline. H1299 cells were seeded at $7.5\times10^5$ cells per 60 mm dish. At 48 h post-seeding, triplicate dishes of cells were infected with QREO5-F at an MOI of 0.25 PFU/cell in a volume of 0.5 ml. After 1.5 h of incubation at 37° C., the inocula were removed and the cells were washed twice with acid-glycine saline (to remove membrane-bound extracellular virions) and then twice by DMEM. QREO5-F infections were carried out in the absence or presence of various amounts of doxycycline. Infected cells were harvested at 48 h post-infection. Viral titers were determined on U2OS monolayers in the presence of tetracycline. Viral titers are expressed as means±standard deviation. Numbers located above each bar column represent the fold difference in viral yield between the presence of indicated doxycycline concentration and the absence of doxycycline.

Doxycycline-dose dependent de novo viral production of QREO5-F. To finely assess the dependence of QREO5-F replication on the presence of tetracycline, H1299 cells were infected with QREO5-F at an MOI of 0.25 PFU/cell in either the absence or presence of different concentration of doxycycline. Infected cells were harvested at 48 h post-infection (FIG. 6). While the yield of QREO5-F at 48 h post-infection was $1.4\times10^7$ PFU/ml in the presence of 0.05 ug/ml of doxycycline, yield of QREO5-F was 0.33 PFU/ml in cells in the absence of doxycycline, indicating that the regulation of QREO5-F viral replication by doxycycline is close to $5\times10^7$-fold in infected H1299 cells.

Figure 7A:
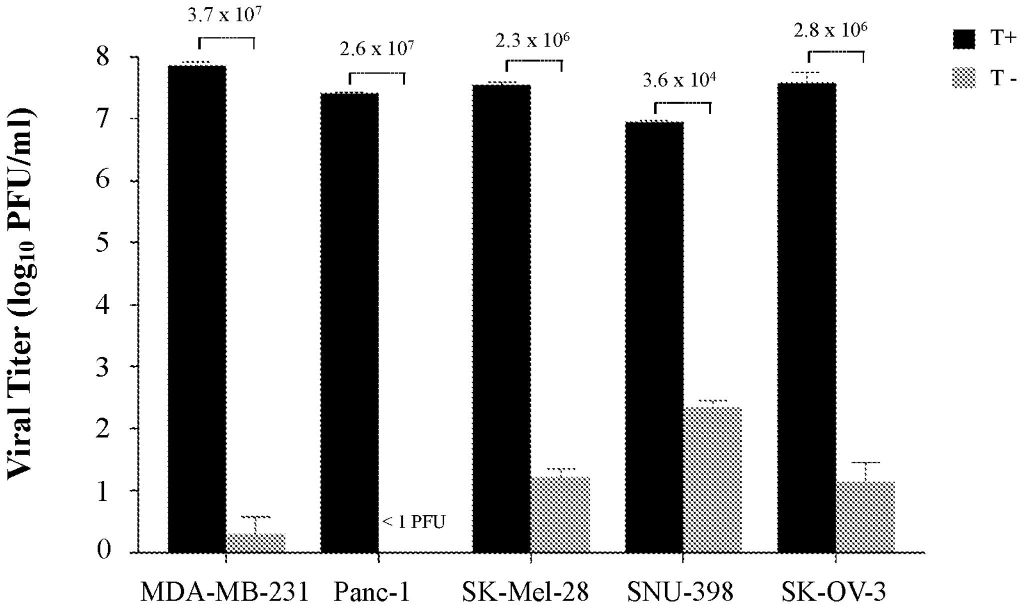
FIGS. 7A and 7B show QREO5-F replication is efficient and highly regulated in various human tumor cell lines.
Figure 7B:
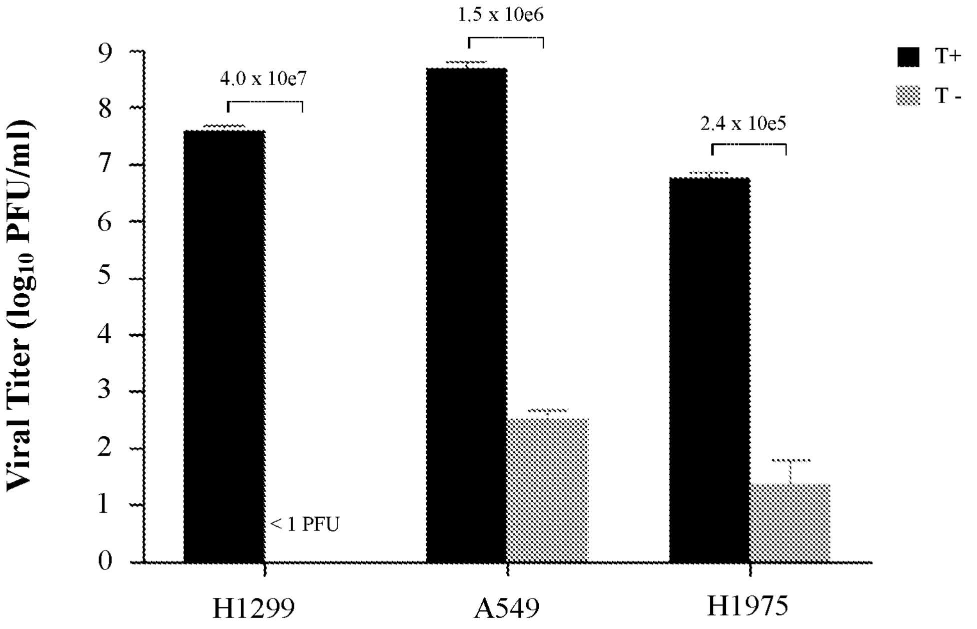

Doxycycline-dependent replication of QREO5-F in cultured human tumor cells and primary cells. Having demonstrated that the replication of QREO5-F is as productive as that of QREO5 in Vero cells and H1299 cells, the replicative and regulative abilities of QREO5-F in various human tumor cell lines were then investigated. As depicted in FIGS. 7A and 7B, QREO5-F infection of human breast, lung, ovary, pancreas, and skin tumor cell lines demonstrated that QREO5-F regulatability ranges from ~240,000-fold to ~$4\times10^7$-fold, whereas the degree of QREO5-F regulation in human SNU-398 liver cancer cell line is about 36,000-fold.

Figure 8A:
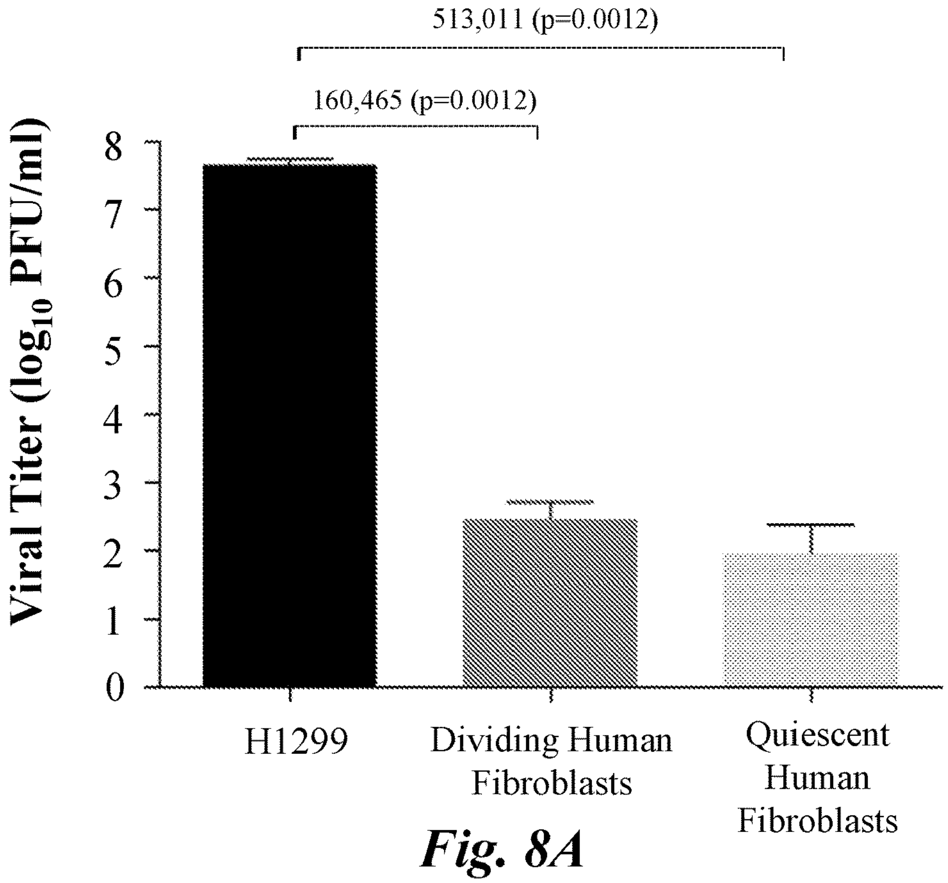
FIGS. 8A-8C show cytotoxicity and replication of QREO5-F are significantly enhanced in human lung cancer cells versus in normal primary human fibroblasts. For results labeled "HF-serum free," primary human fibroblasts (HF) were seeded at $1.5\times10^6$ cells per 60 mm dish in normal growth medium. 24 h post-seeding, normal medium was removed and replaced with serum-free DMEM containing antibiotics. These cells were infected at 45 h post-serum starvation. H1299 cells were seeded at $7.5\times10^5$ cells per 60 mm dish in normal growth medium and infected at about 69 h post-seeding. All cells described above were either mock infected or infected with QREO5-F at an MOI of 0.25 PFU/cell in the absence or presence of tetracycline at 2.5 μg/ml in DMEM containing 2% FBS.
Figure 8B:
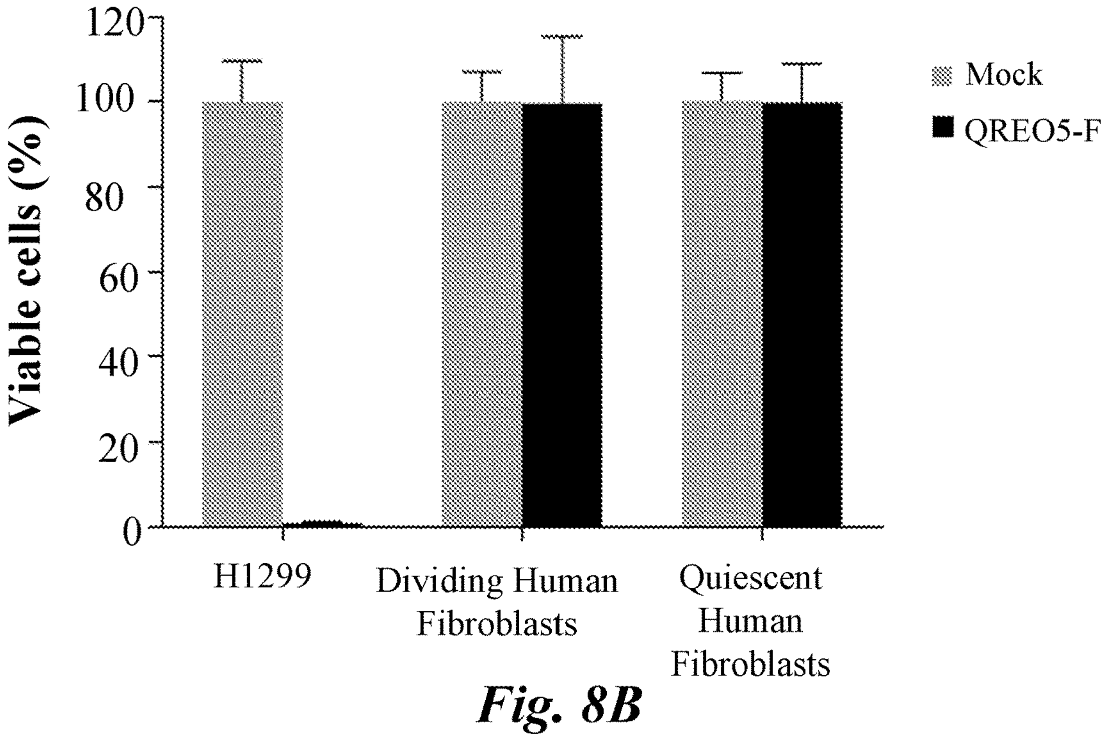
Figure 8C:
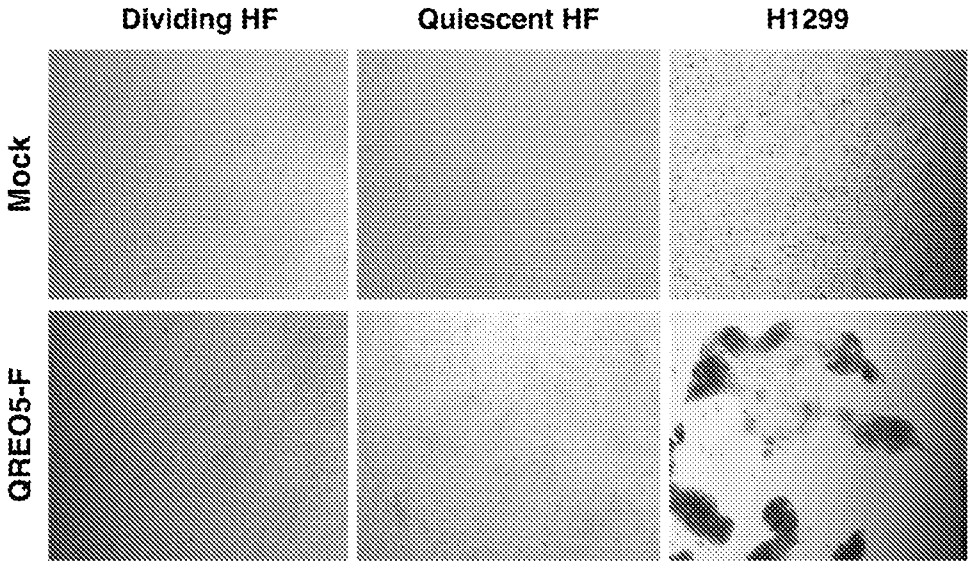

To directly examine the onco-selectivity of QREO5-F in normal primary human cells and human cancer cells, H1299 cells and dividing and non-dividing human breast fibroblasts were infected with QREO5-F at an MOI of 0.25 PFU/cells in the presence and absence of tetracycline as described by Yao et al. (2010). The results of FIG. 8A demonstrate that replication of QREO5-F in primary human fibroblasts, particularly non-dividing fibroblasts, is markedly reduced compared with replication in H1299 cells. Yields of QREO5-F at 72 h post-infection in H1299 cells were more than 510,000-fold higher than those in the serum-starved fibroblasts, and more than 160,000-fold higher than in fibroblasts grown in normal growth medium. Additionally, the cytotoxic effect of QREO5-F infection in the presence of tetracycline was evaluated (FIG. 8B). The results show that QREO5-F exhibits little cytotoxic effect in non-dividing as well as dividing fibroblasts, and drastic cytotoxic effect in H1299 cells (0.86% of infected cells remained viable). The corresponding morphological images of cells from the cytotoxicity assay (FIG. 8C) depict this cytopathic effect in H1299 (note the extensive formation of syncytia). In contrast, very little or no cytotoxic effects are visible among the infected or mock-infected human fibroblasts. Together, the results presented in FIG. 8 indicate that the ability of QREO5-F to replicate in and kill normal primary human fibroblasts is markedly reduced relative to various human tumor cell lines.

Figure 9A:
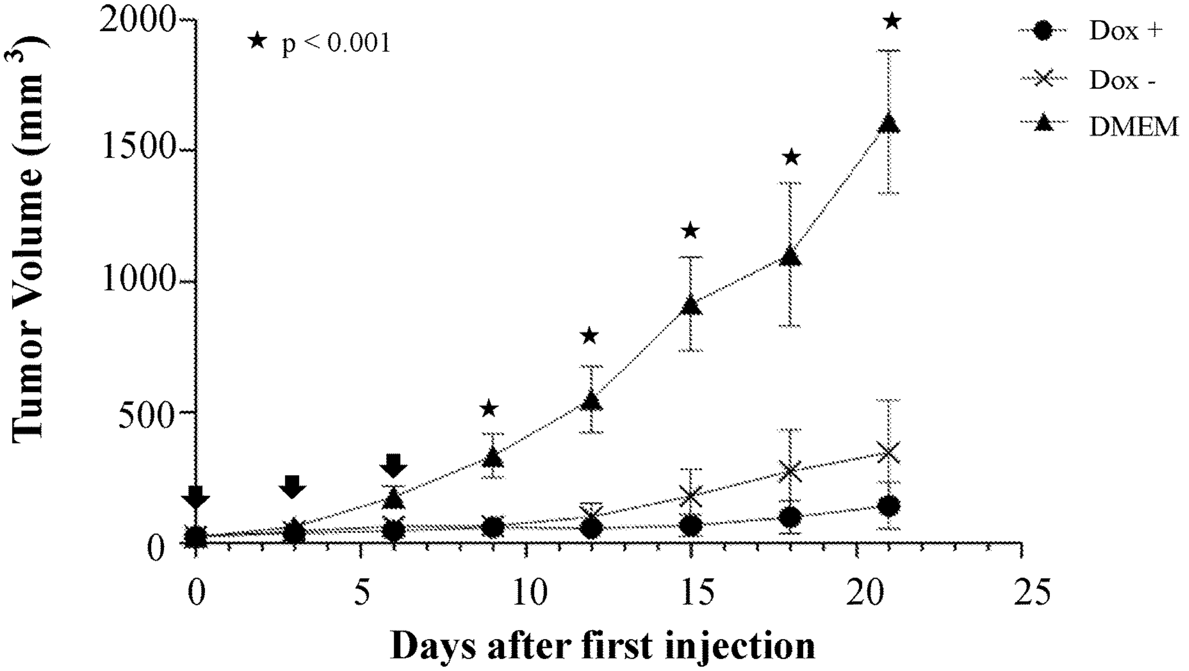
FIGS. 9A and 9B show therapeutic treatment of established bilateral CT26.WT tumors in normal BALB/c mice. Female BALB/c mice, 6 to 7-weeks-old, were implanted s.c. with $5\times10^5$ syngeneic CT26.WT colon cancer cells in a volume of 100 μl at both the left and right flanks. When subcutaneous tumors reached a diameter of tumor size of 3-5 mm, mice were divided into 3 groups of 8 mice each, in which the average of tumor size in each group is essentially the same. Mice were then anesthetized and inoculated with DMEM containing 1 ug doxycycline, QREO5-F at $2\times10^6$ PFU with or without doxycycline in a volume of 100 ul unilaterally. The number of PFU used herein was based on their titers determined on the ICP0-expressing Vero cell monolayers in the presence of tetracycline. The same treatment was repeated on days 3 and 6. Volumes of injected (FIG. 9A) and contralateral (FIG. 9B) tumors were quantified every third day by a caliper using the formula $V=(L\times W^2)/2$ until 21 days after treatment. Mean tumor volumes±SEM are shown.
Figure 9B:
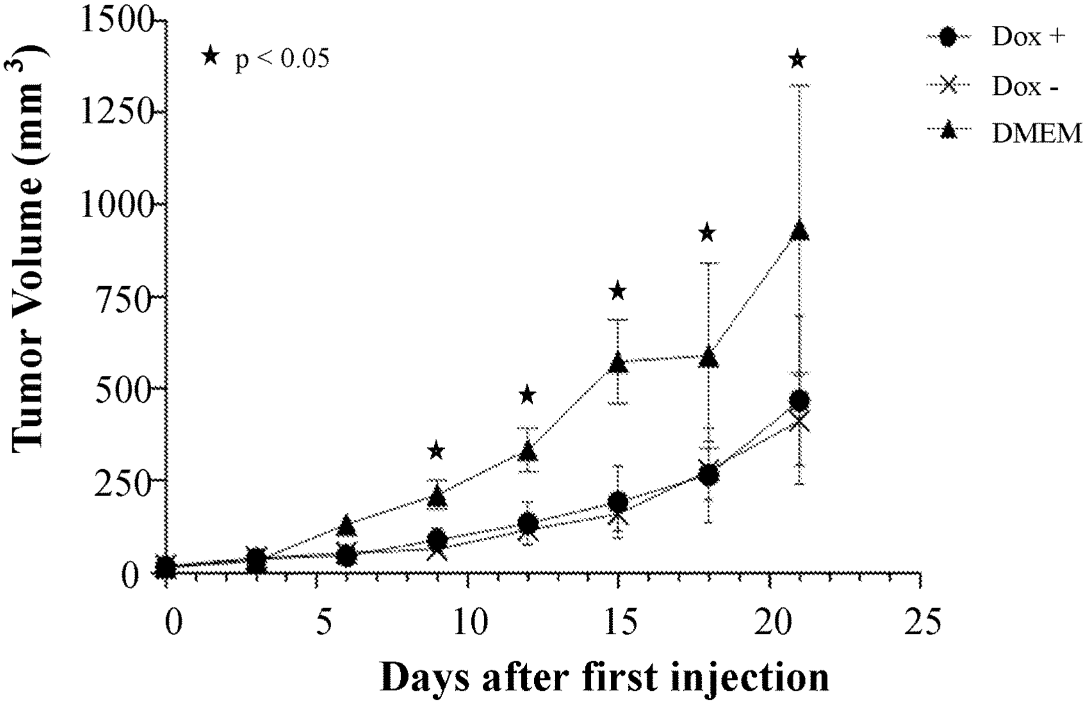

Prevention and induction of tumor-specific immunity against the growth of pre-established CT26. WT tumor in immune-competent mice. Using a syngeneic CT26.WT colon cancer model in immuno-competent BALB/c mice (FIG. 9), it was shown herein that intratumoral inoculation of QREO5-F into pre-established CT26.WT tumors lead to a markedly reduction in overall tumor growth in QREO5-F treated tumors, of particular, in the QREO5-F treated tumor with local co-delivery of 1 ug of doxycycline. There was an average of 11.2-fold reduction in tumor volume in QREO5-F-treated tumor in the presence of doxycycline compared to that of DMEM-treated group on day 21 post-QREO5-F virotherapy ($p<0.001$) (FIG. 9A). Three mice in DMEM-treated group have to be euthanized on day 15 post-initial intratumoral injection due to large tumor sizes. The overall tumor volume in QREO5-F-treated tumor in the presence of doxycycline was 2.4-fold lower than the QREO5-F-treated tumor in the absence of local delivery of doxycycline. Importantly, QREO5-F virotherapy led to a 3.2-fold reduction in growth of the contralateral tumors that received no viruses compared to that of DMEM-treated mice ($p<0.05$) (FIG. 9B), indicating that intratumoral inoculation of QREO5-F can elicit an effective anti-tumor specific immunity that can limit the growth of disseminating tumors. Notably, three of 8 mice treated with QREO5-F plus local delivery of doxycycline were tumor free on both flanks, while only one of 8 mice was tumor free in mice treated with QREO5-F without doxycycline. The described 4 QREO5-F cured mice remain tumor free on day 35 post first QREO5-F treatment.

Figure 10A:
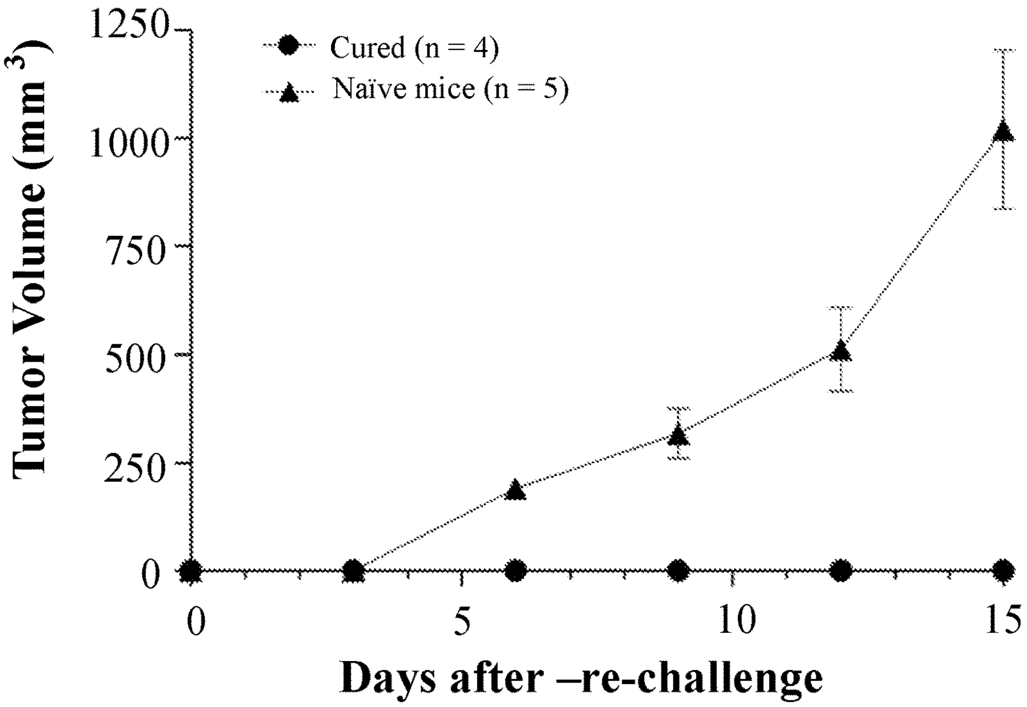
FIGS. 10A and 10B show induction of tumor-specific memory response in QREO5-F cured mice.
Figure 10B:
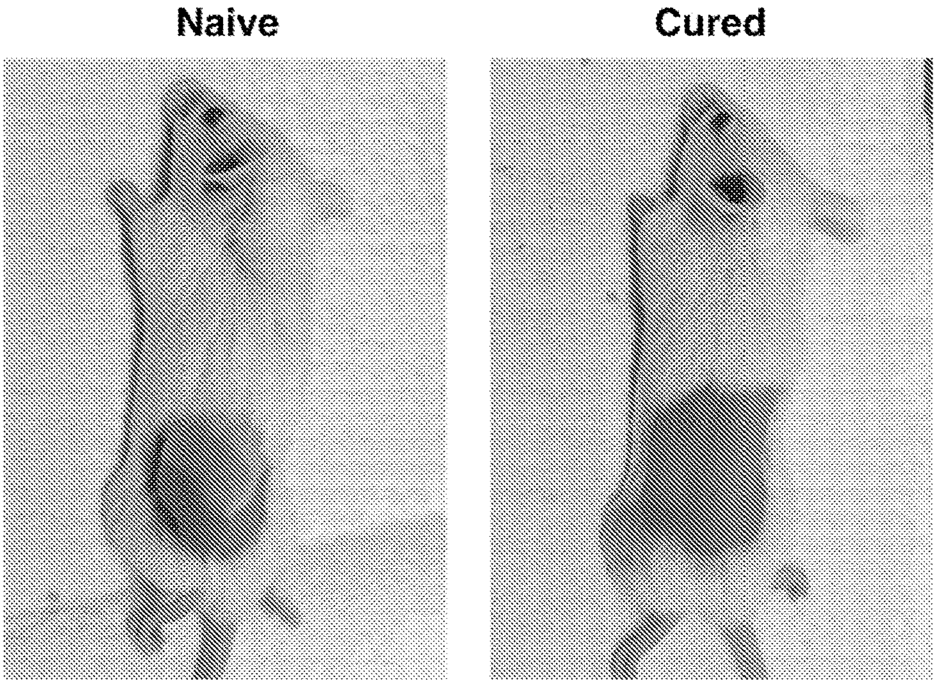

To evaluate the induction of tumor-specific memory response following QREO5-F treatment, 4 QREO5-F cured mice as well as 5 age-matched naïve BALB/c mice were re-challenged with CT26.WT cells. No any sign of tumor growth was detected in 4 QREO5-F cured mice, while all 5 naïve mice developed CT26.WT tumor with an average volume of about 1000 $mm^3$ by day 15 post-challenge (FIG. 10). Collectively, the results presented in FIGS. 9 and 10 strongly indicate that QREO5-F is very effective in prevention of the growth of pre-established CT26.WT tumor in immuno-competent mice, and localized QREO5-F virotherapy is capable of eliciting systemic immune response that can effectively prevent the growth of a distant tumor as well as CT26.WT tumor growth following re-challenge with CT26.WT cells in immuno-competent mice.

Sequence analyses of QREO5-F genome. As expected, sequence analysis of QREO5-F viral genome confirms that QREO5-F encodes tetR at the HSV-1 ICP0 locus, and VP5 under the control of the tetO-containing VP5 promoter. Unlike the first generation tet-regulatable oncolytic virus KTR27 (U.S. Pat. No. 8,236,941), which has both the ICP0 gene and the ICP34.5 gene deleted, QREO5-F encodes wild-type ICP34.5 gene. Using the parental wild-type HSV-1 strain KOS genome as the reference, a total of 53 missense mutations, and 3 frame shift mutations are identified in the QREO5-F genome. The UL36 gene of QREO5-F contains 12 missense mutations and 2 frame shift mutations. Other missense mutations are located in the UL5 gene, the UL6 gene, the UL8 gene, the UL12 gene, UL21 gene, UL23 gene, the UL25 gene, UL26 gene, the UL30 gene, the UL37 gene, the UL38 gene, the UL39 gene, the UL40 gene, the UL44 gene, the UL52 gene, the UL53 gene (gK), the US1 gene, and the US8 gene. Because the UL5 gene encodes the DNA helicase, the UL8 gene encodes the primase, the UL12 gene that encodes alkaline exonuclease, the UL23 gene that encodes TK, the UL30 gene encodes the catalytic subunit of the viral DNA polymerase, the UL39 gene encodes the large subunit of ribonucleotide reductase, the UL40 gene encodes the small subunit of ribonucleotide kinase, the UL52 gene encodes the primase subunit of the HSV-1 helicase-primase complex and all these genes involve in viral DNA replication either directly or indirectly, it is reasonable to predict that some of these described mutations further restrict the virus ability to replicate in normal cells than in cancer cells.

A single amino acid substitution, Ala to Thr at residue 40, is identified in the gK gene of QREO5-F. The same Ala to Thr substitution has been identified in the HSV-1 syncytial mutants, syn20 (Dolter K E et al., J Virol 68:8277-8281, 1994), which was isolated from KOS-infected human embryonic lung (HEL) cells in the presence of mutagens, N-methyl-N'-nitro-N-nitrosoguanidine (Read G S et al., J Virol 35:105-113, 1980), indicating that the Ala to Thr substitution at residue 40 of the gK gene in QREO5-F is a key factor for the observed fusogenic phenotype. Syncytial mutations in the gK gene also include Ala to Val at residue 40 in the HSV-1 syncytial mutants, syn102, syn105 and syn 33 (Dolter K E et al., J Virol 68:8277-8281, 1994), Asp to Asn at residue 99 in syn31 and syn32, Leu to Pro at residue 304 in syn30, and Arg to Leu at residue 310 (Dolter K E et al., J Virol 68:8277-8281, 1994). No mutation is found in the gene encoding gB, the UL20 gene, and the UL24 gene.

REFERENCES

Wan Y, Renner D W, Albert I, Szpara M L. VirAmp: a galaxy-based viral genome assembly pipeline. Gigascience. 2015 Apr. 28; 4:19. doi: 10.1186/si3742-015-0060-y. eCollection 2015 Apr. 28. PubMed PMID: 25918639

Advani, S. J., Sibley, G. S., Song, P. Y., Hallahan, D. E., Kataoka, Y., Roizman, B., and Weichselbaum, R. R. (1998). Enhancement of replication of genetically engineered herpes simplex viruses by ionizing radiation: a new paradigm for destruction of therapeutically intractable tumors. Gene Ther 5, 160-165.

Aghi, M., and Martuza, R. L. (2005). Oncolytic viral therapies—the clinical experience. Oncogene 24, 7802-7816.

Ahmed, A., Jevremovic, D., Suzuki, K., Kottke, T., Thompson, J., Emery, S., Harrington, K., Bateman, A., and Vile, R. (2003). Intratumoral expression of a fusogenic membrane glycoprotein enhances the efficacy of replicating adenovirus therapy. Gene Ther 10, 1663-1671.

Barber, G. N. (2015). STING: infection, inflammation and cancer. Nat Rev Immunol 15, 760-770.

Cai, W. Z., and Schaffer, P. A. (1989). Herpes simplex virus type 1 ICP0 plays a critical role in the de novo synthesis of infectious virus following transfection of viral DNA. J Virol 63, 4579-4589.

Chung, R. Y., Saeki, Y., and Chiocca, E. A. (1999). B-myb promoter retargeting of herpes simplex virus gamma34.5 gene-mediated virulence toward tumor and cycling cells. J Virol 73, 7556-7564.

Critchley-Thorne, R. J., Simons, D. L., Yan, N., Miyahira, A. K., Dirbas, F. M., Johnson, D. L., Swetter, S. M., Carlson, R. W., Fisher, G. A., Koong, A., et al. (2009). Impaired interferon signaling is a common immune defect in human cancer. Proc Natl Acad Sci USA 106, 9010-9015.

Deschamps, T., and Kalamvoki, M. (2017). Impaired STING Pathway in Human Osteosarcoma U2OS Cells Contributes to the Growth of ICP0-Null Mutant Herpes Simplex Virus. J Virol 91.

Errington, F., Jones, J., Merrick, A., Bateman, A., Harrington, K., Gough, M., O'Donnell, D., Selby, P., Vile, R., and Melcher, A. (2006). Fusogenic membrane glycoprotein-mediated tumour cell fusion activates human dendritic cells for enhanced IL-12 production and T-cell priming. Gene Ther 13, 138-149.

Fu, X., Tao, L., Jin, A., Vile, R., Brenner, M. K., and Zhang, X. (2003). Expression of a fusogenic membrane glycoprotein by an oncolytic herpes simplex virus potentiates the viral antitumor effect. Mol Ther 7, 748-754.

Kastan, M. B., and Bartek, J. (2004). Cell-cycle checkpoints and cancer. Nature 432, 316-323.

Kaur, B., Chiocca, E. A., and Cripe, T. P. (2012). Oncolytic HSV-1 virotherapy: clinical experience and opportunities for progress. Curr Pharm Biotechnol 13, 1842-1851.

Lanfranca, M. P., Mostafa, H. H., and Davido, D. J. (2014). HSV-1 ICP0: An E3 Ubiquitin Ligase That Counteracts Host Intrinsic and Innate Immunity. Cells 3, 438-454.

Lawler, S. E., Speranza, M. C., Cho, C. F., and Chiocca, E. A. (2017). Oncolytic Viruses in Cancer Treatment: A Review. JAMA Oncol 3, 841-849.

Leib, D. A., Coen, D. M., Bogard, C. L., Hicks, K. A., Yager, D. R., Knipe, D. M., Tyler, K. L., and Schaffer, P. A. (1989). Immediate-early regulatory gene mutants define different stages in the establishment and reactivation of herpes simplex virus latency. J Virol 63, 759-768.

Li, T., and Chen, Z. J. (2018). The cGAS-cGAMP-STING pathway connects DNA damage to inflammation, senescence, and cancer. J Exp Med 215, 1287-1299.

Martuza, R. L., Malick, A., Markert, J. M., Ruffner, K. L., and Coen, D. M. (1991). Experimental therapy of human glioma by means of a genetically engineered virus mutant. Science 252, 854-856.

McKee, T. D., Grandi, P., Mok, W., Alexandrakis, G., Insin, N., Zimmer, J. P., Bawendi, M. G., Boucher, Y., Breakefield, X. O., and Jain, R. K. (2006). Degradation of fibrillar collagen in a human melanoma xenograft improves the efficacy of an oncolytic herpes simplex virus vector. Cancer Res 66, 2509-2513.

Mohr, I. (2005). To replicate or not to replicate: achieving selective oncolytic virus replication in cancer cells through translational control. Oncogene 24, 7697-7709.

Nagano, S., Perentes, J. Y., Jain, R. K., and Boucher, Y. (2008). Cancer cell death enhances the penetration and efficacy of oncolytic herpes simplex virus in tumors. Cancer Res 68, 3795-3802.

Parato, K. A., Senger, D., Forsyth, P. A., and Bell, J. C. (2005). Recent progress in the battle between oncolytic viruses and tumours. Nat Rev Cancer 5, 965-976.

Phan, V., Errington, F., Cheong, S. C., Kottke, T., Gough, M., Altmann, S., Brandenburger, A., Emery, S., Strome, S., Bateman, A., et al. (2003). A new genetic method to generate and isolate small, short-lived but highly potent dendritic cell-tumor cell hybrid vaccines. Nat Med 9, 1215-1219.

Pluen, A., Boucher, Y., Ramanujan, S., McKee, T. D., Gohongi, T., di Tomaso, E., Brown, E. B., Izumi, Y., Campbell, R. B., Berk, D. A., et al. (2001). Role of tumor-host interactions in interstitial diffusion of macromolecules: cranial vs. subcutaneous tumors. Proc Natl Acad Sci USA 98, 4628-4633.

Rehman, H., Silk, A. W., Kane, M. P., and Kaufman, H. L. (2016). Into the clinic: Talimogene laherparepvec (T-VEC), a first-in-class intratumoral oncolytic viral therapy. J Immunother Cancer 4, 53.

Roizman, B., and D. M. Knipe (2001). Herpes simplex viruses and their replication. In Fields Virology, a.P.M.H.D.M. Knipe, ed. (Philadelphia, Pa: Lippincott Williams & Wilkins), pp. 2399-2459.

Shen, Y., and Nemunaitis, J. (2005). Fighting cancer with vaccinia virus: teaching new tricks to an old dog. Mol Ther 11, 180-195.

Walsh, D., and Mohr, I. (2004). Phosphorylation of eIF4E by Mnk-1 enhances HSV-1 translation and replication in quiescent cells. Genes Dev 18, 660-672.

Yao, F., and Eriksson, E. (1999). A novel anti-herpes simplex virus type 1-specific herpes simplex virus type 1 recombinant. Hum Gene Ther 10, 1811-1818.

Yao, F., Murakami, N., Bleiziffer, O., Zhang, P., Akhrameyeva, N. V., Xu, X., and Brans, R. (2010). Development of a regulatable oncolytic herpes simplex virus type 1 recombinant virus for tumor therapy. J Virol 84, 8163-8171.

Yao, F., and Schaffer, P. A. (1995). An activity specified by the osteosarcoma line U2OS can substitute functionally for ICP0, a major regulatory protein of herpes simplex virus type 1. J Virol 69, 6249-6258.

Yao, F., Theopold, C., Hoeller, D., Bleiziffer, O., and Lu, Z. (2006). Highly efficient regulation of gene expression by tetracycline in a replication-defective herpes simplex viral vector. Mol Ther 13, 1133-1141.

Zitvogel, L., Galluzzi, L., Kepp, O., Smyth, M. J, and Kroemer, G. (2015). Type I interferons in anticancer immunity. Nat Rev Immunol 15, 405-414.

Sequences
SEQ ID NO: 1 is a nucleotide sequence that encodes QREO5-F Linear Genome (142,090 bp).

GAGGAGCGGCTAGACCCCGGAAACGGGCCCCCCCAAAACACACCCCCCGGGGGCGCGCGCGGCCCTTTA

AAGGCGGGCGGCGGGCAGCCCGGGCCCCCCGCGGCCGCGACTAGCGAGTTAGACAGGCAAGCACTACTCG

CCTCTGCACGCACATGCTTGCCTGTCAAACTCTACCACCCCGGCACGCTCTCTGTCTCCATGGCCCGCCG

CCGCCATCGCGGCCCCCGCCGCCCCCGGCCGCCCGGGCCCACGGGCGCGGTCCCAACCGCACAGTCCCAG

GTAACCTCCACGCCCAACTCGGAACCCGTGGTCAGGAGCGCGCCCGCGGCCGCCCCGCCGCCGCCCCCCG

CCCCCCATTAGCATGCCCCTCCCGCCGACGCAACAGGGGCTTGGCCTGCGTCGGTGCCCCGGGGCTTCCC

GCCTTCCCGAAGAAACTCATTACCATACCCGGAACCCCAGGGGACCAATGCGGGTTCATTGAGCGACCCG

CGGGCCAATGCGCGAGGGGCCGTGTGTTCCGCCAAAAAAGCAATTAACATAACCCGGAACCCCAGGGGAG

TGGTTACGCGCGGCGCGGGAGGCGGGGAATACCGGGGTTGCCCATTAAGGGCCGCGGGAATTGCCGGAAG

CGGGAAGGGCGGCCGGGGCCGCCCATTAATGAGTTTCTAATTACCATCCGGGAAGCGGAACAAGGCCTCT

GCAATTTTTTAATTCCCAGCCCGGGAAGGGGGCGGCCCGGCCCACTGGGCGGGGGTTACCGCCCAGTGGG

CCGGGCCCCGACGACTCGGCGGACGCTGGTTGGCCGGGCCCCGCCGCGCTGGCGGCCGCCGATTGGCCAG

TCCCGCCCTCCGAGGGCGGGCCCGCCTCGGGGGCGGGCCGGCTCCAAGCGTATATATGCGCGGCTCCTGC

CATCGTCTCTCCGGAGAGCGGCTTGGTGCGGAGCTCCCGGGAGCTCCGCGGAAGACCCAGGCCGCCTCGG

GTGTAACGTTAGACCGAGTTCGCCGGGCCGGCTCCGCGGGCCAGGGCCCGGGCACGGGCCTCGGGCCCCA

GGCACGGCCCGATGACCGCCTCGGCCTCCGCCACCCGGCGCCGGAACCGAGCCCGGTCGGCCCGCTCGCG

GGCCCACGAGCCGCGGCGCGCCAGGCGGGCGGCCGAGGCCCAGACCACCAGGTGGCGCACCCGGACGTGG

GGCGAGAAGCGCACCCGCGTGGGGGTCGCGGGGGTCGCGGGGGTCGCGGGGGGCTTCGGCGCCCCCTCCC

CGCCCGCGCGTCGCAGGCGCAGGCGCGCCAGGTGCTCTGCGGTGACGCGCAGGCGGAGGGCGAGGCGCGG

CGGAAGGCGGAAGGGGGGAGGGGGGGTGGGAGGGGTTAGCCCCGCCCCCCGGGCCCGCGCCGGGCGGTGG

GGACCGGGGGCGGGGGGCGGCGGCGGTGGGCCGGGCCTCTGGCGCCGGCTCGGGCGGGGGGCTGTCCGGC

CAGTCGTCGTCGTCGTCGTCGGACGCGGACTCGGGAACGTGGAGCCACTGGCGCAGCAGCAGCGAACAAG

AAGGCGGGGGCCCCTGGCGGGGGGCGGCGGCGGGGCGGCCGCGGGCGCGCTCCTGACCACGGGTTCCGAG

TTGGGCGTGGAGGTTACCTGGGACTGGCGGTTGGGACCGCGCCCGTGGGCCCGGGCGGCCGGGGGCGGCG

GGGGCCGCGATGGCGGCGGCGGGCCATGGAGACAGAGAGCGTGCCGGGGTGGTAGAGTTTGACAGGCAAG

CATGTGCGTGCAGAGGCGAGTAGTGCTTGCCTGTCTAACTCGCTAGTCTCGGCCGGGGGGGGCCCGGGCT

GCCCGCCGCCCGCCTTTAAAGGGCCGCGCGCCCCCCGCCAGTGGGCCCCCGCCTTCTTGTTCGCTGCTGC

TGCGCCAGTGGCTCCACGTTCCCGAGTCCGCGTCCGACGACGACGACGACGACTGGCCGGACAGCCCCCC

GCCCGAGCCGGCGCCAGAGGCCCGGCCCACCGCCGCCGCCCCCCGCCCCCGGTCCCCACCGCCCGGCGCG

GGCCCGGGGGGCGGGGCTAACCCCTCCCACCCCCCCTCCGCCCCTTCCGCCTTCCGCCGCGCCTCGCCCT

CCGCCTGCGCGTCACCGCCGAGCACCTGGCGCGCCTGCGCCTGCGACGCGCGGGCGGGGGGGGCGCCGA

AGCCCCCCCGACCCCCGCGACCCCCGCGACCCCCACGCGGGTGCGCTTCTCGCCCCACGTCCGGGTGCGC

CACCTGGTGGTCTGGGCCTCGGCCGCCCGCCTGGCGCGCCGCGGCTCGTGGGCCCGCGAGCGGGCCGACC

-continued

GGGCTCGGTTCCGGCGCCGGGTGGCGGAGGCCGAGGCGGTCATCGGGCCGGCCTGGGGCCCGAGGCCCGT

GCCCGGGCCCGGCCCGCGGAGCCGGCCCGGCGAACTCGGTCTAACGTTACACCCGAGGCGGCCTGGGTCT

TCCGCGGAGCTCCCGGGAGCTCCGCACCAAGCCGCTCTCCGGAGAGACGATGGCAGGAGCCGCGCATATA

TACGCTTGGAGCCGGCCCGCCCCCGAGGCGGGCCCGCCCTCGGAGGGCGGGACTGGCCAATCGGCGGCCG

CCAGCGCGGCGGGGCCCGGCCAACCAGCGTCCGCCGAGTCGTCGGGGCCCGGCCCACTGGGCGGTAACTC

CCGCCCAGTGGGCCGGGCCGCCCACTTCCCGGTATGGTAATTAAAAACTTGCAGAGGCCTTGTTCCGCTT

CCCGGTATGGTAATTAGAAACTCATTAATGGGCGGCCCCGGCCGCCCTTCCCGCTTCCGGCAATTCCCGC

GGCCCTTAATGGGCAACCCCGGTATTCCCCGCCTCCCGCGCCGCGCGTAACCACTCCCCTGGGGTTCCGG

GTTATGTTAATTGCTTTTTTGGCGGAACACACGGCCCCTCGCGCATTGGCCCGCGGGTCGCTCAATGAAC

CCGCATTGGTCCCCTGGGGTTCCGGGTATGGTAATGAGTTTCTTCGGGAAGGCGGGAAGCCCCGGGGCAC

CGACGCAGGCCAAGCCCCTGTTGCGTCGGCGGGAGGGGCATGCTAATGGGGTTCTTTGGGGGACACCGGG

TTGGTCCCCCAAATCGGGGGCCGGGCCGTGCATGCTAATGATATTCTTTGGGGGCGCCGGGTTGGTCCCC

GGGGACGGGGCCGCTCCGCGGTGGGCCTGCCTCCCCTGGGACGCGCGGCCATTGGGGGAATCGTCACTGC

CGCCCCTTTGGGGAGGGGAAAGGCGTGGGGTATAAGTTAGCCCTGGCCCGACGGTCTGGTCGCATTTGCA

CCTCGGCACTCGGAGCGAGACGCAGCAGCCAGGCAGACTCGGGCCGCCCCCTCTCCGCATCACCACAGAA

GCCCCGCCTACGTTGCGACCCCCAGGGACCCTCCGTCAGCGACCCTCCAGCCGCATACGACCCCCCGGGG

ATCCTCTAGGGCCTCTGAGCTATTCCAGAAGTAGTGAAGAGGCTTTTTTGGAGGCCTAGGCTTTTGCAAA

AAGCTCCGGATCGATCCTGAGAACTTCAGGGTGAGTTTGGGGACCCTTGATTGTTCTTTCTTTTTCGCTA

TTGTAAAATTCATGTTATATGGAGGGGGCAAAGTTTTCAGGGTGTTGTTTAGAATGGGAAGATGTCCCTT

GTATCACCATGGACCCTCATGATAATTTTGTTTCTTTCACTTTCTACTCTGTTGACAACCATTGTCTCCT

CTTATTTTCTTTTCATTTTCTGTAACTTTTTCGTTAAACTTTAGCTTGCATTTGTAACGAATTTTTAAAT

TCACTTTTGTTTATTTGTCAGATTGTAAGTACTTTCTCTAATCACTTTTTTTTCAAGGCAATCAGGGTAT

ATTATATTGTACTTCAGCACAGTTTTAGAGAACAATTGTTATAATTAAATGATAAGGTAGAATATTTCTG

CATATAAATTCTGGCTGGCGTGGAAATATTCTTATTGGTAGAAACAACTACATCCTGGTCATCATCCTGC

CTTTCTCTTTATGGTTACAACGATATACACTGTTTGAGATGAGGATAAAATACTCTGAGTCCAAACCGGG

CCCCTCTGCTAACCATGTTCATGCCTTCTTCTTTTTCCTACAGCTCCTGGGCAACGTGCTGGTTATTGTG

CTGTCTCATCATTTTGGCAAAGAATTGTAATACGACTCACTATAGGGCGAATTGATATGTCTAGATTAGA

TAAAAGTAAAGTGATTAACAGCGCATTAGAGCTGCTTAATGAGGTCGGAATCGAAGGTTTAACAACCCGT

AAACTCGCCCAGAAGCTAGGTGTAGAGCAGCCTACATTGTATTGGCATGTAAAAAATAAGCGGGCTTTGC

TCGACGCCTTAGCCATTGAGATGTTAGATAGGCACCATACTCACTTTTGCCCTTTAGAAGGGGAAAGCTG

GCAAGATTTTTTACGTAATAACGCTAAAAGTTTTAGATGTGCTTTACTAAGTCATCGCGATGGAGCAAAA

GTACATTTAGGTACACGGCCTACAGAAAAACAGTATGAAACTCTCGAAAATCAATTAGCCTTTTTATGCC

AACAAGGTTTTTCACTAGAGAATGCATTATATGCACTCAGCGCTGTGGGGCATTTTACTTTAGGTTGTGT

ATTGGAAGATCAAGAGCATCAAGTCGCTAAAGAAGAAAGGGAAACACCTACTACTGATAGTATGCCGCCA

TTATTACGACAAGCTATCGAATTATTTGATCACCAAGGTGCAGAGCCAGCCTTCTTATTCGGCCTTGAAT

TGATCATATGCGGATTAGAAAAACAACTTAAATGTGAAAGTGGGTCCGCGTACAGCGGATCCCGGGAATT

CAGATCTTATTAAAGCAGAACTTGTTTATTGCAGCTTATAATGGTTACAAATAAAGCAATAGCATCACAA

ATTTCACAAATAAAGCATTTTTTTCACTGCATTCTAGTTGTGGTTTGTCCAAACTCATCAATGTATCTTA

TCATGTCTGGTCGACCCGGGACGAGGGAAAACAATAAGGGACGCCCCCGTGTTTGTGGGGAGGGGGGGGT

CGGGCGCTGGGTGGTCTCTGGCCGCGCCCACTACACCAGCCAATCCGTGTCGGGGAGGTGGAAAGTGAAA

GACACGGGCACCACACACCAGCGGGTCTTTTGTGTTGGCCCTAATAAAAAAAACTCAGGGGATTTTTGCT

-continued

GTCTGTTGGGAAATAAAGGTTTACTTTTGTATCTTTTCCCTGTCTGTGTTGGATGTATCGCGGGGGTGCG

TGGGAGTGGGGGTGCGTGGGAGTGGGGGTGCGTGGGAGTGGGGGTGCGTGGGAGTGGGGGCCCACGCACC

CCCACTCCCACGCACCCCCACACCCACGCACCCCCGCGATACATCCAACACAGACAGGGAAAAGATACAA

AAGTAAACCTTTATTTCCCAACAGACAGCAAAAATCCCCTGAGTTTTTTTATTAGGGCCAACACAAAAG

ACCCGCTGGTGTGTGGTGCCCGTGTCTTTCACTTTCCACCTCCCCGACACGGATTGGCTGGTGTAGTGGG

CGCGGCCAGAGACCACCCAGCGCCCGACCCCCCCCTCCCCACAAACGGGGGGCCCGGAGAGCCGCGGCAC

CCGGACGCGCCCGGAAAGTCTTTCGCACCACCGGCGATCGGCACGGCCGCGCCCCCGCTTTTATAAAGGC

TCAGATGACGCAGCAAAAACAGGCCACAGCACCACATGGGTAGGTGATGTAATTTTATTTTCCTCGTCTG

CGGCCTAATGGATTTCCGGGCGCGGTGCCCCTGTCTGCAGAGCACTTAACGGATTGATATCTCGCGGGCA

CGCGCGCCCTTAATGGACCGGCGCGGGGCGGGGGGCCGGATACCCACACGGGCGGGGGGGGGTGTCGCGG

GCCGTCTGCTGGCCCGCGGCCACATAAACAATGACTCGGGGCCTTTCTGCCTCTGCCGCTTGTGTGTGCG

CGCGCCGGCTCTGCGGTGTCGGCGGCGGCGGCGGTGGCCGCCGTGTTCGGTCTCGGTAGCCGGCCGG

CGGGTGGACTCGCGGGGGGCCGGAGGGGGGGAGGCAGGGGGGGGGAGGGTGGGGATCAGGACTTCCACTT

CCCGTCCTTCCATCCCCCGTTCCCCTCGGTTGTTCCTCGCCTCCCCCAACACCCCGCCGCTTTCCGTTGG

GGTTGTTATTGTTGTCGGGATCGTGCGGGCCGGGGGTCGCCGGGGCAGGGGCGGGGGCGTGGGCGGGGGT

GCTCGTCGATCGACCGGGCTCAGTGGGGGCGTGGGGTGGGTGGGAGAAGGCGAGGAGACTGGGGTGGGGG

TGTCGGTGGGTGGTTGTTTTTTCCCCCCTGCCTTCCACCCTCCGGCCCCCCGCGAGTCCACCCGCCGGCC

GGCTACCGAGACCGAACACGGCGGCCACCGCCGCCGCCGCCGCCGACACCGCAGAGCCGGCGCGCGCACA

CACAAGCGGCAGAGGCAGAAAGGCCCCGAGTCATTGTTTATGTGGCCGCGGGCCAGCAGACGGCCCGCGA

CACCCCCCCCCCCCCGTGTGGGGATCCGGCCCCCCGCCCCCGCCGCCCATTAAGGGCGCGCGTGCCCGCG

GATATCATCCGTTAAGTGCTCTGCAGACAGGGGCACCGCGCCCGGAAATCCATTAGGCCGCAGACGAGGA

AAATAAAATTACATCCCTACCCATGTGGTGCTGTGGCCTGTTTTTGCTGCGTCATCTGAGCCTTTATAAA

AGCGGGGGCGCGGCCGTGCCGATCGCCGGTGGTGCGAAAGACTTTCCGGGCGCGTCCGGGCCCCCCGCCG

CTAAACCCCATCCCGCCCCCGGGACCCCACATATAAGCCCCCAGCCACACGCAAGAACAGACACGCAGAA

CGGCTGTGTTTATTTTAAATAAACCGATGTCGGAATAAACAAACACAAACACCCGCGACGGGGGGACGGC

GGGGACGGAGGGAGGGGGGGGACGGGGGACGGAAACAGACACAAAAAACAACCACAAAAAAAAAAAACAA

CCACCCACCGACACCCCCCCCCCAGTCTCCTCGCCTTCTCCCCCCACCCCACGCCCCCACTGAGCCCGGT

CGATCGACGAGCACCCCCGCCCCCGCCCCCGCCCCTGCCCCGGCGACCCCCGGCCCGCACGATCCCGACA

ACAATAATCCGTCCCCCGTCCCCCCCTCCCTCCGTCCCCTCCGTCCCCCCTCGCGGGGGTTTGTGTTTGT

TTATTCCGACATCGGTTTATTTAAAATAAACACAGCCGTTCTGCGTGTCTGTTCTTGCGTGTGGCTGGGG

GCTTATATGTGGGGTCCCGGGGGCGGGATGGGGTTTAGCGGCGGGGGGCGGCGCGCCGGACGGGGCGCTG

GAGATAGCGGCCCCCGGGGACCGGGGGACCGGGGCTGGGTATCCCGAGGTGGGGATGTGGGCGGGGGTGC

GCGGGAGGGGTCGGTGGTGGGGGTGGTGGTGGTGGGGGTAGTAGGAATGGTGGGGGGGGGGAGGGCGCTG

GTTGGTCAAAAAAGGGAGGGACGGGGGCCGGCAGACCGACGGCGACAACGCTCCCCGGCGGCCGGGTCGC

GGCTCTTACGAGCGGCCCGGCCCGCGCTCCCACCCCCCGGGCCGTGTCCTTGCTTTCCCCCCGTCTCCCC

CCCCGCCTTCTCCTCCTCCTCCTCGTTTTTCCAAACCCCGCCCACCCGGCCCGGCCCGGCCCGGCCCGGC

CACCGCCGCCCACCCACCCACCTCGGGATACCCAGCCCCGGTCCCCCGTTCCCCGGGGGCCGTTATCTCC

AGCGCCCCGTCCGGCGCGCCGCCCCCCGCCGCTAAACCCCATCCCGCCCCCGGGACCCCACATATAAGCC

CCCAGCCACACGCAAGAACAGACACGCAGAACGGCTACGAGGAGGAGGAGGAGAAGGCGGGGGGGGAGAC

GGGGGGAAAGCAAGGACACGGCCCGGGGGGTGGAGCGCGGGCCGGGCCGCTCGTAAGAGCCGCGACCCG

-continued

GCCGCCGGGGAGCGTTGTCGCCGTCGGTCTGCCGGCCCCCGTCCCTCCCTTTTTTGACCAACCAGCGCCC

TCCCCCCCGCGCGGGCCGGGCCGCTCGTAAGAGCCGCGACCCGGCCGCCGGGGAGCGTTGTCGCCGTCGG

TCTGCCGGCCCCCGTCCCTCCCTTTTTTGACCAACCAGCGCCCTCCCCCCCACCACCATTCCTACTACCA

CCACCACCACCACCCCCACCACCGACACCTCCCGCGCACCCCCGCCCACATCCCCCCACCCCGCACCACG

AGCACGGGGTGGGGGTAGCAGGGGATCAAAGGGGGGCAAAGCCGGCGGGGCGGTTCGGGGGGGCGGGAGA

CCGAGTAGGCCCGCCCATACGCGGCCCCTCCCGGCAGCCACGCCCCCCAGCGTCGGGTGTCACGGGGAAA

GAGCAGGGGAGAGGGGGGGAGAGGGGAGAGGGGGGGAGAGGGGGTATATAAACCAACGAAAAGCGCGGGA

ACGGGGATACGGGGCTTGTGTGGCACGACGTCGTGGTTGTGTTACTGGGCAAACACTTGGGGACTGTAGG

TTTCTGTGGGTGCCGACCCTAGGCGCTATGGGGATTTTGGGTTGGGTCGGGCTTATTGCCGTTGGGGTTT

TGTGTGTGCGGGGGGGCTTGTCTTCAACCGAATATGTTATTCGGAGTCGGGTGGCTCGAGAGGTGGGGGA

TATATTAAAGGTGCCTTGTGTGCCGCTCCCGTCTGACGATCTTGATTGGCGTTACGAGACCCCCTCGGCT

ATAAACTATGCTTTGATAGACGGTATATTTTTGCGTTATCACTGTCCCGGATTGGACACGGTCTTGTGGG

ATAGGCATGCCCAGAAGGCATATTGGGTTAACCCCTTTTTATTTGTGGCGGGTTTTCTGGAGGACTTGAG

TCACCCCGCGTTTCCTGCCAACACCCAGGAAACAGAAACGCGCTTGGCCCTTTATAAAGAGATACGCCAG

GCGCTGGACAGTCGCAAGCAGGCCGCCAGCCACACACCTGTGAAGGCTGGGTGTGTGAACTTTGACTATT

CGCGCACCCGCCGCTGTGTAGGGCGACAGGATTTGGGACCTACCAACGGAACGTCTGGACGGACCCCGGT

TCTGCCGCCGGACGATGAAGCGGGCCTGCAACCGAAGCCCCTCACCACGCCGCCGCCCATCATCGCCACG

TCGGACCCCACCCCGCGACGGGACGCCGCCACAAAAAGCAGACGCCGACGACCCCACTCCCGGCGCCTCT

AACGATGCCTCGACGGAAACCCGTCCGGGTTCGGGGGGCGAACCGGCCGCCTGTCGCTCGTCAGGGCCGG

CGGGCGCTCCTCGCCGCCCTAGAGGCTGTCCCGCTGGTGTGACGTTTTCCTCGTCCGCGCCCCCCGACCC

TCCCATGGATTTAACAAACGGGGGGGTGTCGCCTGCGGCGACCTCGGCGCCTCTGGACTGGACCACGTTT

CGGCGTGTGTTTCTGATCGACGACGCGTGGCGGCCCCTGATGGAGCCTGAGCTGGCGAACCCCTTAACCG

CCCACCTCCTGGCCGAATATAATCGTCGGTGCCAGACCGAAGAGGTGCTGCCGCCGCGGGAGGATGTGTT

TTCGTGGACTCGTTATTGCACCCCCGACGAGGTGCGCGTGGTTATCATCGGCCAGGACCCATATCACCAC

CCCGGCCAGGCGCACGGACTTGCGTTTAGCGTGCGCGCGAACGTGCCGCCTCCCCCGAGTCTTCGGAATG

TCTTGGTGGCCGTCAAGAACTGTTATCCCGAGGCACGGATGAGCGGCCACGGTTGCCTGGAAAAGTGGGC

GCGGGACGGCGTCCTGTTACTAAACACGACCCTGACCGTCAAGCGCGGGGCGGCGGCGTCCCACTCTAGA

ATCGGTTGGGACCGCTTCGTGGGCGGAGTTATCCGCCGGTTGGCCGCGCGCCGCCCCGGCCTGGTGTTTA

TGCTCTGGGGCGCACACGCCCAGAATGCCATCAGGCCGGACCCTCGGGTCCATTGCGTCCTCAAGTTTTC

GCACCCGTCGCCCCTCTCCAAGGTTCCGTTCGGAACCTGCCAGCATTTCCTCGTGGCGAACCGATACCTC

GAGACCCGGTCGATTTCACCCATCGACTGGTCGGTTTGAAAGGCATCGACGTCCGGGGTTTTTGTCGGTG

GGGGCTTTTGGGTATTTCCGATGAATAAAGACGGTTAATGGTTAAACCTCTGGTCTCATACGGGTCGGTG

ATGTCGGGCGTCGGGGGAGAGGGAGTTCCCTCTGCGCTTGCGATTCTAGCCTCGTGGGGCTGGACGTTCG

ACACGCCAAACCACGAGTCGGGGATATCGCCAGATACGACTCCCGCAGATTCCATTCGGGGGGCCGCTGT

GGCCTCACCTAACCAACCTTTACACGGGGGCCCGGAACGGGAGGCCACAGCGCCGTCTTTCTCCCCAACG

CGCGCGGATGACGGCCCGCCCTGTACCGACGGGCCCTACGTGACGTTTGATACCCTGTTTATGGTGTCGT

CGATCGACGAATTAGGGCGTCGCCAGCTCACGGACACCATCCGCAAGGACCTGCGGTTGTCGCTGGCCAA

GTTTAGCATTGCGTGCACCAAGACCTCCTCGTTTTCGGGAAACGCCCCGCGCCACCACAGACGCGGGGCG

TTCCAGCGCGGCACGCGGGCGCCGCGCAGCAACAAAAGCCTCCAGATGTTTGTGTTGTGCAAACGCGCCC

ACGCCGCTCGAGTGCGAGAGCAGCTTCGGGTCGTTATTCAGTCCCGCAAGCCGCGCAAGTATTACACGCG

ATCTTCGGACGGGCGGCTCTGCCCCGCCGTCCCCGTGTTCGTCCACGAGTTCGTCTCGTCCGAGCCAATG

-continued

CGCCTCCACCGAGATAACGTCATGCTGGCCTCGGGGGCCGAGTAACCGCCCCCCCCCCCCCCCCGCCCCC

CCCCCCCCCCCCCCCCCCCCCCTCCCCCCCCCCCCCCCCCTCTTCCCCCGTGACACCCGACGCTGGGGGG

CGTGGCTGCCGGGAGGGGCCGCGTATGGGCGGGCCTACTCGGTCTCCCGCCCCCCCGAACCGCCCCGCCG

GCTTTGCCCCCCGCGATCTTCGGACGGGCGGCTCTGCCCCGCCGTCCCCGTGTTCGTCCACGAGTTCGTC

TCGTCCGAGCCAATGCGCCTCCACCGAGATAACGTCATGCTGGCCTCGGGGGCCGAGTAACCGCCCCCCC

CCCATGCCACCCTCACTGCCCGTCGCGCGTGTTTGATGTTAATAAATAACACATAAATTTGGCTGGTTGT

TTGTTGTCTTTAATGGACCGCCCGCAAGGGGGGGGGGGCGTTTCAGTGTCGGGTGACGAGCGCGATCCGG

CCGGGATCCTAGGACCCCAAAAGTTTGTCTGCGTATTCCAGGGTGGGGCTCAGTTGAATCTCCCGCAGCA

CCTCTACCAGCAGGTCCGCGGTGGGCTGGAGAAACTCGGCCGTCCCGGGGCAGGCGGTTGTCGGGGGTGG

AGGCGCGGCGCCCACCCCGTGTGCCGCGCCTGGCGTCTCCTCTGGGGGCGACCCGTAAATGGTTGCAGTG

ATGTAAATGGTGTCCGCGGTCCAGACCACGGTCAAAATGCCGGCCGTGGCGCTCCGGGCGCTTTCGCCGC

GCGAGGAGCTGACCCAGGAGTCGAACGGATACGCGTACATATGGGCGTCCCACCCGCGTTCGAGCTTCTG

GTTGCTGTCCCGGCCTATAAAGCGGTAGGCACAAAATTCGGCGCGACAGTCGATAATCACCAACAGCCCA

ATGGGGGTGTGCTGGATAACAACGCCTCCGCGCGGCAGGCGGTCCTGGCGCTCCCGGCCCCGTACCATGA

TCGCGCGGGTGCCGTACTCAAAAACATGCACCACCTGCGCGGCGTCGGGCAGTGCGCTGGTCAGCGAGGC

CCTGGCGTGGCATAGGCTATACGCGATGGTCGTCTGTGGATTGGACATCTCGCGGTGGGTAGTGAGTCCC

CCGGGCCGGGTTCGGTGGAACTGTAAGGGGACGGCGGGTTAATAGACAATGACCACGTTCGGATCGCGCA

GAGCCGATAGTATGTGCTCACTAATGACGTCATCGCGCTCGTGGCGCTCCCGGAGCGGATTTAAGTTCAT

GCGAAGGAATTCGGAGGAGGTGGTGCGGGACATGGCCACGTACGCGCTGTTGAGGCGCAGGTTGCCGGGC

GTAAAGCAGATGGCGACCTTGTCCAGGCTAAGGCCCTGGGAGCGCGTGATGGTCATGGCAAGCTTGGAGC

TGATGCCGTAGTCGGCGTTTATGGCCATGGCCAGCTCCGTAGAGTCAATGGACTCGACAAACTCGCTGAT

GTTGGTGTTGACGACGGACATGAAGCCGTGTTGGTCCCGCAAGACCACGTAAGGCAGGGGGGCCTCTTCC

AGTAACTCGGCCACGTTGGCCGTCGCGTGCCGCCTCCGCAGCTCGTCCGCAAAGGCAAACACCCGTGTGT

ACGTGTATCCCATGAGCGTATAATTGTCCGTCTGCAGGGCGACGGACATCAGCCCCCCGCGCGGCGAGCC

GGTCAGCATCTCGCAGCCCCGGAAGATAACGTTGTCCACGTACGTGCTAAAGGGGGCGACTTCAAATGCC

TCCCCGAAGAGCTCTTGGAGGATTCGGAATCTCCCGAGGAAGGCCCGCTTCAGCAGCGCAAACTGGGTGT

GAACGGCGGCGGTGGTCTCCGGTTCCCCGGGGGTGTAGTGGCAGTAAAACACGTCGAGCTGTTGTTCGTC

CAGCCCCGCGAAAATAACGTCGAGGTCGTCGTCGGGAAAATCGTCCGGGCCCCCGTCCCGCGGCCCCAGT

TGCTTAAAATCAAACGCACGCTCGCCGGGGGCGCCTGCGTCGGCCATTACCGACGCCTGCGTCGGCACCC

CCGAAGATTTGGGGCGCAGAGACAGAATCTCCGCCGTTAGTTCTCCCATGCGGGCGTACGCGAGGGTCCT

CTGGGTCGCATCCAGGCCCGGGCGCTGCAGAAAGTTGTAAAAGGAGATAAGCCCGCTAAATATGAGCCGC

GACAGGAACCTGTAGGCAAACTCCACCGAAGTCTCCCCCTGAGTCTTTACAAAGCTGTCGTCACGCAACA

CTGCCTCGAAGGCCCGGAACGTCCCACTAAACCCAAAAACCAGTTTTCGCAGGCGCGCGGTCACCGCGAT

CTGGCTGTTGAGGACGTAAGTGACGTCGTTGCGGGCCACGACCAGCTGCTGTTTGCTGTGCACCTCGCAG

CGCATGTGCCCCGCGTCCTGGTCCTGGCTCTGCGAGTAGTTGGTGATGCGGCTGGTGTTGGCCGTGAGCC

ACTTTTCAATAGTCAGGCCGGGCTGGTGTGTCAGCCGTCGGTATTCGTCAAACTCCTTGACCGACACGAA

CGTAAGCACGGGGAGGGTTAACACGACGAACTCCCCCTCACGGGTCACCTTCAGGTAGGCGTGGAGCTTG

GCCATGTACGCGCTCACCTCTTTGTGGGAGGAGAACAGCCGCGTCCAGCCGGGGAGGTTGGCGGGGTTGG

TGATGTAGTTTTCCGGGACGACGAAGCGATCCACGAACTGCATGTGCTCCTCGGTGATGGGCAGGCCGTA

CTCCAGCACCTTCATGAGGTTACCGAACTCGTGCTCGACGCACCGTTTGTTGTTAATAAAAATGGCCCAG

-continued
CTATACGAGAGGCGGGCGTACTCGCGCAGCGTGCGGGTGCAGATGAGGTACGTGAGCACGTTCTCGCTCT
GGCGGACGGAACACCGCAGTTTCTGGTGCTCGAAGGCGACTCCAGGGACGCCGTCTGCGTCGGCGAGCCC
ACACACACCAACACGGGCCGCAGGCGGGCCGCGTACTGGGGGGTGTGGTACAGGGCGTTAATCATCCACC
AGCAATACACCACGGCCGTGAGGAGGTGACGCCCAAGGAGCCCGGCCTCGTCGATGACGATCACGTTGCT
GCGGGTAAAGGCCGGCAGCGCCCCGTGGGTGGCCGGGGCCAACCGCGTCAGGGCGCCCTCGGCCAACCCC
AGGGTCCGTTCCAGGGCGGCCAGGGCGCGAAACTCGTTCCGCAACTCCTCGCCCCCGGAGGCGGCCAGGG
CGCGCTTCGTGAGGTCCAAAATCACCTCCCAGTAGTACGTCAGATCTCGTCGCTGCAGGTCCTCCAGCGA
GGCGGGGTTGCTGGTCAGGGTGTACGGGTACTGTCCCAGTTGGGCCTGGACGTGATTCCCGCGAAACCCA
AATTCATGAAAGATGGTGTTGATGGGTCGGCTGAGAAAGGCGCCCGAGAGTTTGGCGTACATGTTTTGGG
CCGCAATGCGCGTGGCGCCCGTCACCACACAGTCCAAGACCTCGTTGATTGTCTGCACGCACGTGCTCTT
TCCGGAGCCAGCGTTGCCGGTGATAAGATACACCGCGAACGGAAACTCCCTGAGGGGCAGGCCTGCGGGG
GACTCTAAGGCCGCCACGTCCCGGAACCACTGCAGACGGGGCACTTGCGCTCCGTCGAGCTGTTGTTGCG
AGAGCTCTCGGATGCGCTTAAGGATTGGCTGCACCCCGTGCATAGACGTAAAATTTAAAAAGGCCTCGGC
CCTCCCTGGAACGGCTGGTCGGTCCCCGGGTTGCTGAAGGTGCGGCGGGCCGGGTTTCTGTCCGTCTAGC
TGGCGCTCCCCGCCGGCCGCCGCCATGACCGCACCACGCTCGTGGGCCCCCACTACGCGTGCGCGGGGGG
ACACGGAAGCGCTGTGCTCCCCCGAGGACGGCTGGGTAAAGGTTCACCCCACCCCCGGTACGATGCTGTT
CCGTGAGATTCTCCACGGGCAGCTGGGGTATACCGAGGGCCAGGGGGTGTACAACGTCGTCCGGTCCAGC
GAGGCGACCACCCGGCAGCTGCAGGCGGCGATCTTTCACGCGCTCCTCAACGCCACCACTTACCGGGACC
TCGAGGCGGACTGGCTCGGCCACGTGGCGGCCCGCGGTCTGCAGCCCCAACGGCTGGTTCGCCGGTACAG
GAACGCCCGGGAGGCGGATATCGCCGGGGTGGCCGAGCGGGTGTTCGACACGTGGCGGAACACGCTTAGG
ACGACGCTGCTGGACTTTGCCCACGGGTTGGTCGCCTGCTTTGCGCCGGGCGGCCCGAGCGGCCCGTCAA
GCTTCCCCAAATATATCGACTGGCTGACGTGCCTGGGGCTGGTCCCCATATTACGCAAGCGACAAGAAGG
GGGTGTGACGCAGGGTCTGAGGGCGTTTCTCAAGCAGCACCCGCTGACCCGCCAGCTGGCCACGGTCGCG
GAGGCCGCGGAGCGCGCCGGCCCCGGGTTTTTTGAGCTGGCGCTGGCCTTCGACTCCACGCGCGTGGCGG
ACTACGACCGCGTGTATATCTACTACAACCACCGCCGGGGCGACTGGCTCGTGCGAGACCCCATCAGCGG
GCAGCGCGGAGAATGTCTGGTGCTGTGGCCCCCCTTGTGGACCGGGGACCGTCTGGTCTTCGATTCGCCC
GTCCAGCGGCTGTTTCCCGAGATCGTCGCGTGTCACTCCCTCCGGGAACACGCGCACGTCTGCCGGCTGC
GCAATACCGCGTCCGTCAAGGTGCTGCTGGGGCGCAAGAGCGACAGCGAGCGCGGGGTGGCCGGTGCCGC
GCGGGTCGTTAACAAGGTGTTGGGGGAGGACGACGAGACCAAGGCCGGGTCGGCCGCCTCGCGCCTCGTG
CGGCTTATCATCAACATGAAGGGCATGCGCCACGTAGGCGACATTAACGACACCGTGCGTGCCTACCTCG
ACGAGGCCGGGGGGCACCTGATAGACGCCCCGGCCGTCGACGGTACCCTCCCTGGATTCGGCAAGGGCGG
AAACAACCGCGGGTCTGCGGGCCAGGACCAGGGGGGGCGGGCGCCGCAGCTTCGCCAGGCCTTCCGCACG
GCCGTGGTTAACAACATCAACGGCGTGTTGGAGGGCTATATAAATAACCTGTTTGGAACCATCGAGCGCC
TGCGCGAGACCAACGCGGGCCTGGCGACCCAATTGCAGGAGCGCGACCGCGAGCTCCGGCGCGCAACAGC
GGGGGCCCTGGAGCGCCAGCAGCGCGCGGCCGACCTGGCGGCCGAGTCCGTGACCGGTGGATGCGGCAGC
CGCCCTGCGGGGGCGGACCTGCTCCGGGCCGACTATGACATTATCGACGTCAGCAAGTCCATGGACGACG
ACACGTACGTCGCCAACAGCTTTCAGCACCCGTACATCCCTTCGTACGCCCAGGACCTGGAGCGCCTGTC
GCGCCTCTGGGAGCACGAGCTGGTGCGCTGTTTTAAAATTCTGTGTCACCGCAACAACCAGGGCCAAGAG
ACGTCGATCTCGTACTCCAGCGGGGCGATCGCCGCATTCGTCGCCCCCTACTTTGAGTCAGTGCTTCGGG
CCCCCCGGGTAGGCGCGCCCATCACGGGCTCCGATGTCATCCTGGGGGAGGAGGAGTTATGGGATGCGGT
TTTAAAAAACCCGCCTGCAAACGTACCTGACAGACATCGCGGCCCTGTTCGTCGCGGACGTCCAGCACGC -continued

AGCGCTGCCCCCGCCCCCCTCCCCGGTCGGCGCCGATTTCCGGCCCGGCGCGTCCCCGCGGGGCCGGTCC

AGATCGCGGTCGCCCGGAAGAACTGCGCCAGGCGCGCCGGACCAGGGCGGGGGCATCGGGCACCGGGATG

GCCGCCGCGACGGCCGACGATGAGGGGTCGGCCGCCACCATCCTCAAGCAGGCCATCGCCGGGGACCGCA

GCCTGGTCGAGGCGGCCGAGGCGATTAGCCAGCAGACGCTGCTCCGCCTGGCCTGCGAGGTGCGCCAGGT

CGGCGACCGCCAGCCGCGGTTTACCGCCACCAGCATCGCGCGCGTCGACGTCGCGCCTGGGTGCCGGTTG

CGGTTCGTTCTGGACGGGAGTCCCGAGGACGCCTATGTGACGTCGGAGGATTACTTTAAGCGCTGCTGCG

GCCAGTCCAGTTATCGCGGCTTCGCGGTGGCGGTCCTGACGGCCAACGAGGACCACGTGCACAGCCTGGC

CGTGCCCCCCCTCGTTCTGCTGCACCGGTTCTCCCTGTTCAACCCCAGGGACCTCCTGGACTTTGAGCTT

GCCTGTCTGCTGATGTACCTGGAGAACTGCCCCCGAAGCCACGCCACCCCGTCGACCTTTGCCAAGGTTC

TGGCGTGGCTCGGGGTCGCGGGTCGCCGCACGTCCCCATTCGAACGCGTTCGCTGCCTTTTCCTCCGCAG

TTGCCACTGGGTCCTAAACACACTCATGTTCATGGTGCACGTAAAACCGTTCGACGACGAGTTCGTCCTG

CCCCACTGGTACATGGCCCGGTACCTGCTGGCCAACAACCCGCCCCCCGTTCTCTCGGCCCTGTTCTGTG

CCACCCCGACGAGCTCCTCATTCCGGCTGCCGGGGCCGCCCCCCCGCTCCGACTGCGTGGCCTATAACCC

CGCCGGGATCATGGGGAGCTGCTGGGCGTCGGAGGAGGTGCGCGCGCCTCTGGTCTATTGGTGGCTTTCG

GAGACCCCAAAACGACAGACGTCGTCGCTGTTTTATCAGTTTTGTTGAATTTTAGGAAATAAACCCGGTT

TTGTTTCTGTGGCCTCCCGACGGATGCGCGTGTCCTTCCTCCGTCTTGGTGGGTGGGTGTCTGTGTATCG

CGTCCCATCTGTGCGGAGAGGGGGGGCATGTCGGCACGTATTCGGACAGACTCAAGCACACACGGGGGAG

CGCTCTTGTCTCAGGGCAATGTTTTTATTGGTCAAACTCAGGCAAACAGAAACGACATCTTGTCGTCAAA

GGGATACACAAACTTCCCCCCCTCTCCCCATACTCCCGCCAGCACCCCGGTAAACACCAACTCAATCTCG

CGCAGGATTTCGCGCAGGTGATGAGCGCAGTCCACGGGGGGGAGCACAAGGGGCCGCGGGTATAGATCGA

CGGGGACGCCGACCGACTCCCCGCCTCCGGGACAGACACGCACGACGCGCCGCCAGTAGTGCTCTGCGTC

CAGCAAGGCGCCGCCGCGGAAGGCAGTGGGGGGCAAGGGGTCGCTAGCCTCAAAGGGGGACACCCGAACG

CTCCAGTACTCCGCGTCCAACCGTTTATTAAACGCGTCCACGATAAGGCGGTCGCAGGCGTCCTCCATAA

GGCCCCGGGCCGTGAGTGCGTCCTCCTCCGGCACGCCTGCCGTTGTCAGGCCCAGGACCCGTCGCAGCGT

GTCGCGTACGACCCCGGCCGCCGTGGTGTACGCGGGCCCGCGGAGAGGAAATCCCCCAAGATGGTCAGTG

TTGTCGCGGGAGTTCCAGAACCACACTCCCGCCTGGTTCCAGGCGACTGCGTGGGTGTAGACGCCCTCGA

GGGCCAGGCACAGTGGGTGCCGCAGCCGGAGGCCGTTGGCCCTAAGCACGGCTCCCACGGCCGTCTCGAT

GGCCCGCCGGGCGTCCTCGATCACCCCGGAAGCCGCATCCGCGTCTTGGGGGTCCACGTTAAAGACACCC

CAGAACGCACCCCCATCGCCCCCGCAGACCGCGAACTTCACCGAGCTGGCCGTCTCCTCGATCTGCAGGC

AGACGGCGGCCATTACCCCACCCAGGAGCTGCCGCAGCGCAGGGCAGGCGTCGCACGTGTCCGGGACCAG

GCGCTCCAAGACGGCCCCGGCCCAGGGCTCTGAGGGAGCGGCCACCACCAGCGCGTCCAGTCTTGCTAGG

CCCGTCCGGCCGTGGGGGTCCGCCAGCCCGCTCCCCCCGAGGTCGGCCAGGGCCACCAGGAGCTGGGCGC

GAAGTCCGGGGAAGCAAAACCGCGCCGTCCAGACGGGCCCGACGGCCGCGGGCGGGTCTAACAGTTGGAT

GATTTTAGTGGCGGGATGCCACCGCGCCACCGCCTCCCGCACCGCGGGCAGGAGGCATCCGGCTGCCGCC

GAGGCCACGCCGGGCCAGGCTCGCGGGGGGAGGACGACCCTGGCCCCCACCGCGGGCCAGGCCCCCAGGA

GCGCGGCGTAAGCGGCCGCGGCCCCGCGCACCAGGTCCCGTGCCGACTCGGCCGTGGCCGGCACGGTGAA

CGTGGGCCAACCCGGAAACCCCAGGACGGCAAAGTACGGGACGGGTCCCCCCCGGACCTCAAACTCGGGC

CCCAGAAAGGCAAAGACGGGGGCCAGGGCCCCGGGGGCGGCGTGGACCGTGGTATGCCACTGCCGGAAAA

GGGCGACGAGCGCCGGCGCGGAGAACTTCTCGCCGGCGCTTACAAAGTAGTCGTAATCGCGGGGCAGCAG

CACCCGTGCCGTGACTCGTTGCGGGTGCCCGCGTGGCCGCAGGCCCACCTCGCACACCTCGACCAGGTCC

-continued

CCGAACGCGCCCTCCTTCTTGATCGGCGGAAACGCAAGAGTCTGGTATTCGCGCGCAAATAGCGCGGTTC

CGGTGGTGATGTTAACGGTCAGCGAAGCGGCGGACGCGCACTGGGGGGTGTCGCGAATGGCCGCCAGGCG

CGCCCACGCCAGCCGCGCGTCGGGATGCTCGGCAACGCGCGCCGCCAGGGCCATAGGGTCGATGTCAATG

TTGGCCTCCGCGACCAGGAGAGCGGCGCGAGGGGCGGCGGGCGGGCCCCACGACGCTCTCTCAACTTTCA

CCACCAGTCCCGTGCGTGGGTCCGAGCCGATACGCAGCGGGGCGAACAGGGCCACCGGCCCGGTCTGGCG

CTCCAGGGCCGCCAGGACGCACGCGTACAGCGCCCGCCACAGAGTCGGGTTCTCCAGGGGCTCCAGCGGG

GAGGCGGCCGGCGTCGTCGCGGCGCGGGCGGCCGCCACGACGGCCTGGACGGAGACGTCCGCGGAGCCGT

AGAAATCCCGCAGCTCCGTCGCGGTGACGGAGACCTCCGCAAAGCGCGCGCGACCCTCCCCTGCGGCGTT

GCGACATACAAAATACACCAGGGCGTGGAAGTACTCGCGAGCGCGGGGGGGCAGCCATACCGCGTAAAGG

GTAATGGCGCTGACGCTCTCCTCCACCCACACGATATCTGCGGTGTCCATCGCACGGCCCCTAAGGATCA

CGGGCGGTCTGTGGGTCCCATGCTGCCGTGCCTGGCCGGGCCCGGTGGGTCGCGGAAACCGGTGACGGGG

GGGGGGCGGTTTTTGGGGTTGGGGTGGGGGTGGGAAACGGCCCGGGTCCGGGGGCCAACTTGGCCCCTCG

GTGCGTTCCGGCAACAGCGCCGCCGGTCCGCGGACGACCACGTACCGAACGAGTGCGGTCCCGAGACTTA

TAGGGTGCTAAAGTTCACCGCCCCCTGCATCATGGGCCAGGCCTCGGTGGGGAGCTCCGACAGCGCCGCC

TCCAGGATGATGTCAGCGTTGGGGTTGGCGCTGGATGAGTGCGTGCGCAAACAGCGCCCCCACGCAGGCA

CGCGTAGCTTGAAGCGCGCGCCCGCAAACTCCCGCTTGTGGGCCATAAGCAGGGCGTACAGCTGCCTGTG

GGTCCGGCAGGCGCTGTGGTCGATGTGGTGGGCGTCCAACAACCCCACGATTGTCTGTTTGGTGAGGTTT

TTAACGCGCCCCGCCCCGGGAAACGTCTGCGTGCTTTTGGCCATCTGCACGCCAAACAGTTCGCCCCAGA

TTATCTTGAACAGCGCCACCGCGTGGTCCGTCTCGCTAACGGACCCGCGCGGGGGACAGCCGCTTAGGGC

GTCGGCGACGCGCTTGACGGCTTCCTCCGAGAGCAGAAGTCCGTCGGTTACGTTACAGTGGCCCAGTTCG

AACACCAGCTGCATGTAGCGGTCGTAGTGGGGGGTCAGTAGGTCCAGCACGTCATCGGGGCCGAAGGTCC

TCCCAGATCCCCCGGCCGCCGAGTCCCAATGCAGGCGCGCGGCCATGGTGCTGCACAGGCACAACAGCTC

CCAGACGGGGGTTACGTTCAGGGTGGGGGGCAGGGCCACGAGCTCCAGCTCTCCGGTGACGTTGATCGTG

GGGATGACGCCCGTGGCGTAGTGGTCATAGATCCGCCGAAATATGGCGCTGCTGCGGGTGGCCATGGGAA

CGCGGAGACAGGCCTCCAGCAACGCCAGGTAAATAAACCGCGTGCGTCCCATCAGGCTGTTGAGGTTGCG

CATGAGCGCGACAATTTCCGCCGGCGCGACATCGGACCGGAGGTATTTTTCGACGAAAAGACCCACCTCC

TCCGTCTCGGCGGCCTGGGCCGGCAGCGACGCCTCGGGATCCCGGCACCGCAGCTCCCGTAGATCGCGCT

GGGCCCTGAGGGCGTCGAAATGTACGCCCCGCAAAAACAGACAGAAGTCCTTTGGGGTCAGGGTATCGTC

GTGTCCCCAGAAGCGCACGCGTATGCAGTTTAGGGTCAGCAGCATGTGAAGGATGTTAAGGCTGTCCGAG

AGACACGCCAGCGTGCATCTCTCAAAGTAGTGTTTGTAACGGAATTTGTTGTAGATGCGCGACCCCCGCC

CCAGCGACGTGTCGCATGCCGACGCGTCACAGCGCCCCTTGAACCGGCGACACAGCAGGTTTGTGACCTG

GGAGAACTGCGCGGGCCACTGGCCGCAGGAACTGACCACGTGATTAAGGAGCATGGGCGTAAAGACGGGC

TCCGAGCGCGCCCCGGAGCCGTCCATGTAAATCAGTAGCTCCCCCTTGCGGAGGGTGCGCACCCGTCCCA

GGGACTGGTACACGGACACCATGTCCGGTCCGTAGTTCATGGGTTTTACGTAGGCGAACATGCCATCAAA

GTGCAGGGGATCGAAGCTGAGGCCCACGGTTACGACCGTCGTGTATATAACCACGCGGTATTGGCCCCAC

GTGGTCACGTCCCCGAGGGGGGTGAGCGAGTGAAGCAACAGCACGCGGTCCGTAAACTGACGGCAGAACC

GGGCCACGATCTCCGCGAAGGAGACCGTCGACGAAAAAATGCAGATGTTATCGCCCCCGCCAAGGCGCGC

TTCCAGCTCCCCAAAGAACGTGGCCCCCCGGGCGTCCGGAGAGGCGTCCGGAGACGGGCCGCTCGGCGGC

CCGGGCGGGCGCAGGGCAGCCTGCAGGAGCTCGGTCCCCAGACGCGGGAGAAACAGGCACCGGCGCGCCG

AAAACCCGGGCATGGCGTACTCGCCGACCACCACATGCACGTTTTTTTCGCCCCGGAGACCGCACAGGAA

GTCCACCAACTGCGCGTTGGCGGTTGCGTCCATGGCGATGATCCGAGGACAGGTGCGCAGCAGGCGTAGC

-continued

ATTAACGCATCCACGCGGCCCAGTTGCTGCATCGTTGGCGAATAGAGCTGGCCCAGCGTCGACATAACCT

CGTCCAGAACGAGGACGTCGTAGTTGTTCAGAAGGTTGGGGCCCACGCGATGAAGGCTTTCCACCTGGAC

GATAAGTCGGTGGAAGGGGCGGTCGTTCATAATGTAATTGGTGGATGAGAAGTAGGTGACAAAGTCGACC

AGGCCTGACTCAGCGAACCGCGTCGCCAGGGTCTGGGTAAAACTCCGACGACAGGAGACGACGAGCACAC

TCGTGTCCGGAGAGTGGATCGCTTCCCGCAGCCAGCGGATCAGCGCGGTAGTTTTTCCCGACCCCATTGG

CGCGCGGACCACAGTCACGCACCTGGCCGTCGGGGCGCTCGCGTTGGGGAAGGTGACGGGTCCGTGCTGC

TGCCGCTCGATCGTTGTTTTCGGGTGAACCCGGGGCACCCATTCGGCCAAATCCCCCCGTACAACATCC

GCGCTAGCGATACGCTCGACGTGTACTGTTCGCACTCGTCGTCCCCAATGGGACGCCCGGCCCCCAGAGG

ATCTCCCGACTCCGCGCCCCCACGAAAGGCATGACCGGGGCGCGGACGGCGTGGTGGGTCTGGTGTGTG

CAGGTGGCGACGTTTGTGGTCTCTGCGGTCTGCGTCACGGGGCTCCTCGTCCTGGCCTCTGTGTTCCGGG

CACGGTTTCCCTGCTTTTACGCCACGGCGAGCTCTTATGCCGGGGTGAACTCCACGGCCGAGGTGCGCGG

GGGTGTAGCCGTGCCCCTCAGGTTGGACACGCAGAGCCTTGTGGGCACTTATGTAATCACGGCCGTGTTG

TTGTTGGCCGCGGCCGTGTATGCCGTGGTCGGCGCCGTGACCTCCCGCTACGACCGCGCCCTGGACGCGG

GCCGCCGTCTGGCTGCGGCCCGCATGGCCATGCCGCACGCCACGCTGATCGCCGGAAACGTCTGCTCTTG

GTTGCTGCAGATCACCGTCCTGTTGCTGGCCCATCGCACCAGCCAGCTGGCCCACCTGGTTTACGTCCTG

CACTTTGCGTGTCTGGTGTATTTTGCGGCCCATTTTTGCACCAGGGGGGTCCTGAGCGGGACGTATCTGC

GTCAGGTGCACGGCCTGATGGAGCCGGCCCCGACTCATCATCGCGTCGTTGGCCCGGCTCGAGCCGTGCT

GACAAACGCCTTGCTGTTGGGCGTCTTCCTGTGCACGGCCGACGCCGCGGTATCCCTGAATACCATCGCC

GCGTTCAACTTTAATTTTTCGGCCCCGGGCATGCTCATATGCCTGACCGTGCTGTTCGCCCTTCTCGTCG

TATCGCTGTTGTTGGTGGTCGAGGGGGTGTTGTGTCACTACGTGCGCGTGTTGGTGGGCCCCCACCTGGG

GGCCGTGGCCGCCACGGGCATCGTCGGCCTGGCATGCGAGCACTATTACACCAACGGCTACTACGTIGTG

GAGACGCAGTGGCCGGGGGCCCAGACGGGAGTCCGCGTCGCCCTCGCCCTGGTCGCCGCCTTTGCCCTCG

GCATGGCCGTGCTCCGCTGCACCCGCGCCTATCTGTATCACAGGCGGCACCACACCAAATTTTTTATGCG

CATGCGCGACACGCGACACCGCGCACATTCCGCCCTCAAGCGCGTACGCAGTTCCATGCGCGGATCGCGA

GACGGCCGCCACAGGCCCGCACCCGGCAGCCCGCCCGGGATTCCCGAATATGCGGAAGACCCCTACGCGA

TCTCATACGGCGGCCAGCTCGACCGGTACGGAGATTCCGACGGGGAGCCGATTTACGACGAGGTGGCGGA

CGACCAAACCGACGTATTGTACGCCAAGATACAACACCCGCGGCACCTGCCCGACGACGAGCCCATCTAT

GACACCGTTGGGGGGTACGACCCCGAGCCCGCCGAGGACCCCGTGTACAGCACCGTCCGCCGTTGGTAGC

TGITTGGTTCCGTTTTAATAAACCGTTTGTGTTTAACCCGACCGTGGTGTATGTCTGGTGTGTGGCGTCC

GATCCCGTTACTATCACCGTTCCCCCCAAACCCCGGCGATTGTGGGTTTTTTTAAAAACGACACGCGTGC

GACCGTATACAGAACATTGTTGTTTTTTATTCGCTATCGGACATGGGGGGTGGAAACTGGGTGGCGGGGC

AGGCGCCTCCGGGGGTTCGCCGGTGAGTGTGGCGCGAGGGGGGATCCGACGAACGCAGGCGCTGTCTCCC

CGGGGCCCGCGTAACCCCGCGCATATCCGGGGGCACGTAGAAATTACCTTCCTCTTCGGACTCGATATCC

ACGACGTCAAAGTCGTGGGCGGTCAGCGAGACGACCTCCCCGTCGTCGGTGATGAGGACGTTGTTTCGGC

AGCAGCAGGGCCGGGTCCCGGAGAACGAGAGGCCCATAGCTCGGCGAGCGTGTCGTCGAACGCCAGGCGG

CTGCTTCGCTGTATGGCCTTATAGATCTCCGGATCGATGCGGACGGGGGTAATGATCAGGGCGATCGGAA

CGGCCTGGTTCGGGAGAATGGACGCCTTGCTGGGTCCTGCGGCCCCGAGAGCCCCGGCGCCGTCCTCCAG

GCGGAACGTTACGCCCTCCTCCGCGCTAGTGCGGTGCCTGCCGATAAACGTCACCAGATGCGGGTGGGGG

GGGCAGTCGGGGAAGTGGCTGTCGAGCACGTAGCCCTGCACCAAGATCTGCTTAAAGTTCGGGTGACGGG

GGTTCGCGAAGACGGGCTCGCGGCGTACCAGATCCCCGGAGCTCCAGGACACGGGGGAGATGGTGTGGCG

-continued

TCCGAGGTCGGGGGTGCCAAACAGAAGCACCTCCGAGACAACGCCGCTATTTAACTCCACCAAGGCCCGA

TCCGCGGCGGAGCACCGCCTTTTTTCGCCCGAGGCGTGGGCCTCTGACCAGGCCTGGTCTTGCGTGACGA

GAGCCTCCTCCGGGCCGGGGACGCGCCCGGGCGCGAAGTATCGCACGCTGGGCTTCGGGATCGACCGGAT

AAATGCCCGGAACGCCTCCGGGGACCGGTGTGCCATCAAGTCCTCGTACGCGGAGGCCGTGGGGTCGCTG

GGGTCCATGGGGTCGAAAGCGTACTTGGCCCGGCATTTGACCTCGTAAAAGGCCAGGGGGGTCTTGGGGA

CTGGGGCCAAGTAGCCGTGAATGTCCCGAGGACAGACGAGAATATCCAGGGACGCCCCGACCATCCCCGT

GTGACCGTCCATGAGGACCCCACACGTATGCACGTTCTCTTCGGCGAGGTCGCCGGGTTCGTGGAAGATA

AAGCGCCGCGTGTCGGCGCCGGCCTCGCCGCCGTCGTCCGCGCGGCCCACGCAGTAGCGAAACAGCAGGC

TTCGGGCCGTCGGCTCGTTCACCCGCCCGAACATCACCGCCGAAGACTGTACATCCGGCCGCAGGCTGGC

GTTGTGCTTCAGCCACTGGGGCGAGAAACACGGACCCTGGGGGCCCCAGCGGAGGGTGGATGCGGTCGTG

AGGCCCCGCCGGAGCAGGGCCCATAGCTGGCAGTCGGCCTGGTTTTGCGTGGCCGCCTCGTAAAACCCCA

TGAGGGGCCGGGGCGCCACGGCGTCCGCGGCGGCCGGGGGCCCGCGGCGCGTCAGGCGCCATAGGTGCCG

GCCGAGTCCGCGGTCCACCATACCCGCCTCCTCGAGGACCACGGCCAGGGAACACAGATAATCCAGGCGG

GCCCAGAGGGGACCGATGGCCAGAGGGGCGCGGACGCCGCGCAGCAACCCGCGCAGGGGCGCTCGAACGT

CTCGGCTAGTATATGGGAGGGCAGCGCGTTGGGGATCACCGACGCCGACCACATAGAGTCAAGGTCCGGG

GAGTCGGGATCGGCGTCCGGGTCGCGGGCGTGGGTGCCCCCAGGAGATAGCGGAATGTCTGGGGTCGGAG

GCCCTGAGGCGTCAGAAAGTGCCGGCGACGCGGCCCGGGGCTTTTCGTCTGCGGTGTCGGTGGCGTGCTG

ATCACGTGGGGGGTTAACGGGCGAATGGGAGCTCGGGTCCACAACTGACGTCGTCTGGGGTGGGGGGGGC

AGGGGACGGAAGGTGGTTGTTAGCGGAAGACTGTTAGGGCGGGGGCGCTTGGGGGGGCTGTCGGGGCCAC

GAGGGGTGTCCTCGGCCAGGGCCCAGGAACGCTTAGTCACGGTGCGTCCCGGCGGACATGCTGGGCCTCC

CGTGGACTCCATTTCCGAGACGACGTGGGGGGAGCGGTGGTTGAGCGCGCCGCCGGGTGAACGCTGATTC

TCACGACAGCGCGTGCCGCGCGCACGGGTTGGTGTGACACAGGCGGGACACCAGCACCAGGAGAGGCTTA

AGCTCGGGAGGCAGCGCCACCGACGACAGTATCGCCTTGTGTGTGTGCTGGTAATTTATACACCGATCCG

TAAACGCGCGCCGAATCTTGGGATTGCGGAGGTGGCGCCGGATGCCCTCTGGGACGTCATACGCCAGGCC

GTGGGTGTTGGTCTCGGCCGAGTTGACAAACAGGGCTGGGTGCAGCACGCGGCGATAGGCGAGCAGGGCC

AGGGCGAAGTCCAGCGACAGCTGGTTGTTGAAATACTGGTAACCGGGAAACCGGGTCACGGGTACGCCCA

GGCTCGGGGCGACGTACACGCTAACCACCAACTCCAGCAGCGTCTGGCCAAGGGCGTACAGGTCAACCGC

TAACCCGACGTCGTGCTTCAGGCGGTGGTTGGTAAATTCGGCCCGTTCGTTGTTAAGGTATTTCACCAAC

AGCTCCGGGGGCTGGTTATACCCGTGACCCACCAGGGTGTGAAAGTTGGCTGTGGTTAGGGCGGTGGGCA

TGCCAAACATCCGGGGGGACTTGAGGTCCGGCTCCTGGAGGCAAAACTGCCCCCGGGCGATCGTGGAGTT

GGAGTTGAGGGTGACGAGGCTAAAGTCGGCGAGGACGGCCCGCCGGAGCGAGACGGCGTCCGACCGCAGC

ATGACGAGGATGTTGGCGCACTTGATATCCAGGTGGCTGATCCCGCAGGTGGTGTTTAAAAACACAACGG

CGCGGGCCAGCTCCGTGAAGCACTGGTGGAGGGCCGTCGAGACCGAGGGGTTTGTTGTGCGCAGGGACGC

CAGTTGGCCGATATACTTACCGAGGTCCATGTCGTACGCGGGGAACACTATCTGTCGTTGTTGCAGCGAG

AACCCGAGGGGCGCGATGAAGCCGCGGATGTTGTGGGTGCGGCCGGCGCGTAGAGCGCACTCCCCGACCA

ACAGGGTCGCGATGAGCTCAACGGCAAACCACTCCTTTTCCTTTATGGTCTTAACGGCAAGCTTATGTTC

GCGAATCAGTTGGACGTCGCCGTATCCCCCAGACCCCCCGAAGCTTCGGGCCCCGGGGATCTCGAGGGTC

GTGTAGTGTAGGGCGGGGTTGATGGCGAACACGGGGCTGCATAGCTTGCGGATGCGCGTGAGGGTAAGGA

TGTGCGAGGGGGACGAGGGGGGTGCGGTTAACGCCGCCTGGGATCTGCGCAGGGGCGGGCGGTTCAGTTT

GGCCGCCGTACCGGGCGTCTCGGGGGACGCGCGGCGATGAGACGAGCGGCTCATTCGCCATCGGGATAGT

CCCGCGCGAAGCCGCTCGCGGAGGCCGGATCGGTGGCGGGACCCGTGGGAGGAGCGGGAGCCGGCGGCGT

-continued

CCTGGAGAGAGGGGCCGCTGGGGCGCCCGGAGGCCCCGTGTGGGTTGGAGTGTATGTAGGATGCGAGCCA

ATCCTTGAAGGACTGTTGGCGTGCACCTTGGGGGCTGAGGTTAGCTGCCACATGACCAGCAGGTCGCTGT

CTGCGGGACTCATCCATCCTTCGGCCAGGTCGCCGTCTTCCCACAGAGAAGCGTTGGTCGCTGCTTCCTC

GAGTTGCTCCTCCTGGTCCGCAAGACGATCGTCCACGGCGTCCAGGCGCTCACCAAGCGCCGGATCGAGG

TACCGTCGGTGTGCGGTTAGAAAGTCACGACGCGCCGCTTGCTCCTCCACGCGAATTTTAACACAGGTCG

CGCGCTGTCGCATCATCTCTAAGCGCGCGCGGGACTTTAGCCGCGCCTCCAATTCCAAGTGGGCCGCCTT

TGCAGCCATAAAGGCGCCAACAAACCGAGGATCTTGGGTGCTGACGCCCTCCCGGTGCAGCTGCAGGGTC

TGGTCCTTGTAAATCTCGGCTCGGAGGTGCGTCTCGGCCAGGCGTCGGCGCAGGGCCGCGTGGGCGGCAT

CTCGGTCCATTCCGCCACCCTGCGGGCGACCCGGGGGGTGCTCTGATAGTCTCGCGTGCCCAAGGCCCGT

GATCGGGGTACTTCGCCGCCGCGACCCGCCACCCGGTGTGCGCGATGTTTGGTCAGCAGCTGGCGTCCGA

CGTCCAGCAGTACCTGGAGCGCCTCGAGAAACAGAGGCAACTTAAGGTGGGCGCGGACGAGGCGTCGGCG

GGCCTCACAATGGGCGGCGATGCCCTACGAGTGCCCTTTTTAGATTTCGCGACCGCGACCCCCAAGCGCC

ACCAGACCGTGGTCCCGGGCGTCGGGACGCTCCACGACTGCTGCGAGCACTCGCCGCTCTTCTCGGCCGT

GGCGCGGCGGCTGCTGTTTAATAGCCTGGTGCCGGCGCAACTAAAGGGGCGTGATTTCGGGGGCGACCAC

ACGGCCAAGCTGGAATTCCTGGCCCCCGAGTTGGTACGGGCGGTGGCGCGACTGCGGTTTAAGGAGTGCG

CGCCGGCGGACGTGGTGCCTCAGCGTAACGCCTACTATAGCGTTCTGAACACGTTTCAGGCCCTCCACCG

CTCCGAAGCCTTTCGCCAGCTGGTGCACTTTGTGCGGGACTTTGCCCAGCTGCTTAAAACCTCCTTCCGG

GCCTCCAGCCTCACGGAGACCACGGGCCCCCCAAAAAAACGGGCCAAGGTGGACGTGGCCACCCACGGCC

GGACGTACGGCACGCTGGAGCTGTTCCAAAAAATGATCCTTATGCACGCCACCTACTTTCTGGCCGCCGT

GCTCCTCGGGGACCACGCGGAGCAGGTCAACACGTTCCTGCGTCTCGTGTTTGAGATCCCCCTGTTTAGC

GACGCGGCCGTGCGCCACTTCCGCCAGCGCGCCACCGTGTTTCTCGTCCCCCGGCGCCACGGCAAGACCT

GGTTTCTAGTGCCCCTCATCGCGCTGTCGCTGGCCTCCTTTCGGGGGATCAAGATCGGCTACACGGCGCA

CATCCGCAAGGCGACCGAGCCGGTGTTTGAGGAGATCGACGCCTGCCTGCGGGGCTGGTTCGGTTCGGCC

CGAGTGGACCACGTTAAAGGGGAAACCATCTCCTTCTCGTTTCCGGACGGGTCGCGCAGTACCATCGTGT

TTGCCTCCAGCCACAACACAAACGTAAGTCCTCTTTTCTTTCGCATGGCTCTCCCAAGGGGCCCCGGGTC

GACCCGACCCACACCCACCCACCCACCCACATACACACACAACCAGACGCGGGAGGAAAGTCTGCCCCGT

GGGCACTGATTTTTATTCGGGATCGCTTGAGGAGGCCCGGGCAACGGCCCGGGCAACGGTGGGGCAACTC

GTAGCAAATAGGCGACTGATGTACGAAGAGAAGACACACAGGCGCCACCCGGCGCTGGTCGGGGGGATGT

TGTCCGCGCCGCACCGTCCCCCGACGACCTCTTGCAGACGGTCCGTGATGCAAGGACGGCGGGGGGCCTG

CAGCAGGGTGACCGTATCCACGGGATGGCCAAAGAGAAGCGGACACAGGCTAGCATCCCCCTGGACCGCC

AGGGTACACTGGGCCATCTTGGCCCACAGACACGGGGCGACGCAGGGACAGGACTCCGTTACGACGGAGG

AGAGCCACAGTGCGTTGGCGGAATCGATGTGGGGCGGCGGGGCGCAGGACTCGCAGCCCCCCGGGTGGTT

GGTGATCCTGGCCAGGAGCCATCCCAGATGGCGGGCCCTGCTTCCCGGTGGACAGAGCGACCCCAGGTCG

CTGTCCATGGCCCAGCAGTAGATCTGGCCGCTGGGGAGGTGCCACCAGGCCCCCGGGCCCAAGGCGCAAC

ACGCGCCCGGCTCCGGGGGGGTCTTCGCGGGGACCAGATACGCGCCATCCAGCTCGCCGACCACTGGCTC

CTCCGCGAGCTGTTCGGTGGTTGGGTCGGGGGTTTCCTCCGGGGGGGTGGCCGCCCGTATGCGGGCGAAC

GTGAGGGTGCACAGGAGCGGGGTCAGGGGGTGCGTCACGCTCCGGAGGTGGACGATCGCGCAGTAGCGGC

GCTCGCGGTTAAAGAAAAAGAGGGCAAAGAAGGTGTTCGGGGGCAACCGCAGCGCCTTGGGGCGCGTCAG

ATACAGAAAAATCTCGCAGAAGAGGGCGCGCCCGGGGTCTGGGTTAGGAAGGGCCACCTGACACAGAGGC

TCGGTGAGGACCGTTAGACACCGAAAGATCTTGAGCCGCTCGTCCGCCCGAACGACGCGCCACACAAAGA

-continued

CGGAGTTGACAATGCGCGCGATAGAGTCGACGTCCGTCCCCAGGTCGTCGACTCTGTCGCGCGTGCCGCG

AGCTCCGGCCCGGGAATCCGGCCGGGGCAAGGTCCCCGGGGGACCAGGCGGCGCCAGGGGCCGCCGGGGT

CCCAGCTGCGCCATGCCGGGGGCGGGGGGAGGGCAAACCCCAGAGGCGGGGGCCAACGGCGCGGGGAGGA

GTGGGTGGGCGAGGTGGCCGGGGGAAGGCGCCCGCTAGCGAGAACGGCCGTTCCCGGACGACACCTTGCG

ACAAAACCTAAGGACAGCGGCCCGCGCGACGGGGTCCGAGAGGCTAAGGTAGGCCGCGATGTTAATGGTG

AACGCAAAGCCGCCGGGAAAGACAACTATGCCACAGAGGCGGCGATTAAACCCCAGGCAGAGGTAGGCGT

AGCTTTCCCCGGGCAGGTATTGCTCGCAGACCCTGCGTGGGGCTGTGGAGGGGACGGCCTCCATGAAGCG

ACATTTACTCTGCTCGCGTTTACTGACGTCACCATCCATCGCCACGGCGATTGGACGATTGTTAAGCCGC

AGCGTGTCTCCGCTTGTGCTGTAGTAGTCAAAAACGTAATGGCCGTCGGAGTCGGCAAAGCGGGCCGGGA

GGTCGTCGCCGAGCGGGACGACCCGCCGCCCCCGACCGCCCCGTCCCCCCAGGTGTGCCAGGACGGCCAG

GGCATACGCGGTGTGAAAAAAGGCGTCGGGGGCGGTCCCCTCGACGGCGCGCATCAGGTTCTCGAGGAGA

ATGGGGAAGCGCCTGGTCACCTCCCCCAGCCACGCGCGTTGGTCGGGGCCAAAGTCATAGCGCAGGCGCT

GTGAGATTCGAGGGCCGCCCTGAAGCGCGGCCCGGATGGCCTGGCCCAGGGCCCGGAGGCACGCCAGATG

TATGCGCGCAGTAAAGGCGACCTCGGCGGCGATGTCAAAGGGCGGCAGGACGGGGCGCGGGTGGCGCAGG

GGCACCTCGAGCGCGGGAAAGCGGAGCAGCAGCTCCGCCTGCCCAGCGGGAGACAGCTGGTGGGGGCGCA

CGACGCGTTCTGCGGCGCAGGCCTCGGTCAGGGCCGTGGCCAGCGCCGAGGACAGCAGCGGGGGCGGGCG

CGTCGCCCGCCCCACGCCACGGAGTTCTCGTAGGAGACGACGACGAAGCGCTGCTTGGTTCCGTAGTGGT

GGCGCAGGACCACGGAGATAGAACGACGGCTCCACAGCCAGTCCGGCCGGTCGCCGCCGGCCAGGGCTTC

CCATCCGCGATCCAACCACTCGACCAGCGACCGCGGCTTTGCGGTACCAGGGGTCAGGGTTAGAACGTCG

TTCAGGATGTCCTCGCCCCCGGGCCCGTGGGGCACTGGGGCCACAAAGCGGCCCCCGCCTGGGGGCTCCA

GACCCGCCAACACCGCATCTGCGTCAGCCGCCCCCATGGCGCCCCCGCTGACGGCCTGGTGAACCAGGGC

GCCCTGGCGGAGCCCCGATGCAACGCCACAGGCCGCACGCCCGGTCCGAGCGCGGACCGGGTGGCGGCGG

GTGACGTCCTGCACTGCCCGCTGAACCAACGCGAGGATCTCCTCGTTCTCCTGCGCGATGGACACGTCCT

GGGCCGCGGTCGTGTCGCCGCCGGGGGCCGTCAGCTGCTCCTCCGGGGAGATGGGGGGGTCGGACGCCCC

GACGATGGGCGGGTCTGCGGGCGCCCCCGCGTGGGGCCGGGCCAAGGGCTGCGGACGCGGGGACGCGCTT

TCCCCCAGACCCATGGACAGGTGGGCCGCAGCCTCCTTCGCGGCCGGCGGGGCGGCGGCGCCAAGCAGAG

CGACGTAGCGGCACAAATGCCGACAGACGCGCATGATGCGCGTGCTGTCGGCCGCGTAGCGCGTGTTGGG

GGGGACGAGCTCGTCGTAACTAAACAGAATCACGCGGGCACAGCTCGCCCCCGAGCCCCACGCAAGGCGC

AGCGCCGCCACGGCGTACGGGTCATAGACGCCCTGTGCGTCACACACCACGGGCAAGGAGACGAACAACC

CCCCGGCGCTGGACGCACGCGGAAGGAGGCCAGGGTGTGCCGGCACGACGGGGGCCAGAAGCTCCCCCAC

CGCATCCGCGGGCACGTAGGCGGCAAACGCCGTGCACCACGGGGTACAGTCGCCGGTGGCATGAGCCCGA

GTCTGGATTTCGACCTGGAAGTTTGCGGCCGTCCCGAGTCCGGGGCGGCCGCGCATCAGGGCGGCCAGAG

GGATTCCCGCGGCCGCCAGGCACTCGCTGGATATGATGACGTGAACCAAAGACGAGGGCCGACCCGGGAC

GTGGCCGAGATCGTACTGGACCTCGTTGGCCAAGTGCGCGTTCATGGTTCGGGGGTGGGTGTGGGTGTGT

AGGCGATGCGGGTCCCCCGAGTCCGCGGGAAGGGCGCGGGTTTGGCGCGCGTATGCGTATTCGCCAACGG

AGGCGTGCGTGCTTATGCGCGGCGCGTTTCTTCTGTCTCCAGGGAATCCGAGGCCAGGACTTTAACCTGC

TCTTTGTCGACGAGGCCAACTTTATTCGCCCGGATGCGGTCCAGACGATTATGGGCTTTCTCAACCAGGC

CAACTGCAAGATTATCTTCGTGTCGTCCACCAACACCGGGAAGGCCAGTACGAGCTTTTTGTACAACCTC

CGCGGGGCCGCCGACGAGCTTCTCAACGTGGTGACCTATATATGCGATGATCACATGCCGCGGGTGGTGA

CGCACACAAACGCCACGGCCTGTTCTTGTTATATCCTCAACAAGCCCGTTTTCATCACGATGGACGGGGC

GGTTCGCCGGACCGCCGATTTGTTTCTGGCCGATTCCTTCATGCAGGAGATCATCGGGGGCCAGGCCAGG

-continued

GAGACCGGCGACGACCGGCCCGTTCTGACCAAGTCTGCGGGGGAGCGGTTTCTGTTGTACCGCCCCTCGA

CCACCACCAACAGCGGCCTCATGGCCCCCGATTTGTACGTGTACGTGGATCCCGCGTTCACGGCCAACAC

CCGAGCCTCCGGGACCGGCGTCGCTGTCGTCGGGCGGTACCGCGACGATTATATCATCTTCGCCCTGGAG

CACTTTTTTCTCCGCGCGCTCACGGGCTCGGCCCCCGCCGACATCGCCCGCTGCGTCGTCCACAGTCTGA

CGCAGGTCCTGGCCCTGCATCCCGGGGCGTTTCGCGGCGTCCGGGTGGCGGTCGAGGGAAATAGCAGCCA

GGACTCGGCCGTCGCCATCGCCACGCACGTGCACACAGAGATGCACCGCCTACTGGCCTCGGAGGGGGCC

GACGCGGGCTCGGGCCCCGAGCTTCTCTTCTACCACTGCGAGCCTCCCGGGAGCGCGGTGCTGTACCCCT

TTTTCCTGCTCAACAAACAGAAGACGCCCGCCTTTGAACACTTTATTAAAAAGTTTAACTCCGGGGGCGT

CATGGCCTCCCAGGAGATCGTTTCCGCGACGGTGCGCCTGCAGACCGACCCGGTCGAGTATCTGCTCGAG

CAGCTGAATAACCTCACCGAAACCGTCTCCCCCAACACGGACGTCCGTACGTATTCCGGAAAACGGAACG

GCGCCTCGGATGACCTTATGGTCGCCGTCATTATGGCCATCTACCTTGCGGCCCAGGCCGGACCTCCGCA

CACATTCGCTCCCATCACACGCGTTTCGTGAGCGCCCAATAAACACACCCAGGTATGCTACGCACGACCA

CGGTGTCGCCTGTTAAGGGGGGGGGGAAGGGGGTGTTGGCGGGAAGCGTGGGAACACGGGGGATTCTCTCA

CGACCGGCACCAGTACCACCCCCCTGTGAACACAGAAACCCCAACCCAAATCCCATAAACATACGACACA

CAGGCATATTTTGGAATTTCTTAGGTTTTTATTTATTTAGGTATGCTGGGGTTTCTCCCTGGATGCCCAC

CCCCACCCCCCCCGTGGGTCTAGCCGGGCCTTAGGGATAGCGTATAACGGGGGCCATGTCTCCGGACCG

CACAACGGCCGCGCCGTCAAAGGTGCACACCCGAACCACGGGAGCCAGGGCCAAGGTGTCTCCTAGTTGG

CCCGCGTGGGTCAGCCAGGCGACGAGCGCCTCGTAGAGCGGCAGCCTTCGCTCTCCATCCTGCATCAGGG

CCGGGGCTTCGGGGTGAATGAGCTGGGCGGCCTCCCGCGTGACACTCTGCATCTGCAGGAGAGCGTTCAC

GTACCCGTCCTGGGCACTTAGCGCAAAGAGCCGGGGGATTAGCGTAAGGATGATGGTGGTTCCCTCCGTG

ATCGAGTAAACCATGTTAAGGACCAGCGATCGCAGCTCGGCGTTTACGGGGCCGAGTTGTTGGACGTCCG

CCAGCAGCGAGAGGCGACTCCCGTTGTAGTACAGCACGTTGAGGTCTGGCAGCCCTCCGGGGTTTCTGGG

GCTGGGGTTCAGGTCCCGGATGCCCCTGGCCACGAGCCGCGCCACGATTTCGCGCGCCAGGGGCGATGGA

AGCGGAACGGGAAACCGCAACGTGAGGTCCAGCGAATCCAGGCGCACGTCCGTCGCTTGGCCCTCGAACA

CGGGCGGGACGAGGCTGATGGGGTCCCCGTTACAGAGATCTACGGGGGAGGTGTTGCGAAGGTTAACGGT

GCCGGCGTGGGTGAGGCCCACGTCCAGGGGGCAGGCGACGATTCGCGTGGGAAGCACCCGGGTGATGACC

GCGGGGAAGCGCCTTCGGTACGCCAGCAACAGCCCCAACGTGTCGGGACTGACGCCTCCGGAGACGAAGG

ATTCGTGCGCCACGTCGGCCAGCGTCAGTTGCCGGCGGATGGTCGGCAGGAATACCACCCGCCCTTCGCA

GCGCTGCAGCGCCGCCGCATCGGGGCGCGAGATGCCCGAGGGTATCGCGATGTCAGTTTCAAAGCCGTCC

GCCAGCATGGCGCCGATCCACGCGGCAGGGAGTGCAGTGGTGGTTCGGGTGGCGGGAGGAGCGCGGTGGG

GGTCAGCGGCGTAGCAGAGACGGGCGACCAACCTCGCATAGGACGGGGGGTGGGTCTTAGGGGGTTGGGA

GGCGACAGGGACCCCAGAGCATGCGCGGGGAGGTCTGTCGGGCCCAGACGCACCGAGAGCGAATCCGTCC

ATGGAGTCCCGGCCTGGGTTTTATGGGGCCCGGCCCTCGGAATCGCGGCTTGTCGGCGGGGACAAAGGGG

GCGGGGCTAGGGGGCTTGCGGAAACAGAAGACGTGTGGGATAAAAGAATCGCACTACCCCAAGGAAGGGC

GGGGCGGTTTATTACAGAGCCAGTCCCTTGAGCGGGGATGCGTCATAGACGAGATACTGCGCGAAGTGGG

TCTCCCGCGCGTGGGCTTCCCCGTTGCGGGCGCTGCGGAGGAGGGCGGGGTCGCTGGCGCAGGTGAGCGG

GTAGGCCTCCTGAAACAGGCCACACGGGTCCTCCACGAGTTCGCGGCACCCCGGGGGGCGCTTAAACTGT

ACGTCGCTGGCGGCGGTGGCCGTGGACACCGCCGAACCCGTCTCCACGATCAGGCGCTCCAGGCAGCGAT

GTTTGGCGGCGATGTCGGCCGACGTAAAGAACTTAAAGCAGGGGCTGAGCACCGGCGAGGCCCCGTTGAG

GTGGTAGGCCCCGTTATAGAGCAGGTCCCCGTACGAAAATCGCTGCGACGCCCACGGGTTGGCCGTGGCC

-continued

GCGAAGGCCCGGGACGGGTCGCTCTGGCCGTGGTCGTACATGAGGGCGGTGACATCCCCCTCCTTGTCCC

CCGCGTAAACGCCCCCGGCGGCGCGTCCCCGGGGGTTGCAGGGCCGGCGGAAGTAGTTGACGTCGGTCGA

CACGGGGGTGGCGATAACTCACACACGGCGTCCTGGCCGTGGTCCATCCCTGCGCGCCGCGGCACCTGGG

CGCCCCCGAACACGGGGACGGGCTGGGCCGGCCCCAGGCGGTTTCCCGCCACGACCGCGTTCCGCAGGTA

CACGGCTGCCGCGTTGTCCAGTAGAGGGGGAGCCCCGCGGCCCAGGTAAAAGTTTTGGGGAAGGTTGCCC

ATGTCGGTGACGGGGTTGCGGACGGTTGCCGTGGCCACGACGGCGGTGTAGCCCACGCCCAGGTCCACGT

TCCCGCGCGGCTGGGTGAGCGTGAAGTTTACCCCCCCGCCAGTTTCATGCCGGGCCACCTGGAGCTGGCC

CAGGAAGTACGCCTCCGACGCGCGCTCCGAGAACAGCACGTTCTCAGTCACAAAGCGGTCCTGTCGGACG

ACGGTGAACCCAAACCCGGGATGGAGGCCCGTCTTGAGCTGATGATGCAAGGCCACGGGACTGATCTTGA

AGTACCCCGCCATGAGCGCGTAGGTCAGCGCGTTCTCCCCGGCCGCGCTCTCGCGGACGTGCTGCACGAC

GGGCTGTCGGATCGACGAAAAGTAGTTGGCCCCCAGAGCCGGGGGGACCAGGGGGACCTGCCGCGACAGG

TCGCGCAGGGCCGGGGGGAAATTGGGCGCGTTCGCCACGTGGTCGGCCCCGGCGAACAGCGCGTGGACGG

GGAGGGGGTAAAAATAGTCGCCATTTTGGATGGTATGGTCCAGATGCTGGGGGGCCATCAGCAGGATTCC

GGCGTGCAACGCCCCGTCGAATATGCGCATGTTGGTGGTGGACGCGGTGTTGGCGCCCGCGTCGGGCGCC

GCCGAGCAGAGCAGCGCCGTTGTGCGTTCGGCCATGTTGTGGGCCAGCACCTGCAGCGTGAGCATGGCGG

GCCCGTCCACTACCACGCGCCCGTTGTGAAACATGGCGTTGACCGTGTTGGCCACCAGATTGGCCGGGGC

AGGGGGTGCGCGGGGCCGTCACGGGGCGCTGGGGCAATCCTCGCCGGGGGTGATCTCCGGGACCACCATG

TTCTGCAGGGTGGCGTATACGCGGTCGAAGCGAACCCCCGCGGTGCAGCAGCGGCCCCGCGAGAAGGCGG

GCACCATCACGTAGTAGTAAATCTTGTGGTGCACGGTCCAGTCCGCCCCCCGGTGCGGCCGGTCGTCCGC

GGCGTCCGCGGCTCGGGCCTGGGTGTTGTGCAGCAGCTGGCCGTCGTTGCGGTTGAAGTCCGCGGTCGCC

ACGTTACACGCCGCTGCGTACACGGGGTCGTGGCCCCCCGCGCTAACCCGGCAGTCGCGATGGCGGTCCA

GGGCCGCGCGCCGCATCAGGGCGTCGCAGTCCCACACGAGGGGTGGCAGCAGCGCCGGGTCTCGCATTAG

GTGATTCAGTTCGGCTTGCGCCTGCCCGCCCAGTTCCGGGCCGGTCAGGGTAAAGTCATCAACCAGCTGG

GCCAGGGCCTCGACGTGCGCCACCAGGTCCCGGTACACGGCCATGCACTCCTCGGGAAGGTCTCCCCCGA

GGTAGGTCACGACGTACGAGACCAGCGAGTAGTCGTTCACGAACGCCGCGCACCGCGTGTTGTTCCAGTA

GCTGGTGATGCACTGGACCACGAGCCGGGCCAGGGCGCAGAAGACGTGCTCGCTGCCGTGTATGGCGGCC

TGCAGCAGGTAAAACACCGCCGGGTAGTTGCGGTCTTCGAACGCCCCGCGAACGGCGGCGATGGTGGCGG

GGGCTGGCGTGGCGTCCCACCCCCAGCTCCAGGCCCCGGGCGTCCCGGAACGCCGCCGGACATAGCGCCA

GGGGCAAGTTGCCGTTCACCACGCGCCAGGTGGCCTGGATCTCCCCCGGGCCGGCCGGGGGAACGTCCCC

CCCCGGCAGCTCCACGTCGGCCACCCCCACGAAGAAGTCGAACGCGGGGTGCAGCTCAAGAGCCAGGTTG

GCGTTGTCGGGCTGCATAAACTGCTCCGGGGTCATCTGGCCTTCCGCGACCCATCGGACCCGCCCGTGGG

CCAGGCGCTGCCCCCAGGCGTTCAAAAACAGCTGCTGCATGTCTGCGGCGGGGCCGGCCGGGGCCGCCAC

GTACGCCCCGTACGGATTGGCGGCTTCGACGGGGTCGCGGTTAAGGCCCCCGACCGCCGCGTCAACGTTC

ATCAGCGAAGGGTGGCACACGGTCCCGATCGCGTGTTCCAGAGACAGGCGCAGCACCTGGCGGTCCTTCC

CCCAAAAAAACAGCTGGCGGGGCGGGAAGGCGCGGGGATCCGGGTGGCCGGGGGCGGGGCTAGGTCCCCG

GCGTGCGCGGCAAACCGTTCCATGACCGGATTGAACAGGCCCAGGGGCAGGACGAACGTCAGGTCCATGG

CGCCCACCAGGGGGTAGGGAACGTTGGTGGCGGCGTAGATGCGCTTCTCCAGGGCCTCCAAAAAGATCAG

CTTCTCGCCGATGGACACCAGATCCGCGCGCACGCGCGTCGTCTGGGGGGCGCTCTCGAGCTCGTCCAGC

GTCTGCCGGTTCAGGTCGAGCTGCTCCTCCTGCATCTCCAGCAGGTGGCGGCCCACGTCGTCCAGACTTC

GCACGGCCTTGCCCATCACGAGCGCCGTGACCAGGTTGGCCCCGTTCAGGACCATCTCGCCGTACGTCAC

CGGCACGTCGGCTTCGGTGTCCTCCACTTTCAGGAAGGACTGCAGGAGGCGCTGTTTGATCGGGGCGGTG

-continued

GTGACGAGCACCCCGTCGACCGGACGCCCGCGCGTGTCGGCATGCGTCAGACGGGGCACGGCCACGGAGG

GCTGCGTGGCCGTGGTGAGGTCCACGAGCCAGGCCTCGACGGCCTCCCGGCGGTGGCCCGCCTTGCCCAG

GAAAAAGCTCGTCTCGCAGAAGCTTCGCTTTAGCTCGGCGACCAGGGTCGCCCGGGCCACCCTGGTGGCC

AGGCGGCCGTTGTCCAGGTATCGTTGCATCGGCAACAACAAAGCCAGGGGCGGCGCCTTTTCCAGCAGCA

CGTGCAGCATCTGGTCGGCCGTGCCGCGCTCAAACGCCCCGAGGACGGCCTGGACGTTGCGAGCGAGCTG

TTGGATGGCGCGCAACTGGCGATGCGCGCTGATACCCGTCCCGTCCAGGGCCTCCCCCGTGAGCAGGGCG

ATGGCCTCGGTGGCCAGGCTGAAGGCGGCGTTCAGGGCCCGGCGGTCGATAATCTTGGTCATGTAATTGT

GTGTGGGTTGCTCGATGGGGTGCGGGCCGTCGCGGGCAATCAGCGGCTGGTGGACCTCGAACTGTACGCG

CCCCTCGTTCATGTAGGCCAGCTCCGGAAACTTGGTACACACGCACGCCACCGACAACCCGAGCTCCAGA

AAGCGCACGAGCGACAGGGTGTTGCAATACGACCCCAACAGGGCGTCGAACTCGACGTCATACAGGCTGT

TTGCATCGGAGCGCACGCGGGAAAAAAAATCGAACAGGCGTCGATGCGACGCCACCTCGATCGTGCTAAG

GAGGGACCCGGTCGGCACCATGGCCGCGGCATACCGGTATCCCGGAGGGTCGCGGTTGGGAGCGGCCATG

GGGTCGCGTGGAGATCGGCTGTCTCTAGCGATATTGGCCCGGGGAGGCTAAGATCCACCCCAACGCCCGG

CCACCCGTGTACGTGCCCGACGGCCCAAGGTCCACCGAAAGACACGACGGGCCCGGACCCAAAAAGGCGG

GGGATGCTGTGTGAGAGGCCGGGTGTCGGTCGGGGGGGAAAGGCACCGGGAGAAGGCTGCGGCCTCGTTC

CAGGAGAACCCAGTGTCCCCAACAGACCCGGGGACGTGGGATCCAAGCTTGATCTCTATCACTGATAGGG

AGATCTCTATCACTGATAGGGATCCCAGGCCTTATATACCCCCCCCGCCCCCCCCCGTTAGAACGCGACG

GGTGCATTCAAGATGGCCCTGGTCCAAAAGCGTGCCAGGAAGAAATTGGCAGAGGCGGCAAAGCTGICCG

CCGCCGCCACCCACATCGAGGCCCCGGCCGCGCAGGCTATCCCCAGGGCCCGTGTGCGCAGGGGATCGGT

GGGCGGCAGCATTTGGTTGGTGGCGATAAAGTGGAAAAGCCCGTCCGGACTGAAGGTCTCGTGGGCGGCG

GCGAACAAGGCACACAGGGCCGTGCCTCCCAAAAACACGGACATCCCCCAAAACACGGGCGCCGACAACG

GCAGACGATCCCTCTTGATGTTAACGTACAGGAGGAGCGCCCGCACCGCCCACGTAACGTAGTAGCCGAC

GATGGCGGCCAGGATACAGGCCGGCGCCACCACCCTTCCGGTCAGCCCGTAATACATGCCCGCTGCCACC

ATCTCCAACGGCTTCAGGACCAAAAACGACCAAAGGAACAGAATCACGCGCTTTGAAAAGACCGGCTGGG

TATGGGGCGGAAGACGCGAGTATGCCGAACTGACAAAAAAGTCAGAGGTGCCGTACGAGGACAATGAAAA

CTGTTCCTCCAGTGGCAGTTCTCCCTCCTCCCCCCCAAAGGCGGCCTCGTCGACCAGATCTCGATCCACC

AGAGGAAGGTCATCCCGCATGGTCATGGGGTGTGCGGTGGAGGTGGGGAGACCGAAACCGCAAAGGGTCG

CTTACGTCAGCAGGATCCCGAGATCAAAGACACCCGGGTTCTTGCACAAACACCACCCGGGTTGCATCCG

CGGAGGCGAGTGTTTTGATAAGGCCGTTCCGCGCCTTGATATAACCTTTGATGTTGACCACAAAACCCGG

AATTTACGCCTACGCCCCAATGCCCACGCAAGATGAGGTAGGTAACCCCCCCCCCGTGGGTGTGACGTTG

CGTTTAGTTCATTGGAGGCCAAGGGGAAAATGGGGTGGGGAGGAAACGGAAAACCCAGTAGGCCGTGTTG

GGAACACGCCCGGGGTTGTCCTCAAAAGGCAGGGTCCATACTACGGAAGCCGTCGTTGTATTCGAGACCT

GCCTGTGCGACGCACGTCGGGGTTGCCTGTGTCCGGTTCGGCCCCACCGCGTGCGGCACGCACGAGGACG

AGTCCGCGTGCTTTATTGGCGTTCCAAGCGTTGCCCTCCAGTTTCTGTTGTCGGTGTTCCCCCATACCCA

CGCCCACATCCACCGTAGGGGGCCTCTGGGCCGTGTCACGTCGCCGCCCGCGATGGAGCTTAGCTACGCC

ACCACCATGCACTACCGGGACGTTGTGTTTTACGTCACAACGGACCGAAACCGGGCCTACTTTGTGTGCG

GGGGGTGTGTTTATTCCGTGGGGCGGCCGTGTGCCTCGCAGCCCGGGGAGATTGCCAAGTTTGGTCTGGT

CGTTCGAGGGACAGGCCCAGACGACCGCGTGGTCGCCAACTATGTACGAAGCGAGCTCCGACAACGCGGC

CTGCAGGACGTGCGTCCCATTGGGGAGGACGAGGTGTTTCTGGACAGCGTGTGTCTTCTAAACCCGAACG

TGAGCTCCGAGCTGGATGTGATTAACACGAACGACGTGGAAGTGCTGGACGAATGTCTGGCCGAGTACTG

-continued

CACCTCGCTGCGAACCAGCCCGGGTGTGCTAATATCCGGGCTGCGCGTGCGGGCGCAGGACAGAATCATC

GAGTTGTTTGAACACCCAACGATAGTCAACGTTTCCTCGCACTTTGTGTATACCCCGTCCCCATACGTGT

TCGCCCTGGCCCAGGCGCACCTCCCCCGGCTCCCGAGCTCGCTGGAGGCCCTGGTGAGCGGCCTGTTTGA

CGGCATCCCCGCCCCACGCCAGCCACTTGACGCCCACAACCCGCGCACGGATGTGGTTATCACGGGCCGC

CGCGCCCCACGACCCATCGCCGGGTCGGGGGCGGGGTCGGGGGGCGCGGGCGCCAAGCGGGCCACCGTCA

GCGAGTTCGTGCAAGTCAAACACATTGACCGCGTGGGCCCCGCTGGCGTTTCGCCGGCGCCTCCGCCAAA

CAACACCGACTCAAGTTCCCTGGTGCCCGGGGCCCAGGATTCCGCCCCGCCCGGCCCCACGCTAAGGGAG

CTGTGGTGGGTGTTTTATGCCACAGACCGGGCGCTGGAGGAGCCCCGCGCCGACTCTGGCCTCACCCGCG

AGGAGGTACGTGCCGTACGTGGGTTCCGGGAGCAGGCGTGGAAACTGTTTGGCTCCGCGGGGGCCCCGCG

GGCGTTTATCGGGGCCGCGTTGGGCCTGAGCCCCCTCCAAAAGCTAGCCGTTTACTACTATATCATCCAC

CGAGAGAGGCGCCTGTCCCCCTTCCCCGCGCTAGTCCGGCTCGTAGGCCGGTACACACAGCGCCACGGCC

TGTACGTCCCTCGGCCCGACGACCCAGTCTTGGCCGATGCCATCAACGGGCTGTTTCGCGACGCGCTGGC

GGCCGGAACCACAGCCGAGCAGCTCCTCATGTTCGACCTTCTCCCCCCAAAGGACGTGCCGGTGGGAAGC

GACGTGCAGGCCGACAGCACCGCTCTGCTGCGCTTTATAGAATCGCAACGTCTCGCCGTCCCCGGGGGGG

TGATCTCCCCCGAGCACGTCGCGTACCTTGGTGCGTTCCTGAGCGTGCTGTACGCTGGCCGCGGGCGCAT

GTCCGCAGCCACGCACACCGCGCGGCTGACAGGGGTGACCTCCCTGGTGCTAGCGGTGGGTGACGTGGAC

CGTCTTTCCGCGTTTGACCGCGGAGCGGCGGGCGCGGCCAGCCGCACGCGGGCCGCCGGGTACCTGGATG

TGCTTCTTACCGTTCGTCTCGCTCGCTCCCAACACGGACAGTCTGTGTAACAGACCCCAATAAACGTATG

TCGCTACCACACCCTTGTGTGTCAATGGACGCCTCTCCGGGGGGGAAGGGAAAACAAAGAGGGGCTGGGG

GAGCGGCACCACCGGGGCCTGAACAAACAAACCACAGACACGGTTACAGTTTATTCGGTCGGGCGGAGAA

ACGGCCGAAGCCACGCCCCCTTTATTCGCGTCTCCAAAAAAACGGGACACTTGTCCGGAGAACCTTTAGG

ATGCCAGCCAGGGCGGCGGTAATCATAACCACGCCCAGCGCAGAGGCGGCCAGAAACCCGGGCGCAATTG

CGGCCACGGGCTGCGTGTCAAAGGCTAGCAAATGAATGACGGTTCCGTTTGGAAATAGCAACAAGGCCGT

GGACGGCACGTCGCTCGAAAACACGCTTGGGGCGCCCTCCGTCGGCCCGGCGGCGATTTGCTGCTGTGTG

TTGTCCGTATCCACCAGCAACACAGACATGACCTCCCCGGCCGGGGTGTAGCGCATAAACACGGCCCCCA

CGAGCCCCAGGTCGCGCTGGTTTTGGGTGCGCACCAGCCGCTTGGACTCGATATCCCGGGTGGAGCCTTC

GCATGTCGCGGTGAGGTAGGTTAGGAACAGTGGGCGTCGGACGTCGACGCCGGTGAGCTTGTAGCCGATC

CCCCGGGGCAGAGGGGAGTGGGTGACGACGTAGCTGGCGTTGTGGGTGATGGGTACCAGGATCCGTGGCT

CGACGTTGGCAGACTGCCCCCCGCACCGATGTGAGGCCTCAGGGACGAAGGCGCGGATCAGGGCGTTGTA

GTGTGCCCAGCGCGTCAGGGTCGAGGCGAGGCCGTGGGTCTGCTGGGCCAGGACTTCGACCGGGGTCTCG

GATCGGGTGGCTTGAGCCAGCGCGTCCAGGATAAACACGCTCTCGTCTAGATCAAAGCGCAGGGAGGCCG

CGCATGGCGAAAAGTGGTCCGGAAGCCAAAAGAGGGTTTTCTGGTGGTCGGCCCGGGCCAGCGCGGTCCG

GAGGTCGGCGTTGGTCGCTGCGGCGACGTCGGACGTACACAGGGCCGAGGCTATCAGAAGGCTCCGGCGG

GCGCGTTCCCGCTGCACCGCCGAGGGGACGCCCGCCAAGAACGGCTGCCGGAGGACAGCCGAGGCGTAAA

ATAGCGCCCGGTGGACGACCGGGGTGGTCAGCACGCGGCCCCCTAGAAACTCGGCATACAGGGCGTCGAT

GAGATGGGCTGCGCTGGGCGCCACTGCGTCGTACGCCGAGGGGCTATCCAGCACGAAGGCCAGCTGATAG

CCCAGCGCGTGTAATGCCAAGCTCTGTTCGCGCTCCAGAATCTCGGCCACCAGGTGCTGGAGCCGAGCCT

CTAGCTGCAGGCGGGCCGTGGGATCCAAGACTGACACATTAAAAAACACAGAATCCGCGGCACAGCCCGC

GGCCCCGCGGGCGGCCAACCCGGCAAGCGCGCGCGAGTGGGCCAAAAAGCCTAGCAGGTCGGAGAGGCAG

ACCGCGCCGTTTGCGTGGGCGGCGTTCACGAAAGCAAAACCCGACGTCGCGAGCAGCCCCGTTAGGCGCC

AGAAGAGAGGGGGACGCGGGCCCTGCTCGGCGCCCGCGTCCCCCGAGAAAAACTCCGCGTATGCCCGCGA

-continued

CAGGAACTGGGCGTAGTTCGTGCCCTCCTCCGGGTAGCCGCCCACGCGGCGGAGGGCGTCCAGCGCGGAG

CCGTTGTCGGCCCGCGTCAGGGACCCTAGGACAAAGACCCGATACCGGGGGCCGCCCGGGGGCCCGGGAA

GAGCCCCCGGGGGGTTTTCGTCCGCGGGGTCCCCGACCCGATCTAGCGTCTGGCCCGCGGGGACCACCAT

CACTTCCACCGGAGGGCTGICGTGCATGGATATCACGAGCCCCATGAATTCCCGCCCGTAGCGCGCGCGC

ACCAGCGCGGCATCGCACCCGAGCACCAGCTCCCCCGTCGTCCAGATGCCCACGGGCCACGTCGAGGCCG

ACGGGGAGAAATACACGTACCTACCTGGGGATCTCAACAGGCCCCGGGTGGCCAACCAGGTCGTGGACGC

GTTGTGCAGGTGCGTGATGTCCAGCTCCGTCGTCGGGTGCCGCCGGGCCCCAACCGGCGGTCGGGGGGGC

GGTGTATCACGCGGCCCGCTCGGGTGGCTCGCCGTCGCCACGTTGTCTCCCCGCGGGAACGTCAGGGCCT

CGGGGTCAGGGACGGCCGAAAACGTTACCCAGGCCCGGGAACGCAGCAACACGGAGGCGGTTGGATTGTG

CAAGAGACCCTTAAGGGGGGCGACCGCGGGGGGAGGCTGGGCGGTCGGCTCGACCGTGATGGGGGCGGGC

AGGCTCGCGTTCGGGGGCCGGCCGAGCAGGTAGGTCTTCGAGATGTAAAGCAGCTGGCCGGGGTCCCGCG

GAAACTCGGCCGTGGTGACCAATACAAAACAAAAGCGCTCCTCGTACCAGCGAAGAAGGGGCAGAGATGC

CGTAGTCAGGTTTAGTTCGTCCGGCGGCGCCAGAAATCCGCGCGGTGGTTTTTGGGGGTCGGGGGTGTTT

GGCAGCCACAGACGCCCGGTGTTCGTGTCGCGCCAGTACATGCGGTCCATGCCCAGGCCATCCAAAAACC

ATGGGTCTGTCTGCTCAGTCCAGTCGTGGACCTGACCCCACGCAACGCCCAAAAGAATAACCCCCACGAA

CCATAAACCATTCCCCATGGGGGACCCCGTCCCTAACCCACGGGGCCCGTGGCTATGGCAGGGCTTGCCG

CCCCGACGTTGGCTGCGAGCCCTGGGCCTTCACCCGAACTTGGGGGTTGGGGTGGGGAAAAGGAAGAAAC

GCGGGCGTATTGGCCCCAATGGGGTCTCGGTGGGGTATCGACAGAGTGCCAGCCCTGGGACCGAACCCCG

CGTTTATGAACAAACGACCCAACACCCGTGCGTTTTATTCTGTCTTTTTATTTCCGTCATAGCGCGGGTT

CCTTCCGGTATTGTCTCCTTCCGTGTTTCAGTTAGCCTCCCCCATCTCCCGGGCAAACGTGCGCGCCAGG

TCGCAGATCGTCGGTATGGAGCCTGGGGTGGTGACGTGGGTCTGGACCATCCCGGAGGTAAGTTGCAGCA

GGGCGTCCCGGCAGCCGGCGGGCGATTGGTCGTAATCCAGGATAAAGACGTGCATGGGACGGAGGCGTTT

GGCCAAGACGTCCAAGGCCCAGGCAAACACGTTATACAGGTCGCCGTTGGGGGCCAGCAACTCGGGGGCC

CGAAACAGGGTAAATAACGTGTCCCCGATATGGGGTCGTGGGCCCGCGTTGCTCTGGGGCTCGGCACCCT

GGGGCGGCACGGCCGTCCCCGAAAGCTGTCCCCAATCCTCCCGCCACGACCCGCCGCCCTGCAGATACCG

CACCGTATTGGCAAGCAGCCCGTAAACGCGGCGAATCGCGGCCAACATAGCCAGGTCAAGCCGCTCGCCG

GGGCGCTGGCGTTTGGCCAGGCGGTCGATGTGTCTGTCCTCCGGAAGGGCCCCCAACACGATGTTTGTGC

CGGGCAAGGTCGGCGGGATGAGGGCCACGAACACCAGCACGGCCTGGGGGGTCATGCTGCCCATAAGGTA

TCGCGCGGCCGGGTAGCACAGGAGGGCGGCGATGGGATGGCGGTCGAAGATGAGGGTGAGGGCCGGGGGC

GGGGCATGTGAGCTCCCAGCCTCCCCCCCGATATGAGGAGCCAGAACGGCGTCGGTCACGGCATAAGGCA

TGCCCATTGTTATCTGGGCGCTTGTCATTACCACCGCCGCGTCCCCGGCCGATATCTCACCCTGGTCGAG

GCGGTGTTGTGTGGTGTAGATGTTCGCGATTGTCTCGGAAGCCCCCAGCACCTGCCAGTAAGTCATCGGC

TCGGGTACGTAGACGATATCGTCGCGCGAACCCAGGGCCACCAGCAGTTGCGTGGTGGTGGTTTTCCCCA

TCCCGTGAGGACCGTCTATATAAACCCGCAGTAGCGTGGGCATTTTCTGCTCCAGGCGGACTTCCGTGGC

TTCTTGCTGCCGGCGAGGGCGCAACGCCGTACGTCGGTTGCTATGGCCGCGAGAACGCGCAGCCTGGTCG

AACGCAGACGCGTGTTGATGGCAGGGGTACGAAGCCATACGCGCTTCTACAAGGCGCTTGCCAAAGAGGT

GCGGGAGTTTCACGCCACCAAGATCTGCGGCACGCTGTTGACGCTGTTAAGCGGGTCGCTGCAGGGTCGC

TCGGTGTTCGAGGCCACACGCGTCACCTTAATATGCGAAGTGGACCTGGGACCGCGCCGCCCCGACTGCA

TCTGCGTGTTCGAATTCGCCAATGACAAGACGCTGGGCGGGGTTTGTGTCATCATAGAACTAAAGACATG

CAAATATATTTCTTCCGGGGACACCGCCAGCAAACGCGAGCAACGGGCCACGGGGATGAAGCAGCTGCGC

-continued

CACTCCCTGAAGCTCCTGCAGTCCCTCGCGCCTCCGGGTGACAAGATAGTGTACCTGTGCCCCGTCCTGG

TGTTTGTCGCCCAACGGACGCTCCGCGTCAGCCGCGTGACCCGGCTCGTCCCGCAGAAGGTCTCCGGTAA

TATCACCGCAGTCGTGCGGATGCTCCAGAGCCTGTCCACGTATACGGTCCCCATGGAGCCTAGGACCCAG

CGAGCCCGTCGCCGCCGCGGCGGCGCTGCCCGGGGGTCTGCGAGCAGACCGAAAAGGTCACCCTCTGGGG

CACGCGACCCGCCCGGGCCAGCGGCCCGCCAGGTACCACCCGCCGACCAAACCCCCGCCTCCACGGAGGG

CGGGGGGGTGCTTAAGAGGATCGCGGCGCTCTTCTGCGTGCCCGTGGCCACCAAGACCAAACCCCGAGCT

GCCTCCGAATGAGAGTGTTTCGTTCCTTCCCCCTCCCCCCGCGTCAGACAAACCCTAACCACCGCTTAAG

CGGCCCCCGCGAGGTCCGAAGACTCATTTGGATCCGGCGGGAGCCACCTGACAACAGCCCCCGGGTTTCC

CCACGCCAGACGCCGGTCCGCTGTGCCATCGCTCCCCTTCATCCCACCCCCATCTTGTCCCCAAATAAAA

CAAGGTCTGGTAGTTAGGACAACGACCGCAGTTCTCGTGTGTTATTGTCGCTCTCCGCCTCTCGCAGATG

GACCCGTATTGCCCATTTGACGCTCTGGACGTCTGGGAACACAGGCGCTTCATAGTCGCCGATTCCCGAA

ACTTCATCACCCCCGAGTTCCCCCGGGACTTTTGGATGTCGCCCGTCTTTAACCTCCCCCGGGAGACGGC

GGCGGAGCAGGTGGTCGTCCTGCAGGCCCAGCGCACAGCGGCTGCCGCTGCCCTGGAGAACGCCGCCATG

CAGGCGGCCGAGCTCCCCGTCGATATCGAGCGCCGGTTACGCCCGATCGAACGGAACGTGCACGAGATCG

CAGGCGCCCTGGAGGCGCTGGAGACGGCGGCGGCCGCCGCCGAAGAGGCGGATGCCGCGCGCGGGGATGA

GCCGGCGGGTGGGGGCGACGGGGGGGCGCCCCCGGGTCTGGCCGTCGCGGAGATGGAGGTCCAGATCGTG

CGCAACGACCCGCCGCTACGATACGACACCAACCTCCCCGTGGATCTGCTACATATGGTGTACGCGGGCC

GCGGGGCGACCGGCTCGTCGGGGGTGGTGTTCGGGACCTGGTACCGCACTATCCAGGACCGCACCATCAC

GGACTTTCCCCTGACCACCCGCAGTGCCGACTTTCGGGACGGCCGGATGTCCAAGACCTTCATGACGGCG

CTGGTCCTGTCCCTGCAGTCGTGCGGCCGGCTGTATGTGGGCCAGCGCCACTATTCCGCCTTCGAGTGCG

CCGTGTTGTGTCTCTACCTGCTGTACCGAAACACGCACGGGGCCGCCGACGATAGCGACCGCGCTCCGGT

CACGTTCGGGGATCTGCTGGGCCGGCTGCCCCGCTACCTGGCGTGCCTGGCCGCGGTGATCGGGACCGAG

GGCGGCCGGCCACAGTACCGCTACCGCGACGACAAGCTCCCCAAGACGCAGTTCGCGGCCGGCGGGGGCC

GCTACGAACACGGAGCGCTGGCGTCGCACATCGTGATCGCCACGCTGATGCACCACGGGGTGCTCCCGGC

GGCCCCGGGGGACGTCCCCCGGGACGCGAGCACCCACGTTAACCCCGACGGCGTGGCGCACCACGACGAC

ATAAACCGCGCCGCCGCCGCGTTCCTCAGCCGGGGCCACAACCTATTCCTGTGGGAGGACCAGACTCTGC

TGCGGGCAACCGCGAACACCATAACGGCCCTGGGCGTTATCCAGCGGCTCCTCGCGAACGGCAACGTGTA

CGCGGACCGCCTCAACAACCGCCTGCAGCTGGGCATGCTGATCCCCGGAGCCGTCCCTTCGGAGGCCATC

GCCCGTGGGGCCTCCGGGTCCGACTCGGGGGCCATCAAGAGCGGAGACAACAATCTGGAGGCGCTATGTG

CCAATTACGTGCTTCCGCTGTACCGGGCCGACCCGGCGGTCGAGCTGACCCAGCTGTTTCCCGGCCTGGC

CGCCCTGTGTCTTGACGCCCAGGCGGGGCGGCCGGTCGGGTCGACGCGGCGGGTGGTGGTATGTCATCGG

GGGCCCGCCAGGCGGCGCTGGGCGCCTCACCGCCCTGGAACTCATCAACCGCACCCGCACAAACCCCACC

CCCGTGGGGGAGGTTATCCACGCCCACGACGCCCTGGCGATCCAATACGAACAGGGGCTTGGCCTGCTGG

CGCAGCAGGCACGCATTGGCTTGGGCTCCAACACCAAGCGTTTCTCCGCGTTCAACGTTAGCAGCGACTA

CGACATGTTGTACTTTTTATGTCTGGGGTTCATTCCACAGTACCTGTCGGCGGTTTAGTGGGTGGTGGGC

GAGGGGGGAGGGGGCATTAGGGAGAAAGAACAAGAGCCTCCGTTGGGTTTTCTTTGTGCCTGTACTCAAA

AGGTCATACCCCGTAAACGGCGGGCTCCAGTCCCGGCCCGGCGGTTGGCGTGAACGCAACGGCGGGAGCT

GGGTTAGCGTTTAGTTTAGCATTCGCTCTCGCCTTTCCGCCCGCCCCCGACCGTTGAGCCTTTTTTTTTT

TTTTTTTTTTTTCGTCCACCAAAGTCTCTGTGGGTGCGCGCATGGCAGCCGATGCCCCGGGAGACCGGAT

GGAGGAGCCCCTGCCAGACAGGGCCGTGCCCATTTACGTGGCTGGGTTTTTGGCCCTGTATGACAGCGGG

GACTCGGGCGAGTTGGCATTGGATCCGGATACGGTGCGGGCGGCCCTGCCTCCGGATAACCCACTCCCGA

-continued

TTAACGTGGACCACCGCGCTGGCTGCGAGGTGGGGCGGGTGCTGGCCGTGGTCGACGACCCCCGCGGGCC

GTTTTTTGTGGGGCTGATCGCCTGCGGCAACTGGAGCGCGTCCTCGAGACGGCCGCCAGCGCTGCGATTT

TCGAGCGCCGCGGGCCGCCGCTCTCCCGGGAGGAGCGCCTGTTGTACCTGATCACCAACTACCTGCCCTC

GGTCTCCCTGGCCACAAAACGCCTGGGGGGCGAGGCGCACCCCGATCGCACGCTGTTCGCGCACGTAGCG

CTGTGCGCGATCGGGCGGCGCCTTGGCACTATCGTCACCTACGACACCGGTCTCGACGCCGCCATCGCGC

CCTTTCGCCACCTGTCGCCGGCGTCTCGCGAGGGGGCGCGGCGACTGGCCGCCGAGGCCGAGCTCGCGCT

ATCCGGACGCACCTGGGCGCCCGGCGTGGAGGCGCTGCCCACCCGCTGCTTTCCACCGCCGTTAACAACA

TGATGCTGCGGGACCGCTGGAGCCTGGTGGCCGAGCGGCGGCGGCAGGCCGGGATCGCCGGACACACCTA

CCTCCAGGCGAGCGAAAAATTCAAAATGTGGGGGGCGGAGCCTGTTTCCGCGCCGGCGCGCGGGTATAAG

AACGGGGCCCCGGAGTCCACGGACATACCGCCCGGCTCGATCGCTGCCGCGCCGCAGGGTGACCGGTGCC

CAATCGTCCGTCAGCGCGGGGTCGCCTCGCCCCCGGTACTGCCCCCCATGAACCCCGTTCCAACATCGGG

CACCCCGGCCCCCGCGCCGCCCGGCGACGGGAGCTACCTGTGGATCCCGGCCTCCCATTACAACCAGCTC

GTCGCCGGCCACGCCGCGCCCCAACCCCAGCCGCATTCCGCGTTTGGTTTCCCGGCTGCGGCGGGGGCCG

TGGCCTATGGGCCTCACGGCGCGGGTCTTTCCCAGCATTACCCTCCCCACGTCGCCCATCAGTATCCCGG

GGTGCTGTTCTCGGGACCCAGCCCACTCGAGGCGCAGATAGCCGCGTTGGTGGGGGCCATAGCCGCGGAC

CGCCAGGCGGGCGGTCAGCCGGCCGCGGGAGACCCTGGGGTCCGGGGGTCGGGAAAGCGTCGCCGGTACG

AGGCGGGGCCGTCGGAGTCCTACTGCGACCAGGACGAACCGGACGCGGACTACCCGTACTACCCCGGGGA

GGCTCGAGGCGGGCCGCGCGGGGTCGACTCTCGGCGCGCGGCCCGCCAGTCTCCCGGGACCAACGAGACC

ATCACGGCGCTGATGGGGGCGGTGACGTCTCTGCAGCAGGAACTGGCGCACATGCGGGCTCGGACCAGCG

CCCCCTATGGAATGTACACGCCGGTGGCGCACTATCGCCCTCAGGTGGGGGAGCCGGAACCAACAACGAC

CCACCCGGCCCTTTGTCCCCCGGAGGCCGTGTATCGCCCCCCACCACACAGCGCCCCCTACGGTCCTCCC

CAGGGTCCGGCGTCCCATGCCCCCACTCCCCCGTATGCCCCAGCTGCCTGCCCGCCAGGCCCGCCACCGC

CCCCATGTCCTTCCACCCAGACGCGCGCCCCTCTACCGACGGAGCCCGCGTTCCCCCCCGCCGCCACCGG

ATCCCAACCGGAGGCATCCAACGCGGAGGCCGGGGCCCTTGTCAACGCCAGCAGCGCAGCACACGTGGAC

GTTGACACGGCCCGCGCCGCCGATTTGTTCGTCTCTCAGATGATGGGGGCCCGCTGATTCGCCCCGGTCT

TTGGTACCATGGGATGTCTTACTGTATATCTTTTTAAATAAACCAGGTAATACCAAATAAGACCCATTGG

TGTATGTTCTTTTTTTTTTATTGGGAGGGGCGGGTAGGCGGGTAGCTTTACAATGCAAAAGCCTTTGACG

TGGAGGAAGGCGTGGGGGGGAGGAAATCGGCACTGACCAAGGGGGTCCGTTTTGTCACGGGAAAGGAAGA

GGAAAAGGCGCGGCACCCGGGGGAGTTATGTGTTCCTTTTTCTTTCTTCCCACACACACACAAAAGGCGT

ACCAAACAAAAAAACCAAAAGATGCGCATGCGGTTTAACACCCGTGGTTTTTATTTACAACAAACCCCCC

GTCACAGGTCGTCCTCGTCGGCGTCACCGTCTTTGTTGGGAACTTGGGTGTAGTTGGTGTTGCGGCGCTT

GCGCATGACCATGTCGGTGACCTTGGCGCTGAGCAGCGCGCTCGTGCCCTTCTTCTTGGCCTTGTGTTCC

GTGCGCTCCATGGCCGACACCAGGGCCATGTACCGTATCATCTCCCTGGCCTCGGCTAGCTTGGCCTCGT

CAAAGTCGCCGCCCTCCTCGCCCTCCCCGGACGCGTCCGGGTTGGTGGGGTTCTTGAGCTCCTTGGTGGT

TAGAGGGTACAGGGCCTTCATGGGGTTGCTCTGCAGCCGCATGACGTAACGAAAGGCGAAGAAGGCCGCC

GCCAGGCCGGCCAGGACCAACAGACCCACGGCCAGCGCCCCAAAGGGGTTGGACATGAAGGAGGACACGC

CCGACACGGCCGATACCACGCCGCCCACGATGCCCATCACCACCTTGCCGACCGCGCGCCCCAGGTCGCC

CATCCCCTCGAAGAACGCGCCCAGGCCCGCGAACATGGCGGCGTTGGCGTCGGCGTGGATGACCGTGTCG

ATGTCGGCGAAGCGCAGGTCGTGCAGCTGGTTGCGGCGCTGGACCTCCGTGTAGTCCAGCAGGCCGCTGT

CCTTGATCTCGTGGCGGGTGTACACCTCCAGGGGGACAAACTCGTGATCCTCCAGCATGGTGATGTTGAG

-continued

GTCGATGAAGGTGCTGACGGTGGTGATGTCGGCGCGGCTCAGCTGGTGGGAGTACGCGTACTCCTCGAAG

TACACGTAGCCCCCACCGAAGGTGAAGTAGCGCCGGTGTCCCACGGTGCACGGCTCGATCGCATCGCGCG

TCAGCCGCAGCTCGTTGTTCTCCCCCAGCTGCCCCTCGACCAACGGGCCCTGGTCTTCGTACCGAAAGCT

GACCAGGGGGCGGCTGTAGCAGGCCCCGGGCCGCGAGCTGATGCGCATCGAGTTTTGGACGATCACGTTG

TCCGCGGCGACCGGCACGCACGTGGAGACGGCCATCACGTCGCCGAGCATCCGCGCGCTCACCCGCCGGC

CCACGGTGACCGAGGCGATGGCGTTGGGGTTCAGCTTGCGGGCCTCGTTCCACAGGGTCAGCTCGTGATT

CTGTAGCTCGCACCACGCGATGGCAACGCGGCCCAACATATCGTTGACATGGCGCTGTATGTGGTTGTAC

GTAAACTGCAGCCGGGCGAACTCGATGGAGGAGGTGGTCTTGATGCGCTCCACGGACGCGTTGGCGCTGG

CCCCGGGCGGCGGGGGCGTGGGGTTTGGGGGCTTGCGGCTCTGCTCTCGGAGGTGTTCCCGCACGTACAG

CTCCGCGAGCGTGTTGCTGAGAAGGGGCTGGTACGCGATCAGAAAGCCCCCATTGGCCAGGTAGTACTGC

GGCTGGCCCACCTTGATGTGCGTCGCGTTGTACCTGCGGGCGAAGATGCGGTCCATGGCGTCGCGGGCGT

CCTTGCCGATGCAGTCCCCCAGGTCCACGCGCGAGAGCGGGTACTCGGTCAGGTTGGTGGTGAAGGTGGT

GGATATGGCGTCGGAGGAGAATCGGAAGGAGCCGCCGTACTCGGAGCGCAGCATCTCGTCCACTTCCTGC

CACTTGGTCATGGTGCAGACCGACGGGCGCTTTGGCACCCAGTCCCAGGCCACGGTGAACTTGGGGGTCG

TGAGCAGGTTCCGGGTGGTCGGCGCCGTGGCCCGGGCCTTGGTGGTGAGGTCGCGCGCGTAGAAGCCGTC

GACCTGCTTGAAGCGGTCGGCGGCGTAGCTGGTGTGTTCGGTGTGCGACCCCTCCCGGTAGCCGTAAAAC

GGGGACATGTACACAAAGTCGCCAGTCGCCAGCACAAACTCGTCGTACGGGTACACCGAGCGCGCGTCCA

CCTCCTCGACGATGCAGTTTACCGTCGTCCCGTACCGGTGGAACGCCTCCACCCGCGAGGGGTTGTACTT

GAGGTCGGTGGTGTGCCAGCCCCGGCTCGTGCGGGTCGCGGCGTTGGCCGGTTTCAGCTCCATGTCGGTC

TCGTGGTCGTCCCGGTGAAACGCGGTGGTCTCCAGGTTGTTGCGCACGTACTTGGCCGTGGACCGACAGA

CCCCCTTGGCGTTGATCTTGTCGATCACCTCCTCGAAGGGGACGGGGGCGCGGTCCTCAAAGATCCCCAT

AAACTGGGAGTAGCGGTGGCCGAACCACACCTGCGAAACGGTGACGTCTTTGTAGTACATGGTGGCCTTG

AACTTGTACGGGGCGATGTTCTCCTTGAAGACCACCGCGATGCCCTCCGTGTAGTTCTGACCCTCGGGCC

GGGTCGGGCAGCGGCGCGGCTGCTCGAACTGCACCACCGTGGCGCCCGTGGGGGGTGGGCACACGTAAAA

GTTTGCATCGGTGTTCTCCGCCTTGATGTCCCGCAGGTGCTCGCGCAGGGTGGCGTGGCCCGCGGCGACG

GTCGCGCCCCCTTGGCGTTGATCTTGTCGATCACCTCCTCGAAGGGGACGGGGGCGCGGTCCTCAAAGAT

CCCCATAAACTGGGAGTAGCGGTGGCCGAACCACACCTGCGAAACGGTGACGTCTTTGTAGTACATGGTG

GCCTTGAACTTGTACGGGGCGATGTTCTCCTTGAAGACCACCGCGATGCCCTCCGTGTAGTTCTGACCCT

CGGGCCGGGTCGGGCAGCGGCGCGGCTGCTCGAACTGCACCACCGTGGCGCCCGTGGGGGGTGGGCACAC

GTAAAAGTTTGCATCGGTGTTCTCCGCCTTGATGTCCCGCAGGTGCTCGCGCAGGGTGGCGTGGCCCGCG

GCGACGGTCGCGTTGTCGCCGGCGGGGCGGGGGCGTTGGGTTTTCGGTTTTTGTTCTTCTTCGGTTTCGG

GTCCCCCGTTGGGGCGGCGCCAAGGGCGGGCGGCGCCGGAGTGGCAGGGCCCCCGTTCGCCGCCTGGGTC

GCGGCCGCGACCCCAGGCGTGCCGGGGGAACTCGGAGCCGCCGACGCCACCAGGACCCCCAGCGTCAACC

CCAAGAGCGCCCATACGACGAACCACCGGCGCCCCCACGAGGGGGCGCCCTGGTGCATGGCGGGACTACG

GGGGCCCGTCGTGCCCCCCGTCAGGTAGCCTGGGGGCGAGGTGCTGGAGGACCGAGTAGAGGATCGAGAA

AACGTCGCGGTCGTAGACCACGACCGACCGGGGGCCGATACAGCCGTCGGGGGCGCTCTCGACGATGGCC

ACCAGCGGACAGTCGGAGTCGTACGTGAGATATACGCCGGGCGGGTAACGGTAACGACCTTCGGAGGTCG

GGCGGCTGCAGTCCGGGCGGCGCAACTCGAGCTCCCCGCACCGGTAGACCGAGGCAAAGAGTGTGGTGGC

GATAATCAGCTCGCGAATATATCGCCAGGCGGCGCGCTGAGTGGGCGTTATTCCGGAAATGCCGTCAAAA

CAGTAAAACCTCTGAAATTCGCTGACGGCCCAATCAGCACCCGAGCCCCCCGCCCCCATGATGAACCGGG

CGAGCTCCTCCTTCAGGTGCGGCAGGAGCCCCACGTTCTCGACGCTGTAATACAGCGCGGTGTTGGGGGG

-continued

CTGGGCGAAGCTGTGGGTGGAGTGATCAAAGAGGGGCCCGTTGACGAGCTCGAAGAAGCGATGGGTGATG

CTGGGGAGCAGGGCCGGGTCCACCTGGTGTCGCAGGAGAGACGCTCGCATGAACCGGTGCGCGTCGAACA

CGCCCGGCGCCGAGCGGTTGTCGATGACCGTGCCCGCGCCCGCCGTCAGGGCGCAGAAGCGCGCGCGCGC

CGCAAAGCCGTTGGCGACCGCGGCGAACGTCGCGGGCAGCACCTCGCCGTGGACGCTGACCCGCAGCATC

TTCTCGAGCTCCCCGCGCTGCTCGCGGACGCAGCGCCCCAGGCTGGCCAACGACCGCTTCGTCAGGCGGT

CCGCGTACAGCCGCCGTCGCTCCCGTACGTCCGCGGCCGCTTGCGTGGCGATGTCCCCCCACGTCTCGGG

CCCCTGCCCCCCGGGCCCGCGGCGACGGTCTTCGTCCTCGCCCCCGCCCCCGGGAGCTCCCAACCCCCGT

GCCCCTTCCTCTACGGCGACACGGTCCCCGTCGTCGTCGGGGCCCGCGCCGCCCTTGGGCGCGTCCGCCG

CGCCCCCCGCCCCCATGCGCGCCAGCACGCGACGCAGCGCCTCCTCGTCGCACTGTTCGGGGCTGACGAG

GCGCCGCAAGAGCGGCGTCGTCAGGTGGTGGTCGTAGCACGCGCGGATGAGCGCCTCGATCTGATCGTCG

GGTGACGTGGCCTGACCGCCGATTATTAGGGCGTCCACCATATCCAGCGCCGCCAGGTGGCTCCCGAACG

CGCGATCGAAATGCTCCGCCCGCCGCCCGAACAGCGCCAGTTCCACGGCCACCGCGGCGGTCTCCTGCTG

CAACTCGCGCCGCGCCAGCGCGGTCAGGTTGCTGGCAAACGCGTCCATGGTGGTCTGGCCGGCGCGGTCG

CCGGACGCGAGCCAGAATCGCAATTCGCTGATGGCGTACAGGCCGGGCGTGGTGGCCTGAAACACGTCGT

GCGCCTCCAGCAGGGCGTCGGCCTCCTTGCGGACCGAGTCGTTCTCGGGCGACGGGTGGGGCTGCCCGTC

GCCCCCCGCGGTCCGGGCCAGCGCATGGTCCAACACGGAGAGCGCCCGCGCGCGGTCGGCGTCCGACAGC

CCGGCGGCGTGGGGCAGGTACCGCCGCAGCTCGTTGGCGTCCAGCCGCACCTGCGCCTGCTGGGTGACGT

GGTTACAGATACGGTCCGCCAGGCGGCGGGCGATCGTCGCCCCCTGGTTCGCCGTCACACACAGTTCCTC

GAAACAGACCGCGCAGGGGTGGGACGGGTCGCTAAGCTCCGGGGGGACGATAAGGCCCGACCCCACCGCC

CCCACCATAAACTCCCGAACGCGCTCCAGCGCGGCGGTGGCGCCGCGCGAGGGGGTGATGAGGTGGCAGT

AGTTTAGCTGCTTTAGAAAGTTCTCGACGTCGTGCAGGAAACACAGCTCCATATGGACGGTCCCGCCATA

CGTATCCAGCCTGACCCGTTGGTGATACGGACAGGGTCGGGCCAGGCCCATGGTCTCGGTGAAAAACGCC

GCGACGTCTCCCGCGGTCGCGAACGTCTCCAGGCTGCCCAGGAGCCGCTCGCCCTCGCGCCACGCGTACT

CTAGCAGCAACTCCAGGGTGACCGACAGCGGGGTGAGAAAGGCCCCGGCCTGGGCCTCCAGGCCCGGCCT

CAGACGACGCCGCAGCGCCCGCACCTGAAGCGCGTTCAGCTTCAGTTGGGGGAGCTTCCCCCGTCCGATG

TGGGGGTCGCACCGCCGGAGCAGCTCTATCTGAAACACATAGGTCTGCACCTGCCCGAGCAGGGCTAACA

ACTTTTGACGGGCCACGGTGGGCTCGGACACCGGGGCGGCCATCTCGCGGCGCCGATCTGTACCGCGGCC

GGAGTATGCGGTGGACCGAGGCGGTCCGTACGCTACCCGGTGTCTGGCTGAGCCCCGGGGTCCCCCTCTT

CGGGGCGGCCTCCCGCGGGCCCGCCGACCGGCAAGCCGGGAGTCGGCGGCGCGTGCGTTTCTGTTCTATT

CCCAGACACCGCGGAGAGGAATCGCGGCCCGCCCAGAGATATAGACACGGAACACAAACAAGCACGGATG

TCGTAGCAATAATTTATTTTACACACATCCCCGCCCCGCCCTAGGTTCCCCCACCCCCCAACCCCTCACA

GCATATCCAACGTCAGGTCTCCCTTTTTGTCGGGGGGCCCCTCCCCAAACGGGTCATCCCCGTGGAACGC

CCGTTTGCGGCCGGCAAATGCCGGTCCCGGGGCCCCCGGGCCGCCGAACGGCGTCGCGTTGTCGTCCTCG

CAGCCAAAATCCCCAAAGTTAAACACCTCCCCGGCGTTGCCGAGTTGGCTGACTAGGGCCTCGGCCTCGT

GCGCCACCTCCAGGGCCGCGTCCGTCGACCACTCGCCGTTGCCGCGCTCCAGGGCACGCGCGGTCAGCTC

CATCATCTCCTCGCTTAGGTACTCGTCCTCCAGGAGCGCCAGCCAGTCCTCGATCTGCAGCTGCTGGGTG

CGGGGCCCCAGGCTTTTCACGGTCGCCACGAACACGCTACTGGCGACGGCCGCCCCGCCCTCGGAGATAA

TGCCCCGGAGCTGCTCGCACAGCGAGCTTTCGTGCGCTCCGCCGCCGAGGTTCGAGGCCGCGCACACAAA

CCCGGCCCGGGGACAGGCCAGGACGAACTTGCGGGTGCGGTCAAAAATAAGGAGCGGGCACGCGTTTTTG

CCGCCCATCAGGCTGGCCCAGTTCCCGGCCTGAAACACACGGTCGTTGCCGGCCATGCCGTAGTATTTGC

-continued

TGATGCTCAACCCCAACACGACCATGGGGCGCGCCGCCATGACGGGCCGCAGCAGGTTGCAGCTGGCGAA

CATGGACGTCCACGCGCCCGGATGCGCGTCCACGGCGTCCATCAGCGCGCGGGCCCCGGCCTCCAGGCCC

GCCCCGCCCTGCGCGGACCACGCGGCCGCCGCCTGCACGCTGGGGGGACGGCGGGACCCCGCGATGATGG

CCGTGAGGGTGTTGATGAAGTATGTCGAGTGATCGCAGTACCGCAGAATCTGGTTTGCCATGTAGTACAT

CGCCAGCTCGCTCACGTTGTTGGGGGCCAGGTTAATAAAGTTTATCGCGCCGTAGTCCAGGGAAAACTTT

TTAATGAACGCGATGGTCTCGATGTCCTCGCGCGACAGGAGCCGGGCGGGAAGCTGGTTGCGTTGGAGGG

CCGTCCAGAACCACTGCGGGTTCGGCTGGTTGGACCCCGGGGGCTTGCCGTTGGGGAAGATGGCCGCGTG

GAACTGCTTCAGCAGAAAGCCCAGCGGTCCGAGGAGGATGTCCACGCGCTTGTCGGGCTTCTGGTAGGCG

CTCTGGAGGCTGGCGACCCGCGCCTTGGCGGCCTCGGACGCGTTGGCGCTCGCGCCCGCGAACAACACGC

GGCTCTTGACGCGCAGCTCCTTGGGAAACCCCAGGGTCACGCGGGCAACGTCGCCCTCGAAGCTGCTCTC

GGCGGGGGCCGTCTGGCCGGCCGTTAGGCTGGGGGCGCAGATAGCCGCCCCCTCCGAGAGCGCGACCGTC

AGCGTTTTGGCCGACAGAAACCCGTTGTTAAACATGTCCATCACGCGCCGCCGCAGCACCGGTTGGAATT

GATTGCGAAAGTTGCGCCCCTCGACCGACTGCCCGGCGAACACCCCGTGGCACTGGCTCAGGGCCAGGTC

CTGATACACGGCGAGGTTGGATCGCCGCCCGAGAAGCTGAAGCAGGGGGCATGGCCCGCACGCGTACGGG

TCCAGCGTCAGGGACATGGCGTGGTTGGCCTCGCCCAGACCGTCGCGAAACTTGAAGTTCCTCCCCTCCA

CCAGGTTGCGCATCAGCTGCTCCACCTCGCGGTCCACGACCTGCCTGACGTTGTTCACCACCGTATGCAG

GGCCTCGCGGTTGGTGATGATGGTCTCCAGCCGCCCCATGGCCGTGGGGACCGCCTGGTCCACGTACTGC

AGGGTCTCGAGTTCGGCCATGACGCGCTCGGTCGCCGCGCGGTACGTCTCCTGCATGATGGTCCGGGCGG

TCTCGGATCCGTCCGCGCGCTTCAGGGCCGAGAAGGCGGCGTAGTTTCCCAGCACGTCGCAGTCGCTGTA

CATGCTGTTCATGGTCCCGAAGACGCCGATGGCTCCGCGGGCGGCGCTGGCGAACTTGGGATGGCGCGCC

CGGAGGCGCATGAGCGTCGTGTGTACGCAGGCGTGGCGCGTGTCGAAGGTGCACAGGTTGCAGGGCACGT

CGGTCTGGTTGGAGTCCGCGACGTATCGAAACACGTCCATCTCCTGGCGCCCGACGATCACGCCGCCGTC

GCAGCGCTCCAGGTAAAACAGCATCTTGGCCAGCAGCGCCGGGGAAAACCCACACAGCATGGCCAGGTGC

TCGCCGGCAAATTCCTGGGTTCCGCCGACGAGGGGCGCGGTGGGCCGACCCTCGAACCCGGGCACCACGT

GTCCCTCGCGGTCCACCTGTGGGTTGGCCGCCACGTGGGTCCCGGGCACGAGGAAGAAGCGGTAAAAGGA

GGGTTTGCTGTGGTCCTTTGGGTCCGCCGGACCGGCGTCGTCCACCTCGGTGAGATGGAGGGCCGAGTTG

GTGCTAAATACCATGGCCCCCACGAGTCCCGCGGCGCGCGCCAGGTACGCCCCGACGGCGTTGGCGCGGG

CCGCGGCCGTGTCCTGGCCCTCGCACAGCGGCCACGCGGAGATGTCGGTGGGCGGCTCGTCGAAGACGGC

CATCGACACGATAGACTCGAGGGCCAGGGCGGCGTCTCCGGCCATGACGGAGGCCAGGCGCTGTTCGAAC

CCGCCCGCCGGGCCCTTGCCGCCGCCGTCGCGCCCACCCCGCGGGGTCTTACCCTGGCTGGCTTCGAAGG

CCGTGAACGTAATGTCGGCGGGGAGGGCGGCGCCCTCGTGGTTTTCGTCAAACGCCAGGTGGGCGGCCGC

GCGGGCCACGGCGTCCACGTTTCGGCATCGCAGTGCCACGGCGGCGGGTCCCACGACCGCCTCGAACAGG

AGGCGGTTGAGGGGGCGGTTAAAAAACGGAAGCGGGTAGGTAAAATTCTCCCCGATCGATCGGTGGTTGG

CGTTGAACGGCTCGGCGATGACCCGGCTAAAATCCGGCATGAACAGCTGCAACGGATACACGGGTATGCG

GTGCACCTCCGCCCCGCCTATGGTTACCTTGTCCGAGCCTCCCAGGTGCAGAAAGGTGTTGTTGATGCAC

ACGGCCTCCTTGAAGCCCTCGGTAACGACCAGATACAGGAGGGCGCGGTCCGGGTCCAGGCCGAGGCGCT

CACACAGCGCCTCCCCCGTCGTCTCGTGTTTGAGGTCGCCGGGCCGGGGGGTGTAGTCCGAAAAGCCAAA

ATGGCGGCGTGCCCGCTCGCAGAGTCGCGTCAGGTTTGGGGCCTGGGTGCTGGGGTCCAGGTGCCGGCCG

CCGTGAAAGACGTACACGGACGAGCTGTAGTGCGATGGCGTCAGTTTCAGGGACACCGCGGTACCCCCGA

GCCCCGTCGTGCGAGAACCCACGACCACGGCTACGTTGGCCTCAAAGCCGCTCTCCACGGTCAGGCCCAC

GACCAGGGGCGCCACGGCGACGTCGGCATCGCCGCTGCGCGCCGACAGTAACGCCAGAAGCTCGATGCCT

-continued

TCGGACGGACACGCGCGAGCGTACACGTATCCCAGGGGCCCGGGGGGGACCTTGATGGTGGTTGCCGTCT

TGGGCTTTGTCTCCATGTCCTCCTGGCAATCGGTCCGCAAACGGAGGTAATCCCGGCACGACGACGGACG

CCCGACGAGGTATGTCTCCCGAGCGTCAAAATCCGGGGGGGGGGGGGGGGGGGGGGCGGCGACGGTCAAG

GGGAGGGTGGGAGACCGGGGTTGGGGAATGAATCCCTACCCTTCACAGACAACCCCCGGGTAACCACGGG

GTGCCGATGAACCCCGGCGGCTGGCAACGCGGGGTCCCTGCGAGAGGCACAGATGCTTACGGTCAGGTGC

TCCGGGCCGGGTGCGTCTGATATGCGGTTGGTATATGTACACTTTACCTGGGGGCGTGCCGGACCGCCCC

AGCCCCTCCCACACCCCGCGCGTCATCAGCCGGTGGGCGTGGCCGCTATTATAAAAAAAGTGAGAACGCG

AAGCGTTCGCACTTTGTCCTAATAATATATATATTATTAGGACAAAGTGCGAACGCTTCGCGTTCTCACT

TTTTTTATAATAGCGGCCACGCCCACCGGCTACGTCACGCTCCTGTCGGCCGCCGGCGGTCCATAAGCCC

GGCCGGCCGGGCCGACGCGAATAAACCGGGCCGCCGGCCGGGGCGCCGCGCAGCAGCTCGCCGCCCGGAT

CCGCCAGACAAACAAGGCCCTTGCACATGCCGGCCCGGGCGAGCCTGGGGGTCCGGTAATTTTGCCATCC

CACCCAAGCGGCTTTTGGGGTTTTTCCTCTTCCCCCCTCCCCACATCCCCCCTCTTTAGGGGTTCGGGTG

GGAACAACCGCGATGTTTTCCGGTGGCGGCGGCCCGCTGTCCCCCGGAGGAAAGTCGGCGGCCAGGGCGG

CGTCCGGGTTTTTTGCGCCCGCCGGCCCTCGCGGAGCCGGCCGGGGACCCCCGCCTTGTTTGAGGCAAAA

CTTTTACAACCCCTACCTCGCCCCAGTCGGGACGCAACAGAAGCCGACCGGGCCAACCCAGCGCCATACG

TACTATAGCGAATGCGATGAATTTCGATTCATCGCCCCGCGGGTGCTGGACGAGGATGCCCCCCCGGAGA

AGCGCGCCGGGGTGCACGACGGTCACCTCAAGCGCGCCCCCAAGGTGTACTGCGGGGGGGACGAGCGCGA

CGTCCTCCGCGTCGGGTCGGGCGGCTTCTGGCCGCGGCGCTCGCGCCTGTGGGGCGGCGTGGACCACGCC

CCGGCGGGGTTCAACCCCACCGTCACCGTCTTTCACGTGTACGACATCCTGGAGAACGTGGAGCACGCGT

ACGGCATGCGCGCGGCCCAGTTCCACGCGCGGTTTATGGACGCCATCACACCGACGGGGACCGTCATCAC

GCTCCTGGGCCTGACTCCGGAAGGCCACCGGGTGGCCGTTCACGTTTACGGCACGCGGCAGTACTTTTAC

ATGAACAAGGAGGAGGTTGACAGGCACCTACAATGCCGCGCCCCACGAGATCTCTGCGAGCGCATGGCCG

CGGCCCTGCGCGAGTCCCCGGGCGCGTCGTTCCGCGGCATCTCCGCGGACCACTTCGAGGCGGAGGTGGT

GGAGCGCACCGACGTGTACTACTACGAGACGCGCCCCGCTCTGTTTTACCGCGTCTACGTCCGAAGCGGG

CGCGTGCTGTCGTACCTGTGCGACAACTTCTGCCCGGCCATCAAGAAGTACGAGGGTGGGGTCGACGCCA

CCACCCGGTTCATCCTGGACAACCCCGGGTTCGTCACCTTCGGCTGGTACCGTCTCAAACCGGGCCGGAA

CAACACGCTAGCCCAGCCGCGGGCCCCGATGGCCTTCGGGACATCCAGCGACGTCGAGTTTAACTGTACG

GCGGACAACCTGGCCATCGAGGGGGGCATGAGCGACCTACCGGCATACAAGCTCATGTGCTTCGATATCG

AATGCAAGGCGGGGGGGGAGGACGAGCTGGCCTTTCCGGTGGCCGGGCACCCGGAGGACCTGGTTATTCA

GATATCCTGTCTGCTCTACGACCTGTCCACCACCGCCCTGGAGCACGTCCTCCTGTTTTCGCTCGGTTCC

TGCGACCTCCCCGAATCCCACCTGAACGAGCTGGCGGCCAGGGGCCTGCCCACGCCCGTGGTTCTGGAAT

TCGACAGCGAATTCGAGATGCTGTTGGCCTTCATGACCCTTGTGAAACAGTACGGCCCCGAGTTCGTGAC

CGGGTACAACATCATCAACTTCGACTGGCCCTTCTTGCTGGCCAAGCTGACGGACATTTACAAGGTCCCC

CTGGACGGGTACGGCCGCATGAACGGCCGGGGCATGTTTCGCGTGTGGGACATAGGCCAGAGCCACTTCC

AGAAGCGCAGCAAGATAAAGGTGAACGGCATGGTGAACATCGACATGTACGGGATCATAACCGACAAGAT

CAAGCTCTCGAGCTACAAGCTCAACGCCGTGGCCGAAGCCGTCCTGAAGGACAAGAAGAAGGACCTGAGC

TATCGCGACATCCCCGCCTACTACGCCACCGGGCCCGCGCAACGCGGGGTGATCGGCGAGTACTGCATAC

AGGATTCCCTGCTGGTGGGCCAGCTGTTTTTTAAGTTTTTGCCCCATCTGGAGCTCTCGGCCGTCGCGCG

CTTGGCGGGTATTAACATCACCCGCACCATCTACGACGGCCAGCAGATCCGCGTCTTTACGTGCCTGCTG

CGCCTGGCCGACCAGAAGGGCTTTATTCTGCCGGACACCCAGGGGCGATTTAGGGGCGCCGGGGGGGAGG

-continued

CGCCCAAGCGTCCGGCCGCAGCCCGGGAGGACGAGGAGCGGCCAGAGGAGGAGGGGGAGGACGAGGACGA

ACGCGAGGAGGGCGGGGGCGAGCGGGAGCCGGAGGGCGCGCGGGAGACCGCCGGCCGGCACGTGGGGTAC

CAGGGGGCCAGGGTCCTTGACCCCACTTCCGGGTTTCACGTGAACCCCGTGGTGGTGTTCGACTTTGCCA

GCCTGTACCCCAGCATCATCCAGGCCCACAACCTGTGCTTCAGCACGCTCTCCCTGAGGGCCGACGCAGT

GGCGCACCTGGAGGCGGGCAAGGACTACCTGGAGATCGAGGTGGGGGGGCGACGGCTGTTCTTCGTCAAG

GCTCACGTGCGAGAGAGCCTCCTCAGCATCCTCCTGCGGGACTGGCTCGCCATGCGAAAGCAGATCCGCT

CGCGGATTCCCCAGAGCAGCCCCGAGGAGGCCGTGCTCCTGGACAAGCAGCAGGCCGCCATCAAGGTCGT

GTGTAACTCGGTGTACGGGTTCACGGGAGTGCAGCACGGACTCCTGCCGTGCCTGCACGTTGCCGCGACG

GTGACGACCATCGGCCGCGAGATGCTGCTCGCGACCCGCGAGTACGTCCACGCGCGCTGGGCGGCCTTCG

AACAGCTCCTGGCCGATTTCCCGGAGGCGGCCGACATGCGCGCCCCCGGGCCCTATTCCATGCGCATCAT

CTACGGGGACACGGACTCCATATTTGTGCTGTGCCGCGGCCTCACGGCCGCCGGGCTGACGGCCATGGGC

GACAAGATGGCGAGCCACATCTCGCGCGCGCTGTTTCTGCCCCCCATCAAACTCGAGTGCGAAAAGACGT

TCACCAAGCTGCTGCTGATCGCCAAGAAAAAGTACATCGGCGTCATCTACGGGGGTAAGATGCTCATCAA

GGGCGTGGATCTGGTGCGCAAAAACAACTGCGCGTTTATCAACCGCACCTCCAGGGCCCTGGTCGACCTG

CTGTTTTACGACGATACCGTATCCGGAGCGGCCGCCGCGTTAGCCGAGCGCCCCGCAGAGGAGTGGCTGG

CGCGACCCCTGCCCGAGGGACTGCAGGCGTTCGGGGCCGTCCTCGTAGACGCCCATCGGCGCATCACCGA

CCCGGAGAGGGACATCCAGGACTTTGTCCTCACCGCCGAACTGAGCAGACACCCGCGCGCGTACACCAAC

AAGCGCCTGGCCCACCTGACGGTGTATTACAAGCTCATGGCCCGCCGCGCGCAGGTCCCGTCCATCAAGG

ACCGGATCCCGTACGTGATCGTGGCCCAGACCCGCGAGGTAGAGGAGACGGTCGCGCGGCTGGCCGCCCT

CCGCGAGCTAGACGCCGCCGCCCCAGGGGACGAGCCCGCCCCCCCCGCGGCCCTGCCCTCCCCGACCAAG

CGCCCCCGGGAGACGCCGTCGCATGCCGACCCCCCGGGAGGCGCGTCCAAGCCCCGCAAGCTGCTGGTGT

CCGAGCTGGCCGAGGATCCCGCATACGCCATTGCCCACGGCGTCGCCCTGAACACGGACTATTACTTCTC

CCACCTGTTGGGGGCGGCGTGCGTGACATTCAAGGCCCTGTTTGGGAATAACGCCAAGATCACCGAGAGT

CTGTTAAAAAGGTTTATTCCCGAAGTGTGGCACCCCCCGGACGACGTGGCCGCGCGGCTCCGGGCCGCAG

GGTTCGGGGCGGTGGGTGCCGGCGCTACGGCGGAGGAAACTCGTCGAATGTTGCATAGAGCCTTTGATAC

TCTAGCATGAGCCCCCCGTCGAAGCTGATGTCCCTCATTTTACAATAAATGTCTGCGGCCGACACGGTCG

GAATCTCCGCGTCCGTGGGTTTCTCTGCGTTGCGCCGGACCACGAGCACAAACGTGCTCTGCCACACGTG

GGCGACGAACCGGTACCCCGGGCACGCGGTGAGCATCCGGTCTATGAGCCGGTAGTGCAGGTGGGCGGAC

GTGCCGGGAAAGATGACGTACAGCATGTGGCCCCCGTAAGTGGGGTCCGGGTAAAACAACAGCCGCGGGT

CGCACGCCCCGCCTCCGCGCAGGATCGTGTGGACGAAAAAAAGCTCGGGTTGGCCAAGAATCCCGGCCAA

GAGGTCCTGGAGGGGGGCGTTGTGGCGGTCGGCCAACACGACCAAGGAGGCCAGGAAGGCGCGATGCTCG

AATATCGTGTTGATCTGCTGCACGAAGGCCAGGATTAGGGCCTCGCGGCTGGTGGCGGCGAACCGCCCGT

CTCCCGCGTTGCACGCGGGACAGCAACCCCCGATGCCTAGGTAGTAGCCCATCCCGGAGAGGGTCAGGCA

GTTGTCGGCCACGGTCTGGTCCAGACAGAAGGGCAGCGACACGGGAGTGGTCTTCACCAGGGGCACCGAG

AACGAGCGCACGATGGCGATCTCCTCGGAGGGCGTCTGGGCGAGGGCGGCGAAAAGGCCCCGATAGCGCT

GGCGCTCGTGTAAACACAGCTCCTGTTTGCGGGCGTGAGGCGGCAGGCTCTTCCGGGAGGCCCGACGCAC

CACGCCCAGAGTCCCGCCGGCCGCAGAGGAGCACGACCGCCGGCGCTCCTTGCCGTGATAGGGCCCGGGC

CGGGAGCCGCGGCGATGGGGGTCGGTATCATACATAGGTACACAGGGTGTGCTCCAGGGACAGGAGCGAG

ATCGAGTGGCGTCTAAGCAGCGCGCCCGCCTCACGGACAAATGTGGCGAGCGCGGTGGGCTTTGGTACAA

ATACCTGATACGTCTTGAAGGTGTAGATGAGGGCACGCAACGCTATGCAGACACGCCCCTCGAACTCGTT

CCCGCAGGCCAGCTTGGCCTTGTGGAGCAGCAGCTCGTCGGGATGGGTGGCGGGGGGATGGCCGAACAGA

-continued

ACCCAGGGGTCAACCTCCATCTCCGTGATGGCGCACATGGGGTCACAGAACATGTGCTTAAAGATGGCCT

CGGGCCCCGCGGCCCGCAGCAGGCTCACAAACCGGCCCCCGTCCCCGGGCTGCGTCTCGGGGTCCGCCTC

GAGCTGGTCGACGACGGGTACGATACAGTCGAAGAGGCTCGTGTTGTTTTCCGAGTAGCGGACCACGGAG

GCCCGGAGTCTGCGCAGGGCCAGCCAGTAAGCCCGCACCAGTAACAGGTTACACAGCAGGCATTCTCCGC

CGGTGCGCCCGCGCCCCCGGCCGTGTTTCAGCACGGTGGCCATCAGAGGGCCCAGGTCGAGGTCGGGCTG

GGCATCGGGTTCGGTAAACTGCGCAAAGCGCGGAGCCACGTCGCGCGTGCGTGCCCCGCGATGCGCTTCC

CAGGACTGGCGGACCGTGGCGCGACGGGCCTCCGCGGCAGCGCGCAGCTGGGGCCCCGACTCCCAGACGG

CGGGGGTGCCGGCGAGGAGCAGCAGGACCAGATCCGCGTACGCCCACGTATCCGGCGACTCCTCCGGCTC

GCGGTCCCCGGCGACCGTCTCGAATTCCCCGTTGCGAGCGGCGGCGCGCGTACAGCAGCTGTCCCCGCCC

CCGCGCCGACCCTCCGTGCAGTCCAGGAGACGGGCGCAATCCTTCCAGTTCATCAGCGCGGTGGTGAGCG

ACGGCTGCGTGCCGGATCCCGCCGCCGACCCCGCCCCCTCCTCGCCCCCGGAGGCCAAGGTTCCGATGAG

GGCCCGGGTGGCAGACTGCGCCAGGAACGAGTAGTTGGAGTACTGCACCTTGGCGGCTCCCGGGGAGGGC

GAGGGCTTGGGTTGCTTCTGGGCATGCCGCCCGGGCACCCCGCCGTCGGTACGGAAGCAGCAGTGGAGAA

AAAAGTGCCGGTGGATGTCGTTTATGGTGAGGGCAAAGCGTGCGAAGGAGCCGACCAGGGTCGCCTTCTT

GGTGCGCAGAAAGTGGCGGTCCATGACGTACACAAACTCGAACGCGGCCACGAAGATGCTAGCGGCGCAG

TGGGGCGCCCCCAGGCATTTGGCACAGAGAAACGCGTAATCGGCCACCCACTGGGGCGAGAGGCGGTAGG

TTTGCTTGTACAGCTCGATGGTGCGGCAGACCAGACAGGGCCGGTCCAGCGCGAAGGTGTCGATGGCCGC

CGCGGAAAAGGGCCCGGTGTCCAAAAGCCCCTCCCCACAGGGATCCGGGGGCGGGTTGCGGGGTCCTCCG

CGCCCGCCCGAACCCCCTCCGTCGCCCGCCCCCCCGCGGGCCCTTGAGGGGGCGGTGACCACGTCGGCGG

CGACGTCCTCGTCGAGCGTACCGACGGGCGGCACACCTATCACGTGACTGGCCGCCAGGAGCTCGGCGCA

GAGAGCCTCGTTAAGAGCCAGGAGGCTGGGATCGAAGGCCACATACGCGCGCTCGAACGCCCCCGCCTTC

CAGCTGCTGCCGGGGGACTCTTCGCACACCGCGACGCTCGCCAGGACCCCGGGGGGCGAAGTTGCCATGG

CTGGGCGGGAGGGGCGCACGCGCCAGCGAACTTTACGGGACACAATCCCCGACTGCGCGCTGCGGTCCCA

GACCCTGGAGAGTCTAGACGCGCGCTACGTCTCGCGAGACGGCGCGCATGACGCGGCCGTCTGGTTCGAG

GATATGACCCCCGCCGAGCTGGAGGTTGTCTTCCCGACTACGGACGCCAAGCTGAACTACCTGTCGCGGA

CGCAGCGGCTGGCCTCCCTCCTGACGTACGCCGGGCCTATAAAAGCGCCCGACGACGCCGCCGCCCCGCA

GACCCCGGACACCGCGTGTGTGCACGGCGAGCTGCTCGCCCGCAAGCGGGAAAGATTCGCGGCGGTCATT

AACCGGTTCCTGGACCTGCACCAGATTCTGCGGGGCTGACGCGCGCGCTGTTGGGCGGGACGGTTCGCGA

ACCCTTTGGTGGGTTTACGCGGGCACGCACGCTCCCATCGCGGGCGCCATGGCGGGACTGGGCAAGCCCT

ACCCCGGCCACCCAGGTGACGCCTTCGAGGGTCTCGTTCAGCGAATTCGGCTTATCGTCCCATCTACGTT

GCGGGGCGGGGACGGGGAGGCGGGCCCCTACTCTCCCTCCAGCCTCCCCTCCAGGTGCGCCTTTCAGTTT

CATGGCCATGACGGGTCCGACGAGTCGTTTCCCATCGAGTATGTACTGCGGCTTATGAACGACTGGGCCG

AGGTCCCGTGCAACCCTTACCTGCGCATACAGAACACCGGCGTGTCGGTGCTGTTTCAGGGGTTTTTTCA

TCGCCCACACAACGCCCCCGGGGGCGCGATTACGCCAGAGCGGACCAATGTGATCCTGGGCTCCACCGAG

ACGACGGGGCTGTCCCTCGGCGACCTGGACACCATCAAGGGGCGGCTCGGCCTGGATGCCCGGCCGATGA

TGGCCAGCATGTGGATCAGCTGCTTTGTGCGCATGCCCCGCGTGCAGCTCGCGTTTCGGTTCATGGGCCC

CGAAGATGCCGGACGGACGAGACGGATCCTGTGCCGCGCCGCCGAGCAGGCTATTACCCGTCGCCGCCGA

ACCCGGCGGTCCCGGGAGGCGTACGGGGCCGAGGCCGGGCTGGGGGTGGCTGGAACGGGTTTCCGGGCCA

GGGGGGACGGTTTTGGCCCGCTCCCCTTGTTAACCCAAGGGCCCTCCCGCCCGTGGCACCAGGCCCTGCG

GGGTCTTAAGCACCTACGGATTGGCCCCCCCGCGCTCGTTTTGGCGGCGGGACTCGTCCTGGGGGCCGCT

-continued

ATTTGGTGGGTGGTTGGTGCTGGCGCGCGCCTATAAAAAAGGACGCACCGCCGCCCTAATCGCCAGTGCG

TTCCGGACGCCTTCGCCCCACACAGCCCTCCCGTCCGACACCCCCATATCGCTTCCCGACCTCCGGTCCC

GATGGCCGTCCCGCAATTTCACCGCCCCAGCACCGTTACCACCGATAGCGTCCGGGCGCTTGGCATGCGC

GGGCTCGTCTTGGCCACCAATAACTCTCAGTTTATCATGGATAACAACCACCCGCACCCCCAGGGCACCC

AAGGGGCCGTGCGGGAGTTTCTCCGCGGTCAGGCGGCGGCGCTGACGGACCTTGGTCTGGCCCACGCAAA

CAACACGTTTACCCCGCAGCCTATGTTCGCGGGCGACGCCCCGGCCGCCTGGTTGCGGCCCGCGTTTGGC

CTGCGGCGCACCTATTCACCGTTTGTCGTTCGAGAACCTTCGACGCCCGGGACCCCGTGAGGCCCGGGGA

GTTCCTTCTGGGGTGTTTTAATCAATAAAAGACCACACCAACGCACGAGCCTTGCGTTTAATGTCGTGTT

TATTCAAGGGAGTGGGATAGGGTTCGACGGTTCGAAACTTAACACACAAAATAATCGAGCGCGTCTAGCC

CAGTAACATGCGCACGTGATGTAGGCTGGTCAGCACGGCGTCGCTGTGATGAAGCAGCGCCCGGCGGGTC

CGCTGTAACTGCTGTTGTAGGCGGTAACAGGCGCGGATCAGCACCGCCAGGGCGCTACGACCGGTGCGTT

GCACGTAGCGTCGCGACAGAACTGCGTTTGCCGATACGGGCGGGGGGCCGAATTGTAAGCGCGTCACCTC

TTGGGAGTCATCGGCGGATAACGCACTGAATGGTTCGTTGGTTATGGGGGAGTGTGGTTCCCGAGGGAGT

GGGTCGAGCGCCTCGGCCTCGGAATCCGAGAGGAACAACGAGGTGGTGTCGGAGTCTTCGTCGTCAGAGA

CATACAGGGTCTGAAGCAGCGACACGGGCGGGGGGGTAGCGTCAATGTGTAGCGCGAGGGAGGATGCCCA

CGAAGACACCCCAGACAAGGAGCTGCCCGTGCGTGGATTTGTGGACGACGCGGAAGCCGGGACGGATGGG

CGGTTTTGCGGTGCCCGGAACCGAACCGCCGGATACTCCCCGGGTGCTACATGCCCGTTTTGGGGCTGGG

GTTGGGGCTGGGGCTGGGGCGGGGGGTGGGGGGGGTTGGGGTGGGGCTGGGGTGGGGCTGGGGTTGGGGC

TGGGGCTGGGGCTGGGGCTGGGGTGGGGTTGGGGTTGGGGCTGGGGCTGGGGTGGGGTGGGGCTGGGGTG

GGGTTGGGGCTGGGGTTGGGGCTGGGGTTGGGGCTGGGGTGGGGCTGGGGTTGGGGTTGGGGTTGGGGCT

GGGGTTGGGGCTGGGGCGCGGACAGGCGGTTGACGGTCAAATGCCCCCGGGGGCGCGCAGATGTGGTGGG

CGTGGCCACCGGCTGCCGGGTAGGGGGGCGGCGGGGAACCGGGCCTCCGGGCGTAACACCGCCCTCCAGC

GTCAAGGATGTGGGGGGCGGGCCTGACGTCGGGGGCGGGGTGACGGGTTGGACCGCGGGAGGCGGGGGAG

AGGGACCTGCGGGAGAGGATGAGGTCGGCTCGGCCGGGTTGCGGCCTAAAACAGGGGCCGTGGGGTCGGC

GGGGTCCCAGGGTGAAGGGAGGGATTCCCGCGATTCGGACAGCGACGCGACAGCGGGGCGCGTAAGGCGC

CGCTGCGGCCCGCCTACGGGAACCCTGGGGGGGGTTGGCGCGGGACCCGAGGTTAGCGGGGGGCGGCGGT

TTTCGCCCCCGGGCAAAACCGTGCCGGTTGCGACCGGGGGCGGAACGGGATCGATAGGGAGAGCGGGAGA

AGCCTGGCCGGCGAACTGGGGACCGAGCGGGAGGGGCACACCAGACACCAAAGCGTGGAGCGCTGGCTCT

GGGGGTTTGGGAGGGGCCGGGGGGCGCGCGAAATCGGTAACCGGGGCGACCGTGTCGGGGAGGGCAGGCG

GCCGCCAACCCTGGGTGGTCGCGGAAGCCTGGGTGGCGCGCGCCAGGGAGCGTGCCCGGCGGTGTCGGCG

CGCGCGCGACCCGGACGAAGAAGCGGCAGAAGCGCGGGAGGAGGCGGGGGGGCGGGGGGCGGTGGCATCG

GGGGGCGCCGGGGAACTTTGGGGGGACGGCAAGCGCCGGAAGTCGTCGCGGGGGCCCACGGGCGCCGGCC

GCGTGCTTTCGGCCGGGACGCCCGGTCGTGCTTCGCGAGCCGTGACTGCCGGCCCAGGGGGCCGCGGTGC

ACACTGGGACGTGGGGACGGACTGATCGGCGGTGGGCGAAAGGGGGTCCGGGGCAAGGAGGGGCGCGGGG

CCGCCGGAGTCGTCAGACGCGAGCTCCTCCAGGCCGTGAATCCATGCCCACATGCGAGGGGGGACGGGCT

CGCCGGGGGTGGCGTCGGTGAATAGCGTGGGGGCCAGGCTTCCGGGCCCCAACGAGCCCTCCGTCCCAAC

AAGGTCCGCCGGGCCGGGGGTCGGGTTCGGGACCGAGGGGCTCTGGTCGTCGGGGGCGCGCTGGTACACC

GGATGCCCCGGGAATAGCTCCCCCGACAGGAGGGAGGCGTCGAACGGCCGCCCGAGGATAGCTCGCGCGA

GGAAGGGGTCCTCGTCGGTGGCGCTGGCGGCGAGGACGTCCTCGCCGCCCGCCACAAACGGGAGCTCCTC

GGTGGCCTCGCTGCCAACAAACCGCACGTCGGGGGGGCCGGGGGGGTCCGGGTTTTCCCACAACACCGCG

ACCGGGGTCATGGAGATGTCCACGAGCACCAGACACGGCGGGCCCCGGGCGAGGGGCCGCTCGGCGATGA

-continued

GCGCGGACAGGCGCGGGAGCTGTGCCGCCAGACACGCGTTTTCAATCGGGTTCAGGTCGGCGTGCAGGAG

GCGGACGGCCCACGTCTCGATGTCGGACGACACGGCATCGCGCAAGGCGGCGTCCGGCCCGCGAGCGCGT

GAGTCAAACAGCGTGAGACACAGCTCCAGCTCCGACTCGCGGGAAAAGGCCGTGGTGTTGCGGAGCGCCA

CGACGACGGGCGCGCCCAGGAGCACTGCCGCCAGCACCAGGTCCATGGCCGTAACGCGCGCCGCGGGGGT

GCGGTGGGTGGCGGCGGCCGGCACGGCGACGTGCTGGCCCGTGGGCCGGTAGAGGGCGTTGGGGGGAGCG

GGGGGTGACGCCTCGCGCCCCCCCGAGGGGCTCAGCGTCTGCCCAGATTCCAGACGCGCGGTCAGAAGGG

CGTCGAAACTGTCATACTCTGTGTAGTCGTCCGGAAACATGCAGGTCCAAAGAGCGGCCAGAGCGGTGCT

TGGGAGACACATGCGCCCGAGGACGCTCACCGCCGCCAGCGCCTGGGCGGGACTCAGCTTTCCCAGCGCG

GCGCCGCGCTCGGTTCCCAGCTCGGGGACCGAGCGCCAGGGCGCCAGGGGGTCGGTTTCGGACAACTTGC

CGCGGCGCCAGTCTGCCAGCCGCGTGCCGAACATGAGGCCCCGGGTCGGAGGGCCTCCGGTCGAAAACAC

TGGCAGCACGCGGATGCGGGCGTCTGGATGCGGGGTCAGGCGCTGCACGAATAGCATGGAATCTGCTGCG

TTCTGAAACGCACGGGGGAGGGTGAGATGCATGTACTCGTGTTGGCGGACCAGATCCAGGCGCCAAAAGG

TGTAAATGTGTTCCGGGGAGCTGGCCACCAGCGCCACCAGCACGTCGTTCTCGTTAAAGGAAACGCGGTG

CCTAGTGGAGCTGTGGGGCCCGAGCGGCGGTCCCGGGGCCGCCGCGTCACCCCCCCATTCCAGCTGGGCC

CAGCGACACCCAAACTCGCGCGTGAGAGTGGTCGCGACGAGGGCGACGTAGAGCTCGGCCGCCGCATCCA

TCGAGGCCCCCCATCTCGCCTGGCGGTGGCGCACAAAGCGTCCGAAGAGCTGAAAGTTGGCGGCCTGGGC

GTCGCTGAGGGCCAGCTGAAGCCGGTTGATGACGGTGATGACGTACATGGCCGTGACGGTCGAGGCCGAC

TCCAGGGTGTCCGTCGGAAGCGGGGGGCGAATGCATGCCGCCTCGGGACACATCAGCAGCGCGCCGAGCT

TGTCGGTCACGGCCGGGAAGCAGAGCGCGTACTGCAGTGGCGTTCCATCCGGGACCAAAAAGCTGGGGGC

GAACGGCCGATCCAGCGTACTGGTGGCCTCGCGCAGCACCAGGGGCCCCGGGCCTCCGCTCACTCGCAGG

TACGCCTCGCCCCGGCGGCGCAGCATCTGCGGGTCGGCCTCTTGGCCGGGTGGGGCGGACGCCCGGGCGC

GGGCGTCTAGGGCGCGAAGATCCACGAGCAGGGGCGCGGGCGCGGCGGCCGCGCCCGCGCCCGTCTGGCC

TGTGGCCTTGGCGTACGCGCTATATAAGCCCATGCGGCGTTGGATGAGCTCCCGCGCGCCCCGGAACTCC

TCCACCGCCCATGGGGCCAGGTCCCCGGCCACCGCGTCGAATTCCGCCAACAGGCCCCCCAGGGTGTCAA

AGTTCATCTCCCAGGCCACCCTTGGCACCACCTCGTCCCGCAGCCGGGCGCTCAGGTCGGCGTGTTGGGC

CACGCGCCCCCCGAGCTCCTCCACGGCCCCGGCCCGCTCGGCGCTCTTGGCGCCCAGGACGCCCTGGTAC

TTGGCGGGAAGGCGCTCGTAGTCCCGCTGGGCTCGCAGCCCCGACACAGTGTTGGTGGTGTCCTGCAGGG

CGCGAAGCTGCTCGCATGCCGCGCGAAATCCCTCGGGCGATTTCCAGGCCCCCCCGCGAACGCGGCCGAA

GCGACCCCATACCTCGTCCCACTCCGCCTCGGCCTCCTCGAGAGACCTCCGCAGGGCCTCGACGCGGCGA

CGGGTGTCGAAGAGCGCCTGCAGGCGCGCGCCCTGTCGCGTCAGGAGGCCCGGGCCGTCGCCGCTGGCCG

CGTTTAGCGGGTGCGTCTCAAAGGTACGCTGGGCATGTTCCAACCAGGCGACCGCCTGCACGTCGAGCTC

GCGCGCCTTCTCCGTCTGGTCCAACAGAATTTCGACCTGATCCGCGATCTCCTCCGCCGAGCGCGCCTGG

TCCAGCGTCTTGGCCACGGTCGCCGGGACGGCGACCACCTTCAGCAGGGTCTTCAGATTGGCCAGACCCT

CGGCCTCGAGCTGGGCCCGGCGCTCGCGCGCGGCCAGCACCTCCCGCAGCCCCGCCGTGACCCGCTCGGT

GGCTTCGGCGCGCTGCTGTTTGGCGCGCACCACGGCGTCCTTGGTATCGGCCAGGTCCTGTCGGGTCACG

AATGCGACGTAGTCGGCGTACGCCGTGTCCTTCACGGGGCTCTGGTCCACGCGCTCCAGCGCCGCCACGC

ACGCCACCAGCGCGTCCTCGCTCGGGCAGGGCAGGGTGACCCCTGCCCGGACAAGCTCGGCGGCCGCCGC

CGGGTCGTTGCGCACCGCGGATATCTCCTCCGCGGCGGCGGCCAGGTCCAGCGCCACGCTTCCGATCGCG

CGCCGCGCGTCGGCCCGGAGGGCGTCCAGGCGATCGCGGATATCCACGTACTCGGCGTAGCCCTTTTGAA

AAAACGGCACGTACTGGCGCAGGGCCGGCACGCCCCCCAAGTCTTCCGACAGGTGTAGGACGGCCTCGTG

-continued

GTAGTCGATAAACCCGTCGTTCGCCTGGGCCCGCTCCAGCAGCCCCCCGCCAGCCGCAGAAGCCGCGCC

AGGGGCTCGGTGTCCACCCGAAACATGTCGGCGTACGTGTCGGCCGCGGCCCCGAAGGCCGCGCTCCAGT

CGATGCGGTGAATGGCTGCGAGCGGGGGGAGCATGGGGTGGCGCTGGTTCTCGGGGGTGTATGGGTTAAA

CGCAAGGGCCGTCTCCAGGGCAAGGGTCACCGCCTTGGCGTTGGTTCCCAGCGCCTGTTCGGCCCGCTTT

CGGAAGTCCCGGGGGTTGTAGCCGTGCGTGCCCGCCAGCGCCTGCAGGCGACGGAGCTCGACCACGTCAA

ACTCGGCACCGCTTTCCACGCGGTCCAGCACGGCCTCCACGTCGGCGGCCCAGCGCTCGTGGCTACTGCG

GGCGCGCTGGGCCGCCATCTTCTCTCTCAGGTCGGCGATGGCGGCCTCAAGTTCGTCGGCGCGGCGTCGC

GTGGCGCCGATGACCTTTCCCAGCTCCTGCAGGGCGCGCCCGCTGGGGGAGTGGTCCCCGGCCGTCCCTT

CGGCGTGCAACAGGCCCCCGAACCTGCCCTCGTGGCCCGCGAGGCTTTCCCGCGCGCCGGTGGTCGCGCG

CGTCGCGGCCTGGATCAGGGAGGCATGCTCTCCCTCCGGTTGGTTGGCGGCCCGGCGCACCTGGACGACA

AGGTCGGCTGCCGCCGACCCTAAGGTCGTGAGCTGGGCGATGGCCCCCCGCGCGTCCAGGGCCAACCGAG

TCGCCTTGACGTATCCCGCGGCGCTGTCGGCCATGGCCGCTAGGAAGGCCAGGGGGGAGGCCGGGTCGCT

GGCGGCCGCGCCCAGGGCCGTCACCGCGTCGACCAGGACGCGGTGCGCCCGCACGGCCGCATCCACCGTC

GACGCGGGGTCTGCCGTCGCGACGGCGGCGCTGCCGGCGTTGATGGCGTTCGAGACGGCGTGGGCTATGA

TCGGGGCGTGATCGGCGAAGAACTGCAAGAGAAACGGAGTCTCTGGGGCGTCGGCGAACAGGTTCTTCAG

CACCACCACGAAGCTGGGATGCAAGCCAGACAGAGCCGTCGCCGTGTCCGGAGTCGGGTGCTCCAGGGCA

TCTCGGTACTGCCCCAGCAGCCCCCACATGTCCGCCCGCAGTGCCGCCGTAACCTCAGGGGGCGCCCCCC

GAACGGCCTCGGGGAGGTCCGACCAGCCCGCCGGCAGGGAGGCCCGCAGGGTCGCCAGGACGGCCGGACA

GGCCTTTAGCCCCACAAAGTCAGGGAGGGGGCGCAGGACCCCCTGGAGTTTGTGCAAGAACTTCTCCCGG

GCGTCGCGGGCCACCTTCGCCCGCTCCCGCGCTCCCTCGAGCATTGCCTCCAGGGAGCGCGCGCGCTCCC

GCAAACGGGCACGCGCATCGGGGGCGAGCTCTGCCGTCAGCTTGGCGGCATCCATGGCCCGCGCCTGCCG

CAGCGCTTCCTCGGCCATGCGCGTGGCCTCTGGCGACAGCCCGCCGTCGTCGGGGTAGGGCGACGCGCCG

GGCGCAGGAACAAAGGCCGCGTCGCTGTCCAGCTGCTGGCCCAGGGCCGCATCTAGGGCGTCGAAGCGCC

GCAGCTCGGCCAGACCCGAGCTGCGGCGCGCCTGCTGGTCGTTAATGTCGCGGATGCTGCGCGCCAGCTC

GTCCAGCGGCTTGCGTTCTATCAGCCCTTGGTTGGCGGCGTCCGTCAGGACGGAGAGCCAGGCCGCCAGG

TCCTCGGGGGCGTCCAGCGTCTGGCCCCGCTGGATCAGATCCCGCAACAGGATGGCCGTGGGGCTGGTCG

CGATCGGGGGCGGGGCGGGAATGGCGGCGCGCTGCGCGATGTCCCGCGTGTGCTGGTCGAAGACAGGCAG

GGACTCGAGCAGCTGGACCACGGGCACGACGGCGGCCGAAGCCACGTGAAACCGGCGGTCGTTGTTGTCG

CTGGCCTGTAGAGCCTTGGCGCTGTATACGGCCCCCCGGTAAAAGTACTCCTTAACCGCGCCCTCGATCG

CCCGACGGGCCTGGGTCCGCACCTCCTCCAGCCGAACCTGAACGGCCTCGGGGCCCAGGGGGGGTGGGCG

CGGAGCCCCCTGCGGGGCCGCCCCGGCCGGGGCGGGCATTACGCCGAGGGGCCCGGCGTGCTGTGAGACC

GCGTCGACCCCGCGAGCGAGGGCGTCGAGGGCCTCGCGCATCTGGCGATCCTCCGCCTCCACCCTAATCT

CTTCGCCACGGGCAAATTTGGCCAGAGCCTGGACTCTATACAGAAGCGGTTCTGGGTGCGTCGGGGTGGC

GGGGGCAAAAAGGGTGTCCGGGTGGGCCTGCGAGCGCTCCAGAAGCCACTCGCCGAGGCGTGTATACAGA

TTGGCCGGCGGGGCCGCGCGAAGCTGCAGCTCCAGGTCCGCGAGTTCCCCGTAAAAGGCGTCCGTCTCCC

GAATGACATCCCTAGCCACAAGGATCAGCTTCGCCAGCGCCAGGCGACCGATCAGAGAGTTTTCGTCCAG

CACGTGCTGGACGAGGGGCAGATGGGCGGCCACGTCGGCCAGGCTCAGGCGCGTGGAGGCCAGAAAGTCC

CCCACGGCCGTTTTCCGGGGCAGCATGCTCAGGGTAAACTCCAGCAGGGCGGCGGCCGGGCCGGCCACCC

CGGCCTGGGTGTGCGTCCGGGCCCCGTTCTCGATGAGAAAGGCGAGGACGCGTTCAAAGAAAAAAATAAC

ACAGAGCTCCAGCAGCCCCGGAGAAGCCGGATACGGCGACCGTAAGGCGCTGATGGTGAGCCGCGAACAC

GCGGCGCCCTCGCGGGCCAGGGTGGCGGAGCACGCGGTGAACTTAACCGCCGTGGCGGCCACGTTTGGGT

-continued

GGGCCTCGAACAGCTGGGCGAGGTCTGCGCCCGGGGGCTCGGGTGAGCGGCGAGTCTTCAGCGCCTCGAG

GGCCTGTGAGGACGCCGGAACCATGGGCCCGTCGTCCTCGCCCGCCTCGGCGACCGGCGGCCCGGCCGGG

TCGGGGGGTGCCGAGGCGAGGACAGGCTCCGGAACGGAGGCGGGGACCGCGGCCCCGACGGGGGTTTGCC

TTTGGGGGTGGGTTTCTTCTTGGTTTTGGCAGGGGGGGCCGAGCGTTTCGTTTTCTCCCCCGAAGTCAGG

TCTTCGACGCTGGAAGGCGGAGTCCAGGTGGGTCGGCGGCGCTTGGGAAGGCCGGCCGAGTAGCGTGCCC

GGTGCCGACCAACCGGGACGACGCCCATCTCCAGGACCCGCATGTCGTCGTCATCTTCTTCGGCCGCCTC

TGCGGCGGGGGTCTTGGGGGCGGAGGGAGGCGGTGGTGGGATCGCGGAGGGTGGGTCGGCGGAGGGGGGA

TCCGTGGGTGGGGTACCCTTTAGGGCCACCGCCCATACATCGTCGGGCGCCCGATTCGGGCGCTTGGCCT

CTGGTTTTGCCGACGGACCGGCCGTCCCCCGGGATGTCTCGGAGGCCCTGTCGTCGCGACGGGCCCGGGT

CGGTGGCGGCGACTGGGCGGCTGTGGGCGGGTGTGGCCCCGGCCCCCCTCCCCCCTCCCGGGGGCCCACG

CCGACGCAGGGCTCCCCCAGGCCCGCGATCTCGCCCCGCAGGGGGTGCGTGATGGCCACGCGCCGTTCGC

TGAACGCTTCGTCCTGCATGTAAGTCTCGCTGGCCCCGTAAAGATGCAGAGCCGCGGCCGTCAAGTCCGC

AGGAGCCGCGGGTTCCGGGCCCGACGGCACGAAAAACACCATGGCTCCCGCCCACCGTACGTCCGGGCGA

TCGCGGGTGTAATACGTCAGGTATGGATACATGTCCCCCGCCCGCACTTTGGCGATGAACGCGGGGGTGC

CCTCCGGAAGGCCATGCGGGTCAAAAAGGTATGCGGTGTCGCCGTCCCTGAACAGCCCCATCCCTAGGGG

GCCAATGGTTAGGAGCGTGTACGACAGGGGGCGCAGGGCCCACGGGCCGGCGAAGAACGTGTGTGCGGGG

CATTGTGTCTCCAGCAGGCCTGCCGCGGGCTCCCCGAAGAAGCCCACCTCGCCGTATACGCGCGAGAAGA

CACAGCGCAGTCCGCCGCGCGCCCCTGGGTACTCGAGGAAGTTGGGGAGCTCGACGATCGAACACATGCG

CGGCGGCCCAGGGCCCGCAGTCGCGCGCGTCCACTCGCCCCCCTCGACCAAACATCCCTCGATGGCCTCC

GCGGACAGAACGTCGCGAGGGCCCACATCAAATATGAGGCTGAGAAAGGACAGCGACGAGCGCATGCACG

ATACCGACCCCCCCGGCTCCAGGTCGGGCGCGAACTGGTTCCGAGCACCGGTGACCACGATGTCGCGATC

CCCCCCGCGTTCCATCGTGGAGTGCGGTGGGGTGCCCGCGATCATATGTGCCCTGCGGGCCAGAGACCCG

GCCTGTTTATGGACCGGACCCCCGGGGTTAGTGTTGTTTCCGCCACCCACGCCCCCGTACCATGGCCCCG

GTTCCCCTGATTAGGCTACGAGTCGCGGTGATCGCTTCCCAAAAACCGAGCTGCGTTTGTCTGTCTTGGT

CTTCCCCCCCCCCAGCCCGCACACCATAACACCGAGAACAACACACGGGGGTGGGCGGAACATAATAAAG

CTTTATTGGTAACTAGTTAACGGCAAGTCCGTGGGTGGCGCGACGGTGTCCTCCGGGATCATCTCGTCGT

CCTCGACGGGGGTGTTGGAATGAGGCGCCTCCTCGCGGTCCACCTGGCGTGGGCCGTGCCCATAGGCCTC

CGGCTTCTGTGCGTCCATGGGCGTAGGCGCGGGGAGACTGTTTCCGGCGTCGCGGACCTCCAGGTCCCTG

GGAGCCTCCGGTCCGGCTAACGGACGAAACGCGGAAGCGCGAAACACGCCGTCGGTGACCCGCAGGAGCT

CGTTCATCAGTAACCAATCCATACTCAGCGTAACGGCCAGCCCCTGGCGAGACAGATCCACGGAGTCCGG

AACCGCGGTCGTCTGGCCCAGGGGGCCGAGGCTGTAGTCCCCCCAGGCCCCTAGGTCGCGACGGCTCGTA

AGCACGACGCGGTCGGCCGCGGGGCTTTGCGGGGGGGCGTCCTCGGGCGCATGCGCCATTACCTCTCGGA

TGGCCGCGGCGCGCTGGTCGGCCGAGCTGACCAAGGGCGCCACGACCACGGCGCGCTCCGTCTGCAGGCC

CTTCCACGTGTCGTGGAGTTCCTGGACAAACTCGGCCACGGGCTCGGGTCCCGCGGCCGCGCGCGCGGCT

TGATAGCAGGCCGACAGACGCCGCCAGCGCGCTAGAAACTGACCCATGAAACAAAACCCGGGGACCTGGT

CTCCCGACAGCAGCTTCGACGCCCGGGCGTGAATGCCGGACACGACGGACAGAAACCCGTGAATTTCGCG

CCGGACCACGGCCAGCACGTTGTCCTCGTGCGACACCTGGGCTGCCAGCTCGTCGCACACCCCCAGGTGC

GCCGTGGTTTCGGTGATGACGGAACGCAGGCTCGCGAGGGACGCGACCAGCGCGCGCTTGGCGTCGTGAT

ACATGCTGCAGTACTGACTCACCGCGTCCCCCATGGCCTCGGGGGGCCAGGGCCCCAGGCGGTCGGGCGT

GTCCCCGACCACCGCATACAGGCGGCGCCCGTCGCTCTCGAACCGACACTCGAAAAAGGCGGAGAGCGTG

-continued

CGCATGTGCAGCCGCAGCAGCACGATGGCGTCCTCCAGTTGGCGAATCAGGGGGTCGGCGCGCTCGGCGA

GGTCCTGCAGCACCCCCCGGGCAGCCAGGGCGTACATGCTAATCAACAGGAGGCTGGTGCCCACCTCGGG

GGGCGGGGGGGGCTGCAGTTGGACCAGGGGCCGCAGCTGCTCGACGGCACCCCTGGAGATCACGTACAGC

TCCCGGAGCAGCTGCTCTATGTTGTCGGCCATCTGCATAGTGGGGCCGAGGCCGCCCCGGGCGGCCGGTT

CGAGGAGAGTGATCAGCGCGCCCAGTTTGGTGCGATGGCCCTCGACCGTGGGGAGATAGCCCAGCCCAAA

GTCCCGGGCCCAGGCCAACACACGCAGGGCGAACTCGACCGGGCGGGGAAGGTAGGCCGCGCTACACGTG

GCCCTCAGCGCGTCCCCAACCACCAGGGCCAGAACGTAGGGGACGAAGCCCGGGTCGGCGAGGACGTTGG

GGTGAATGCCCTCGAGGGCGGGGAAGCGGATCTGGGTCGCCGCGGCCAGGTGGACAGAGGGGGCATGGCT

GGGCTGCCCGACGGGGAGAAGCGCGGACAGCGGCGTGGCCGGGGTGGTGGGGGTGATGTCCCAGTGGGTC

TGACCATACACGTCGATCCAGATGAGCGCCGTCTCGCGGAGAAGGCTGGGTTGACCGGAACTAAAGCGGC

GCTCGGCCGTCTCAAACTCCCCCACGAGCGCCCGCCGCAGGCTCGCCAGATGTTCCGTCGGCACGGCCGG

CCCCATGATACGCGCCAGCGTCTGGCTCAGAACGCCCCCCGACAGGCCGACCGCCTCACAGAGCCGCCCG

TGCGTGTGCTCGCTGGCGCCCTGGACCCGCCTGAAAGTTTTTACGTAGTTGGCATAGTACCCGTATTCCC

GCGCCAGACCAAACACGTTCGACCCCGCGAGGGCAATGCACCCAAAGAGCTGCTGGACTTCGCCGAGTCC

GTGGCCGGCGGGCGTCCGCGCGGGGACGCCCGCCGCCAGAAACCCCTCCAGGGCCGAAAGGTAGTGCGTG

CAGTGCGAGGGCGTGAACCCAGCGTCGATCAGGGTGTTGATCACCACGGAGGGCGAATTGGTATTCTGGA

TCAACGTCCACGTCTGCTGCAGCAGAGCCAGCAGCCGCTGCTGGGCGCCGGCGGAGGGCTGCTCCCCGAG

CTGCAGCAGGCTGGAGACGGCAGGCTGGAAGACTGCCAGTGCCGACGAACTCAGGAACGGCACGTCGGGA

TCAAACACGGCCACGTCCGTCCGCACGCGCGCCATTAGCGTCCCCGGGGGCGCACAGGCCGAGCGCGGGC

TGACGCGGCTGAGGGCCGTCGACACGCGCACCTCCTCGCGGCTGCGAACCATCTTGTTGGCCTCCAGTGG

CGGAATCATTATGGCCGGGTCGATCTCCCGCACGGTGTGCTGAAACTGCGCCAACAGGGGCGGCGGGACC

ACAGCCCCCCGCTCGGGGGTCGTCAGGTACTCGTCCACCAGGGCCAACGTAAAGAGGGCCCGTGTGAGGG

GAGTGAGGGTCGCGTCGTCTATGCGCTGGAGGTGCGCCGAGAACAGCGTCACCCGATTACTCACCAGGGC

CAAGAACCGGAGGCCCTCTTGCACGAACGGGGCGGGGAAGAGCAGGCTGTACACCGGGGTGGTAAGGTTC

GCGCTGGGCTGCCCCAACGGGACCGGCGCCAGCTTGAGCGACGTCTCCCCAAGGGCCTCGATGGAGGTCC

GCGGGCTCATGGCCAAGCAGCTCTTGGTGACGGTTTGCCAGCGGTCTATCCACTCCACGGCGCACTGGCG

GACGCGGACCGGCCCCAGGGCCGCCGCGGTGCGCAGGCCGGCGGACTCCAGCGCATGGGACGTGTCGGAG

CCGGTGACCGCGAGGATGGTGTCCTTGATGACCTCCATCTCCCGGAAGGCCTGGTCGGGGGCCTCGGGGA

GAGCCACCACCAAGCGGTGTACGAGCAACCCGGGGAGGTTCTCGGCCAAGAGCGCCGTCTCCGGAAGCCC

GTGGGCCCGGTGGAGCGCGCACAGGTGTTCCAGCAGCGGCCGCCAGCATGCCCGCGCGTCTGCCGGGGCG

ATGGCCGTTCCCGACAACAGAAACGCCGCCATGGCGGCGCGCAGCTTGGCCGTGGCCAGAAACGCCGGGT

CGTCCGCCCCGTTTGCCGTCTCGGCCGTGGGGGTTGGCGGTTGGCGAAGGCCGGCTAGGCTCGCCAATAG

GCGCTGCATAGGTCCGTCCGAGGGCGGACCGGCGGGTGAGGTCGTGACGACGGGGGCCTCGGACGGGAGA

CCGCGGTCTGCCATGACGCCCGGCTCGCGTGGGTGGGGGACAGCGTAGACCAACGACGAGACCGGGCGGG

AATGACTGTCGTGCGCTGTAGGGAGCGGCGAATTATCGATCCCCCGCGGCCCTCCAGGAACCCCGCAGGC

GTTGCGAGTACCCCGCGTCTTCGCGGGGTGTTATACGGCCACTTAAGTCCCGGCATCCCGTTCGCGGACC

CAGGCCCGGGGGATTGTCCGGATGTGCGGGCAGCCCGGACGGCGTGGGTTGCGGACTTTCGGCGGGGCGG

CCCAAATGGCCCTTTAAACGTGTGTATACGGACGCGCCGGGCCAGTCGGCCAACACAACCCACCGGAGGC

GGTAGCCGCGTTTGGCTGTGGGGTGGGTGGTTCCGCCTTGCGTGAGTGTCCTTTCGACCCCCCCCTCCCC

CGGGTCTTGCTAGGTCGCGATCTGTGGTCGCAATGAAGACCAATCCGCTACCCGCAACCCCTTCCGTGTG

GGGCGGGAGTACCGTGGAACTCCCCCCCACCACACGCGATACCGCGGGGCAGGGCCTGCTTCGGCGCGTC

-continued

CTGCGCCCCCCGATCTCTCGCCGCGACGGCCCAGTGCTCCCCAGGGGGTCGGGACCCCGGAGGGCGGCCA

GCACGCTGTGGTTGCTTGGCCTGGACGGCACAGACGCGCCCCCTGGGGCGCTGACCCCCAACGACGATAC

CGAACAGGCCCTGGACAAGATCCTGCGGGGCACCATGCGCGGGGGGGCGGCCCTGATCGGCTCCCCGCGC

CATCATCTAACCCGCCAAGTGATCCTGACGGATCTGTGCCAACCCAACGCGGATCGTGCCGGGACGCTGC

TTCTGGCGCTGCGGCACCCCGCCGACCTGCCTCACCTGGCCCACCAGCGCGCCCCGCCAGGCCGGCAGAC

CGAGCGGCTGGGCGAGGCCTGGGGCCAGCTGATGGAGGCGACCGCCCTGGGGTCGGGGCGAGCCGAGAGC

GGGTGCACGCGCGCGGGCCTCGTGTCGTTTAACTTCCTGGTGGCGGCGTGTGCCGCCTCGTACGACGCGC

GCGACGCCGCCGATGCGGTACGGGCCCACGTCACGGCCAACTACCGCGGGACGCGGGTGGGGGCGCGCCT

GGATCGTTTTTCCGAGTGTCTGCGCGCCATGGTTCACACGCACGTCTTCCCCCACGAGGTCATGCGGTTT

TTCGGGGGGCTGGTGTCGTGGGTCACCCAGGACGAGCTAGCGAGCGTCACCGCCGTGTGCGCCGGGCCCC

AGGAGGCGGCGCACACCGGCCACCCGGGCCGGCCCCGCTCGGCCGTGATCCTCCCGGTGTGTGCGTTCGT

GGACCTGGACGCCGAGCTGGGGCTGGGGGGCCCGGGCGCGGCGTTTCTGTACCTGGTATTCACTTACCGC

CAGCGCCGGGACCAGGAGCTGTGTTGTGTGTACGTGATCAAGAGCCAGCTCCCCCCGCGCGGGTTGGAGC

CGGCCCTGGAGCGGCTGTTTGGGCGCCTCCGGATCACCAACACGATTCACGGCACCGAGGACATGACGCC

CCCGGCCCCAAACCGAAACCCCGACTTCCCCCTCGCGGGCCTGGCCGCCAATCCCCAAACCCCGCGTTGC

TCTGCTGGCCAGGTCACGAACCCCCAGTTCGCCGACAGGCTGTACCGCTGGCAGCCGGACCTGCGGGGGC

GCCCCACCGCACGCACCTGTACGTACGCCGCCTTTGCAGAGCTCGGCATGATGCCCGAGGATAGTCCCCG

CTGCCTGCACCGCACCGAGCGCTTTGGGGCGGTCAGCGTCCCCGTTGTCATCCTGGAAGGCGTGGTGTGG

CGCCCCGGCGAGTGGCGGGCCTGCGCGTGAGCGTAGCAAACGCCCCGCCCACACAACGCTCCGCCCCCAA

CCCCTTCCCCGCTGTCACTCGTTGTTCGTTGACCCGGACGTCCGCCAAATAAAGCCACTGAAACCCGAAA

CGCGAGTGTTGTAACGTCCTTTGGGCGGGAGGAAGCCACAAAATGCAAATGGGATACATGGAAGGAACAC

ACCCCCGTGACTCAGGACATCGGCGTGTCCTTTTGGGTTTCACTGAAACTGGCCCGCGCCCCACCCCTGC

GCGATGTGGATAAAAAGCCAGCGCGGGTGGTTTAGGGTACCACAGGTGGGTGCTTTGGAAACTTGTCGGT

CGCCGTGCTCCTGTGAGCTTGCGTCCCTCCCCGGTTTCCTTTGCGCTCCCGCCTTCCGGACCTGCTCTCG

CCTATCTTCTTTGGCTCTCGGTGCGATTCGTCAGGCAGTGGCCTTGTCGAATCTCGACCCCACCACTCGC

CGGACCCGCCGACGTCCCCTCTCGAGCCCGCCGAAACCCGCCGCGTCTGTTGAAATGGCCAGCCGCCCCG

CCGCATCCTCTCCCGTCGAAGCGCGGGCCCCGGTTGGGGGACAGGAGGCCGGCGGCCCCAGCGCAGCCAC

CCAGGGGGAGGCCGCCGGGGCCCCTCTCGCCCGCGGCCACCACGTGTACTGCCAGCGAGTCAATGGCGTG

ATGGTGCTTTCCGACAAGACGCCCGGGTCCGCGTCCTACCGCATCAGCGATAGCAACTTTGTCCAATGTG

GTTCCAACTGCACCATGATCATAGACGGAGACGTGGTGCGCGGGCGCCCCCAGGACCCGGGGGCCGCGGC

ATCCCCCGCTCCCTTCGTTGCGGTGACAAACATCGGAGCCGGCAGCGACGGCGGGACCGCCGTCGTGGCA

TTCGGGGGAACCCCACGTCGCTCGGCGGGGACGTCTACCGGTACCCAGACGACCGACGTCCCCACCGAGG

CCCTTGGGGGCCCCCCTCCTCCTCCCCGCTTCACCCTGGGTGGCGGCTGTTGTTCCTGTCGCGACACACG

GCGCCGCTCTGCGGTATTCGGGGGGGAGGGGGATCCCGTCGGCCCCGCGGAGTTCGTCTCGGACGACCGG

TCGTCCGATTCCGACTCGGATGACTCGGAGGACACCGACTCGGAGACGCTGTCACACGCCTCCTCGGACG

TGTCCGGCGGGGCCACGTACGACGACGCCCTTGACTCCGATTCGTCATCGGATGACTCCCTGCAGATAGA

TGGCCCCGTGTGTCGCCCGTGGAGCAATGACACCGCGCCCCTGGATGTTTGCCCCGGGACCCCCGGCCCG

GGCGCCGACGCCGGTGGTCCCTCAGCGGTAGACCCACACGCACCGACGCCAGGGGCCGGCGCTGGTCTTG

CGGCCGATCCCGCCGTGGCCCGGGACGACGCGGAGGGGCTTTCGGACCCCCGGCCACGTCTGGGAACGGG

CACGGCCTACCCCGTCCCCCTGGAACTCACGCCCGAGAACGCGGAGGCCGTGGCGCGCTTTCTGGGAGAT

-continued

GCCGTGAACCGCGAACCCGCGCTCATGCTGGAGTACTTTTGCCGGTGCGCCCGCGAGGAAACCAAGCGTG

TCCCCCCCAGGACATTCTGCAGCCCCCCTCGCCTCACGGAGGACGACTTTGGGCTTCTCAACTACGCGCT

CGTGGAGATGCAGCGCCTGTGTCTGGACGTTCCTCCGGICCCGCCGAACGCATACATGCCCTATTATCTC

AGGGAGTATGTGACGCGGCTGGTCAACGGGTTCAAGCCGCTGGTGAGCCGGTCCGCTCGCCTTTACCGCA

TCCTGGGGGTTCTGGTGCACCTGCGGATCCGGACCCGGGAGGCCTCCTTTGAGGAGTGGCTGCGATCCAA

GGAAGTGGCCCTGGACTTTGGCCTGACGGAAAGGCTTCGCGAGCACGAAGCCCAGCTGGTGATCCTGGCC

CAGGCTCTGGACCATTACGACTGICTGATCCACAGCACACCGCACACGCTGGTCGAGCGGGGGCTGCAAT

CGGCCCTGAAGTATGAGGAGTTTTACCTAAAGCGCTTTGGCGGGCACTACATGGAGTCCGTCTTCCAGAT

GTACACCCGCATCGCCGGCTTTTTGGCCTGCCGGGCCACGCGCGGCATGCGCCACATCGCCCTGGGGCGA

GAGGGGTCGTGGTGGGAAATGTTCAAGTTCTTTTCCACCGCCTCTACGACCACCAGATCGTACCGTCGAC

CCCCGCCATGCTGAACCTGGGGACCCGCAACTACTACACCTCCAGCTGCTACCTGGTAAACCCCCAGGCC

ACCACAAACAAGGCGACCCTGCGGGCCATCACCAGCAACGTCAGCGCCATCCTCGCCCGCAACGGGGGCA

TCGGGCTATGCGTGCAGGCGTTTAACGACTCCGGCCCCGGGACCGCTAGCGTCATACCCGCCCTCAAGGT

CCTCGACTCGCTGGTGGCGGCGCACAACAAAGAGAGCGCGCGTCCAACCGGCGCGTGCGTGTACCTGGAG

CCGTGGCACACCGACGTGCGGGCCGTGCTCCGGATGAAGGGGGTCCTCGCCGGCGAAGAGGCCCAGCGCT

GCGACAATATCTTCAGCGCCCTCTGGATGCCAGACCTGTTTTTCAAGCGCCTGATTCGCCACCTGGACGG

CGAGAAGAACGTCACATGGACCCTGTTCGACCGGGACACCAGCATGTCGCTCGCCGACTTTCACGGGGAG

GAGTTCGAGAAGCTCTACCAGCACCTCGAGGTCATGGGGTTCGGCGAGCAGATACCCATCCAGGAGCTGG

CCTATGGCATTGTGCGCAGTGCGGCCACGACCGGGAGCCCCTTCGTCATGTTCAAAGACGCGGTGAACCG

CCACTACATCTACGACACCCAGGGGGCGGCCATCGCCGGCTCCAACCTCTGCACCGAGATCGTCCATCCG

GCCTCCAAGCGATCCAGTGGGGTCTGCAATCTGGGAAGCGTGAATCTGGCCCGATGCGTCTCCAGGCAGA

CGTTTGACTTTGGGCGGCTCCGCGACGCCGTGCAGGCGTGCGTGCTGATGGTGAACATCATGATCGACAG

CACGCTACAACCCACGCCCCAGTGCACCCGCGGCAACGACAACCTGCGGTCCATGGGAATCGGCATGCAG

GGCCTGCACACGGCCTGCCTGAAGCTGGGGCTGGATCTGGAGTCTGTCGAATTTCAGGACCTGAACAAAC

ACATCGCCGAGGTGATGCTGCTGTCGGCGATGAAGACCAGCAACGCGCTGTGCGTTCGCGGGGCCAGTCC

CTTCAACCACTTTAAGCGCAGCATGTATCGCGCCGGCCGCTTTCACTGGGAGCGCTTTCCGGACGCCCGG

CCGCGGTACGAGGGCGAGTGGGAGATGCTACGCCAGAGCATGATGAAACACGGCCTGCGCAACAGCCAGT

TTGTCGCGCTGATGCCCACCGCCGCCTCGGCGCAGATCTCGGACGTCAGCGAGGGCTTTGCCCCCCTGTT

CACCAACCTGTTCAGCAAGGTGACCCGGGACGGCGAGACGCTGCGCCCCAACACGCTCCTGCTAAAGGAA

CTGGAACGCACGTTTAGCGGGAAGCGCCTCCTGGAGGTGATGGACAGTCTCGACGCCAAGCAGTGGTCCG

TGGCGCAGGCGCTCCCGTGCCTGGAGCCCACCCACCCCCTCCGGCGATTCAAGACCGCGTTTGACTACGA

CCAGAAGTTGCTGATCGACCTGTGTGCGGACCGCGCCCCCTACGTCGACCATAGCCAATCCATGACCCTG

TATGTCACGGAGAAGGCGGACGGGACCCTCCCAGCCTCCACCCTGGTCCGCCTTCTGGTCCACGCATATA

AGCGCGGACTAAAAACAGGGATGTACTACTGCAAGGTTCGCAAGGCGACCAACAGCGGGGTCTTTGGCGG

CGACGACAACATTGTCTGCACGAGCTGCGCGCTGTGCCCGACAACCCCCTCCGCGCCAGGCCCGCCGCCA

CTGTCGTCGCCGTCCCACGCGCTCCCCCGCTGCCATGGATTCCGCGGCCCCAGCCCTCTCCCCCGCTCTG

ACGGCCCATACGGGCCAGAGCACGCCGGCGGACCTGGCGATCCAGATTCCAAAGTGCCCCGACCCCGAGA

GGTACTTCTACACCTCCCAGTGTCCCGACATTAACCACCTGCGCTCCCTCAGCATCCTTAACCGCTGGCT

GGAAACCGAGCTTGTTTTCGTGGGGGACGAGGAGGACGTCTCCAAGCTTTCCGAGGGCGAGCTCAGCTTT

TACCGCTTCCTCTTCGCTTTCCTGTCGGCCGCCGACGACCTGGTTACGGAAAACCTGGGCGGCCTCTCCG

GCCTGTTTGAGCAGAAGGACATTCTCCACTACTACGTGGAGCAGGAATGCATCGAAGTCGTACACTCGCG

-continued

CGTGTACAACATCATCCAGCTGGTGCTTTTTCACAACAACGACCAGGCGCGCCGCGAGTACGTGGCCGGC

ACCATCAACCACCCGGCCATCCGCGCCAAGGTGGACTGGCTGGAAGCGCGGGTGCGGGAATGCGCCTCCG

TTCCGGAAAAGTTCATCCTCATGATCCTCATCGAGGGCATCTTTTTTGCCGCCTCGTTTGCCGCCATCGC

CTACCTTCGCACCAACAACCTTCTGCGGGTCACCTGCCAGTCAAACGACCTCATCAGCCGGGACGAGGCC

GTGCACACGACGGCCTCGTGTTACATCTACAACAACTACCTCGGCGGGCACGCCAAGCCCCCGCCCGACC

GCGTGTACGGGCTGTTCCGCCAGGCGGTCGAGATCGAGATCGGATTTATCCGATCCCAGGCGCCGACGGA

CAGCCATATCCTGAGCCCGGCGGCGCTGGCGGCCATCGAAAACTACGTGCGATTCAGCGCGGATCGCCTG

TTGGGCCTTATCCACATGAAGCCACTGTTTTCCGCCCCACCCCCCGACGCCAGCTTTCCGCTGAGCCTCA

TGTCCACCGACAAACACACCAATTTTTTCGAGTGTCGCAGCACCTCCTACGCCGGGGCGGTCGTCAACGA

TCTGTGAGGGTCGCGGCGCGCTTCTACCCGTGTTTGCCCATAATAAACCTCTGAACCAAACTTTGGGTCT

CATTGTGATTCTTGTCAGGGACGCGGGGGTGGGAGAGGATAAAAGGCGGCGCAAAAAGCAGTAACCAGGT

CCGTCCAGATTCTGAGGGCATAGGATACCATAATTTTATTGGTGGGTCGTTTGTTCGGGGACAAGCGCGC

TCGTCTGACGTTTGGGCTACTCGTCCCAGAATTTGGCCAGGACGTCCTTGTAGAACGCGGGTGGGGGGGC

CTGGGTCCGCAGCTGCTCCAGAAACCTGTCGGCGATATCAGGGGCCGTGATATGCCGGGTCACAATAGAT

CGCGCCAGGTTTTCGTCGCGGATGTCCTGGTAGATAGGCAGGCGTTTCAGAAGAGTCCACGGCCCCCGCT

CCTTGGGGCCGATAAGCGATATGACGTACTTAATGTAGCGGTGTTCCACCAGCTCGGTGATGGTCATGGG

ATCGGGGAGCCAGTCCAGGGACTCTGGGGCGTCGTGGATGACGTGGCGTCGCCGGCTGGCCACATAACTG

CGGTGCTCTTCCAGCAGCTGCGCGTTCGGGACCTGGACGAGCTCGGGCGGGGTGAGTATCTCCGAGGAGG

ACGACCTGGGGCCGGGGTGGCCCCCGGTAACGTCCCGGGGATCCAGGGGGAGGTCCTCGTCGTCTTCGTA

TCCGCCGGCGATCTGTTGGGTTAGAATTTCGGTCCACGAGACGCGCATCTCGGTGCCGCCGGCGGCCGGC

GGCAAAGGGGGCCTGGTTTCCGTGGAGCGCGAGCTGGTGTGTTCCCGGCGGATGGCCCGCCGGGTCTGAG

AGCGACTCGGGGGGGTCCAGTGACATTCGCGCAGCACATCCTCCACGGAGGCGTAGGTGTTATTGGGATG

GAGGTCGGTGTGGCAGCGGACAAAGAGGGCCAGGAACTGGGGGTAGCTCATCTTAAAGTACTTTAGTATA

TCGCGACAGTTGATCGTGGGAATGTAGCAGGCGCTAATATCCAACACAATATCACAGCCCATCAACAGGA

GGTCAGTGTCTGTGGTGTACACGTACGCGACCGTGTTGGTGTGATAGAGGTTGGCGCAGGCATCGTCCGC

CTCCAGCTGACCCGAGTTAATGTAGGCGTACCCCAGGGCCCGGAGAACGCGAATACAGAACAGATGCGCC

AGACGCAGGGCCGGCTTCGAGGGCGCGGCGGACGGCAGCGCGGCTCCGGACCCGGCCGTCCCCCGGGTCC

CCGAGGCCAGAGAGGTGCCGCGCCGGCGCATGTTGGAAAAGGCAGAGCTGGGTCTGGAGTCGGTGATGGG

GGAAGGCGGTGGAGAGGCGTCCACGTCACTGGCCTCCTCGTCCGTCCGGCATTGGGCCGTCGTGCGGGCC

AGGATGGCCTTGGCTCCAAACACAACCGGCTCCATACAATTGACCCCGCGATCGGTAACGAAGATGGGGA

AAAGGGACTTTTGGGTAAACACCTTTAATAAGCGACAGAGGCAGTGTAGCGTAATGGCCTCGCGGTCGTA

ACTGGGGTATCGGCGCTGATATTTGACCACCAACGTGTACATGACGTTCCACAGGTCCACGGCGATGGGG

GTGAAGTACCCGGCCGGGGCCCCAAGGCCCTGGCGCTTGACCAGATGGTGTGTGTGGGCAAACTTCATCA

TCCCGAACAAACCCATGTCAGGTCGATTGTAACTGCGGATCGGCCTAACTAAGGCGTGGTTGGTGCGACG

GTCCGGGACACCCGAGTCTGTCTCTCTGTGTATGGTGACCCAGACAACAACACCGACACAAGAGGACAAT

AATCCGTTAGGGGACGCTCTTTATAATTTCGATGGCCCAACTCCACGCGGATTGGTGCAGCACCCTGCAT

GCGCCGGTGTGGGCCAAACTTCCCCCCGCTCATTGCCTCTTCCAAAAGGGTGTGGCCTAACGAGCTGGGG

GCGTATTTAATCAGGCTAGCGCGGCGGGCCTGCCGTAGTTTCTGGCTCGGTGAGCGACGGTCCGGTTGCT

TGGGTCCCCTGGCTGCCAGCAAAACCCCACCCTCGCAGCGGCATACGCCCCCTCCGCGTCCCGCACCCGA

GACCCCGGCCCGGCTGCCCTCACCACCGAAGCCCACCTCGTCACTGTGGGGTGTTCCCAGCCCGCATTGG

-continued

GATGACGGATTCCCCTGGCGGTGTGGCCCCCGCCTCCCCCGTGGAGGACGCGTCGGACGCGTCCCTCGGG

CAGCCGGAGGAGGGGGCGCCCTGCCAGGTGGTCCTGCAGGGCGCCGAACTTAATGGAATCCTACAGGCGT

TTGCCCCGCTGCGCACGAGCCTTCTGGACTCGCTTCTGGTTATGGGCGACCGGGGCATCCTTATCCATAA

CACGATCTTTGGGGAGCAGGTGTTCCTGCCCCTGGAACACTCGCAATTCAGTCGGTATCGCTGGCGCGGA

CCCACGGCGGCGTTCCTGTCTCTCGTGGACCAGAAGCGCTCCCTCCTGAGCGTGTTTCGCGCCAACCAGT

ACCCGGACCTACGTCGGGTGGAGTTGGCGATCACGGGCCAGGCCCCGTTTCGCACGCTGGTTCAGCGCAT

ATGGACGACGACGTCCGACGGCGAGGCCGTTGAGCTAGCCAGCGAGACGCTGATGAAGCGCGAACTGACG

AGCTTTGTGGTGCTGGTTCCCCAGGGAACCCCCGACGTTCAGTTGCGCCTGACGAGGCCGCAGCTCACCA

AGGTCCTTAACGCGACCGGGGCCGATAGTGCCACGCCCACCACGTTCGAGCTCGGGGTTAACGGCAAATT

TTCCGTGTTCACCACGAGTACCTGCGTCACATTTGCTGCCCGCGAGGAGGGCGTGTCGTCCAGCACCAGC

ACCCAGGTCCAGATCCTGTCCAACGCGCTCACCAAGGCGGGCCAGGCGGCCGCCAACGCCAAGACGGTGT

ACGGGGAAAATACCCATCGCACCTTCTCTGTGGTCGTCGACGATTGCAGCATGCGGGCGGTGCTCCGGCG

ACTGCAGGTCGCCGGGGGCACCCTCAAGTTCTTCCTCACGACCCCCGTCCCCAGTCTGTGCGTCACCGCC

ACCGGTCCCAACGCGGTATCGGCGGTATTTCTCCTGAAACCCCAGAAGATTTGCCTGGACTGGCTGGGTC

ATAGCCAGGGGTCTCCTTCAGCCGGGAGCTCGGCCTCCCGGGCCTCTGGGAGCGAGCCAACAGACAGCCA

GGACTCCGCGTCGGACGCGGTCAGCCACGGCGATCCGGAAGACCTCGATGGCGCTGCCCGGGCGGGAGAG

GCGGGGGCCTCGCACGCCTGTCCGATGCCGTCGTCGACCACGCGGGTCACTCCCACGACCAAGCGGGGGC

GCTCGGGGGGCGAGGATGCGCGCGCGGACACGGCCCTAAAGAAACCTAAGACGGGGTCGCCCACCGCACC

CCCGCCCACAGATCCAGTCCCCCTGGACACGGAGGACGACTCCGATGCGGCGGACGGGACGGCGGCCCGT

CCCGCCGCTCCAGACGCCCGGAGCGGAAGCCGTTACGCGTGTTACTTTCGCGACCTCCCGACCGGAGAAG

CAAGCCCCGGCGCCTTCTCCGCCTTCCGGGGGGGCCCCCAAACCCCGTATGGTTTTGGATTCCCCTGACG

GGGCGGGGCCTTGGCGGCCGCCCAACTCTCGCACCATCCCGGGTTAATGTAAATAAACTTGGTATTGCCC

AACACTCTCCCGCGTGTCGCGTGTGGTTCATGTGTGTGCCTGGCGTCCCCCACCCTCGGGTTCGTGTATT

TCCTTTCCCTGTCCTTATAAAAGCCGTATGTGGGGCGCTGACGGAACCACCCCGCGTGCCATCACGGCCA

AGGCGCGGGATGCTCCGCAACGACAGCCACCGGGCCGCGTCCCCGGAGGACGGCCAGGGACGGGTCGACG

ACGGACGGCCACACCTCGCGTGCGTGGGGGCCCTGGCGCGGGGGTTCATGCATATCTGGCTTCAGGCCGC

CACGCTGGGTTTTGCGGGATCGGTCGTTATGTCGCGCGGGCCGTACGCGAATGCCGCGTCTGGGGCGTTC

GCCGTCGGGTGCGCCGTGCTGGGCTTTATGCGCGCACCCCCTCCCCTCGCGCGGCCCACCGCGCGGATAT

ACGCCTGGCTCAAACTGGCGGCCGGTGGAGCGGCCCTTGTTCTGTGGAGTCTCGGGGAGCCCGGAACGCA

GCCGGGGGCCCCGGGCCCGGCCACCCAGTGCCTGGCGCTGGGCGCCGCCTATGCGGCGCTCCTGGTGCTC

GCCGATGACGTCTATCCGCTCTTTCTCCTCGCCCCGGGGCCCCTGTTCGTCGGCACCCTGGGGATGGTCG

TCGGCGGGCTGACGATCGGAGGCAGCGCGCGCTACTGGTGGATCGGTGGGCCCGCCGCGGCCGCCTTGGC

CGCGGCGGTGTTGGCGGGCCCGGGGGCGACCACCGCCAGGGACTGCTTCTCCAGGGCGTGCCCCGACCAC

CGCCGCGTCTGCGTCATCGTCGCAGGCGAGTCTGTTTCCCGCCGCCCCCCGGAGGACCCAGAGCGACCCG

GGGACCCCGGGCCACCGTCCCCCCCGACACCCCAACGATCCCAGGGGCCGCCGGCCGATGAGGTCGCACC

GGCCGGGGTAGCGCGGCCCGAAAACGTCTGGGTGCCCGTGGTCACCTTTCTGGGGGCGGGCGCGCTCGCC

GTCAAGACGGTGCGAGAACATGCCCGGGAAACGCCGGGCCCGGGCCTGCCGCTGTGGCCCCAGGTGTTTC

TCGGAGGCCATGTGGCGGTGGCCCTGACGGAGCTGTGTCAGGCGCTTATGCCCTGGGACCTTACGGACCC

GCTGCTGTTTGTTCACGCCGGACTGCAGGTCATCAACCTCGGGTTGGTGTTTCGGTTTTCCGAGGTTGTC

GTGTATGCGGCGCTAGGGGGTGCCGTGTGGATTTCGTTGGCGCAGGTGCTGGGGCTCCGGCGTCGCCTGC

ACAGGAAGGACCCCGGGGACGGGGCCCGGTTGGCGGCGACGCTTCGGGGCCTCTTCTTCTCCGTGTACGC

-continued

GCTGGGGTTTGGGGTGGGGGCGCTGCTGTGCCCTCCGGGGTCAACGGGCGGGTGGTCGGGCGATTGATAT

ATTTTTCAATAAAAGGCATTAGTCCCGAAGACCGCCGGTGTGTGATGATTTCGCCATAACACCCAAACCC

CGGATGGGGCCCGGGTATAAATTCCGGAAGGGGACACGGGCTACCCTCACTACCGAGGGCGCTTGGTCGG

GAGGCCGCATCGAACGCACACCCCCATCCGGTGGTCCGTGTGGAGGTCGTTTTTCAGTGCCCGGTCTCGC

TTTGCCGGGAACGCTAGCCGATCCCTCGCGAGGGGGAGGCGTCGGGCATGGCCCCGGGGCGGGTGGGCCT

TGCCGTGGTCCTGTGGAGCCTGTTGTGGCTCGGGGCGGGGGTGGCCGGGGGCTCGGAAACTGCCTCCACC

GGGCCCACGATCACCGCGGGAGCGGTGACGAACGCGAGCGAGGCCCCCACATCGGGGTCCCCCGGGTCAG

CCGCCAGCCCGGAAGTCACCCCCACATCGACCCCAACCCCCAACAATGTCACACAAAACAAAACCACCCC

CACCGAGCCGGCCAGCCCCCCAACAACCCCCAAGCCCACCTCCACGCCCAAAAGCCCCCCCACGTCCCCC

CGCCCCAACCCAAGAACAACACCCCCCCCGCCAAGTCGGGCCGCCCCACTAAACCCCCCGGGCCCGTGTG

GTGCGACCGCCGCGACCCATTGGCCCGGTACGGCTCGCGGGTGCAGATCCGATGCCGGTTTCGGAATTCC

ACCCGCATGGAGTTCCGCCTCCAGATATGGCGTTACTCCATGGGTCCGTCCCCCCCAATCGCTCCGGCTC

CCGACCTAGAGGAGGTCCTGACGAACATCACCGCCCCACCCGGGGGACTCCTGGTGTACGACAGCGCCCC

CAACCTGACGGACCCCCACGTGCTCTGGGCGGAGGGGGCCGGCCCGGGCGCCGACCCTCCGTTGTATTCT

GTCACCGGGCCGCTGCCGACCCAGCGGCTGATTATCGGCGAGGTGACGCCCGCGACCCAGGGAATGTATT

ACTTGGCCTGGGGCCGGATGGACAGCCCGCACGAGTACGGGACGTGGGTGCGCGTCCGCATGTTCCGCCC

CCCGTCTCTGACCCTCCAGCCCCACGCGGTGATGGAGGGTCAGCCGTTCAAGGCGACGTGCACGGCCGCC

GCCTACTACCCGCGTAACCCCGTGGAGTTTGTCTGGTTCGAGGACGACCGCCAGGTGTTTAACCCGGGCC

AGATCGACACGCAGACGCACGAGCACCCCGACGGGTTCACCACAGTCTCTACCGTGACCTCCGAGGCTGT

CGGCGGCCAGGTCCCCCCGCGGACCTTCACCTGCCAGATGACGTGGCACCGCGACTCCGTGATGTTCTCG

CGACGCAATGCCACCGGGCTGGCCCTGGTGCTGCCGCGGCCAACCATCACCATGGAATTTGGGGICCGGC

ATGTGGTCTGCACGGCCGGCTGCGTCCCCGAGGGCGTGACGTTTGCCTGGTTCCTGGGGGACGACCCCTC

ACCGGCGGCTAAGTCGGCCGTTACGGCCCAGGAGTCGTGCGACCACCCCGGGCTGGCTACGGTCCGGTCC

ACCCTGCCCATTTCGTACGACTACAGCGAGTACATCTGTCGGTTGACCGGATATCCGGCCGGGATTCCCG

TTCTAGAGCACCACGGCAGTCACCAGCCCCCACCCAGGGACCCCACCGAGCGGCAGGTGATCGAGGCGAT

CGAGTGGGTGGGGATTGGAATCGGGGTTCTCGCGGCGGGGGTCCTGGTCGTAACGGCAATCGTGTACGTC

GTCCGCACATCACAGTCGCGGCAGCGTCATCGGCGGTAACGCGAGACCCCCCCGTTACCTTTTTAATATC

TATATAGTTTGGTCCCCCTCTATCCCGCCCACCGCTGGGCGCTATAAAGCCGCCACCCTCTCTTCCCTCA

GGICATCCTTGGTCGATCCCGAACGACACACGGCGTGGAGCAAAACGCCTCCCCCTGAGCCGCTTTCCTA

CCAACACAACGGCATGCCTCTGCGGGCATCGGAACACGCCTACCGGCCCCTGGGCCCCGGGACACCCCCC

ATGCGGGCTCGGCTCCCCGCCGCGGCCTGGGTTGGCGTCGGGACCATCATCGGGGGAGTTGTGATCATTG

CCGCGTTGGTCCTCGTGCCCTCGCGGGCCTCGTGGGCACTTTCCCCATGCGACAGCGGATGGCACGAGTT

CAACCTCGGGTGCATATCCTGGGATCCGACCCCCATGGAGCACGAGCAGGCGGTCGGCGGCTGTAGCGCC

CCGGCGACCCTGATCCCCCGCGCGGCTGCCAAACAGCTGGCCGCCGTCGCACGCGTCCAGTCGGCAAGAT

CCTCGGGCTACTGGTGGGTGAGCGGAGACGGCATTCGGGCCTGCCTGCGGCTCGTCGACGGCGTCGGCGG

TATTGACCAGTTTTGCGAGGAGCCCGCCCTCGCATATGCTACTATCCCCGCAGTCCCGGGGGCTTTGTTC

AGTTTGTAACTTCGACCCGCAACGCGCTGGGGCTGCCGTGAGGCGCGTGTACTGCGGTCTGTCTCGTCTC

CTCTTCTCCCCTTCCCTCCCCCTCCGCATCCCAGGATCACACCGGCCAACGAGGGTTGGGGGGGTCCGGC

ACGGACCCAAAATAATAAACACACAATCACGTGCGATAAAAAGAACACGCGGTCCCCTGTGGTGTTTTTG

GTTATTTTTATTAAATCTCGTCGACAAACAGGGGGAAAGGGGCGTGGTCTAGCGACGGCAGCACGGGCGG

-continued

AGGCGTTCACCGGCTCCGGCGTCCTTCGCGTTTAAGCTTGGTCAGGAGGGCGCTCAGGGCGGCGACGTTG

GTCGGGCCGTCGTTGGTCAGGGCGTTGGCTCGATGGCGGGCGAGGACGGGCGAGGGGCTCAACGGCGGGG

GCGGGGGCCGGGGCGGCCCGGGGGGGGAAATAGGGCGGATCCCCCCCCGTCGTACAGGGGGTTTTCCGCC

TCAATGTACGGGGAGGCCGGCGCTGCATTCGCCGTGTTCACGCAGACGGTTTCGTAGACCCGCATCCATG

GTATTTCCTCGTAGACACGCCCCCCGTCCTCGCTCACGGTCTCGTATATTGACTCGTCGTCCTCGTAGGG

GGCGTGCCGTTCGCGGGCCGAGGCGGCGTGGGTGGCTTTGCGGCGGGCGTCGTCGTCGTCGTCGTCGGCC

GTCAGATACGTGGCTTCCATCTGGTCGGGTTCTCCCTCCGGGGCGGGTCCCCACACCCGTGGCCGATCGA

GGCTCCCCAGAGACGCGCGCCGGACAAGAAGGGGGCACGTCGCCGCCGGCGGTCGCCTGTCGGGTCCCGC

GACGTTACGGGCCGGGAGGCGCGGGGGCACCTCCCCCATGTGCGTGTAATACGTGGCCGGCTGTGCGGCC

GCAGCGGGGGGCTCGGCGACCGGGTCGTCCGCATCCGGAAGCGGGGGCCCCGCGCCGTCCGCACGGCGCC

TCCGGAACCGCCGGGTGGACGGCGCGGGGGTCGAGTGTAGGCGAGGTCGGGGGAGGGGCGGGGGCTCGTT

GTCGCGCCGCGCCCGCTGAATCTTTTCCCGACAGGTCCCACCCCCCGCGCGATGCCCCCCCGGGCCGCGG

GCCATGTCGTCCGGGGGAGGCCCCGCGGACCACGTCGTCCGGCGAGACGCCACGAGCCGCAGGATGGACT

CGTAGTGGAGCGACGGCGCCCCGCTGCGGAGCAGATCCGCGGCCAGGGCGGCCCCGAACCAAGCCTTGAT

GCTCAACTCCATCCGGGCCCAGCTGGGGGCGGTCATCGTGGGGAACAGGGGGGCGGTGGTCCGACAGAAA

CGCTCCTGGCTGTCCACCGCGGCCCGCAGATACTCGTTGTTCAGGCTGTCGGTGGCCCAGACGCCGTACC

CGGTGAGGGTCGCGTTGATGATATACTGGGCGTGGTGATGGACGATCGACAGAACCTCCACCGTGGATAC

CACGGTATCCACGGTCCCGTACGTACCGCCGCTCCGCTTGCCGGTCTGCCACAGGTTGGCTAGGCACGTC

AGGTGGCCCAGGACGTCGCTGACCGCCGCCCTGAGCGCCATGCACTGCATGGAGCCGGTCGTGCCGCTGG

GACCCCGGTCCAGATGGCGCGCGAACGTTTCCGCGGGCGCCTCCGGGCTGCCGCCGAGCGGGAGGAACCG

GCGATTGGAGGGACTCAGCCGGTGACATACGTGCTTGTCCGTCGTCCACAGCATCCAGGACGCCCACCGG

TACAGCACGGAGACGTAGGCCAGGAGCTCGTTGAGCCGCAGTGCGGTGTCGGTGCTGGGGCGGCTTGGGT

CCGCCGGGCGCATAAAGAACATGTACTGCTGAATCCGATGGAGGGCGTCGCGCAGGCCGGCCACGGTGGC

GGCGTACTTGGCCGCCGCGGCCCCGCTCTTGAACGGGGTGCGCGCCAGCAGCTTTGGCGCCAGGGTGGGC

CGCAGCAGCACGTGAAGGCTGGGGTCGCAGTCGCCCACGGGGTCCTCGGGGACGTCCAGGCCGCTGGGCA

CCACCGTCTGCAGGTACTTCCAGTACTGCGTGAGGATGGCGCGGCTCAACTGGCCGCCGGGCAGCTCCAC

CTCGCCCAGCGCCTGGGTGGCGGCCGAAGCGTAGTGCCGGATGTACTCGTAGTGCGGGTCGCTGGCGAGC

CCGTCCACGATCAAACTCTCGGGAACCGTGTTGTGTTGCCGCGCGGCCAACCGGACGCTGCGATCGGTGC

AGGTCAGAAACGCCGGCTGCGCGTCGTCGGAGCGCTGCCGCAAGGCGCCCACGGCCGCGCTAAGGAGCCC

CTCCGGGGTGGGGAGCAGACACCCGCCGAAGATGCGCCGCTCGGGAACGCCCGCGTTGTCGCCGCGGATC

AGGTTGGCAGGCGTCAGGCACCGCGCCAGCCGCAGGGAGCTCGCGCCGCGCGTCCGGCGCTGCATGGTGA

CGCCCGTTCGGTCGGGACCCGCCGGTCGGAGTTATGCCGCGTCCAGGGCCATCGGGGCGCTTTTTATCGG

GAGGAGCTTATGGGCGTGGCGGGCCTCCCAGCCCGGTCGCGCGCCTCCCCGACACGTGCGCCCGCAGGGC

GGCGGCCCCCTCGTCTCCCATCAGCAGTTTCCTAAACTGGGACATGATGCCACCCGCGGACCCGCGGGCC

AACACGGACCCGCCGCTTACGGGGGCGGGGGGGAAGGGCTCCAGGTCCTTGAGCAGAAAGGCGGGGTCTG

CCGTCCCGGACACGGGGGCCCGGGGCGCGGAGGAGGCGGGGCGCAGATCCACGTGCTCCGCGGCCGCGCG

GACGTCCGCCCAGAACTTGGCGGGGGTGGTGCGCGCGTACAGGGGCTGGGTCGCTCGGAGGACACACGCG

TAGCGCAGGGGGGTGTACGTGCCCACCTCGGGGGCCGTGAATCCCCCGTCAAACGCGGCCAGTGTCACGC

ACGCCACCACGGTGTCGGCAAAACCCAGCAGCCGCTGCAGGACGAGCCCGGCGGCCAGAATGGCGCGCGT

GGTCGCAGCGTCGTCCCGGCGCCGGTGCGCGTCCCCGCACGCCCGGGCGTACTTTAAGGTCACTGTCGCC

AGGGCCGTGTGCAGCGCGTACACCGCAGCGCCCAGCACGGCGTTGAGCCCGCTGTTGGCGAGCAGCCGGC

-continued

GCGCTGCGGTGTCGCCCAGCGCCTCGTGCTCGGCCCCCACGACCGCGGGGCTTCCCAGGGGCAGGGCGCG

AAACAGCTCCTCCCGCGCCACGTCCGCAAAGGCGGGGTGGTGCACGTGCGGGTGCAGGCGCGCCCCCACG

ACCACCGAGAGCCACTGGACCGTCTGCTCCGCCATCACCGCCAACACATCCAGCACGCGCCCCAGGAAGG

CGGCCTCCCGCGTCAAAACGCACCGGACGGCGTCGGGATTGAAGCGGGCGAGCAGGGCCCCGGTGGCCAG

GTACGTCATGCGGCCGGCATAGCGGGCGGCCACGCGACAGTCGCGGTCCAGCAGCGCGCGCACCCCGGGC

CAGTACAGCAGGGACCCCAGCGAGCTGCGAAACACCGCGGCGTCGGGGCCGGATTGGGGGGACACTAACC

CCCCCGCGCTCAGTAACGGCACGGCCGCGGCCCCGACGGGACGCAACGCCGTGAGGCTCGCGAACTGCCG

CCTCAGCTCGGCAGCCCTGTCGTCCAGGTCCGACCCGCGCGCCTCTGCGTGAAGGCGCGTCCCGCATACC

CACCCGTTGATGGCCAGCCGCACGACGGCATCCGCCAAAAAGCTCATCGCCTGGGCGGGGCTGGTTTTTG

TTCGACGATCCGTCAGGTCAAGAATCCCATCGCCCGTGATATACCAGGCCAACGCCTCGCCCTGCTGCAG

GGTTTGGCGGAAAAACACCGCGGGGTTGTCGGGGGAGGCGAAGTGCATGACCCCCACGCGCGATAACCCG

AACGCGCTATCCGGACACGGGTAAAACCCGGCCGGATGCCCCAGGGCTAGGGCGGAGCGCACGGACTCGT

CCCACACGGCAACCTGAGGGGCCAGTCGATCCAACGGGAATGCCGCCCGGAGCTCCGGGCCCGGCACGCG

TCCCTCCAGAACCTCCACCTTGGGCGGGGAACGGGCCCCGCCGCCGTCCTCCGGCCCGACGTCTTCCGGG

TAGTCGTCCTCCTCGTACTGCAGTTCCTCTAGGAACAGCGGCGACGGCGCCACCCGCGAACCGCCGACCC

GCCCCAAAATAGCCCGCGCGTCGACGGGACCCAGGTATCCCCCCTGCCGGGCCTGCGGAGGACCGCGGGG

AACCTCATCATCATCGTCCAGGCGACCGCGCACCGACTGGCTACGGGCCGCATCGGGCCCGGGGCGCTGC

CGGGACGCTCGGCGATGGGATGAGGGCGGGGCTTCCGACGCGCGCCGTCGTCGGGCTCGCGGGCCTTCCC

GTCGACGGCGCACGGGCGGCTCGTCGCCCGCCATCTCCTCCAGAGCCTCTAGCTCGCTGTCGTCATCCCC

GCGGAACACCGCACGCAGGTACCCCATGAACCCCACCCCATCGCCCGCTGGCTCGTCCGCCACGGGCGAG

GCGCGGGGGCGGGTGGATGCGCGCCTCCTGCGCCCCGCGGGTTCGCGAGCCGACATGGTGGCGATAGACG

CGGGTTATCGGATGTCCGCTACCCCCCAAAAAAGAAAAAGACCCCACAGCGCGGATGGAGGTCGGGGTAG

GTGCCGCCGGACCCCCTCGCGATGGGAATGGACGGGAGCGACGGGGCCGGCGCAAAAAACGCAGTATCTC

CCGCGAAGGCTACCCGCCGCCCCAGCCCCCGGCCAAATGCGGAAACGGTCCCGCGCTCTCGCCTTTATAC

GCGGGCCGCCCTGCGACACAATCACCCGTCCGTGGTTTCGAATCTACACGACAGGCCCGCAGACGCGGCT

AACACACACGCCGGCAACCCAGACCCCAGTGGGTTGGTTGCGCGGTCCCGTCTCCTGGCTAGTTCTTTCC

CCCACCACCAAATAATCAGACGACAACCGCAGGTTTTTGTAATGTATGTGCTCGTGTTTATTGTGGATAC

GAACCGGGGACGGGAGGGGAAAACCCAGACGGGGGATGCGGGTCCGGTCGCGCCCCCTACCCACCGTACT

CGTCAATTCCAAGGGCATCGGTAAACATCTGCTCAAACTCGAAGTCGGCCATATCCAGAGCGCCGTAGGG

GGCGGAGTCGTGGGGGGTAAATCCCGGACCCGGGGAATCCCCGTCCCCCAACATGTCCAGATCGAAATCG

TCTAGCGCGTCGGCATGCGCCATCGCCACGTCCTCGCCGTCTAAGTGGAGCTCGTCCCCCAGGCTGACAT

CGGTCGGGGGGGCCGTCGACAGTCTGCGCGTGTGTCCCGCGGGGAGAAAGGACAGGCGCGGAGCCGCCAG

CCCCGCCTCTTCGGGGGCGTCGTCGTCCGGGAGATCGAGCAGGCCCTCGATGGTAGACCCGTAATTGTTT

TTCGTACGCGCGCGGCTGTACGCGTGTTCCCGCATGACCGCCTCGGAGGGCGAGGTCGTGAAGCTGGAAT

ACGAGTCCAACTTCGCCCGAATCAACACCATAAAGTACCCAGAGGCGCGGGCCTGGTTGCCATGCAGGGT

GGGAGGGGTCGTCAACGGCGCCCCTGGCTCCTCCGTAGCCGCGCTGCGCACCAGCGGGAGGTTAAGGTGC

TCGCGAATGTGGTTTAGCTCCCGCAGCCGGCGGGCCTCGATTGGCACTCCCCGGACGGTGAGCGCTCCGT

TGACGAACATGAAGGGCTGGAACAGACCCGCCAACTGACGCCAGCTCTCCAGGTCGCAACAGAGGCAGTC

AAACAGGTCGGGCCGCATCATCTGCTCGGCGTACGCGGCCCATAGGATCTCGCGGGTCAAAAATAGATAC

AAATGCAAAAACAGAACACGCGCCAGACGAGCGGTCTCTCGGTAGTACCTGTCCGCGATCGTGGCGCGCA

-continued

GCATTTCTCCCAGGTCGCGATCGCGTCCGCGCATGTGCGCCTGGCGGTGCAGCTGCCGGACGCTGGCGCG

CAGGTACCGGTACAGGGCCGAGCAGAAGTTGGCCAACACGGTTCGATAGCTCTCCTCCCGCGCCCGTAGC

TCGGCGTGGAAGAAACGAGAGAGCGCTTCGTAGTAGAGCCCGAGGCCGTCGCGGGTGGCCGGAAGCGTCG

GGAAGGCCACGTCGCCGTGGGCGCGAATGTCGATTTGGGCGCGTTCGGGGACGTACGCGTCCCCCCATTC

CACCACATCGCTGGGCAGCGTTGATAGGAATTTACACTCCCGGTACAGGTCGGCGTTGGTCGGTAACGCC

GAAAACAAATCCTCGTTCCAGGTATCGAGCATGGTACATAGCGCGGGGCCCGCGCTAAAGCCCAAGTCGT

CGAGGAGACGGTTAAAGAGGGCGGCGGGGGGGACGGGCATGGGCGGGGAGGGCATGAGCTGGGCCTGGCT

CAGGCGCCCCGTTGCGTACAGCGGAGGGGCCGCCGGGGTGTTTTTGGGACCCCCGGCCGGGCGGGGGGGT

GGTGGCGAAGCGCCGTCCGCGTCCATGTCGGCAAACAGCTCGTCGACCAAGAGGTCCATTGGGTGGGGTT

GATACGGGAAAGACGATATCGGGCTTTTGATGCGATCGTCCCCGCCCGCCCAGAGAGTGTGGGACGCCCG

ACGGCGCGGGAAGAGAAAAACCCCCAAACGCGTTAGAGGACCGGACGGACCTTATGGGGGGAAGTGGGCA

GCGGGAACCCCGTCCGTTCCCGAGGAATGACAGCCCGTGGTCGCCACCCCGCATTTAAGCAACCCGCACG

GGCCGCCCCGTACCTCGTGACTTCCCCCCACATTGGCTCCTGTCACGTGAAGGCAAACCGAGGGCGGCTG

TCCAACCCACCCCCCGCCACCCAGTCACGGTCCCCGTCGGATTGGGAAACAAAGGCACGCAACGCCAACA

CCGAATGAACCCCTGTTGGTGCTTTATTGTCTGGGTACGGAAGTTTTTCACTCGACGGGCCGTCTGGGGC

GAGAAGCGGAGCGGGCTGGGGCTCGAGGTCGCTCGGTGGGGCGCGACGCCGCAGAACGCCCTCGAGTCGC

CGTGGCCGCGTCGACGTCCTGCACCACGTCTGGATTCACCAACTCGTTGGCGCGCTGAATCAGGTTTTTG

CCCTCGCAGACCGTCACGCGGATGGTGGTGATGCCAAGGAGTTCGTTGAGGTCTTCGTCTGTGCGCGGAC

GCGACATGTCCCAGAGCTGGACCGCCGCCATCCGGGCATGCATGGCCGCCAGGCGCCCAACCGCGGCGCA

GAAGACGCGCTTGTTAAAGCCGGCCACCCGGGGGGTCCATGGCGCGTCGGGGTTTGGGGGGGCGGTGCTA

AAGTGCAGCTTTCTGGCCAGCCCCTGCGCGGGTGTCTTGGATCGGGTTGGCGCCGTCGACGCGGGGGCGT

CTGGGAGTGCGGCGGATTCTGGCTGGGCCGATTTCCTGCCGCGGGTGGTCTCCGCCGCCGGGGCCGCGGG

GGCCTTAGTCGCCACCCGCTGGGTTCGGGGGGCCCGGGGGGCGGTGGTGGGTGTGCGTCCGGCCCCTCCG

GACCCAGCGGGCGGCGGAGGCGCCCGCGCAGGCCCCGGGGCGGACAAAACCGCCCCGGAAACGGGACGCC

GCGTCCGGGGGACCTCCGGGTGTTCGTCGTCTTCGGATGACGAGCCCCCGTAGAGGGCATAATCCGACTC

GTCGTACTGGACGAAACGGACCTCGCCCCTTGGGCGCGCGCGTGTCTGTAGGGCGCCACGGCGGGAGGTG

TCAGGCGGACTATCGGGACTCGCCATACATGAAGACGGGGTGTAGTACAGATCCTCGTACTCATCGCGCG

GAACCTCCCGCGGACCCGACTTCACGGAGCGGCGAGAGGTCATGGTTCCACGAACACGCTAGGGTCGGAT

GCGCGGACAATTAGGCCTGGGTTCGGACGGCGGGGGTGGTGCAGGTGTGGAGAGGTCGAGCGATAGGGGC

GGCCCGGGAGAGAAGAGAGGGTCCGCAAAACCCACTGGGGATGCGTGAGIGGCCCTCTGTGGGCGGTGGG

GGAGAGTCTTATAGGAAGTGCATATAACCACAACCCATGGGTCTAACCAATCCCCAGGGGCCAAGAAACA

GACACGCCCCAAACGGTCTCGGTTTCCGCGAGGAAGGGGAAGTCCTGGGACACCCTCCACCCCCACCCCT

CACCCCACACAGGGCGGGTTCAGGCGTGCCCGGCAGCCAGTAGCCTCTGGCAGATCTGACAGACGTGTGC

GATAATACACACGCCCATCGAGGCCATGCCTACATAAAAGGGCACCAGGGCCCCCGGGGCAGACATTTGG

CCAGCGTTTTGGGTCTCGCACCGCGCGCCCCCGATCCCATCGCGCCCGCCCTCCTCGCCGGGCGGCTCCC

CGTGCGGGCCCGCGTCTCCCGCCGCTAAGGCGACGAGCAAGACAAACAACAGGCCCGCCCGACAGACCCT

TCTGGGGGGGCCCATCGTCCCTAACAGGAAGATGAGTCAGTGGGGATCCGGGGCGATCCTTGTCCAGCCG

GACAGCTTGGGTCGGGGGTACGATGGCGACTGGCACACGGCCGTCGCTACTCGCGGGGGCGGAGTCGTGC

AACTGAACCTGGTCAACAGGCGCGCGGTGGCTTTTATGCCGAAGGTCAGCGGGGACTCCGGATGGGCCGT

CGGGCGCGTCTCTCTGGACCTGCGAATGGCTATGCCGGCTGACTTTTGTGCGATTATTCACGCCCCCGCG

CTATCCAGCCCAGGGCACCACGTAATACTGGGTCTTATCGACTCGGGGTACCGCGGAACCGTTATGGCCG

-continued

TGGICGTAGCGCCTAAAAGGACGCGGGAATTTGCCCCCGGGACCCTGCGGGTCGACGTGACGTTCCTGGA

CATCCTGGCGACCCCCCCGGCCCTCACCGAGCCGATTTCCCTGCGGCAGTTCCCGCAACTGGCGCCCCCC

CCTCCAACCGGGGCCGGGATACGCGCAGATCCTTGGTTGGAGGGGGCGCTCGGGGACCCAAGCGTGACTC

CTGCCCTACCGGCGCGACGCCGAGGGCGGTCCCTCGTCTATGCCGGCGAGCTGACGCCGGTTCAGACGGA

ACACGGGGACGGCGTACGAGAAGCCATCGCCTTCCTTCCAAAACGCGAGGAGGATGCCGGTTTCGACATT

GTCGTCCGTCGCCCGGTCACCGTCCCGGCAAACGGCACCACGGTCGTGCAGCCATCCCTCCGCATGCTCC

ACGCGGACGCCGGGCCCGCGGCCTGCTATGTGCTGGGGCGGTCGTCGCTCAACGCCCGCGGCCTCCTGGT

CGTTCCTACGCGCTGGCTCCCCGGGCACGTATGTGCGTTTGTTGTTTACAACCTTACGGGGGTTCCTGTG

ACCCTCGAGGCCGGCGCCAAGGTCGCCCAGCTCCTGGTTGCGGGGGCGGACGCTCTTCCTTGGATCCCCC

CGGACAACTTTCACGGGACCAAAGCGCTTCGAAACTACCCCAGGGGTGTTCCGGACTCAACCGCCGAACC

CAGGAACCCGCCGCTCCTGGTGTTTACGAACGAGTTTGACGCGGAGGCCCCCCCGAGCGAGCGCGGGACC

GGGGGTTTTGGCTCTACCGGTATTTAGCCCATAGCTTGGGGTTCGTTCCGGGCAATAAAAAACGTTTGTA

TCTCATCTTTCCTGTGTGTAGTTGTTTCTGTTGGATGCCTGTGGGTCTATCACACCCGCCCCTCCATCCC

ACAAACACAGAACACACGGGTTGGATGAAAACACGCATTTATTGACCCAAAACACACGGAGCTGCTCGAG

ATGGGCCAGGGCGAGGTGCGGTTGGGGAGGCTGTAGGTCTGGGAACGGACACGCGGGGACACGATTCCGG

TTIGGGGTCCGGGAGGGCGTCGCCGTTTCGGGCGGCAGGCGCCAGCGTAACCTCCGGGGGCGGCGTGTGG

GGGTGCCCCAAGGAGGGCGCCTCGGTCACCCCAAGCCCCCCCGAGCGGGTTCCCCCGGCAACCCCGAAGG

CGGAGAGGCCAAGGGCCCGTTCGGCGATGGCCACATCCTCCATGACCACGTCGCTCTCGGCCATGCTCCG

AATAGCCTGGGAGACGAGCACATCCGCGGACTIGTCAGCCGCCCCCACGGACATGTACATCTGCAGGATG

GTGGCCATACACGTGTCCGCCAGGCGCCGCATCTTGTCCTGATGGGCCGCCACGGCCCCGTCGATCGTGG

GGGCCTCGAGCCCGGGGTGGTGGCGCGCCAGTCGTTCTAGGTTCACCATGCAGGCGTGGTACGTGCGGGC

CAAGGCGCGGGCCTTCACGAGGCGTCGGGTGTCGTCCAGGGACCCCAGGGCGTCATCGAGCGTGATGGGG

GCGGGAAGTAGCGCGTTAACGACCACCAGGGCCTCCTGCAGCCGCGGCTCCGCCTCCGAGGGCGGAACGG

CCGCGCGGATCATCTCATATTGTTCCTCGGGGCGCGCTCCCCAGCCACATATAGCCCCGAGAAGAGAAGC

CATCGCGGGCGGGTACTGGCCCTTGGGCGCGCGGACGCAATGGGGCAGGAAGACGGGAACCGCGGGGAGA

GGCGGGCGGCCGGGACTCCCGTGGAGGTGACCGCGCTTTATGCGACCGACGGGGGCGTTATTACCTCTTC

GATCGCCCTCCTCACAAACTCTCTACTGGGGGCCGAGCCGGTTTATATATTCAGCTACGACGCATACACG

CACGATGGCCGTGCCGACGGGCCCACGGAGCAAGACAGGTTCGAAGAGAGTCGGGCGCTCTACCAAGCGT

CGGGCGGGCTAAATGGCGACTCCTTCCGAGTAACCTTTTGTTTATTGGGGACGGAAGTGGGTGGGACCCA

CCAGGCCCGCGGGCGAACCCGACCCATGTTCGTCTGTCGCTTCGAGCGAGCGGACGACGTCGCCGCGCTA

CAGGACGCCCTGGCGCACGGGACCCCGCTACAACCGGACCACATCGCCGCCACCCTGGACGCGGAGGCCA

CGTTCGCGCTGCATGCGAACATGATCCTGGCTCTCACCGTGGCCGTCAACAACGCCAGCCCCCGCACCGG

ACGCGACGCCGCCGCGGCGCAGTATGATCAGGGCGCGTCCCTACGCTCGCTCGTGGGGCGCACGTCCCTG

GGACAACGCGGCCTTACCACGCTATACGTCCACCACGAGGCGCGCGTGCTGGCCGCGTACCGCAGGGCGT

ATTATGGAAGCGCGCAGAGTCCCTTCTGGTTTCTTAGCAAATTCGGGCCTGACGAAAAAAGCCTGGTGCT

CACCACTCGGTACTACCTGCTTCAGGCCCAGCGTCTGGGGGGCGCGGGGGCCACGTACGACCTGCAGGCC

ATCAAGGACATCTGCGCCACCTACGCGATTCCCCACGCCCCCCGCCCCGACACCGTCAGCGCCGCGTCCC

TGACCTCGTTTGCCGCCATCACGCGGTTCTGTTGCACGAGCCAGTACGCCCGCGGGGCCGCGGCGGCCGG

GTTTCCGCTTTACGTGGAGCGCCGTATTGCGGCCGACGTCCGCGAGACCAGTGCGCTGGAGAAGTTCATA

ACCCACGATCGCAGTTGCCTGCGCGTGTCCGACCGTGAATTCATTACGTACATTTACCTGGCCCATTTTG

-continued

AGTGTTTCAGCCCCCCGCGCCTAGCCACGCATCTTCGGGCCGTGACGACCCAGGACCCCAACCCCGCGGC

CAACACGGAGCAGCCCTCGCCCCTGGGCAGGGAGGCCGTGGAACAATTTTTTTGCCACGTGCGCGCCCAA

CTGAATATCGGGGAGTACGTCAAACACAACGTGACCCCCCGGGAGACCGTCCTGGATGGCGATACGGCCA

AGGCCTACCTGCGCGCTCGCACGTACGCGCCCGGGGCCCTGACGCCCGCCCCCGCGTATTGCGGGGCCGT

GGACTCCGCCACCAAAATGATGGGGCGTTTGGCGGACGCCGAAAAGCTCCTGGCCCCCGCGGGTGGCCCG

CGTTGGCGCCCGCCAGTCCCGGGGAGGATACGGCGGGCGGCACGCCGCCCCCACAGACCTGCGGAATCGT

CAAGCGCCTCCTGAGACTGGCCGCCACGGAACAACAGGACACCACGCCCCCGGCGATCGCGGCGCTTATC

CGTAATGCGGCGGTGCAGACTCCCCTGCCCGTCTACCGGATATCCATGGTCCCCACGGGACAGGCATTTG

CCGCGCTGGCCTGGGACGACTGGGCCCGCATAACGCGGGACGCTCGCCTGGCCGAAGCGGTCGTGTCCGC

CGAAGCGGCGGCGCACCCCGACCACGGCGCGCTGGGCAGGCGGCTCACGGATCGCATCCGCGCCCAGGGC

CCCGTGATGCCCCCTGGCGGCCTGGATGCCGGGGGGCAGATGTACGTGAATCGCAACGAGATATTTAACG

GCGCGCTGGCAATCACAAACATCATCCTGGATCTCGACATCGCCCTGAAGGAGCCCGTCCCCTTTCGCCG

GCTCCACGAGGCCCTGGGCCACTTTAGGCGCGGGGCTCTGGCGGCGGTTCAGCTCCTGTTTCCCGCGGCC

CGCGTGGACCCCGACGCATATCCCTGTTATTTTTTCAAAAGCGCATGTCGGCCCGGCCCGGCGTCCGTGG

GTTCCGGCAGCGGACTCGGCAACGACGACGACGGGGACTGGTTTCCCTGCTACGACGACGCCGGTGATGA

GGAGTGGGCGGAGGACCCGGGCGCCATGGACACATCCCACGATCCCCCGGACGACGAGGTTGCCTACTTT

GACCIGTGCCACGAAGTCGGCCCCCACGGCGGAACCTCGCGAAACGGATTCGCCCGTGTGTTCCTGCACCG

ACAAGATCGGACTGCGGGTGTGCATGCCCGTCCCCGCCCCGTACGTCGTCCACGGTTCTCTAACGATGCG

GGGGGTGGCACGGGTCATCCAGCAGGCGGTGCTGTTGGACCGAGATTTTGTGGAGGCCATCGGGAGCTAC

GTAAAAAACTTCCTGTTGATCGATACGGGGGCCCGGGCGCCATGGACACATCCCACGATCCCCCGGACGA

CGAGGTTGCCTACTTTGACCTGTGCCACGAAGTCGGCCCCCACGGCGGAACCTCGCGAAACGGATTCGCCC

GTGTGTTCCTGCACCGACAAGATCGGACTGCGGGTGTGCATGCCCGTCCCCGCCCCGTACGTCGTCCACG

GTTCTCTAACGATGCGGGGGGTGGCACGGGTCATCCAGCAGGCGGTGCTGTTGGACCGAGATTTTGTGGA

GGCCATCGGGAGCTACGTAAAAAACTTCCTGTTGATCGATACGGGGGTGTACGCCCACGGCCACAGCCTG

CGCTTGCCGTATTTTGCCAAAATCGCCCCCGACGGGCCTGCGTGCGGAAGGCTGCTGCCAGTGTTTGTGA

TCCCCCCCGCCTGCAAAGACGTTCCGGCGTTTGTCGCCGCGCACGCCGACCCGCGGCGCTTCCATTTTCA

CGCCCCGCCCACCTATCTCGCTTCCCCCCGGGAGATCCGTGTCCTGCACAGCCTGGGTGGGGACTATGTG

AGCTTCTTTGAAAGGAAGGCGTCCCGCAACGCGCTGGAACACTTTGGGCGACGCGAGACCCTGACGGAGG

TCCTGGGTCGGTACAACGTACAGCCGGATGCGGGGGGGACCGTCGAGGGGTTCGCATCGGAACTGCTGGG

GCGGATAGTCGCGTGCATCGAAACCCACTTTCCCGAACACGCCGGCGAATATCAGGCCGTATCCGTCCGG

CGGGCCGTCAGTAAGGACGACTGGGTCCTCCTACAGCTAGTCCCCGTTCGCGGTACCCTGCAGCAAAGCC

TGTCGTGTCTGCGCTTTAAGCACGGCCGGGCGAGTCGCGCCACGGCGCGGACATTCGTCGCGCTGAGCGT

CGGGGCCAACAACCGCCTGTGCGTGTCCTTGTGTCAGCAGTGCTTTGCCGCCAAATGCGACAGCAACCGC

CTGCACACGCTGTTTACCATTGACGCCGGCACGCCATGCTCGCCGTCCGTTCCCTGCAGCACCTCTCAAC

CGTCGTCTTGATAACGGCGTACGGCCTCGTGCTCGTGTGGTACACCGTCTTCGGTGCCAGTCCGCTGCAC

CGATGTATTTACACGGTACGCCCCACCGGCACCAACAACGACACCGCCCTCGTGTGGATGAAAATGAACC

AGACCCTATTGTTTCTGGGGGCCCCGACGCACCCCCCCAACGGGGGCTGGCGCAACCACGCCCATATCTG

CTACGCCAATCTTATCGCGGGTAGGGTCGTGCCCTTCCAGGTCCCACCCGACGCCACGAATCGTCGGATC

ATGAACGTCCACGAGGCAGTTAACTGTCTGGAGACCCTATGGTACACACGGGTGCGTCTGGTGGTCGTAG

GGTGGTTCCTGTATCTGGCGTTCGTCGCCCTCCACCAACGCCGATGTATGTTTGGTGTCGTGAGTCCCGC

CCACAAGATGGTGGCCCCGGCCACCTACCTCTTGAACTACGCAGGCCGCATCGTATCGAGCGTGTTCCTG

-continued

CAGTCCCCCTACACGAAAATTACCCGCCTGCTCTGCGAGCTGTCGGTCCAGCGGCAAAACCTGGTTCAGT

TGTTTGAGACGGACCCGGTCACCTTCTTGTACCACCGCCCCGCCATCGGGGTCATCGTAGGCTGCGAGTT

GATGCTACGCTTTGTGGCCGTGGGTCTCATCGTCGGCACCGCTTTCATATCCCGGGGGGCATGTGCGATC

ACATACCCCCTGTTTCTGACCATCACCACCTGGTGTTTTGTCTCCACCATCGGCCTGACAGAGCTGTATT

GTATTCTGCGGCGGGGCCCGGCCCCCAAGAACGCAGACAAGGCCGCCGCCCCGGGGCGATCCAAGGGGCT

GTCGGGCGTCTGCGGGCGCTGTTGTTCCATCATCCTGTCGGGCATCGCAATGCGATTGTGTTATATCGCC

GTGGTGGCCGGGGTGGTGCTCGTGGCGCTTCACTACGAGCAGGAGATCCAGAGGCGCCTGTTTGATGTAT

GACGTCACATCCAGGCCGGCGGAAACCGGAACGGCATATGCAAACTGGAAACTGTCCTGTCTTGGGGCCC

ACCCACCCGACGCGTCATATGTAAATGAAAATCGTTCCCCCGAGGCCATGTGTAGCCTGGATCCCAACGA

CCCCGCCCATGGGTCCCAATTGGCCGTCCCGTTACCAAGACCAACCCAGCCAGCGTATCCACCCCCGCCC

GGGTCCCCGCGGAAGCGGAACGGTGTATGTGATATGCTAATTAAATACATGCCACGTACTTATGGTGTCT

GATTGGTCCTTGTCTGTGCCGGAGGTGGGGCGGGGGCCCCGCCCGGGGGGCGGAACTAGGAGGGGTTTGG

GAGAGCCGGCCCCGGCACCACGGGTATAAGGACATCCACCACCCGGCCGGTGGTGGTGTGCAGCCGTGTT

CCAACCACGGTCACGCTTCGGTGCCTCTCCCCGATTCGGGCCCGGTCGCTTGCTACCGGTGCGCCACCAC

CAGAGGCCATATCCGACACCCCAGCCCCGACGGCAGCCGACAGCCCGGTCATGGCGACTGACATTGATAT

GCTAATTGACCTCGGCCTGGACCTCTCCGACAGCGATCTGGACGAGGACCCCCCCGAGCCGGCGGAGAGC

CGCCGCGACGACCTGGAATCGGACAGCAACGGGGAGTGTTCCTCGTCGGACGAGGACATGGAAGACCCCC

ACGGAGAGGACGGACCGGAGCCGATACTCGACGCCGCTCGCCCGGCGGTCCGCCCGTCTCGTCCAGAAGA

CCCCGGCGTACCCAGCACCCAGACGCCTCGTCCGACGGAGCGGCAGGGCCCCAACGATCCTCAACCAGCG

CCCCACAGTGTGTGGTCGCGCCTCGGGGCCCGGCGACCGTCTTGCTCCCCCGAGCGGCACGGGGGCAAGG

TGGCCCGCCTCCAACCCCCACCGACCAAAGCCCAGCCTGCCCGCGGCGGACGCCGTGGGCGTCGCAGGGG

TCGGGGTCGCGGTGGTCCCGGGGCCGCCGATGGTTTGTCGGACCCCCGCCGGCGTGCCCCCAGAACCAAT

CGCAACCCGGGGGGACCCCGCCCCGGGGCGGGGTGGACGGACGGCCCCGGCGCCCCCATGGCGAGGCGT

GGCGCGGAAGTGAGCAGCCCGACCCACCCGGAGGCCCGCGGACACGGAGCGTGCGCCAAGCACCCCCCC

GCTAATGACGCTGGCGATTGCCCCCCCGCCCGCGGACCCCCGCGCCCCGGCCCCGGAGCGAAAGGCGCCC

GCCGCCGACACCATCGACGCCACCACGCGGTTGGTCCTGCGCTCCATCTCCGAGCGCGCGGCGGTCGACC

GCATCAGCGAGAGCTTCGGCCGCAGCGCACAGGTCATGCACGACCCCTTTGGGGGGCAGCCGTTTCCCGC

CGCGAATAGCCCCTGGGCCCCGGTGCTGGCGGGCCAAGGAGGGCCCTTTGACGCCGAGACCAGACGGGTC

TCCTGGGAAACCTTGGTCGCCCACGGCCCGAGCCTCTATCGCACTTTTGCCGGCAATCCTCGGGCCGCAT

CGACCGCCAAGGCCATGCGCGACTGCGTGCTGCGCCAAGAAAATTTCATCGAGGCGCTGGCCTCCGCCGA

CGAGACGCTGGCGTGGTGCAAGATGTGCATCCACCACAACCTGCCGCTGCGCCCCCAGGACCCCATTATC

GGGACGGCCGCGGCGGTGCTGGATAACCTCGCCACGCGCCTGCGGCCCTTTCTCCAGTGCTACCTGAAGG

CGCGAGGCCTGTGCGGCCTGGACGAACTGTGTTCGCGGCGGCGTCTGGCGGACATTAAGGACATTGCATC

CTTCGTGTTTGTCATTCTGGCCAGGCTCGCCAACCGCGTCGAGCGTGGCGTCGCGGAGATCGACTACGCG

ACCCTTGGTGTCGGGGTCGGAGAGAAGATGCATTTCTACCTCCCCGGGGCCTGCATGGCGGGCCTGATCG

AAATCCTAGACACGCACCGCCAGGAGTGTTCGAGTCGTGTCTGCGAGTTGACGGCCAGTCACATCGTCGC

CCCCCCGTACGTGCACGGCAAATATTTTTATTGCAACTCCCTGTTTTAGGTACAATAAAAACAAAACATT

TCAAACAAATCGCCCCACGTGTTGTCCTTCTTTGCTCATGGCCGGCGGGGCGTGGGTCACGGCAGATGGC

GGGGGTGGGCCCGGCGTACGGCCTGGGTGGGCGGAGGGAACTAACCCAACGTATAAATCCGTCCCCGCTC

CAAGGCCGGTGTCATAGTGCCCTTAGGAGCTTCCCGCCCGGGCGCATCCCCCCTTTTGCACTATGACAGC

-continued

GACCCCCCTCACCAACCTGTTCTTACGGGCCCCGGACATAACCCACGTGGCCCCCCCTTACTGCCTCAAC

GCCACCTGGCAGGCCGAAACGGCCATGCACACCAGCAAAACGGACTCCGCTTGCGTGGCCGTGCGGAGTT

ACCTGGTCCGCGCCTCCTGTGAGACCAGCGGCACAATCCACTGCTTTTTCTTTGCGGTATACAAGGACAC

CCACCATACCCCTCCGCTGATTACCGAGCTCCGCAACTTTGCGGACCTGGTTAACCACCCGCCGGTCCTA

CGCGAACTGGAGGATAAGCGCGGGGTGCGGCTGCGGTGTGCGCGGCCGTTTAGCGTCGGGACGATTAAGG

ACGTCTCTGGGTCCGGCGCGTCCTCGGCGGGAGAGTACACGATAAACGGGATCGTGTACCACTGCCACTG

TCGGTATCCGTTCTCAAAAACATGCTGGATGGGGGCCTCCGCGGCCCTACAGCACCTGCGCTCCATCAGC

TCCAGCGGCATGGCCGCCCGCGCGGCAGAGCATCGACGCGTCAAGATTAAAATTAAGGCGTGATTTCCAA

CCCCCCATGAATGTGTGTAACCCCCCCCCCAAAAAAATAAAGAGCCGTAACCCAACCAAACCAGGCGTGG

TGTGAGTTTGTGGACCCAAAGCCCTCAGAGACAATGCGACAGGCCAGTATGGACCGTGATACTTTTATTT

ATTAACTCACAGGGGCGCTTACCGCCACAGGAATACCAGAATAATGACCACCACAATCGCGACCACCCCA

AATACAGCATGGCGCCACACCACGCCACAACAGCCCTGTCGCCGGTATGGGGCATGATCAGACGAGCCGC

GCGCCGCGCGTTGGGCCCTGTACAGCTCGCGCGAATTGACCCTAGGAGGCCGCCACGCGCCCGAGTTTTG

CGTTCGTCGCTGGTCGTCGGGCGCCAAAGCCCCGGACGGCTGTTCGGTCGAACGAACGGCCACGACAGTG

GCATAGGTTGGGGGGTGGTCCGACATAGCCTCGGCGTACGTCGGGAGGCCCGACAAGAGGTCCCTTGTGA

TGTCGGGTGGGGCCACAAGCCTGGTTTCCGGAAGAAACAGGGGGGTTGCCAATAACCCGCCAGGGCCAAA

ACTCCGGCGCTGCGCACGTCGTTCGGCGCGGCGCCGGGCGCGCCGAGCGGCTCGCTGGGCGGCTTGGCGT

GAGCGGCCCCGCTCCGACGCCTCGCCCTCTCCGGAGGAGGTTGGCGGAATTGGCACGGACGACAGGGGCC

CAGCAGAGTACGGTGGAGGTGGGTCCGTGGGGGTGTCCAGATCAATAACGACAAACGGCCCCTCGTTCCT

ACCAGACAAGCTATCGTAGGGGGGCGGGGGATCAGCAAACGCGTTCCCCGCGCTCCATAGACCCGCGTCG

GGTTGCGCCGCCTCCGAAGCCATGGATGCGCCCCAAAGCCACGACTCCCGCGCGCTAGGTCCTTGGGGTA

AGGGAAAAGGCCCTACTCCCCATCCAAGCCAGCCAAGTTAACGGGCTACGCCTTCGGGGATGGGACTGGC

ACCCCGGCGGATTTTGTTGGGCTGGTACGCGTCGCCCAACCGAGGGCCGCGTCCACGGGACGCGCCTTTT

ATAACCCCGGGGTCATTCCCAACGATCACATGCAATCTAACTGGCTCCCCTCTCCCCTCTCCCCCCCTCT

CCCCAGCAGGAGCGGGGTGTTGCGCCGGGGGACGTCTGGAGGAGCGGGAGGTGCGCGGGACGGTGGATGA

GGAACAGGAGTTGTTGCGCGGTGAGTTGTCGCTGTGAGTTGTGTTGTTGGGCAGGTGTGGTGGATGACGT

GACGTGTGACGTGCGGATTGCGCCGTGCTTTGTTGGTGTTGTTTTACCTGTGGCAGCCCGGGCCCCCCGC

GGGCGCGCGCGCGCGCAAAAAAGGCGGGCGGCGGCCCCCGCTCCTCCCCCGCCCCTCCCCCGCTCCTCCC

CCGCTCCCCCCCGCCCCCGGCCCCGCCCCCACCCCCCCCGCGCGCGCACGCCGCCCGGACCGCCGCCCGC

CCTTTTTGCGCCCGCGCGCGCCCGCGGGGGGCCCTGGCTGCCACAGGTAAAACAACACCAACAAAGCACG

GCGCAATCCGCACGTCACACGTCACGTCATCCACCACCCTGCCCAACAACACAACTCACAGCGACAACTC

CCGCGCAACAACTCCTGTTCCTCATCCACACGTCACCGCGCCCCTCCCGCTCCTCCAGACGTACCCCGGC

GCAACACCCGCTCCTGCTACACCCCACCGCCCCTCCCCAGCCCCAGCCCTCCCCAGCCCCAGCCCTCCCC

CGGGAGGGGGCGAGGGGCGGGAGGGGGCGAGGGGCGGGAGGGGGCGAGGGGCGGTGGTGGGGCGCGGGCG

CCCCCGGAGGGTTGGATCTCTGACCTGAGATTGGCGGCACTGAGGAGAGATGCCCGAACCCCCCCGAGGG

AGCGCGGGACGCGGTGGGGAGGGCTGGGGCTGGGGAGGGCGGGGCGGGGGGGCGGGGCGGGGGGGGGGG

GGGGGGGGGCGGGGGCCCCCCCCCCCCCCCCCCCCCCCCCCCCCCCCCCCCCCCCCCGCCCCCCCCCG

CCCCCCGCCCCCCCCCGCCCCTCGCCCCCTCCCGCCCCTCGCCCCCTCCCGCCCCTCGAATAAACAACGC

TACTGCAAAACTTAATCAGGTCGTTGCCGTTTATTGCGTCTTCGGGTTTCACAAGCGCCCCGCCCCGTCC

CGGCCCGTTACAGCACCCCGTCCCCCTCGAACGCGCCGCCGCGTCTTCGTCCCAGGCGCCTTCCCAGTCC

ACAACGTCCCGTCGCGGGGGCGTGGCCAAGCCCGCCTCCGCCCCCAGCACCTCCACGGCCCCCGCCGCCG

-continued

CCAGCACGGTGCCGCTGCGGCCCGTGGCCGAGGCCCAGCGAATCCCGGGCGGCGCCGGCGGCAGGGCCCC

CGGGCCGTCGTCGTCGTCGCCGCGCAGCACCAGCGGGGGGGCGTCGTCGTCGGGCTCCAGCAGGGCGCGG

GCGCAAAAGTCCCTCCGCGGCCCGCGCCACCGGGCCGGGCCGGCGCGCACCGCCTCGCGCCCCAGCGCCA

CGTACACGGGCCGCAGCGGCGCGCCCAGGCCCCAGCGCGCGCAGGCGCGGTGCGAGTGGGCCTCCTCCTC

GCAGAAGTCCGGCGCGCCGGGCGCCATGGCGTCGGTGGTCCCCGAGGCCGCCGCCCGGCCGTCCAGCGCC

GGCAGCACGGCCCGGCGGTACTCGCGCGGGGACATGGGCACCGGCGTGTCCGGGCCGAGCGCGTGCGCAC

GCGGTAGCGCCGTTGCCGCCGCGGCACGGCGCAGCGGCGGCGCGTCGGGGTACAGGCGCGCGTGCGCGGC

CTCCACGCGCGCGAAGACCCCCGGGCCGAACACGCGGCCCGAGGCCAGCACCGTGCGGCGCAGGTCCCGC

GCCGCCGGCCAGCGCACGGCGCACTGCACGGCGGGCAGCAGGTCGCACGCCAGGTAGGCGTGCTGCCGCG

ACACCGCGGGCCCGTCGGCGGGCCAGTCGCAGGCGCGCACGGTGTTGACCACGATGAGCCGCCGGTCGCC

GGCGCTGGCGAGCAGCCCCAGAAACTCCACGGCCCCGGCGAAGGCCAGGTCCCGCGTGGACAGCAGCAGC

ACGCCCTGCGCGCCCAGCGCCGACACGTCGGGGGCGCCGGTCCAGTTGCCCGCCCAGGCGGCCGTGTCCG

GCCCGCACAGCCGGTTGGCCAGGGCCGCCAGCAGGCAGGACAGCCCGCCGCGCTCGGCGGACCACTCCGG

CGGCCCCCCCGAGGCCCCGCCGCCGGCCAGGTCCTCGCCCGGCAGCGGCGAGTACAGCACCACCACGCGC

ACGTCCTCGGGGTCGGGGATCTGGCGCATCCAGGCCGCCAGGCGGCGCAGCGGGCCCGAGGCGCGCGGGG

GGCCAAAGAGGCGGCCCCCGGCGGCCCCGTGGGGGTGGGGGCCCCCACCCCCACGGGGCCGCCGGGGGCC

GCCTCTTTGGCCCCCTGCGCGCCTCGGGCCCGCTGCGCCGCATGGCGGCCTGGATGCGCCAGATCCCCGA

CCCCGAGGACGTGCGCGTGGTGGTGCTGTACTCGCCGCTGCCGGGCGAGGACCTGGCCGGCGGCGGGGCC

TCGGGGGGGCCGCCGGAGTGGTCCGCCGAGCGCGGCGGGCTGTCCTGCCTGCTGGCGGCCCTGGCCAACC

GGCTGTGCGGGCCGGACACGGCCGCCTGGGCGGGCAACTGGACCGGCGCCCCCGACGTGTCGGCGCTGGG

CGCGCAGGGCGTGCTGCTGCTGTCCACGCGGGACCTGGCCTTCGCCGGGGCCGTGGAGTTTCTGGGGCTG

CTCGCCAGCGCCGGCGACCGGCGGCTCATCGTGGCAACACCGTGCGCGCCTGCGACTGGCCCGCCGACGG

GCCCGCGGTGTCGCGGCAGCACGCCTACCTGGCGTGCGACCTGCTGCCCGCCGTGCAGTGCGCCGTGCGC

TGGCCGGCGGCGCGGGACCTGCGCCGCACGGTGCTGGCCTCGGGCCGCGTGTTCGGCCCGGGGGTCTTCG

CGCGCGTGGAGGCCGCGCACGCGCGCCTGTACCCCGACGCGCCGCCGCTGCGCCTGTGCCGCGGCGGCAA

CGTGCGCTACCGCGTGCGCACGCGCTTCGGCCCGGACACGCCGGTGCCCATGTCCCCGCGCGAGTACCGC

CGGGCCGTGCTGCCGGCGCTGGACGGCCGGGCGGCGGCCTCGGGGACCACCGACGCCATGGCGCCCGGCG

CGCCGGACTTCTGCGAGGAGGAGGCCCACTCGCACCGCGCCTGCGCGCGCTGGGGCCTGGGCGCGCCGCT

GCGGCCCGTGTACGTGGCGCTGGGGCGCGAGGCGGTGCGCGCCGGCCCGGCCCGGTGGCGCGGGCCGCGG

AGGGACTTTTGCGCCCGCGCCCTGCTGGAGCCCGACGACGACGCCCCCCCGCTGGTGCTGCGCGGCGACG

ACGACGACGGCCCGGGGGCCCTGCCGCCGGCGCCGCCCGGGATTCGCTGGGCCTCGGCCACGGGCCGCAG

CGGCACCGTGCTGGCGGCGGCGGGGGCCGTGGAGGTGCTGGGGGCGGAGGCGGGCTGGCCACGCCCCCGC

GCGGGACGTTGTGGACTGGGAAGGCGCCTGGGCGAAGACGCGGCGGCGCGTCGAGGGGGACGGGGTGCTG

TACGGGCCGGGACGGGGCGGGGCGCTTGTGAAACCCGAAGACGCAATAAACGGCAACGACCTGATTAAGT

TTTGCAGTAGCGTTGTTTATTCGAGGGGCGGGAGGGGGCGAGGGGCGGCCGGCCCGCACAGCCGGTTGGC

CAGGGCCGCCAGCAGGCAGGACAGCCCGCCGCGCTCGGCGGACCACTCCGGCGGCCCCCCCGAGGCCCCG

CCGCCGGCCAGGTCCTCGCCCGGCAGCGGCGAGTACAGCACCACCACGCGCACGTCCTCGGGGTCGGGGA

TCTGGCGCATCCAGGCCGCCATGCGGCGCAGCGGGCCCGAGGCGCGCAGGGGGCCAAAGAGGCGGCCCCC

GGCGGCCCCGTGGGGGTGGGGGTTCTCGTCGTCGTCGCCGCCGCACGCGGCCTGGGCGGCGGGGGCGGGC

CCGGCGCACCGCGCGGCGATCGAGGCCAGGGCCCGCGGGTCAAACATGAGGGCCGGTCGCCAGGGGACGG

-continued

GGAACAGCGGGTGGTCCGTGAGCTCGGCCACGGCGCGCGGGGAGCAGTAGGCCTCCAGGGCGGCGGCCGC

GGGCGCCGCCGTGTGGCTGGGCCCCCGGGGCTGCCGCCGCCAGCCGCCCAGGGGGTCGGGGCCCTCGGCG

GGCCGGCGCGACAGCGCCAGGGGGCGCGGGCGGGCCTGCGCCGCGGCGCCCGGGCCGCCGCGGGCTGGGC

GGGGGTGGGCTCGGGCCCGGGGGCGTGGAGGGGGGCGCGGGGAGGGGGGCGCGGGCGTCCGAGCCGGGGG

CGTCCGCGCCGCTCTTCTTCGTCTTCGGGGGTCGCGGGCCGCCGCCTCCGGGCGGCCGGGCCGGGCCGGG

ACTCTTGCGCTTGCGCCCCTCCCGCGGCGCGGCGGAGGCGGCGGCGGCCGCCAGCGCGTCGGCGGCGTCC

GGTGCGCTGGCCGCCGCCGCCAGCAGGGGGCGGAGGCTCTGGTTCTCAAACAGCAGGTCCGCGGCGGCGG

CGGCCGCGGAGCTCGGCAGGCGCGGGTCCCGCGGCAGCGCGGGGCCCAGGGCCCCGGCGACCAGGCTCAC

GGCGCGCACGGCGGCCACGGCGGCCTCGCTGCCGCCGGCCACGCGCAGGTCCCCGCGCAGGCGCATGAGC

ACCAGCGCGTCGCGCACGAACCGCAGCTCGCGCAGCCACGCGCGCAGGCGGGGCGCGTCGGCGTGCGGCG

GCGGCGGGGAAGCGGGGCCCGCGGGTCCCTCTGGCCGCGGGGGGCTGGCGGGCCGGGCCCCGGCCAGCCC

CGGGACGGCCGCCAGGTCGCCGTCGAAGCCCTCGGCCAGCGCCTCCAGGATCCCGCGGCAGGCGGCCAGG

CACTCGACGGCCACGCGGCCGGCCTGGGCGCGGCGCCCGGCGTCGGCGTCGGCGTGGCGGGCGGCGTCGG

GGTCGTCGCCCCCCACGGGGGAGGCGGGCGCGGCGGACAGCCGCCCCAGGGCGGCGAGGATCCCCGCGGC

GCCGTACCCGGCGGGCACCGCGCGCTCGCCCGGTGCGGCGGCGGCGACGGCGGCGACCCCCTCGTCATCT

GCGCCGGCGCCGGGGCTCCCCGCGGCCCCCGTCAGCGCCGCGTTCTCGCGCGCCAACAGGGGCGCGTAGG

CGCGGCGCAGGCTGGTCAGCAGGAAGCCCTTCTGCGCGCGGTCGTATCGGCGGCTCATGGCCACGGCGGC

CGCCGCGTGCGCCAGGCCCCGCCGAAGCGGCCGGCCGCCATGGCGTAGCCCAGGTGGGGCACGGCCCGCG

CCACGCTGCCGGTGATGAAGGAGCTGCTGTTGCGCGCGGCGCCCGAGATCCGGAAGCAGGCCTGGTCCAG

CGCCACGTCCCCGGGGACCACGCGCGGGTTCTGGAGCCACCCCATGGCCTCCGCGTCCGGGGGCCTGCGC

GGGGACCTGCGCGTGGCCGGCGGCAGCGGGCCGCCGTGGCCGCCGGCGCGCCGTGGCCGGTCGCCGGGGC

CCTGGGCCCCGCGCTGCCGCGGGACCCGCGCCTGCCGAGCTCCGCGGCCGCCGCCGCCGCGGACCTGCTG

TTTGAGAACCAGAGCCTCCGCCCCCTGCTGGCGGCGGCGGCCAGCGCACCGGACGCCGCCGACGCGCTGG

CGGCCGCCGCCGCCTCCGCCGCGCCGCGGGAGGGGCGCAAGCGCAAGAGTCCCGGCCCGGCCCGGCCGCC

CGGAGGCGGCGGCCCGCGACCCCCGAAGACGAAGAAGAGCGGCGCGGACGCCCCCGGCTCGGCGCCCGCG

CCCCCCTCCCCGCGCCCCCCTCCACGCCCCCGGGCCCAGCCCACCCCCCCCCACCCGCGGCGGCCCGGGG

CGCCGCGGCGCAGGCCCGCCCCCGCCCCTGGCGCTGTCGCGCCGGCCCCCCGAGGGCCCCGACCCCCGGG

CGGCTGGCGGCGGCAGCCCCGGGGGCCCAGCCACACGGCGGCGCCCGCGGCCGCCGCCCTGGAGGCCTAC

TGCTCCCCGCGCGCCGTGGCCGAGCTCACGGACCACCCGCTGTTCCCCGTCCCCTGGCGACCGGCCCTCA

TGTTTGACCCGCGGGCCCTGGCCTCGATCGCCGCGCGGTGCGCCGGGCCCGCCCCCGCCGCCCAGGCCGC

GTGCGGCGGCGACGACGACGAGAACCCCCGGGGGGGGGGGGGGGGGGGGGGGGGGGGGTGGGGGGGGGG

GGGGGGGGGGGGGGGGGGGTGGGTGGGGAGTGGCAAGGAAGAAACAAGCCCGACCACCAGACAGAAAAT

GTAACCATACCCAAACCGACTCTGGGGGCTGTTTGTGGGGTCGGAACCATAGGATGAACAAACCACCCCG

TACCTCCCGCACCCAAGGGTGCGGGTGGCTCATCGGCATCTGTCCGGTATGGGTTGTTCCCCACCCACTC

GCGTTCGGACGTCTTAGAATCATGGCGGTTTTCTATGCCGACATCGGTTTTTCCCCCGCAATAAACACGA

TGCGATAAAAACTGTTTGTAAAATTTATTAAGGGGACAAAATGCCCTAGCACAGGGGTGGGGTTAGGGCC

GGGTCCCCACACCCAAACGCACCAAACAGATGCAGGCAGTGGGTCGAGTACAGCCCCGCGTACGAACACG

TCGATGCGTGTGTCAGACAGCACCAGAAAGCACAGGCCATCAACAGGTCGTGCATGTGTCGGTGGGTTTG

GACGCGGGGGGCCATGGTGGTGATAAAGTTAATGGCCGCCGTCCGCCAGGGCCACAGGGGCGACGTCTCT

TGGTTGGCCCGGAGCCACTGGGTGTGGACCAGCCGCGCGTGGCGGCCCAACATGGCCCCTGTAGCCGGGG

GCGGGGGATCGCGCACGTTTGCAGCGCACATGCGAGACACCTCGACCACGGTTCGAAAGAAGGCCCGGTG

-continued

GTCCGCGGGCAACATCACCAGGTGCGCAAGCGCCCGGGCGTCCAGAGGGTAGAGCCCTGAGTCATCCGAG

GTTGGCTCATCGCCCGGGTCTTGCCGCAAGTGCGTGTGGGTTGGGCTTCCGGTGGGCGGGACGCGAACCG

CGGTGTGGATCCCGACGCGGCCCGAGCGTATGCTCCATCTTGTGGGGAGAAGGGGTCTGGGCTCGCCAG

GGGGGCATACTTGCCCGGGCTATACAGACCCGCGAGCCGTACGTGGTTCGCGGGGGGTGCGTGGGGTCCG

GGGCTCCCTGGGAGACCGGGGTTGTCGTGGATCCCTGGGGTCACGCGGTACCCTGGGGTCTCTGGGAGCT

CGCGGTACTCTGGGTTCCCTAGGTTCTCGGGGTGGTCGCGGAACCCGGGGCTCCCGGGGAACACGCGGTG

TCCTGGGGATTGTTGGCGGTCGGACGGCTTCAGATGGCTTCGAGATCGTAGTGTCCGCACCGACTCGTAG

TAGACCCGAATCTCCACATTGCCCCGCCGCTTGATCATTATCACCCCGTTGCGGGGGTCCGGAGATCATG

CGCGGGTGTCCTCGAGGTGCGTGAACACCTCTGGGGTGCATGCCGGCGGACGGCACGCCTTTTAAGTAAA

CATCTGGGTCGCCCGGCCCAACTGGGGCCGGGGGTTGGGTCTGGCTCATCTCGAGAGACACGGGGGGGAA

CCACCCTCCGCCCAGAGACTCGGGTGATGGTCGTACCCGGGACTCAACGGGTTACCGGATTACGGGGACT

GTCGGTCACGGTCCCGCCGGTTCTTCGATGTGCCACACCCAAGGATGCGTTGGGGGCGATTTCGGGCAGC

AGCCCGGGAGAGCGCAGCAGGGGACGCTCCGGGTCGTGCACGGCGGTTCTGGCCGCCTCCCGGTCCTCAC

GCCCCCTTTTATTGATCTCATCGCGTACGTCGGCGTACGTCCTGGGCCCAACCCGCATGTTGTCCAGGAA

GGTGTCCGCCATTTCCAGGGCCCACGACATGCTTTTCCCGACGAGCAGGAAGCGGTCCACGCAACGGTCG

CCGCCGGTCGCCTCGACGAGGGCGTTCCTCCTGCGGGAAGGCACGAACGCGGGTGAGCCCCCGCGTCCCC

CCTCCTCCGCCCCCGCGTCCCCCCTCCTCCGCCCCCGCGTCCCCCCTCCTCCGCCCCCGCGTCCCCCCTC

CTCCGCCCCCGCGTCCCCCCTCCTCCGCCCCCGCGTCCCCCCTCCTCCGCCCACCCAAGGTGCTTACCCG

TGCAAAAAAGGCGGACCGGTGGGTTTCTGTCGTCGGAGGCCCCCGGGGTGCGTCCCCTGTGTTTCGTGGG

TGGGGTGGGCGGGTCTTTCCCCCCCGCGTCCGCGTGTCCCTTTCCGATGCGATCCCGATCCCGAGCCGGG

GCGTCGCGATGCCGACGCCGTCCGCTCCGACGGCCCTCTGCGACTCCCGCTCCCGGTCCGCGTGCTCCGC

AGCCGCTCCCGTCGTTCGTGGCCGGCGCCGTCTGCGGGCGTCGGTCGCGCCGGGCCTTTATGTGCGCCGG

AGAGACCCGCCCCCCGCCGCCCGGGTCCGCCCCCGGGGCCGGCGCGGAGTCGGGCACGGCGCCAGTGCTC

GCACTTCGCCCTAATAATATATATATATTGGGACGAAGTGCGAACGCTTCGCGTTCTCACTTCTTTTACC

CGGCGGCCCCGCCCCCTTGGGGCGGTCCCGCCCGCCGGCCAATGGGGGGGCGGCAAGGCGGGCGGCCCAA

GGGCCGCCCGCCGTCCCGTGGTCCCGGCGTCCGGCGGGCGGGACCGGGGGCCCGGGGACGGCCAACGGGC

GCGCGGGGCTCGTATCTCATTACCGCCGAACCGGGAAGTCGGGGCCCGGGCCCCGCCCCCTGCCCGTTCC

TCGTTAGCATGCGGAACGGAAGCGGAAACCGCCGGATCGGGCGGTAATGAGATGCCATGCGGGGCGGGGC

GCGGACCCACCCGCCCTCGCGCCCCGTCCATGGCAGATGGCGCGGATGGGCGGGGCCGGGGGTTCGACCA

ACGGGCCGCGGCCACGGGCCCCCGGCGTGCCGGCGTCGGGGCGGGGTCGTGCATAATGGAATTCCGTTCG

GGGTGGGCCCGCCGGGGGGCGGGGGGCCGGCGGCCTCCGCTGCTCCTCCTTCCCGCCGGCCCCTGGGACT

ATATGAGCCCGAGGACGCCCCGATCGTCCACACGGAGCGCGGCTGCCGACACGGATCCACGACCCGACGC

GGGACCGCCAGAGACAGACCGTCAGACGCTCGCCGCGCCGGGACGCCGATACGCGGACGAAGCGCGGGAG

GGGGATCGGCCGTCCCTGTCCTTTTTCCCCACCCAAGCATCGACCGGTCCGCGCTAGTTCCGCGTCGACG

GCGGGGGTCGTCGGGGTCCGTGGGTCTCGCCCCCTCCCCCCATCGAGAGTCCGTAGGTGACCTACCGTGC

TACGTCCGCCGTCGCAGCCGTATCCCCGGAGGATCGCCCCGCATCGGCGATGGCGTCGGAGAACAAGCAG

CGCCCCGGCTCCCCGGGCCCCACCGACGGGCCGCCGCCCACCCCGAGCCCAGACCGCGACGAGCGGGGGG

CCCTCGGGTGGGGCGCGGAGACGGAGGAGGGCGGGGACGACCCCGACCACGACCCCGACCACCCCCACGA

CCTCGACGACGCCCGGCGGGACGGGAGGGCCCCCGCGGCGGGCACCGACGCCGGCGAGGACGCCGGGGAC

GCCGTCTCGCCGCGACAGCTGGCTCTGCTGGCCTCCATGGTAGAGGAGGCCGTCCGGACGATCCCGACGC

-continued

CCGACCCCGCGGCCTCGCCGCCCCGGACCCCCGCCTTTCTAGCCGACGACGATGACGGGGACGAGTACGA

CGACGCAGCCGACGCCGCCGGCGACCGGGCCCCGGCCCGGGGCCGCGAACGGGAGGCCCCGCTACGCGGC

GCGTATCCGGACCCCACGGACCGCCGTCGCCGCGCCCGCCGGCCCAGCCGCCGCGGAGACGTCGTCACGG

CCGGCGGCGGCCATCGGCGTCATCGACCTCGTCGGACTCCGGGTCCTCGTCCTCGTCGTCCGCATCCTCT

TCGTCCTCGTCGTCCGACGAGGACGAGGACGACGACGGCAACGACGCGGCCGACCACGCACGCGAGGCGC

GGGCCGTCGGGCGGGGTCCGTCGAGCGCGGCGCCGGAAGCCCCCGGGCGGACGCCGCCCCCGCCCGGGCC

ACCCCCCCTCTCCGAGGCCGCGCCCAAGCCCCGGGCGGCGGCGAGGACCCCCGCGGCCTCCGCGGGCCGC

ATCGAGCGCCGCCGGGCCCGCGCGGCGGTGGCCGGCCGCGACGCCACGGGCCGCTTCACGGCCGGGCAGC

CCCGGCGGGTCGAGCTGGCGCCGACGCGGCCTCCGGCGCCTTCTCGCGCGCTACGCGACGGGTCGTCGCG

GGGAGCCGTGGCCCGGCGCCGGGCCCCCGCCCCCGGGGCGGGTGCTGTACGGCGGCCTGGGCGACAGCCG

CCCGGGCCTCTGGGGGGCGCCCGAGGCGGAGGAGGCGCGACGCCGGTTCGAGGCCTCGGGCGCCCCGGCG

GCCGTGTGGGCGCCCGAGCTGGGCGACGCCGCGCAGCAGTACGCCCTGATCACGCGGCTGCTGTACACCC

CGGACGCGGAGGCCATGGGGTGGCTCCAGAACCCGCGCGTGGTCCCCGGGGACGTGGCGCTGGACCAGGC

CTGCTTCCGGATCTCGGGCGCCGCGCGCAACAGCAGCTCCTTCATCACCGGCAGCGTGGCGCGGGCCGTG

CCCCACCTGGGCTACGCCATGGCGGCCGGCCGCTTCGGCTGGGGCCTGGCGCACGCGGCGGCCGCCGTGG

CCATGAGCCGCCGATACGACCGCGCGCAGAAGGGCTTCCTGCTGACCAGCCTGCGCCGCGCCTACGCGCC

CCTGTTGGCGCGCGAGAACGCGGCGCTGACGGGGGCCGCGGGGAGCCCCGGCGCCGGCGCAGATGACGAG

GGGGTCGCCGCCGTCGCCGCCGCCGCACCGGGCGAGCGCGCGGTGCCCGCCGGGTACGGCGCCGCGGGGA

TCCTCGCCGCCCTGGGGCGGCTGTCCGCCGCGCCCGCCTCCCCCGTGGGGGGCGACGGGGCGTACAGCAG

CCGCGTGATCAGGGCGTACTGCTGCGCGGCGTCGCCCGCTCGGGCGCCCACACGGCCGCCGGGGCGCCCG

AGGCCTCGACCCGGCGTCGCGCCTCCTCCGCCTCGGGCGCCCCCCAGAGGCCCGGGCGGCTGTCGCCCAG

GCCGCCGTACAGCACCCGCCCCGGGGGCGGGGGCCCGGCGCCGGGCCACGGCTCCCCGCTGACGACCCGT

CGCGATAGCGCGCGTAGAAGGCGCCGGAGGCCGCGTCGGCGTCCAGCTCGACCCGCCGGGGCTGCCCGGC

CGTGAAGCGGCCCGTGGCGTCGCGGCCGGCCACCGCCGCGCGGGCCCGGCGGCGCTCGATGCGGCCCGCG

GAGGCCGCGGGGGTCCTCGCCGCCGCCCGGGGCTTGGGCGCGGCCTCGGAGAGGGGGGGTGGCCCGGGCG

GGGGCGGCGTCCGCCCGGGGGCTTCCGGCGCCGCGCTCGACGGACCCCGCCCGACGGCCCGCGCCTCGCG

TGCGTGGTCGGCCGCGTCGTTGCCGTCGTCGTCCTCGTCCTCGTCGGACGACGAGGACGAAGAGGATGCG

GACGACGAGGACGAGGACCCGGAGTCCGACGAGGTCGATGACGCCGATGGCCGCCGCCGGCCGTGACGAC

GTCTCCGCGGCGGCTGGGCCGGCGGGCGCGGCGACAGGCGGTCCGTGGGGGCCGGATACGCGCCGCGCCG

CCCGGGGGCTTCCGGCGCCGCGCTCGACGGACCCCGCCCGACGGCCCGCGCCTCGCGTGCGTGGTCGGCC

GCGTCGTTGCCGTCGTCGTCCTCGTCCTCGTCGGACGACGAGGACGAAGAGGATGCGGACGACGAGGACG

AGGACCCGGAGTCCGACGAGGTCGATGACGCCGATGGCCGCCGCCGGCCGTGACGACGTCTCCGCGGCGG

CTGGGCCGGCGGGCGCGGCGACAGGCGGTCCGTGGGGTCCGGATACGCGCCGCGTAGCGGGGCCTCCCGT

TCGCGGCCCCGGGCCGGGGCCCGGTCGCCGGCGGCGTCGGCTGCGTCGTCGTACTCGTCCCCGTCATCGT

CGTCGGCTAGAAAGGCGGGGGTCCGGGGCGGCGAGGCCGCGGGGTCGGGCGTCGGGATCGTCCGGACGGC

CTCCTCTACCATGGAGGCCAGCAGAGCCAGCTGTCGCGGCGAGACGGCGTCCCCGGCGTCCTCGCCGGCG

TCGGTGCCCGCCGCGGGGGCCCTCCCGTCCCGCCGGGCGTCGTCGAGGTCGTGGGGGTGGTCGGGGTCGT

GGTCGGGGTCGTCCCCGCCCTCCTCCGTCTCCGCGCCCCACCCGAGGGCCCCCGCTCGTCGCGGTCTGG

GCTCGGGGTGGGCGGCGGCCCGTCGGTGGGGCCCGGGGAGCCGGGGCGCTGCTTGTTCTCCGACGCCATC

GCCGATGCGGGGCGATCCTCCCCCGACGACCCCCGCCGTCGACGCGGAACTAGCGCGGACCGGTCGATGC

TTGGGTGGGGAAAAAGGACAGGGACGGCCGATCCCCCTCCCGCGCTTCGTCCGCGTATCGGCGTCCCGGC

-continued

GCGGCGAGCGTCTGACGGTCTGTCTCTGGCGGTCCCGCGTCGGGTCGTGGATCCGTGTCGGCAGCCGCGC

TCCGTGTGGACGATCGGGGCGTCCTCGGGCTCATATAGTCCCGGGGCCGGCGGGAGGGAGGAGCAGCGGA

GGCCGCCGGCCCCCCGCCCCCCGGCGGGCCCGACCCCGCCCCGACGCCGGCACGCCGGGGGCCCGTGGCC

GCGGCCCGTTGGTCGAACCCCCGGCCCCGCCCATCCGCGCCATCTGCCATGGACGGGGCGCGAGGGCGGG

TGGGTCCGCGCCCCGCCCCGCATGGCATCTCATTACCGCCCGATCCGGCGGTTTCCGCTTCCGTTCCGCA

TGCTAACGAGGAACGGGCAGGGGGCGGGGCCCGGGCCCCGACTTCCCGGTTCGGCGGTAATGAGATACGA

GCCCCGCGCGCCCGTTGGCCGTCCCCGGGCCCCCGTCCCGCCCGCCGGACGCCGGGACCACGGGACGCGG

AGCGGACGGCGTCGGCATCGCGACGCCCCGGCTCGGGATCGGGATCGCATCGGAAAGGGACACGCGGACG

CGGGGGGGAAAGACCCGCCCACCCCACCCACGAAACACAGGGGACGCCCCCGGGGGCCCCGACGACAGAA

ACCCCCGGTCCGCCTTTTTTGCACGGGTAAGCGCCTTGGGTGGGCGGAGGAGGGGGGACGCGGGGGCGGA

GGAGGGGGGACGCGGGGGCGGAGGAGGGGGGAGCGGGGGGGAGGAGGGGGGACGCGGGGGCGGAGGAGGG

GGGACGCGGGGGCGGAGGAGGGGGGGGGGGGGGGAGCCACTGTGGTCCTCCGGGCGTTTTCTGGATGGCC

GACATTTCCCCAGGCGCTTTTGTGCCTTGTGTAAAAGCGCGGCGTCCCGCTCTCCGATCCCCGCCCCTGG

GCACGCGCAAGCGCAAGCGCCCTGCCCGCCCCCTCTCATCGGAGTCTGAGGTCGAATCCGAGACAGCCTT

GGAGTCTGAGGTCGAATCCGAGACAGCATCGGATTCGACCGAGTCTGGGGACCAGGAGGAAGCCCCCCGC

ATCGGTGGCCGTAGGGCCCCCCGGAGGCTTGGGGGGCGGTTTTTTCTGGACATGTCGGCGGAATCCACCA

CGGGGACGGAAACGGATGCGTCGGTGTCGGACGACCCCGACGACACGTCCGACTGGTCTTGTGACGACAT

TCCCCCACGACCCAAGCGGGCCCGGGTAAACCTGCGGCTCACTAGCTCTCCCGATCGGCGGGATGGGGTT

ATTTTTCCTAAGATGGGGCGGGTCCGGTCTACCCGGGAAACGCAGCCCCGGGCCCCCACCCCGTCGGCCC

CAAGCCCAAATGCAATGCTCCGGCGCTCGGTGCGCCAGGCCCAGAGGCGGAGCAGCGCACGATGGACCCC

CGACCTGGGCTACATGCGCCAGTGTATCAATCAGCTGTTTCGGGTCCTGCGGGTCGCCCGGGACCCCCAC

GGCAGTGCCAACCGCCTGCGCCACCTGATACGCGACTGTTACCTGATGGGATACTGCCGAGCCCGTCTGG

CCCCGCGCACGTGGTGCCGCTTGCTGCAGGTGTCCGGCGGAACCTGGGGCATGCACCTGCGCAACACCAT

ACGGGAGGTGGAGGCTCGATTCGACGCCACCGCAGAACCCGTGTGCAAGCTTCCTTGTTTGGAGGCCAGA

CGGTACGGCCCGGAGTGTGATCTTAGTAATCTCGAGATTCATCTCAGCGCGACAAGCGATGATGAAATCT

CCGATGCCACCGATCTGGAGGCCGCCGGTTCGGACCACACGCTCGCGTCCCAGTCCGACACGGAGGATGC

CCCCTCCCCCGTTACGCTGGAAACCCCAGAACCCCGCGGGTCCCTCGCTGTGCGTCTGGAGGATGAGTTT

GGGGAGTTTGACTGGACCCCCCAGGAGGGCTCCCAGCCCTGGCTGTCTGCGGTCGTGGCCGATACCAGCT

CCGTGGAACGCCCGGGCCCATCCGATTCTGGGGCGGGTCGCGCAGCAGAAGACCGCAAGTGTCTGGACGG

CTGCCGGAAAATGCGCTTCTCCACCGCCTGCCCCTATCCGTGCAGCGACACGTTTCTCCGGCCGTGAGTC

CGGICGCCCCGACCCCCTTGTATGTCCCCAAAATAAAAGACCAAAATCAAAGCGTTTGTCCCAGCGTCTT

AATGGCGGGAAGGGGGAGAGAAACAGACCACGCGTACATGGGGGGTGTTTGGGGGTTTATTGACATCGGG

GCTACAGGGTGGTAACCGGATAGCAGATGTGAGGAAGTCTGGGCCGTTCGCCGCGAACGGCGATCAGAGG

GTCCGTTTCTTGCGGACCACGGCCCGGTGATGTGGGTTGCTCGTCTAAAATCTCGGGCATACCCATACAC

GCACAACACGGACGCCGCACCGAATGGGACGTCGTAAGGGGGTGGGAGGTAGCTGGGTGGGGTTTGTGCA

GAGCAATCAGGGACCGCAGCCAGCGCATACAATCGCGCTCCCGTCCGTTGGTCCCGGGCAGGACCACGCC

GTACTGGTATTCGTACCGGCTGAGCAGGGTCTCCAGGGGGTGGTTGGGTGCCGCGGGGAACGGGGTCCAC

GCCACGGTCCACTCGGGCAAAAACCGAGTCGGCACGGCCCACGGTTCTCCCACCCACGCGTCTGGGGTCT

TGATGGCGATAAATCTTACCCCGAGCCGGATTTTTTGGGCGTATTCGAGAAACGGCACACACAGATCCGC

CGCGCCTACCACCCACAAGTGGTAGAGGCGAGGGGGGCTGGGTTGGTCTCGGTGCAACAGTCGGAAGCAC

-continued

GCCACGGCGTCCACGACCTCGGTGCTCTCCAAGGGGCTGTCCTCCGCAAACAGGCCCGTGGTGGTGTTTG

GGGGGCAGCGACAGGACCTAGTGCGCACGATCGGGCGGGTGGGTTTGGGTAAGTCCATCAGCGGCTCGGC

CAACCGTCGAAGGTTGGCCGGGCGAACGACGACCGGGGTACCCAGGGGTTCTGATGCCAAAATGCGGCAC

TGCCTAAGCAGGAAGCTCCACAGGGCCGGGCTTGCGTCGACGGAAGTCCGGGGCAGGGCGTTGTTCTGGT

CAAGGAGGGTCATTACGTTGACGACAACAACGCCCATGTTGGTATATTACAGGCCCGTGTCCGGTTTGGG

GCACTTGCAGATTTGTAAGGCCACGCACGGCGGGGAGACAGGCCGACGCGGGGGCTGCTCTAAAAATTTA

AGGGCCCTACGGTCCACAGACCCGCCTTCCCGGGGGGGCCCTTGGAGCGACCGGCAGCGGAGGCGTCCGG

GGGAGGGGAGGGTTATTTACGGGGGGGTAGGTCAGGGGGTGGGTCGTCAAACTGCCGCTCCTTAAAACCC

CGGGGCCCGTCGTTCGGGGTGCTCGTTGGTTGGCACTCACGGTGCGGCGAATGGCCTGTCGTAAGTTTTG

TCGCGTTTACGGGGGACAGGGCAGGAGGAAGGAGGAGGCCGTCCCGCCGGAGACAAAGCCGTCCCGGGTG

TTTCCTCATGGCCCCTTTTATACCCCAGCCGAGGACGCGTGCCTGGACTCCCCGCCCCCGGAGACCCCCA

AACCTTCCCACACCACACCACCCGGCGATGCCGAGCGCCTGTGTCATCTGCAGGAGATCCTGGCCCAGAT

GTACGGAAACCAGGACTACCCCATAGAGGACGACCCCAGCGCGGATGCCGCGGACGATGTCGACGAGGAC

GCCCCGGACGACGTGGCCTATCCGGAGGAATACGCAGAGGAGCTTTTTCTGCCCGGGGACGCGACCGGTC

CCCTTATCGGGGCCAACGACCACATCCCTCCCCCGCGTGGCGCATCTCCCCCCGGTATACGACGACGCAG

CCGGGATGAGATTGGGGCCACGGGATTTACCGCAGAAGAGCTGGACGCCATGGACAGGCAGGCGGCTCGA

GCCATCAGCCGCGGCGGCAAGCCCCCCTCGACCATGGCCAAGCTGGTGACTGGCATGGGCTTTACGATCC

ACGGAGCGCTCACCCCAGGATCGGAGGGGTGTGTCTTTGACAGCAGCCACCCAGATTACCCCCAACGGGT

AATCGTGAAGGCGGGGTGGTACACGAGCACGAGCCACGAGGCGCGACTGCTGAGGCGACTGGACCACCCG

GCGATCCTGCCCCTCCTGGACCTGCATGTCGTCTCCGGGGTCACGTGTCTGGTCCTCCCCAAGTACCAGG

CCGACCTGTATACCTATCTGAGTAGGCGCCTGAACCCACTGGGACGCCCGCAGATCGCAGCGGTCTCCCG

GCAGCTCCTAAGCGCCGTTGACTACATTCACCGCCAGGGCATTATCCACCGCGACATTAAGACCGAAAAT

ATTTTTATTAACACCCCCGAGGACATTTGCCTGGGGGACTTTGGTGCCGCGTGCTTCGTGCAGGGTTCCC

GATCAAGCCCCTTCCCCTACGGAATCGCCGGAACCATCGACACCAACGCCCCCGAGGTCCTGGCCGGGGA

TCCGTATACCACGACCGTCGACATTTGGAGCGCCGGTCTGGTGATCTTCGAGACTGCCGTCCACAACGCG

TCCTTGTTCTCGGCCCCCCGCGGCCCCAAAAGGGGCCCGTGCGACAGTCAGATCACCCGCATCATCCGAC

AGGCCCAGGTCCACGTTGACGAGTTTTCCCCGCATCCAGAATCGCGCCTCACCTCGCGCTACCGCTCCCG

CGCGGCCGGGAACAATCGCCCGCCTTACACCCGACCGGCCTGGACCCGCTACTACAAGATGGACATAGAC

GTCGAATATCTGGTTTGCAAAGCCCTCACCTTCGACGGCGCGCTTCGCCCCAGCGCCGCAGAGCTGCTTT

GTTTGCCGCTGTTTCAACAGAAATGACCGCCCCCGGGGGGCGGTGCTGTTTGCGGGTTGGCACAAAAAGA

CCCCGACCCGCGTCTGTGGTGTTTTTGGCATCATGTCGCCGGGCGCCATGCGTGCCGTTGTTCCCATTAT

CCCATTCCTTTTGGTTCTTGTCGGTGTATCGGGGGTTCCCACCAACGTCTCCTCCACCACCCAACCCCAA

CTCCAGACCACCGGTCGTCCCTCGCATGAAGCCCCCAACATGACCCAGACCGGCACCACCGACTCTCCCA

CCGCCATCAGCCTTACCACGCCCGACCACACACCCCCCATGCCAAGTATCGGACTGGAGGAGGAGGAGGA

AGAGGAGGAGGGGGCCGGGGATGGCGAACATCTTAAGGGGGGAGATGGGACCCGTGACACCCTACCCCAG

TCCCCGGGTCCAGCCGTCCCGTTGGCCGGGGATGACGAGAAGGACAAACCCAACCGTCCCGTAGTCCCAC

CCCCCGGTCCCAACAACTCCCCCGCGCGCCCCGAGACCAGTCGACCGAAGACACCCCCCACCAGTATCGG

GCCGCTGGCAACTCGACCCACGACCCAACTCCCCTCAAAGGGGCGACCCTTGGTTCCGACGCCTCAACAT

ACCCCGCTGTTCTCGTTCCTCACTGCCTCCCCCGCCCTGGACACCCTCTTCGTCGTCAGCACCGTCATCC

ACACCTTATCGTTTGTGTGTATTGTTGCTATGGCGACACACCTGTGTGGTGGTTGGTCCAGACGCGGGCG

ACGCACACACCCTAGCGTGCGTTACGTGTGCCTGCCGCCCGAACGCGGGTAGGGTATGGGGCGGGGATGG

-continued

GGAGAGCCCACACGCGGAAAGCAAGAACAATAAAGGCGGCGGGATCTAGTTGATATGCGTCTCTGGGTGT

TTTTGGGGTGTGGTGGGCGCGGGGCGGTCATTGGACGGGGGTGCAGTTAAATACATGCCCGGGACCCATG

AAGCATGCGCGACTTCCGGGCCTCGGAACCCACCCGAAACGGCCAACGGACGTCTGAGCCAGGCCTGGCT

ATCCGGAGAAACAGCACACGACTTGGCGTTCTGTGTGTCGCGATGTCTCTGCGCGCAGTCTGGCATCTGG

GGCTTTTGGGAAGCCTCGTGGGGGCTGTTCTTGCCGCCACCCATCTGGGACCTGCGGCCAACACAACGGA

CCCCTTAACGCACGCCCCAGTGTCCCCTCACCCCAGCCCCCTGGGGGGCTTTGCCGTCCCCCTCGTAGTC

GGTGGGCTGTGTGCCGTAGTCCTGGGGGCGGCGTGTCTGCTTGAGCTCCTGCGTCGTACGTGCCGCGGGT

GGGGGCGTTACCATCCCTACATGGACCCAGTTGTCGTATAATTTTTTCCCCCCCCCCCCTTCTCCGCATG

GGTGATGTCGGGTCCAAACTCCCGACACCACCAGCTGGCATGGTATAAATCACCGGTGCGCCCCCCAAAC

CATGTCCGGCAGGGGGATGGGGGGCGAATGCGGAGGGCACCCAACAACACCGGGCTAACCAGGAAATCCG

TGGCCCCGGCCCCCAACAAAGATCGCGGTAGCCCGGCCGTGTGACATTATCGTCCATACCTACCACACCG

ACGAATCCCCTAAGGGGGAGGGGCCATTTTACGAGGAGGAGGGGTATAACAAAGTCTGTCTTTAAAAAGC

AGGGGTTAGGGAGTTGTTCGGTCATAAGCTTCAGTGCGAACGACCAACTACCCCGATCATCAGTTATCCT

TAAGGTCTCTTTTGTGTGGTGCGTTCCGGTATGGGGGGGGCTGCCGCCAGGTTGGGGGCCGTGATTTTGT

TTGTCGTCATAGTGGGCCTCCATGGGGTCCGCGGCAAATATGCCTTGGCGGATGCCTCTCTCAAGATGGC

CGACCCCAATCGCTTTCGCGGCAAAGACCTTCCGGTCCTGGACCAGCTGACCGACCCTCCGGGGGTCCGG

CGCGTGTACCACATCCAGGCGGGCCTACCGGACCCGTTCCAGCCCCCCAGCCTCCCGATCACGGTTTACT

ACGCCGTGTTGGAGCGCGCCTGCCGCAGCGTGCTCCTAAACGCACCGTCGGAGGCCCCCCAGATTGTCCG

CGGGGCCTCCGAAGACGTCCGGAAACAACCCTACAACCTGACCATCGCTTGGTTTCGGATGGGAGGCAAC

TGTGCTATCCCCATCACGGTCATGGAGTACACCGAATGCTCCTACAACAAGTCTCTGGGGGCCTGTCCCA

TCCGAACGCAGCCCCGCTGGAACTACTATGACAGCTTCAGCGCCGTCAGCGAGGATAACCTGGGGTTCCT

GATGCACGCCCCCGCGTTTGAGACCGCCGGCACGTACCTGCGGCTCGTGAAGATAAACGACTGGACGGAG

ATTACACAGTTTATCCTGGAGCACCGAGCCAAGGGCTCCTGTAAGTACGCCCTCCCGCTGCGCATCCCCC

CGTCAGCCTGCCTCTCCCCCCAGGCCTACCAGCAGGGGGTGACGGTGGACAGCATCGGGATGCTGCCCCG

CTTCATCCCCGAGAACCAGCGCACCGTCGCCGTATACAGCTTGAAGATCGCCGGGTGGCACGGGCCCAAG

GCCCCATACACGAGCACCCTGCTGCCCCCGGAGCTGTCCGAGACCCCCAACGCCACGCAGCCAGAACTCG

CCCCGGAAGACCCCGAGGATTCGGCCCTCTTGGAGGACCCCGTGGGGACGGTGGCGCCGCAAATCCCACC

AAACTGGCACATCCCGTCGATCCAGGACGCCGCGACGCCTTACCATCCCCCGGCCACCCCGAACAACATG

GGCCTGATCGCCGGCGCGGTGGGCGGCAGTCTCCTGGCAGCCCTGGTCATTTGCGGAATTGTGTACTGGA

TGCACCGCCGCACTCGGAAAGCCCCAAAGCGCATACGCCTCCCCCACATCCGGGAAGACGACCAGCCGTC

CTCGCACCAGCCCTTGTTTTACTAGATACCCCCCCCCTTAATGGGTGCGGGGGGGGTCAGGTCTGCGGGG

TTGGGATGGGACCTTAACTCCATATAAAGCGAGTCTGGAAGGGGGGAAAGGCGGACAGTCGATAAGTCGG

TAGCGGGGGACGCGCACCTGTTCCGCCTGTCGCACCCACAGCTTTTTCGCGAACCGTCCCGTTTCGGGAT

GCCGTGCCGCCCGTTGCAGGGCCTGGTGCTCGTGGGCCTCTGGGTCTGTGCCACCAGCCTGGTTGTCCGC

CCCCCCCTTAATGGGTGCGGGGGGGGTCAGGTCTGCGGGGTTGGGATGGGACCTTAACTCCATATAAAGC

GAGICTGGAAGGGGGGAAAGGCGGACAGTCGATAAGTCGGTAGCGGGGGACGCGCACCTGTTCCGCCTGT

CGCACCCACAGCTTTTTCGCGAACCGTCCCGTTTCGGGATGCCGTGCCGCCCGTTGCAGGGCCTGGTGCT

CGTGGGCCTCTGGGTCTGTGCCACCAGCCTGGTTGTCCGTGGCCCCACGGTCAGTCTGGTATCAAACTCA

TTTGTGGACGCCGGGGCCTTGGGGCCCGACGGCGTAGTGGAGGAAGACCTGCTTATTCTCGGGGAGCTTC

GCTTTGTGGGGGACCAGGTCCCCCACACCACCTACTACGATGGGGTCGTAGAGCTGTGGCACTACCCCAT

-continued

GGGACACAAATGCCCACGGGTCGTGCATGTCGTCACGGTGACCGCGTGCCCACGTCGCCCCGCCGTGGCA

TTTGCCCTGTGTCGCGCGACCGACAGCACTCACAGCCCCGCATATCCCACCCTGGAGCTGAATCTGGCCC

AACAGCCGCTTTTGCGGGTCCGGAGGGCGACGCGTGACTATGCCGGGGIGTACGTGTTACGCGTATGGGT

CGGGGACGCACCAAACGCCAGCCTGTTTGTCCTGGGGATGGCCATAGCCGCCGAAGGTACTCTGGCGTAC

AACGGCTCGGCCCATGGCTCCTGCGCCCCGAAACTGCTTCCGTCTTCGGCCCCGCGTCTGGCCCCGGCGA

GCGTATACCAACCCGCCCCTAACCCGGCCTCCACCCCCTCGACCACCACCTCCACCCCCTCGACCACCAT

CCCCGCTCCCCAAGCATCGACCACACCCTTCCCCACGGGAGACCCAAAACCCCAACCTCACGGGGTCAAC

CACGAACCCCCATCGAATGCCACGCGAGCGACCCGCGACTCGCGATATGCGCTAACGGTGACCCAGATAA

TCCAGATAGCCATCCCCGCGTCCATTATAGCCCTGGTGTTTCTGGGGAGCTGTATTTGCTTTATACACAG

ATGTCAACGCCGCTACCGACGCTCCCGCCGCCCGATTTACAGCCCCCAGATACCCACGGGCATCTCATGC

GCGGTGAACGAAGCGGCCATGGCCCGCCTCGGAGCCGAGCTCAAATCGCATCCGAGCACCCCCCCCAAAT

CCCGGCGCCGGTCGTCACGCACGCCAATGCCCTCCCTGACGGCCATCGCCGAAGAGTCGGAGCCCGCGGG

GGCGGCTGGGCTTCCGACGCCCCCCGTGGACCCCACGACATCCACCCCAACGCCTCCCCTGTTGGTATAG

GTCCACGGCCACTGGCCGGGGGCACCACATAACCGACCGCAGTCACTGAGTTGGGAATAAACCGGTATTA

TTTACCTATATCCGTGTATGTCCATTTCTTTCTTCCCCCCCCCCCCGGAAACCAAAGAAGGAAGCAAAGA

ATGGATGGGAGGAGTTCAGGAAGCCGGGGAGAGGGCCCGCGGCGCATTTAAGGCGTTGTTGTGTTGACTT

TGGCTCTTCTGGCGGGTTGGTGCGGTGCTGTTTGTTGGGCTCCCATTTTACCCGAAGATCGGCTGCTATC

CCCGGGACATGGATCGCGGGGCGGTGGTGGGGTTTCTTCTCGGTGTTTGTGTTGTATCGTGCTTGGCGGG

AACGCCCAAAACGTCCTGGAGACGGGTGAGTGTCGGCGAGGACGTTTCGTTGCTTCCAGCTCCGGGGCCT

ACGGGGCGCGGCCCGACCCAGAAACTACTATGGGCCGTGGAACCCCTGGATGGGTGCGGCCCCTTACACC

CGTCGTGGGTCTCGCTGATGCCCCCCAAGCAGGTGCCCGAGACGGTCGTGGATGCGGCGTGCATGCGCGC

TCCGGTCCCGCTGGCGATGGCGTACGCCCCCCCGGCCCCATCTGCGACCGGGGGTCTACGAACGGACTTC

GTGTGGCAGGAGCGCGCGGCCGTGGTTAACCGGAGTCTGGTTATTCACGGGGTCCGAGAGACGGACAGCG

GCCTGTATACCCTGTCCGTGGGCGACATAAAGGACCCGGCTCGCCAAGTGGCCTCGGTGGTCCTGGTGGT

GCAACCGGCCCCAGTTCCGACCCCACCCCCGACCCCAGCCGATTACGACGAGGATGACAATGACGAGGGC

GAGGACGAAAGTCTCGCCGGCACTCCCGCCAGCGGGACCCCCCGGCTCCCGCCTCCCCCCGCCCCCCCGA

GGTCTTGGCCCAGCGCCCCCGAAGTCTCACATGTGCGTGGGGTGACCGTGCGTATGGAGACTCCGGAAGC

TATCCTGTTTTCCCCCGGGGAGACGTTCAGCACGAACGTCTCCATCCATGCCATCGCCCACGACGACCAG

ACCTACTCCATGGACGTCGTCTGGTTGAGGTTCGACGTGCCGACCTCGTGTGCCGAGATGCGAATATACG

AATCGTGTCTGTATCACCCGCAGCTCCCAGAATGTCTGTCCCCGGCCGACGCGCCGTGCGCCGCGAGTAC

GTGGACGTCTCGCCTGGCCGTCCGCAGCTACGCGGGGTGTTCCAGAACAAACCCCCCACCGCGCTGTTCG

GCCGAGGCTCACATGGAGCCCGTCCCGGGGCTGGCGTGGCAGGCGGCCTCCGTCAATCTGGAGTTCCGGG

ACGCGTCCCCACAACACTCCGGCCTGTATCTGTGTGTGGTGTACGTCAACGACCATATTCACGCCTGGGG

CCACATTACCATCAGCACCGCGGCGCAGTACCGGAACGCGGTGGTGGAACAGCCCCTCCCACAGCGCGGC

GCGGATTTGGCCGAGCCCACCCACCCGCACGTCGGGGCCCCTCCCCACGCGCCCCCAACCCACGGCGCCC

TGCGGTTAGGGGCGGTGATGGGGGCCGCCCTGCTGCTGTCTGCGCTGGGGTTGTCGGTGTGGGCGTGTAT

GACCTGTTGGCGCAGGCGTGCCTGGCGGGCGGTTAAAAGCAGGGCCTCGGGTAAGGGGCCCACGTACATT

CGCGTGGCCGACAGCGAGCTGTACGCGGACTGGAGCTCGGACAGCGAGGGAGAACGCGACCAGGTCCCGT

GGCTGGCCCCCCCGGAGAGACCCGACTCTCCCTCCACCAATGGATCCGGCTTTGAGATCTTATCACCAAC

GGCTCCGTCTGTATACCCCCGTAGCGACGGGCATCAATCTCGCCGCCAGCTCACAACCTTTGGATCCGGA

AGGCCCGATCGCCGTTACTCCCAGGCCTCCGATTCGTCCGTCTTCTGGTAAGGCGCCCCATCCCGAGGCC

-continued

CCACGTCGGTCGCCGAACTGGGCGACCGCCGGCGAGGTGGACGTCGGAGACGAGCTAATCGCGATTTCCG

ACGAACGCGGACCCCCCCGACATGACCGCCCGCCCCTCGCCACGTCGACCGCGCCCTCGCCACACCCGCG

ACCCCCGGGCTACACGGCCGTTGTCTCCCCGATGGCCCTCCAGGCTGTCGACGCCCCCTCCCTGTTTGTC

GCCTGGCTGGCCGCTCGGTGGCTCCGGGGGGCTTCCGGCCTGGGGGCCGTCCTGTGTGGGATTGCGTGGT

ATGTGACGTCAATTGCCCGAGGCGCACAAAGGGCCGGTGGTCCGCCTAGCCGCAGCAAATTAAAAATCGT

GAGTCACAGCGACCGCAACTTCCCACCCGGAGCTTTCTTCCGGCCTCGATGACGTCCCGGCTCTCCGATC

CCAACTCCTCAGCGCGATCCGACATGTCCGTGCCGCTTTATCCCACGGCCTCGCCAGTTTCGGTCGAAGC

CTACTACTCGGAAAGCGAAGACGAGGCGGCCAACGACTTCCTCGTACGCATGGGCCGCCAACAGTCGGTA

TTAAGGCGTTGACGCAGACGCACCCGCTGCGTCGGCATGGTGATCGCCTGTCTCCTCGTGGCCGTTCTGT

CGGGCGGATTTGGGGCGCTCCTGATGTGGCTGCTCCGCTAAAAGACCGCATCGACACGCGCGTCCTTCTT

GTCGTCTCTCTTCCCCCCCATCACCCCGCAATTTGCACCCAGCCTTTAACTACATTAAATTGGGTTCGAT

TGGCAATGTTGTCTCCCGGTTGATTTTTGGGTGGGTGGGGAGTGGGTGGGTGGGGAGTGG

SEQ ID NO: 9 is a nucleotide sequence that encodes pSH-tetR.

(SEQ ID NO: 9)

tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatcaga gcagattgtactgagagtgcaccatatgcggtgtgaaataccgcacagatgcgtaaggagaaaataccgcatcaggcgcc attcgccattcaggctgcgcaactgttgggaagggcgatcggtgcgggcctcttcgctattacgccagctggcgaaaggg ggatgtgctgcaaggcgattaagttgggtaacgccagggttttcccagtcacgacgttgtaaaacgacggccagtgccaa gcttggctgcaggtcaacaccagagcctgcccaacatggcacccccactcccacgcacccccactcccacgcacccccac tcccacgcacccccactcccacgcacccccactcccacgcacccccactcccacgcacccccactcccacgcacccccac tcccacgcacccccactcccacgcatccccgcgatacatccaacacagacagggaaaagatacaaaagtaaacctttatt tcccaacagacagcaaaaatcccctgagtttttttttattagggccaacacaaaagacccgctggtgtgtggtgcccgtg tctttcacttttcccctccccgacacggattggctggtgtagtgggcgcggccagagaccacccagcgcccgaccccccc ctccccacaaacacgggggggcgtcccttattgttttccctcgtcccgggtcgaccagacatgataagatacattgatgag tttggacaaaccacaactagaatgcagtgaaaaaaatgctttatttgtgaaatttgtgatgctattgctttatttgtaac cattataagctgcaataaacaagttctgctttaataagatctgaattcccgggatccgctgtacgcggacccactttcac atttaagttgtttttctaatccgcatatgatcaattcaaggccgaataagaaggctggctctgcaccttggtgatcaaat aattcgatagcttgtcgtaataatggcggcatactatcagtagtaggtgtttccctttcttctttagcgacttgatgctc ttgatcttccaatacgcaacctaaagtaaaatgccccacagcgctgagtgcatataatgcattctctagtgaaaaacctt gttggcataaaaaggctaattgattttcgagagtttcatactgtttttctgtaggccgtgtacctaaatgtacttttgct ccatcgcgatgacttagtaaagcacatctaaaacttttagcgttattacgtaaaaaatcttgccagctttccccttctaa agggcaaaagtgagtatggtgcctatctaacatctcaatggctaaggcgtcgagcaaagcccgcttatttttacatgcc aatacaatgtaggctgctctacacctagcttctgggcgagtttacgggttgttaaaccttcgattccgacctcattaagc agctctaatgcgctgttaatcactttacttttatctaatctagacatatcaattcgccctatagtgagtcgtattacaat tctttgccaaaatgatgagacagcacaataaccagcacgttgcccaggagctgtaggaaaaagaagaaggcatgaacatg gttagcagaggggcccggtttggactcagagtattttatcctcatctcaaacagtgtatatcattgtaaccataaagaga aaggcaggatgatgaccaggatgtagttgtttctaccaataagaatatttccacgccagccagaatttatatgcagaaat attctaccttatcatttaattataacaattgttctctaaaactgtgctgaagtacaatataatataccctgattgccttg aaaaaaaagtgattagagaaagtacttacaatctgacaaataaacaaaagtgaatttaaaaattcgttacaaatgcaagc taaagtttaacgaaaaagttacagaaaatgaaaagaaaataagaggagacaatggttgtcaacagagtagaaagtgaaag -continued

```
aaacaaaattatcatgagggtccatggtgatacaagggacatcttcccattctaaacaacaccctgaaaactttgccccc
tccatataacatgaattttacaatagcgaaaaagaaagaacaatcaagggtccccaaactcaccctgaagttctcaggat
cgatccggagcttttttgcaaaagcctaggcctccaaaaaagcctcttcactacttctggaatagctcagaggccctagag
gatccccggcggggtcgtatgcggctggagggtcgcggacggagggtccctgggggtcgcaacgtaggcggggcttctgt
ggtgatgcggagagggggcggcccgagtctgcctggctgctgcgtctcgctccgagtgccgaggtgcaaatgcgaccaga
ctgtcgggccagggctaacttataccccacgcctttcccctccccaaaggggcggcagtgacgattcccccaatggccgc
gcgtcccaggggaggcaggcccaccgcggggcggccccgtccccggggaccaacccggcgcccccaaagaatatcattag
catgcacggcccggcccccgatttgggggcccaacccggtgtcccccaaagaaccccattagcatgcccctcccgccgac
gcaacaggggcttggcctgcgtcggtgccccggggcttcccgccttcccgaagaaactcattaccatacccggaacccca
ggggaccaatgcgggttcattgagcgacccgcgggccaatgcgcgaggggccgtgtgttccgccaaaaaagcaattagca
taacccggaaccccaggggagtggttacgcgcggcgcgggaggcggggaataccggggttgcccattaagggccgcggga
attgccggaagcgggaagggcggccggggccgcccattaatgagtttctaattaccataccgggaagcggaacaaggcct
cttgcaagtttttaattaccataccgggaagtgggcggcccggcccattgggcggtaactcccgcccaatgggccgggcc
ccgaagactcggcggacgctggttggccgggccccgccgcgctggcggccgccgattggccagtcccgcccccgaggcgg
cccgccctgtgagggcgggctggctccaagcgtatatatgcgcggctcctgccatcgtctctccggagagcggcttggtg
cggagctcgaattcggtaatcatggtcatagctgtttcctgtgtgaaattgttatccgctcacaattccacacaacatac
gagccggaagcataaagtgtaaagcctggggtgcctaatgagtgagctaactcacattaattgcgttgcgctcactgccc
gctttccagtcgggaaacctgtcgtgccagctgcattaatgaatcggccaacgcgcggggagaggcggtttgcgtattgg
gcgctcttccgcttcctcgctcactgactcgctgcgctcggtcgttcggctgcggcgagcggtatcagctcactcaaagg
cggtaatacggttatccacagaatcaggggataacgcaggaaagaacatgtgagcaaaaggccagcaaaaggccaggaac
cgtaaaaaggccgcgttgctggcgtttttccataggctccgcccccctgacgagcatcacaaaaatcgacgctcaagtca
gaggtggcgaaacccgacaggactataaagataccaggcgtttccccctggaagctccctcgtgcgctctcctgttccga
ccctgccgcttaccggatacctgtccgcctttctcccttcgggaagcgtggcgctttctcaatgctcacgctgtaggtat
ctcagttcggtgtaggtcgttcgctccaagctgggctgtgtgcacgaaccccccgttcagcccgaccgctgcgccttatc
cggtaactatcgtcttgagtccaacccggtaagacacgacttatcgccactggcagcagccactggtaacaggattagca
gagcgaggtatgtaggcggtgctacagagttcttgaagtggtggcctaactacggctacactagaaggacagtatttggt
atctgcgctctgctgaagccagttaccttcggaaaaagagttggtagctcttgatccggcaaacaaaccaccgctggtag
cggtggtttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatc
cttttaaattaaaaatgaagttttaaatcaatctaaagtatatatgagtaaacttggtctgacagttaccaatgcttaat
cagtgaggcacctatctcagcgatctgtctatttcgttcatccatagttgcctgactccccgtcgtgtagataactacga
tacgggagggcttaccatctggccccagtgctgcaatgataccgcgagacccacgctcaccggctccagatttatcagca
ataaaccagccagccggaagggccgagcgcagaagtggtcctgcaactttatccgcctccatccagtctattaattgttg
ccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatcccccatgttgtgcaaa
aaagcggttagctccttcggtcctccgatcgttgtcagaagtaagttggccgcagtgttatcactcatggttatggcagc
actgcataattctcttactgtcatgccatccgtaagatgcttttctgtgactggtgagtactcaaccaagtcattctgag
aatagtgtatgcggcgaccgagttgctcttgcccggcgtcaatacgggataataccgcgccacatagcagaactttaaaa
gtgctcatcattggaaaacgttcttcggggcgaaaactctcaaggatcttaccgctgttgagatccagttcgatgtaacc
cactcgtgcacccaactgatcttcagcatcttttactttcaccagcgtttctgggtgagcaaaaacaggaaggcaaaatg
ccgcaaaaaagggaataagggcgacacggaaatgttgaatactcatactcttcctttttcaatattattgaagcatttat
```

-continued cagggttattgtctcatgagcggatacatatttgaatgtatttagaaaaataaacaaataggggttccgcgcacatttcc ccgaaaagtgccacctgacgtctaagaaaccattattatcatgacattaacctataaaaataggcgtatcacgaggccct ttcgtc SEQ ID NO: 10 is a nucleotide sequence that encodes the open reading frame of gK (strain KOS).

(SEQ ID NO: 10)

atgctcgccg tccgttccct gcagcacctc tcaaccgtcg tcttgataac ggcgtacggc ctcgtgctcg tgtggtacac cgtcttcggt gccagtccgc tgcaccgatg tatttacgcg gtacgcccca ccggcaccaa caacgacacc gccctcgtgt ggatgaaaat gaaccagacc ctattgtttc tgggggcccc gacgcacccc cccaacgggg gctggcgcaa ccacgcccat atctgctacg ccaatcttat cgcgggtagg gtcgtgccct tccaggtccc acccgacgcc acgaatcgtc ggatcatgaa cgtccacgag gcagttaact gtctggagac cctatggtac acacgggtgc gtctggtggt cgtagggtgg ttcctgtatc tggcgttcgt cgccctccac caacgccgat gtatgtttgg tgtcgtgagt cccgcccaca agatggtggc cccggccacc tacctcttga actacgcagg ccgcatcgta tcgagcgtgt tcctgcagta cccctacacg aaaattaccc gcctgctctg cgagctgtcg gtccagcggc aaaacctggt tcagttgttt gagacggacc cggtcacctt cttgtaccac cgccccgcca tcggggtcat cgtaggctgc gagttgatgc tacgctttgt ggccgtgggt ctcatcgtcg gcaccgcttt catatcccgg ggggcatgtg cgatcacata ccccctgttt ctgaccatca ccacctggtg ttttgtctcc accatcggcc tgacagagct gtattgtatt ctgcggcggg gcccggcccc caagaacgca gacaaggccg ccgccccggg gcgatccaag ggctgtcgg gcgtctgcgg gcgctgttgt tccatcatcc tgtcgggcat cgcaatgcga ttgtgttata tcgccgtggt ggccggggtg gtgctcgtgg cgcttcacta cgagcaggag atccagaggc gcctgtttga tgtatga

The invention claimed is:

1. An oncolytic Herpes Simplex Virus (HSV) comprising recombinant DNA, wherein the recombinant DNA comprises:

a) a gene comprising a 5' untranslated region and a HSV-1, or HSV-2, VP5 gene that is operably linked to an VP5 promoter comprising a TATA element;

b) a tetracycline operator sequence positioned between 6 and 24 nucleotides 3' to said TATA element, wherein the VP5 gene lies 3' to said tetracycline operator sequence;

c) a gene sequence encoding tetracycline repressor operably linked to an HSV immediate-early promoter, wherein the gene sequence is located at the ICP0 locus;

d) a variant gene that increases syncytium formation as compared to wild type, wherein the HSV-1, or HSV-2, variant gene is selected from the group consisting of: a glycoprotein K (gK) variant; a glycoprotein B (gB) variant; a UL24 variant; and UL20 gene variant; and e) a gene sequence encoding a functional ICP34.5 protein; wherein said oncolytic HSV does not encode functional ICP0 and does not contain a ribozyme sequence located in said 5' untranslated region of VP5.

2. The oncolytic HSV of claim 1, wherein the variant gene is a gK variant gene that encodes an amino acid substitution selected from the group consisting of: an Ala to Thr amino acid substitution corresponding to amino acid 40 of SEQ ID NO: 2; an Ala to "x" amino acid substitution corresponding to amino acid 40 of SEQ ID NO: 2, wherein "x" is any amino acid; an Asp to Asn amino acid substitution corresponding to amino acid 99 of SEQ ID NO: 2; a Leu to Pro amino acid substitution corresponding to amino acid 304 of SEQ ID NO: 2; and an Arg to Leu amino acid substitution corresponding to amino acid 310 of SEQ ID NO: 2.

3. The oncolytic HSV of claim 1, wherein the tetracycline operator sequence comprises two Op2 repressor binding sites.

4. The oncolytic HSV of claim 1, wherein the VP5 promoter is an HSV-1 or HSV-2 VP5 promoter.

5. The oncolytic HSV of claim 1, wherein the immediate-early promoter is an HSV-1 or HSV-2 immediate-early promoter.

6. The oncolytic HSV of claim 1, wherein the HSV immediate-early promoter is selected from the group consisting of: ICP0 promoter and ICP4 promoter.

7. The oncolytic HSV of claim 1, wherein the recombinant DNA is part of the HSV-1 genome or part of the HSV-2 genome.

8. The oncolytic HSV of claim 1, further encoding at least one polypeptide that can increase the efficacy of the oncolytic HSV to induce an anti-tumor-specific immunity.

9. The oncolytic HSV of claim 8, wherein the at least one polypeptide encodes a product selected from the group consisting of: interleukin 2 (IL2), interleukin 12 (IL12), interleukin 15 (IL15), an anti-PD-1 antibody or antibody reagent, an anti-PD-L1 antibody or antibody reagent, an anti-OX40 antibody or antibody reagent, a CTLA-4 antibody or antibody reagent, a TIM-3 antibody or antibody reagent, a TIGIT antibody or antibody reagent, a soluble interleukin 10 receptor (IL10R), a fusion polypeptide between a soluble IL10R and IgG-Fc domain, a soluble TGFβ type II receptor (TGFBRII), a fusion polypeptide between a soluble TGFBRII and IgG-Fc domain, an anti-IL10R antibody or antibody reagent, an anti-IL10 antibody or antibody reagent, an anti-TGFBRII antibody or antibody reagent, and an anti-TGFBRII antibody or antibody reagent.

10. The oncolytic HSV of claim 1, wherein the oncolytic HSV the further encodes fusogenic activity.

11. A composition comprising an oncolytic HSV of claim 1.

12. A method for treating cancer, the method comprising administering the oncolytic HSV of claim 1 to a subject having cancer.

13. The method of claim 12, wherein the cancer is a benign solid tumor or malignant solid tumor.

14. The method of claim 12, wherein the subject is diagnosed or has been diagnosed as having a cancer selected from the group consisting of: non-small-cell lung cancer, breast cancer, brain cancer, colon cancer, prostate cancer, liver cancer, lung cancer, ovarian cancer, skin cancer, head and neck cancer, kidney cancer, and pancreatic cancer.

15. The method of claim 12, wherein the cancer is metastatic.

16. The method of claim 12, further comprising administering an agent that regulates the tet operator-containing promoter.

17. The method of claim 16, wherein the agent is doxycycline or tetracycline.

18. The method of claim 16, wherein the agent is administered locally or systemically.

19. The method of claim 12, wherein the oncolytic virus is administered directly to the tumor.

* * * * *